(12) United States Patent
Johansson et al.

(10) Patent No.: US 8,415,333 B2
(45) Date of Patent: Apr. 9, 2013

(54) BRONCHODILATING DIAZAHETEROARYLS

(75) Inventors: Martin Johansson, Linhamn (SE); Viveca Thornqvist Otlner, Landskrona (SE); Jorgen Toftered, Lund (SE); David Wensbo, Billeberga (SE); Maria Dalence, Lund (SE)

(73) Assignee: Respiratorious AB, Lund (SE)

( * ) Notice: Subject to any disclaimer, the term of this patent is extended or adjusted under 35 U.S.C. 154(b) by 0 days.

(21) Appl. No.: 13/202,875

(22) PCT Filed: Feb. 24, 2010

(86) PCT No.: PCT/EP2010/052343
§ 371 (c)(1),
(2), (4) Date: Nov. 4, 2011

(87) PCT Pub. No.: WO2010/097410
PCT Pub. Date: Sep. 2, 2010

(65) Prior Publication Data
US 2012/0040942 A1    Feb. 16, 2012

Related U.S. Application Data

(60) Provisional application No. 61/155,027, filed on Feb. 24, 2009.

(30) Foreign Application Priority Data

Aug. 28, 2009 (SE) ...................................... 0950620

(51) Int. Cl.
| | | |
|---|---|---|
| A61K 31/56 | (2006.01) | |
| A61K 31/4375 | (2006.01) | |
| A61K 31/438 | (2006.01) | |
| A61K 31/5377 | (2006.01) | |
| A61K 31/5386 | (2006.01) | |
| A61K 31/541 | (2006.01) | |
| A61P 11/00 | (2006.01) | |
| A61P 11/06 | (2006.01) | |
| A61P 11/08 | (2006.01) | |
| C07D 471/04 | (2006.01) | |
| C07D 491/113 | (2006.01) | |
| C07D 498/08 | (2006.01) | |

(52) U.S. Cl. .................. 514/171; 514/228.2; 514/230.5; 514/234.5; 514/235.04; 514/278; 514/300; 544/58.2; 544/58.6; 544/105; 544/127; 544/362; 546/15; 546/19; 546/122; 546/123

(58) Field of Classification Search .................. 546/122; 514/300
See application file for complete search history.

(56) References Cited

U.S. PATENT DOCUMENTS

| | | |
|---|---|---|
| 4,031,103 A | 6/1977 | Williams et al. |
| 4,753,666 A | 6/1988 | Pastor et al. |
| 5,026,711 A | 6/1991 | Mendes et al. |
| 5,593,943 A | 1/1997 | Nuebling et al. |
| 2006/0040254 A1 | 2/2006 | Skogvall |

FOREIGN PATENT DOCUMENTS

| | | |
|---|---|---|
| EP | 0 346 208 | 12/1989 |
| EP | 0 584 611 | 3/1994 |
| EP | 1669348 A1 * | 4/2005 |
| EP | 1 669 348 | 6/2006 |
| JP | 8-301849 | 11/1996 |
| WO | WO 93/13097 | 7/1993 |
| WO | WO 95/00511 | 1/1995 |
| WO | WO 99/26927 | 6/1999 |
| WO | WO 02/089793 | 11/2002 |
| WO | WO 2004/014377 | 2/2004 |
| WO | WO 2004/052370 | 6/2004 |
| WO | WO 2005/085234 | 9/2005 |
| WO | WO 2008/000407 | 1/2008 |
| WO | WO 2008/000409 | 1/2008 |

OTHER PUBLICATIONS

Nakamoto et. al., "Preparation of heterocyclic compounds as novel antimalaria agents", Hcaplus 2006:152549, 2006.*
Patani et. al., "Bioisosterism: A Rational Approach in Drug Design", Patani et. al., Chem. Rev. 1996, 96, pp. 3147-3176.*
Vippagunta et al., Crystalline solids, 48 ADV. Drug Delivery Rev. 3-26 (2001).*
International Search Report for International Application No. PCT/EP2010/052343 mailed May 27, 2010.
Skogvall et al. "Effects of capsazepine on human small airway responsiveness unravel a novel class of bronchorelaxants." *Pulmonary Pharm. & Therap.* vol. 20. 2007. pp. 273-280.

* cited by examiner

*Primary Examiner* — Janet Andres
*Assistant Examiner* — Timothy R Rozof
(74) *Attorney, Agent, or Firm* — Merchant & Gould P.C.

(57) ABSTRACT

The invention relates to novel compounds having the general formula (I), and which compounds are useful to treat a disorder or disease characterized by bronchoconstriction, e.g. COPD and asthma.

17 Claims, No Drawings

BRONCHODILATING DIAZAHETEROARYLS

This application is a National Stage Application of PCT/EP2010/052343, filed 24 Feb. 2010, which claims benefit of U.S. Ser. No. 61/155,027, filed 24 Feb. 2009 and Ser. No. 0950620-5, filed 28 Aug. 2009 in Sweden and which applications are incorporated herein by reference. To the extent appropriate, a claim of priority is made to each of the above disclosed applications.

TECHNICAL FIELD

The present invention relates to novel bronchorelaxing compounds, pharmaceutical compositions comprising such compounds, and a method of treating or alleviating conditions accompanied by bronchoconstriction and/or vasoconstriction, by use of such compounds.

BACKGROUND

Asthma and chronic obstructive pulmonary disease (COPD) are diseases affecting the respiratory system, which millions of people suffer from. These diseases are today regarded as inflammatory diseases and the symptoms comprise constriction of the airways. Common treatment of the associated bronchoconstriction involves use of beta-agonists, such as terbutalin and formoterol, and anticholinergics, such as ipratropium bromide and tiotropium bromide.

Hypertension, i.e. high blood pressure, increases the risk of stroke, heart attacks, heart failure and kidney disease. Medications presently used for the treatment of hypertension include the administration of beta-blockers, calcium channel blockers, diuretics, angiotensin-converting enzyme inhibitors and angiotensin II receptor antagonists. Vasoconstriction results in an increase in the blood pressure.

The treatments for prevention, revocation or reduction of bronchoconstricion and vasoconstriction are in many ways insufficient and there is a need for alternative treatments.

More specifically, there is a need of compounds also being effective in preventing or revoking bronchoconstriction within the small airways, such as human airways having a diameter of less than 2.0 mm. It is believed that a bronchodilating effect on small airways (noncartilaginous airways of 2.0 mm or less in inner diameter) is of greater relevance for clinically observed relief of symptoms in COPD (i.e. shortness of breath), and maybe even in severe asthma, as compared to bronchodilation of larger bronchi (more than 2 mm in inner diameter), due to the greater total surface area associated with the former.

Furthermore, there is a need for compounds being effective in preventing or revoking bronchoconstriction, whose mechanisms differs from pharmacological established mechanisms of bronchodilation and preferably being effective in preventing or revoking bronchoconstriction within the small airways. Accordingly, there is a need for compounds being effective in preventing or revoking bronchoconstriction and which neither affect adrenergic or muscarinic receptors nor increasing the levels of cAMP through inhibition of phosphodiesterase enzymes, such as PDE3A enzyme.

SUMMARY

The present invention seeks to mitigate, alleviate, circumvent or eliminate at least one, such as one or more, of the above-identified deficiencies.

Accordingly there is provided, according to one aspect of the invention, a compound, which may be represented with the general formula (I)

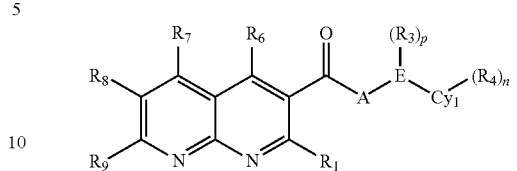

wherein $R_1$ is selected from the group consisting of C1-C3 alkyl, NH2, NH(C1-C3 alkyl), C1-3 fluoroalkyl, OC1-C3 alkyl, OC1-3 fluoroalkyl, N(C1-C3 alkyl)2 in which the C1-3 alkyl may be the same or different, C(O)C0-C3 alkyl, C(O)OC0-C3 alkyl, C(O)N(C0-C3 alkyl)2 in which the C0-3 alkyl may be the same or different and N(C0-C3 alkyl)C(O)C1-C3 alkyl; A is $NR_2$, O, or S, wherein R2 is selected from the group consisting of H and C1-C3 alkyl; E is selected from the group consisting of C1-C3 alkylene, ethene-1,2-diyl, 1-propene-1,3-diyl and 2-propene-1,3-diyl; if E is selected from the group consisting of ethene-1,2-diyl, 1-propene-1,3-diyl and 2-propene-1,3-diyl, then the stereochemistry of the double-bond may be either E or Z; the integer "p" is 0 (zero), 1 or 2; R3 is independently selected from the group consisting of C1-C3 alkyl, C1-C3 alkyleneOC0-C3 alkyl, OMe, C1-5 fluoroalkyl, C0-C3 alkyleneOC1-3 fluoroalkyl, C(O)OC0-C3 alkyl, and C(O)N(C0-C3 alkyl)2, in which the C0-3 alkyl may be the same or different; R3 may, if present, be connected to any of the carbon atom(s) in E; if "p" is 2, then the two R3 may be the connected to the same carbon atom or to different carbon atoms; Cy1 is a 5-membered heteroaryl, a 6-membered heteroaryl, or phenyl; the integer "n" is 0 (zero), 1 or 2; R4 is independently selected from the group consisting of C1-8 alkyl, C1-5 fluoroalkyl, halo, C0-1 alkylene cyano, C0-8 alkyleneOC0-5 alkyl, SC0-5 alkyl, C0-3 alkyleneSO2C0-5 alkyl, C0-3 alkyleneOC0-3 fluororoalkyl, C0-3 alkyleneNHC0-3 alkyl, C0-3 alkyleneN(C1-5 alkyl)2, in which the C1-5 alkyl may be the same or different, C0-3 alkyleneC(O)OC0-5 alkyl, C0-3 alkyleneOC(O)C0-5 alkyl, C0-3 alkyleneN(C0-3 alkyl)C(O)C0-3 alkyl, C0-3 alkyleneC(O)NHC0-3 alkyl, C0-3 alkyleneC(O)N(C1-5 alkyl)$_2$, in which the C1-5 alkyl may be the same or different, nitro, C(O)C0-C5 alkyl, N(C0-C3 alkyl)SO2C1-C3 alkyl, N(C0-C3 alkyl)SO2C1-C3 fluoroalkyl, OC2-C3alkyleneN(C0-C3 alkyl)2, in which the C0-3 alkyl may be the same or different, and wherein D is selected from the group consisting of C0-C3 alkylene, C0-1 alkylene OC0-1 alkylene, C0-1 alkylene OC(O)C0-1 alkylene, C0-1 alkylene C(O)OC0-1 alkylene, C0-1 alkylene C(O)N(C0-3 alkyl) C0-1 alkylene, C0-1 alkylene N(C0-3 alkyl)C(O)C0-1 alkylene, NHSO2, SO2NH, SO2, SO, C0-1 alkylene C(O)C0-1 alkylene, C0-1 alkylene N(C0-3 alkyl)C0-1 alkylene and S; Cy2 is a 5-membered heteroaryl, a 6-membered heteroaryl, phenyl, a 3- to 8-membered non-aromatic heterocycle or a C3-8 non-aromatic carbocycle; the integer "m" is 0 (zero), 1, 2 3, 4, or 5; and R5 is independently selected from C1-5 alkyl, C1-5 fluoroalkyl, halo, C0-1 alkylene cyano, C0-5 alkyleneOC0-5 alkyl, SC0-5 alkyl, C0-3 alkyleneSO2C0-5 alkyl, C0-3 alkyleneOC1-3 fluoroalkyl, C0-3 alkyleneNHC0-3 alkyl, C0-3 alkyleneN(C1-5 alkyl)$_2$, in which the C1-5 alkyl may be the same or different, C0-3 alkyleneC(O)OC0-5 alkyl, C0-3 alkyleneOC(O)C0-5 alkyl, C0-3 alkyleneN(C0-3 alkyl)C(O)C0-3 alkyl, C0-3 alkyleneC(O)NHC0-3 alkyl, C0-3 alkyleneC(O)N(C1-5 alkyl)2, in which the C1-5 alkyl may be the same or different, C0-3 alkyleneC(O)N(C4-5 alkylene), nitro, C(O)C0-C5 alkyl, C(O)C1-C3 fluoroalkyl, N(C0-C3 alkyl)SO2C1-C3 alkyl, N(C0-C3 alkyl)SO2C1-C3 fluoroalkyl, and OC2-C3alkyleneN(C0-C3 alkyl)2, in which the C0-3 alkyl may be the same or different; if Cy2 is a 3- to 8-membered non-aromatic heterocycle or a C3-8 non-aromatic carbocycle and "m" is at least 2, then two R5, being attached to the same carbon atom on said 3- to 8-membered non-aromatic heterocycle or said C3-8 non-aromatic carbocycle, may be connected to each other to form a 3-, 4- or 5-membered spiro ring; said spiro ring being a non-aromatic carbocycle or a non-aromatic heterocycle; if Cy2 is a 3- to 8-membered non-aromatic heterocycle or a C3-8 non-aromatic carbocycle and "m" is at least 2, then two R5, being attached to different atoms in said 3- to 8-membered non-aromatic heterocycle or said C3-8 non-aromatic carbocycle, may be connected to each other to form a C0-3 alkylene bridge; Cy2 thus being a bicyclic residue; if Cy2 is a 3- to 8-membered non-aromatic heterocycle or a C3-8 non-aromatic carbocycle, then R5 may be a double bonded oxygen (═O), being attached to a carbon or sulfur atom in said cycle; R6, R7, and R8 are independently selected from the group consisting of H, halogen, C1-C3 alkyl, NH(C0-C3 alkyl), C1-3 fluoroalkyl, OC0-C3 alkyl, OC1-3 fluoroalkyl, N(C4-5 alkylene), morpholinyl, N(C1-C3 alkyl)2, in which the C0-3 alkyl may be the same or different, and cyano; R9 is selected from the group consisting of H, halogen, C1-C3 alkyl, and C1-3 fluoroalkyl; as a free base, an acid in its non-charged protonated form, a pharmaceutically addition acceptable salt, solvate, solvate of a salt thereof, a pure stereoisomer, a racemic, diastereomeric or scalemic mixture, a corresponding tautomeric form resulting from a hydrogen shift between two hetero-atoms and/or the corresponding tautomeric form resulting from a keto-enol tautomerization; with the proviso that the compound is not any of the following:

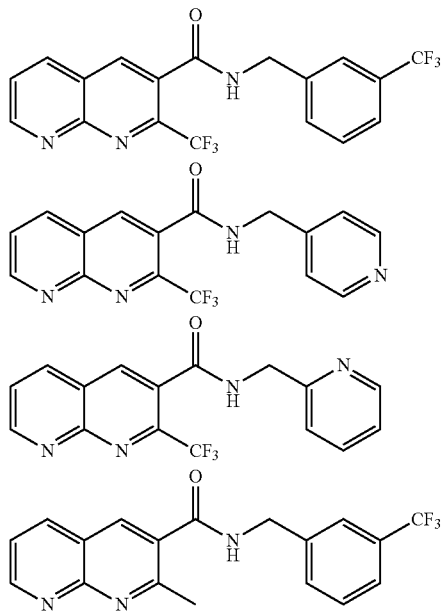

-continued

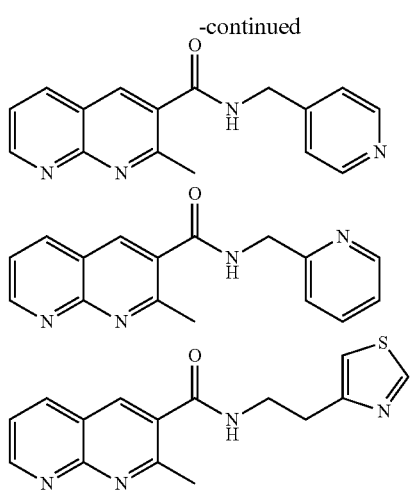

According to another aspect of the invention there is provided a pharmaceutical composition, which may comprise a compound according formula (I) or a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide and at least one pharmaceutically acceptable excipient.

According to another aspect of the invention a compound according to formula (I), a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide or a pharmaceutical composition as disclosed above may be used in therapy.

According to another aspect of the invention, a compound according to formula (I), a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide or a pharmaceutical composition as disclosed above may be used to prevent and/or treat a disease or condition characterized by bronchoconstriction of the respiratory apparatus. Such diseases or conditions characterized by bronchoconstriction of the respiratory apparatus may be asthma, chronic obstructive pulmonary disease, chronic bronchitis, emphysema, bronchiectasis, cystic fibrosis, bronchiolitis and bronchopulmonary dysplasia.

According to another aspect of the invention, a compound according to formula (I), a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide or a pharmaceutical composition as disclosed above may be used to prevent and/or treat bronchoconstriction.

According to another aspect of the invention, a compound according to formula (I), a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide or a pharmaceutical composition as disclosed above may be used to prevent and/or treat diseases and disorders related to smooth muscle dysfunction including hypertension, pulmonary hypertension, incontinence and overactive bladder, irritable bowel syndrome, pre-term labor, vasospasm, subarachnoid hemorrhages and erectile dysfunction.

According to another aspect of the invention there is provided a method of preventing, and/or treating bronchoconstriction of the respiratory apparatus. Such a method comprises the step of administering, to a mammal, including man in need of such prevention and/or treatment, a therapeutically effective amount of a compound according formula (I) or a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide.

According to another aspect of the invention there is provided method of preventing and/or treating a disease or condition characterized by bronchoconstriction of the respiratory apparatus. Such a method comprises the step of administering, to a mammal, including man in need of such prevention and/or treatment, a therapeutically effective amount of a compound according formula (I) or a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide.

According to another aspect of the invention a compound according to formula (I), a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide or a pharmaceutical composition as disclosed above may be used to prevent and/or treat a disease or condition characterized by systemic or respiratory vasoconstriction. Additional, a method of preventing and/or treating a disease or condition characterized by systemic or respiratory vasoconstriction, may comprise the step of administering, to a mammal, including man in need of such prevention and/or treatment, a therapeutically effective amount of a compound according to formula (I) or a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide.

According to another aspect of the invention there is provided a method of preventing, and/or treating diseases and disorders related to smooth muscle dysfunction including hypertension, pulmonary hypertension, incontinence and overactive bladder, irritable bowel syndrome, pre-term labor, vasospasm, subarachnoid hemmorages and erectile dysfunction. Such a method comprises the step of administering, to a mammal, including man in need of such prevention and/or treatment, a therapeutically effective amount of a compound according formula (I) or a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide.

Further, advantageous features of various embodiments of the invention are defined in the dependent claims and within the detailed description below.

DETAILED DESCRIPTION OF EXAMPLE EMBODIMENTS

Definitions

In the context of the present application and invention, the following definitions apply:

The term "addition salt" is intended to mean salts formed by the addition of a pharmaceutical acceptable acid, such as organic or inorganic acids, or a pharmaceutical acceptable base. The organic acid may be, but is not limited to, acetic, propanoic, methanesulfonic, benzenesulfonic, lactic, malic, citric, tartaric, succinic or maleic acid. The inorganic acid may be, but is not limited to, hydrochloric, hydrobromic, sulfuric, nitric acid or phosphoric acid. The base may be, but is not limited to, ammonia and hydroxides of alkali or alkaline earth metals. The term "addition salt" also comprises the hydrates and solvent addition forms, such as hydrates and alcoholates.

As used herein, "halo" or "halogen" refers to fluoro, chloro, bromo, and iodo.

As used herein, "alkyl" used alone or as a suffix or prefix, is intended to include both branched and straight chain saturated aliphatic hydrocarbon groups having from 1 to 12 carbon atoms or if a specified number of carbon atoms is provided then that specific number is intended. For example "C1-6 alkyl" denotes alkyl having 1, 2, 3, 4, 5 or 6 carbon atoms. When the specific number denoting the alkyl-group is the integer 0 (zero), a hydrogen-atom is intended as the substituent at the position of the alkyl-group. For example, "N(C0 alkyl)2" is equivalent to "NH2" (amino).

As used herein, "alkylenyl" or "alkylene" used alone or as a suffix or prefix, is intended to include straight chain saturated aliphatic hydrocarbon groups having from 1 to 12 carbon atoms or if a specified number of carbon atoms is provided then that specific number is intended. For example "C1-6 alkylenyl" "C1-6 alkylene" denotes alkylenyl or alkylene having 1, 2, 3, 4, 5 or 6 carbon atoms. When the specific number denoting the alkylenyl or alkylene-group is the integer 0 (zero), a bond is intended to link the groups onto which the alkylenyl or alkylene-group is substituted. For example, "NH(C0 alkylene)NH2" is equivalent to "NHNH2" (hydrazino). As used herein, the groups linked by an alkylene or alkylenyl-group are intended to be attached to the first and to the last carbon of the alkylene or alkylenyl-group. In the case of methylene, the first and the last carbon is the same. For example, "H2N(C2 alkylene)NH2", "H2N(C3 alkylene) NH2", "N(C4 alkylene)", "N(C5 alkylene)" and "N(C2 alkylene)2NH" is equivalent to 1,2-diamino ethane, 1,3-diamino propane, pyrrolidinyl, piperidinyl and piperazinyl, respectively.

Examples of alkyl include, but are not limited to, methyl, ethyl, n-propyl, i-propyl, n-butyl, i-butyl, sec-butyl, t-butyl, pentyl, and hexyl.

Examples of alkylene or alkylenyl include, but are not limited to, methylene, ethylene, propylene, and butylene.

As used herein, "alkoxy" or "alkyloxy" is intended to mean an alkyl group as defined above with the indicated number of carbon atoms attached through an oxygen bridge. Examples of alkoxy include, but are not limited to, methoxy, ethoxy, n-propoxy, isopropoxy, n-butoxy, isobutoxy, t-butoxy, n-pentoxy, isopentoxy, cyclopropylmethoxy, allyloxy and propargyloxy. Similarly, "alkylthio" or "thioalkoxy" represent an alkyl group as defined above with the indicated number of carbon atoms attached through a sulphur bridge.

As used herein, "fluoroalkyl", "fluoroalkylene" and "fluoroalkoxy", used alone or as a suffix or prefix, refers to groups in which one, two, or three of the hydrogen(s) attached to any of the carbons of the corresponding alkyl, alkylene and alkoxy-groups are replaced by fluoro.

Examples of fluoroalkyl include, but are not limited to, trifluoromethyl, difluoromethyl, fluoromethyl, 2,2,2-trifluoroethyl, 2-fluoroethyl and 3-fluoropropyl.

Examples of fluoroalkylene include, but are not limited to, difluoromethylene, fluoromethylene, 2,2-difluorobutylene and 2,2,3-trifluorobutylene.

Examples of fluoroalkoxy include, but are not limited to, trifluoromethoxy, 2,2,2-trifluoroethoxy, 3,3,3-trifluoropropoxy and 2,2-difluoropropoxy.

As used herein, "non-aromatic carbocycle", whether alone or as a suffix or prefix, is intended to mean non-aromatic saturated and unsaturated carbomonocycles, having from 3 to 8 ring carbon atoms, such as cyclopropanyl, cyclopentanyl, cyclohexanyl, cyclopentenyl and cyclohexenyl. If a prefix, such as C3-C6, is given, when said carbocycle comprises the indicated number of carbon atoms, eg. 3, 4, 5 or 6 carbon atoms. Accordingly, "C6 non-aromatic carbocycle" for example includes cyclohexyl and cyclohexenyl. Non-aromatic unsaturated carbocycles are to be distinguished from aryls, as aryl refers to aromatic ring structures, comprising at least one aromatic ring.

As used herein, "cycloalkyl", whether alone or as a suffix or prefix, is intended to mean a saturated carbomonocycle, having from 3 to 8 ring carbon atoms, such as cyclopropanyl, cyclopentanyl and cyclohexanyl. If a prefix, such as C3-C6, is given, when said cycloalkyl comprises the indicated number of carbon atoms, eg. 3, 4, 5 or 6 carbon atoms. Accordingly, C6 cycloalkyl corresponds to cyclohexyl.

As used herein, "cycloalkenyl", whether alone or as a suffix or prefix, is intended to mean a monounsaturated carbomonocycle, having from 4 to 8 ring carbon atoms, such as cyclopentenyl and cyclohexenyl. If a prefix, such as C3-C6, is given, when said cycloalkenyl comprises the indicated number of carbon atoms, eg. 3, 4, 5 or 6 carbon atoms. Accordingly, C6 cycloalkenyl corresponds to cyclohexenyl.

As used herein, the term "substitutable" refers to an atom to which a hydrogen may be covalently attached, and to which another substituent may be present instead of the hydrogen. A non-limiting example of substitutable atoms include the carbon-atoms of pyridine. The nitrogen-atom of pyridine is not substitutable according to this definition. Further, according to the same definition, the imine nitrogen at position 3 in imidazole is not substitutable, while the amine nitrogen at position 1 is.

As used herein, the term "aryl" refers to a ring structure, comprising at least one aromatic ring, made up of from 5 to 14 carbon atoms. Ring structures containing 5, 6, 7 and 8 carbon atoms would be single-ring aromatic groups, for example phenyl. Ring structures containing 8, 9, 10, 11, 12, 13, or 14 carbon atoms would be polycyclic, for example naphthyl. The aromatic ring may be substituted at one or more ring positions. The term "aryl" also includes polycyclic ring systems having two or more cyclic rings in which two or more carbons are common to two adjoining rings (the rings are "fused rings") wherein at least one of the rings is aromatic, for example, the other cyclic rings may be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

As used herein, "heteroaryl" refers to an aromatic heterocycle, having at least one ring with aromatic character, (e.g. 6 delocalized electrons) or at least two conjugated rings with aromatic character, (e.g. 4n+2 delocalized electrons where "n" is an integer), and comprising up to about 14 carbon atoms, and having at least one heteroatom ring member such as sulfur, oxygen, or nitrogen. Heteroaryl groups include monocyclic and bicyclic (e.g., having 2 fused rings) systems.

Examples of heteroaryl groups include without limitation, pyridyl (i.e., pyridinyl), pyrimidinyl, pyrazinyl, pyridazinyl, triazinyl, furyl (i.e. furanyl), quinolyl, tetrahydroquinolyl, isoquinolyl, tetrahydroisoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, benzimidazolyl, indolinyl, and the like.

As used herein, "non-aromatic heterocycle" refers to a monocycle comprising at least one heteroatom ring member, such as sulfur, oxygen, or nitrogen. Such monocyclic rings may be saturated or unsaturated. However, non-aromatic heterocycles are to be distinguished from heteroaryl groups.

Examples of non-aromatic heterocyclic residues include without limitation morpholinyl, thiomorpholinyl, piperazinyl, 3H-diazirin-3-yl, oxiranyl, aziridinyl, piperidinyl, pyrrolidinyl, tetrahydrofuranyl, tetrahydropyranyl, dihydro-2H-pyranyl, oxazepanyl, and azepanyl.

Embodiments of the Invention

One embodiment of the present invention relates to a compound according to formula (I),

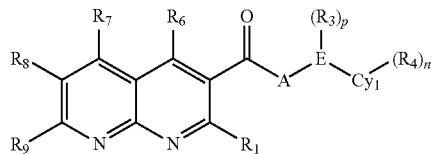

(I)

wherein $R_1$ is selected from the group consisting of C1-C3 alkyl, such as Me, NH2, NH(C1-C3 alkyl), such as NHMe, C1-3 fluoroalkyl, such as CF3, OC1-C3 alkyl, such as OMe, OC1-3 fluoroalkyl, such as $OCF_3$, $N(C1-3 \text{ alkyl})_2$ in which the C1-3 alkyl may be the same or different, such as $N(Me)_2$, C(O)C0-C3 alkyl, such as C(O)H or C(O)Me, C(O)OC0-C3 alkyl, such as C(O)OH or C(O)OMe, C(O)N(C0-C3 alkyl)2 in which the C0-3 alkyl may be the same or different, such as $C(O)NH_2$, and N(C0-C3 alkyl)C(O)C1-C3 alkyl, such NHC(O)Me; A is $NR_2$, O, or S, such as $NR_2$ or O, wherein R2 is selected from the group consisting of H and C1-C3 alkyl, such as methyl; E is selected from the group consisting of C1-C3 alkylene, such as methylene or ethylene, ethene-1,2-diyl, 1-propene-1,3-diyl and 2-propene-1,3-diyl; if E is selected from the group consisting of ethene-1,2-diyl, 1-propene-1,3-diyl and 2-propene-1,3-diyl, then the stereochemistry of the double-bond may be either E or Z; the integer "p" is 0 (zero), 1 or 2; if "p" is 0 (zero), then E is unsubstituted; R3, if present, is independently selected from the group consisting of C1-C3 alkyl, such as methyl or ethyl, C1-C3 alkyleneOC0-C3 alkyl, OMe, C1-5 fluoroalkyl, such as CF3, C0-C3 alkyleneOC1-3 fluoroalkyl, C(O)OC0-C3 alkyl, such as C(O)OH or C(O)OMe, and C(O)N(C0-C3 alkyl)2, in which the C0-3 alkyl may be the same or different, such as C(O)NH2; R3 may, if present, be connected to any of the carbon atom(s) in E; if "p" is 2, then the two R3 may be connected to the same carbon atom or to different carbon atoms; Cy1 is a 5-membered heteroaryl, such as thiazolyl, furanyl or iosoxazolyl, a 6-membered heteroaryl, such as pyridyl, or phenyl; the integer "n" is 0 (zero), 1 or 2; if "n" is 0 (zero), then Cy1 is unsubstituted; R4, if present, is independently selected from the group consisting of C1-8 alkyl, such as methyl, iso-propyl or tert-butyl, C1-5 fluoroalkyl, such as trifluoromethyl, halo, such as fluorine, chlorine or bromine, C0-1 alkylene cyano, such as cyano, C0-8 alkyleneOC0-5 alkyl, such as C0-8 alkyleneOH, such as OH or C1-8 alkyleneOH, or C0-8 alkyleneOMe, such as OMe, SC0-5 alkyl, such as SMe, C0-3 alkyleneSO2C0-5 alkyl, such as SO2Me, C0-3 alkyleneOC1-3 fluoroalkyl, such as OCF3, C0-3 alkyleneNHC0-3 alkyl, such as C0-3 alkyleneNH2, such as NH2, or NHMe, C0-3 alkyleneN(C1-5 alkyl)$_2$, in which the C1-5 alkyl may be the same or different, such as C0-3 alkyleneNMe2, such as NMe2, C0-3 alkyleneC(O)OC0-5 alkyl, such as C1 alkyleneC(O)OH, C(O)OH or C(O)OMe, C0-3 alkyleneOC(O) C0-5 alkyl, such as OC(O)Me, C0-3 alkyleneN(C0-3 alkyl) C(O)C0-3 alkyl, such as NHC(O)Me, C0-3 alkyleneC(O) NHC0-3 alkyl, such as C(O)NH2 or C(O)NHMe, C0-3 alkyleneC(O)N(C1-5 alkyl)2, in which the C1-5 alkyl may be the same or different, such as C(O)NMe2, nitro, C(O)C0-C5 alkyl, such as C(O)H or C(O)Me, N(C0-C3 alkyl)SO2C1-C3 alkyl, such as NHSO2Me, N(C0-C3 alkyl)SO2C1-C3 fluoroalkyl, such as NHSO2CF3, OC2-C3alkyleneN(C0-C3 alkyl)$_2$, in which the C0-3 alkyl may be the same or different, such as OC2 alkyleneNMe2, and

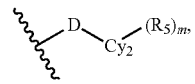

wherein D is selected from the group consisting of C0-C3 alkylene, such as a direct bond or methylene, C0-1 alkylene OC0-1 alkylene, such as OC1 alkylene or C1 alkyleneO, C0-1 alkylene OC(O)C0-1 alkylene, such as OC(O), C0-1 alkylene C(O)OC0-1 alkylene, such as C(O)O, C0-1 alkylene C(O)N (C0-3 alkyl) C0-1 alkylene, such as C(O)NH or C(O)NMe, C0-1 alkylene N(C0-3 alkyl)C(O)C0-1 alkylene, such as NHC(O) or NMe(CO), NHSO2, SO2NH, SO2, SO, C0-1 alkylene C(O)C0-1 alkylene, such as C(O), C0-1 alkylene N(C0-3 alkyl)C0-1 alkylene, such as NH or NMe, and S; The waved line indicates the point of attachment to Cy1; Cy2 is a 5-membered heteroaryl, such imidazolyl, thiazolyl, isoxazolyl or oxazolyl, a 6-membered heteroaryl, such as pyridyl or pyrimidinyl, phenyl, a 3- to 8-membered non-aromatic heterocycle, such as N-piperidinyl, N-piperazinyl, N-morpholinyl, N-thiomorpholinyl, 3H-diazirin-3-yl, tetrahydro-2H-pyranyl, such as tetrahydro-2H-pyran-4-yl, tetrahydrofuranyl, such as tetrahydrofuran-3-yl, or dihydro-2H-pyranyl, such as 3,6-dihydro-2H-pyran-4-yl, oxazepanyl, and azepanyl, or a C3-8 non-aromatic carbocycle, such as C3-8 cycloalkyl, such as cyclopropyl, cyclopentyl or cyclohexyl, or C5-8 cycloalkenyl, such as 1-cyclohexenyl or 1-cyclopentenyl; the integer "m" is 0 (zero), 1, 2, 3, 4, or 5; if "m" is 0 (zero) then Cy2 is unsubstituted; and R5 is, if present, independently selected from C1-5 alkyl, such as methyl, isopropyl or tert-butyl, C1-5 fluoroalkyl, such as trifluormethyl, halo, such as F, Cl or Br, C0-1 alkylene cyano, such as cyano, C0-5 alkyleneOC0-5 alkyl, such as OH, Cl alkyleneOH or OMe, SC0-5 alkyl, C0-3 alkyleneSO2C0-5 alkyl, such as SO2Me, C0-3 alkyleneOC1-3 fluororoalkyl, such as OCF3, C0-3 alkyleneNHC0-3 alkyl, such as NH2 or NHMe, C0-3 alkyleneN(C1-5 alkyl)2, in which the C1-5 alkyl may be the same or different, such as NMe2, C0-3 alkyleneC(O)OC0-5 alkyl, such as C(O)OH or C(O)OMe, C0-3 alkyleneOC(O) C0-5 alkyl, such as OC(O)Me, C0-3 alkyleneN(C0-3 alkyl) C(O)C0-3 alkyl, such as NHC(O)Me or NMeC(O)Me, C0-3 alkyleneC(O)NHC0-3 alkyl, such as C(O)NH2, C0-3 alkyleneC(O)N(C1-5 alkyl)$_2$, in which the C1-5 alkyl may be the same or different, such as C(O)NMe2, C0-3 alkyleneC(O)N (C4-5 alkylene), such as C(O)N(C4-5 alkylene), nitro, C(O) C0-C5 alkyl, such as C(O)H or C(O)Me, C(O)C1-C3 fluoralkyl, such as C(O)CF3, N(C0-C3 alkyl)SO2C1-C3 alkyl, such as NHSO2Me, N(C0-C3 alkyl)SO2C1-C3 fluoroalkyl, such as NHSO2CF3, and OC2-C3alkyleneN(C0-C3 alkyl)$_2$, in which the C0-3 alkyl may be the same or different, such as OC2alkyleneN(Me)$_2$; furthermore, if Cy2 is a 3- to 8-membered non-aromatic heterocycle or a C3-8 non-aromatic carbocycle and "m" is at least 2, then two R5, being attached to the same carbon atom on said 3- to 8-membered non-aromatic heterocycle or a C3-8 non-aromatic carbocycle, may be connected to each other to form a 3,4- or 5-membered spiro ring, said spiro ring being a non-aromatic carbocycle or a non-aromatic heterocycle; examples of such spiro rings includes without limitations spirocyclopropan, spiro-3'-diazirine, spiro-2'-oxirane, spiro-2'-1,3-dioxolane and spiro-2'-oxetane; thus Cy2(R5)$_2$ may represent, without limitations, cyclohexanspiro-3'-diazirin-4-yl, cyclohexanspiro-2'-oxirane-4-yl, cyclohexanespirocyclopropan-4-yl, piperidine-3-spiro-3'-diazirin-N-yl, piperidine-3-spiro-3'-diazirin-N-yl, piperidine-3-spirocyclopropane-N-yl, 1,4-dioxa-8-azaspiro[4.5]decan-N-yl or 1,4-dioxaspiro[4.5]decan-8-yl; furthermore, if Cy2 is a 3- to 8-membered non-aromatic heterocycle or a C3-8 non-aromatic carbocycle and "m" is at least 2, then two R5, being attached to different atoms in said 3- to 8-membered non-aromatic heterocycle or said C3-8 non-aromatic carbocycle, may be connected to each other to form a C0-3 alkylene bridge; Cy2 thus being a bicyclic residue, such as 8-oxa-3-azabicyclo[3.2.1]octan-3-yl; furthermore, if Cy2 is a 3- to 8-membered non-aromatic heterocycle or a C3-8 non-aromatic carbocycle, then R5 may be a double bonded oxygen (=O), being attached to a carbon or sulfur atom in said cycle; such a double bonded oxygen may part of a keto group or a sulfon group; accordingly, Cy2 may thus be a cyclic residue, such as 4-oxocyclohex-1-yl or 1,1-dioxothiomorpholin-N-yl; evidently Cy2 may thus also be a lactone or a lactame; in compounds wherein Cy2 comprises sp3-hybridized carbon atoms, a single carbon atom may be connected to more than one R5, being of the same or different type; similarly, if the atom in Cy2 to which "D" is connected is sp3-hybridized, the atom may be connected to a substituent R5 as well; R6, R7 and R8 are independently selected from the group consisting of H, halogen, C1-C3 alkyl, such as methyl, NH(C0-C3 alkyl), such as NH2, C1-3 fluoroalkyl, such as trifluoromethyl, OC0-C3 alkyl, such as OC1-C3 alkyl, such as OMe, OC1-3 fluoroalkyl, such as OCF3, N(C4-5 alkylene), such N-piperidinyl, morpholinyl, such as N-morpholinyl, N(C1-C3 alkyl)2, in which the C1-3 alkyl may be the same or different, such as NMe2, and cyano; and R9 is selected from the group consisting of H, halogen, C1-C3 alkyl, such as methyl, and C1-3 fluoroalkyl, such as trifluoromethyl; as a free base, an acid in its non-charged protonated form, a pharmaceutically addition acceptable salt, solvate, solvate of a salt thereof, a pure stereoisomer, a racemic, diastereomeric or scalemic mixture, a corresponding tautomeric form resulting from a hydrogen shift between two heteroatoms, such as 1,3-shift in any direction between O and N or between N and N, and/or the corresponding tautomeric form resulting from a keto-enol tautomerization; with the proviso that the compound is not any of the following:

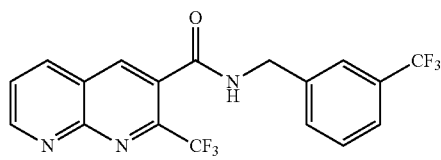

-continued

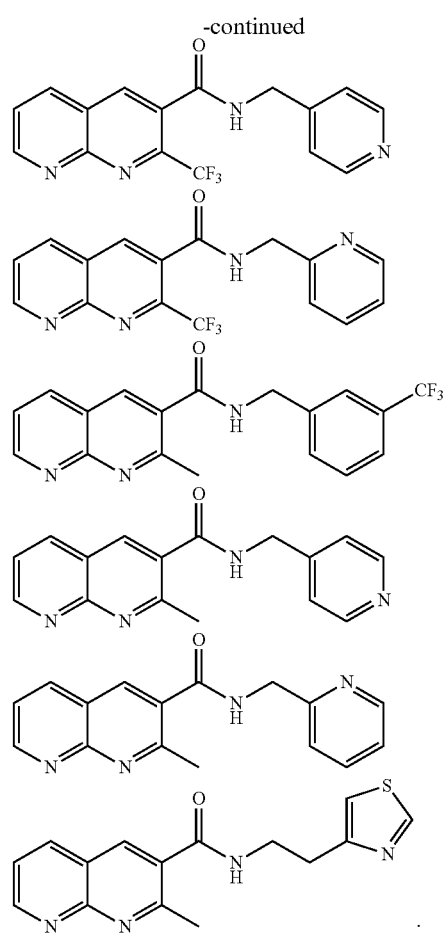

The substances 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide were all found to be commercially available, but without any reported biological activity or use.

According to one embodiment R1 may be a C1-C3 alkyl, such as methyl.

According to one embodiment A may be NR2 or O. Furthermore A may be O. A may also be NR2. In an embodiment, wherein A is NR2, R2 may be H or methyl. Preferably R2 is H, when A is NR2.

According to one embodiment "p" is 0 (zero) or 1. If p is 1, then it is preferred if R3 is C1-C3 alkyl, such as methyl. The integer "p" may be 0 (zero). Furthermore, "p" may 1.

According to one embodiment E is methylene or ethylene, such as methylene. E may also be ethene-1,2-diyl, 1-propene-1,3-diyl or 2-propene-1,3-diyl. However it is preferred for E to be selected from methylene and ethylene, such as methylene.

As both E may be both 1-propene-1,3-diylene and 2-propene-1,3-diylene, formula (I) comprises compounds wherein the double bond is alfa to Cy1 as well as compounds wherein the double bond is alfa to A (see further below).

According to one embodiment, wherein E is ethene-1,2-diylene, 1-propene-1,3-diylene or 2-propene-1,3-diylene, the stereochemistry of the double bond of E is "trans" with respect to the chain A-E-Cy1. In such an embodiment, wherein the double is trans with respect to the chain A-E-Cy1, compounds according to formula (I) may be represented by a formula selected from

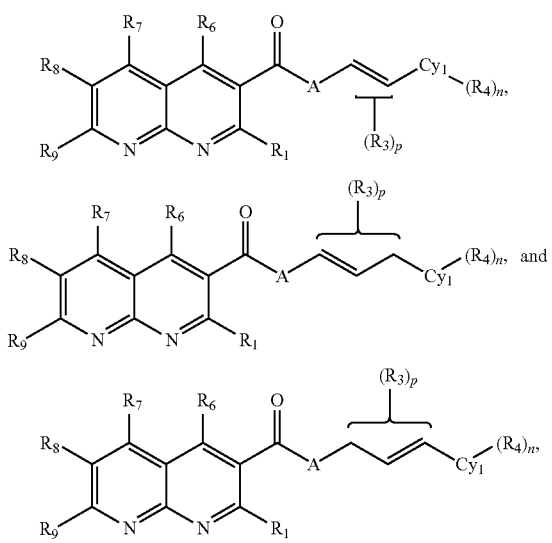

respectively, wherein R3, if present, may be connected to any of the carbon atoms in ethene-1,2-diylene, 1-propene-1,3-diylene or 2-propene-1,3-diylene, respectively.

According to one embodiment, it is preferred if E is methylene and "p" is 0 (zero) or 1. If E is methylene and "p" is 1, then it is preferred if R3 is methyl. Such a compound, wherein E is methylene, "p" is 1 and R3 is methyl, may be present as a mixture of enantiomers. The individual enantiomers in such a mixture may be present in the same amount, thus constituting a racemic mixture, or in different amount, thus constituting a scalemic mixture. However, it is preferred if one of the enantiomers prevails. Accordingly, its is preferred if the enantiomeric excess of one of the enantiomers is more than 50%, such as more than 75%, 90%, 95% or even more than 99%. Furthermore, it is preferred if the enantiomer, which prevails, is the one wherein the hydrogen of E is situated below the plane, if A, E (methylene) and Cy1 defines the plane and if the corresponding structural formula of the compound is drawn as in formula (I) above. If A is given the highest priority, Cy1, the second highest priority and the methyl group the lowest, the stereochemistry of the carbon atom of E would correspond to "S"-configuration according to the IUPAC system of designating stereochemistry.

As disclosed above, Cy1 is a 5-membered heteroaryl, such as thiazolyl, furanyl, thiophenyl, pyrrolyl, pyrazolyl, oxazolyl, or isooxazolyl, a 6-membered heteroaryl, such as pyridyl, or phenyl. Cy1 may be attached to E at any substitutable atom in Cy1. Preferably said atom is a carbon atom. If Cy1 is a 5-membered heteroaryl, then its preferred if said 5-membered heteroaryl is thiazolyl, furanyl or iosoxazolyl. If Cy1 is a 6-membered heteroaryl, then its preferred if said 6-membered heteroaryl is pyridyl.

According to one embodiment, Cy1 may be a 5- or 6-membered heteroaryl. In such an embodiment it is preferred if E is connected to a carbon atom in said heteroaryl. Furthermore, it is preferred if said 5- or 6-membered heteroaryl comprises 1 or 2 heteroatoms, such as nitrogen.

According to one embodiment, Cy1 may be phenyl.

Although Cy1 may be unsubstituted, i.e. the integer "n" may be 0 (zero), it is preferred if Cy1 is substituted, i.e. it is preferred that the integer "n" is at least 1, such as being 1 or 2. Cy1 may be substituted at any substitutable atom(s) in Cy1. Accordingly, R4, if present, may be attached to any substitutable atom(s) in Cy1.

In an embodiment, wherein "n" is 1 or 2, it is preferred if at least one R4 is selected from the group consisting of trifluoromethyl, tert-butyl, cyano, halogen, such as fluorine or chlorine, N(C0-3 alkyl)2, in which the C0-3 alkyl may be the same or different, OC1-C3 alkyl and

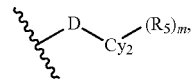

wherein Cy2 is selected from the group consisting of a 5- or 6-membered non-aromatic heterocycle, such as tetrahydro-2H-pyranyl, tetrahydrofuranyl, N(C4-5 alkylene), N-morpholinyl, piperidinyl, or piperazine-N-yl, and a C3-7 non-aromatic carbocycle, such as cyclopentyl, cyclohexyl or cyclopentenyl. More preferably, R4 is selected from the group consisting of trifluoromethyl, tert-butyl, fluorine, and

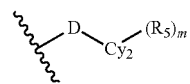

wherein Cy2 is selected from the group consisting of piperidinyl, such as N-piperidinyl, piperazine-N-yl, morpholinyl, such as N-morpholinyl, cyclopentyl and cyclohexyl.

In an embodiment, wherein "n" is 1 or 2, one R4 may be

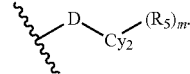

D may be attached to any substitutable atom in Cy2. Furthermore, R5, if present may, be attached to any substitutable atom(s) in Cy2.

In an embodiment, wherein "n" is 2, it is preferred that one R4 is

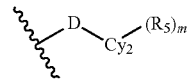

and that the other R4 is selected from the group consisting of trifluoromethyl, C1-4 alkyl, such as methyl, iso-propyl or tert-butyl, halogen, such as fluorine or chlorine, and OC0-3 alkyl, such as hydroxyl and methoxy.

In one embodiment, one R4 is trifluormethyl, the other being

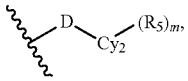

and "n" is 2.

As disclosed above, Cy2 may be a 5-membered heteroaryl, such as thiazolyl, furanyl, thiophenyl, pyrrolyl, pyrazolyl, oxazolyl, or isoxazolyl, a 6-membered heteroaryl, such as pyridyl, such as 3-pyridyl, or pyrimidinyl, phenyl, a 3- to 8-membered non-aromatic heterocycle, such as N-piperidinyl, N-piperazinyl, N-morpholinyl, 3H-diazirin-3-yl, tetrahydro-2H-pyranyl, such as tetrahydro-2H-pyran-4-yl, tetrahydrofuranyl, such as tetrahydrofuran-3-yl, or dihydro-2H-pyranyl, such as 3,6-dihydro-2H-pyran-4-yl, or a C3-8 non-aromatic carbocycle, such as C5-6 cycloalkyl, such as cyclopentyl or cyclohexyl, or C5-6 cycloalkenyl, such as 1-cyclohexenyl or 1-cyclopentenyl, or cyclopropyl.

If Cy2 is a 5-membered heteroaryl, then its preferred if said 5-membered heteroaryl is thiazolyl.

If Cy2 is a 6-membered heteroaryl, then its preferred if said 6-membered heteroaryl is pyridyl, such as 3-pyridyl.

If Cy2 is a 3- to 8-membered non-aromatic heterocycle, then its preferred if said 3- to 8-membered non-aromatic heterocycle is 5- or 6-membered. Furthermore, it is preferred if said 3- to 8-membered non-aromatic heterocycle comprises at least one nitrogen and/or oxygen atom. Even more preferred, said 3- to 8-membered non-aromatic heterocycle is selected from the group consisting of N-piperidinyl, N-piperazinyl, N-morpholinyl, tetrahydro-2H-pyran-4-yl, tetrahydrofuran-3-yl, and 3,6-dihydro-2H-pyran-4-yl.

If Cy2 is a C3-8 non-aromatic carbocycle, then it is preferred if said C3-8 non-aromatic carbocycle is selected from the group consisting of cyclopentyl, cyclohexyl, and C5-6 cycloalkenyl, such as 1-cyclohexenyl or 1-cyclopentenyl.

According to one embodiment, Cy2 is a 5- or 6-membered heteroaryl. In such an embodiment it is preferred if D is connected to a carbon atom in said heteroaryl. Furthermore, it is preferred if said 5- or 6-membered heteroaryl comprises 1 or 2 heteroatoms.

According to one embodiment, Cy2 is phenyl or pyridyl, such as phenyl.

According to one embodiment, Cy2 is a 3- to 8-membered non-aromatic heterocycle or a C3-8 non-aromatic carbocycle. Preferably said 3- to 8-membered non-aromatic heterocycle is 5- or 6-membered. Furthermore, it is preferred if 3- to 8-membered non-aromatic heterocycle comprises at least one nitrogen and/or oxygen atom, but no more than two heteroatoms. It also preferred that said 3- to 8-membered non-aromatic heterocycle is saturated. Similarly, it is preferred if said C3-8 non-aromatic carbocycle, is as C5-6 cycloalkyl. If said C3-8 non-aromatic carbocycle is unsaturated, it is preferred if is monounsaturated.

In one embodiment, wherein "n" is 1 or 2 and at least one of R4 is

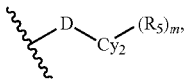

the integer "m" may be 0 (zero).

In an embodiment, wherein "n" is 1 or 2, at least one of R4 is

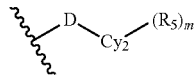

and the integer "m" is 1, 2 or 3, R5 may be independently selected from the group consisting of trifluoromethyl, C1-4 alkyl, such as methyl, OC1-3 alkyl, such as methoxy.

In an embodiment, wherein "n" is 1 or 2, and at least one of R4 is

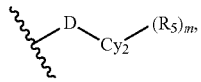

D may be selected from the group consisting of a direct bond, —C(O)NH—, —NHC(O)—, C(O), —OCH2-, —CH2O—, —NHSO2-, —O—, and —SO2NH. In such an embodiment it is preferred for D to be a direct bond. D may be attached to any substitutable atom in Cy2.

In an embodiment, wherein "n" is 2 and at least one R4 is

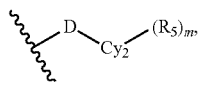

its is preferred that only one R4 is

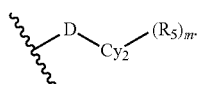

In an embodiment, wherein Cy 2 is a saturated 6-membered non-aromatic heterocycle, such as N-piperidinyl or N-piperazinyl, or a 6-membered non-aromatic carbocycle, such as cyclohexyl or cyclohexenyl, and "m" is at least 1, it is preferred if at least one R5 is in the 4-position (the 1-position being the point of attachment to D) of Cy2. Furthermore, it is preferred if said at least one R5 is methyl in such an embodiment.

According to one embodiment, Cy2 is 6-membered non-aromatic heterocycle, such as N-piperidinyl, or a 5- or 6-membered non-aromatic carbocycle, such as cyclopentyl, cyclohexyl or cyclohexenyl, and "m" is at least 2. In such an embodiment it is preferred that two R5 are attached to the 4-position of said 6-membered non-aromatic heterocycle or said 6-membered non-aromatic carbocycle (the 1-position being the point of attachment to D) or to the 3-position of said 5-membered non-aromatic carbocycle (the 1-position being the point of attachment to D) and both being C1-3 alkyl, such as methyl. Thus, Cy2 being geminally disubstituted.

According to one embodiment, Cy2 is 6-membered non-aromatic heterocycle, such as N-piperidinyl, or a 5- or 6-membered non-aromatic carbocycle, such as cyclohexyl, "m" is at least 2 and two R5, being attached to the same carbon atom on said 6-membered non-aromatic heterocycle or said 5- or 6-membered non-aromatic carbocycle, are connected to each other to form a 3-membered spiro ring, such as spirocyclopropan, spiro-3'-diazirine or spiro-1'-oxirane.

Preferably, "m" is 2 and Cy2(R5)₂ is selected from the group consisting of cyclohexanspiro-3'-diazirin-4-yl, cyclohexanespirocyclopropan-4-yl, piperidine-3-spiro-3'-diazirin-N-yl and piperidine-3-spirocyclopropane-N-yl in such an embodiment. In such a preferred embodiment, a compound according of formula (I) may be represented by any of the general formulas below:

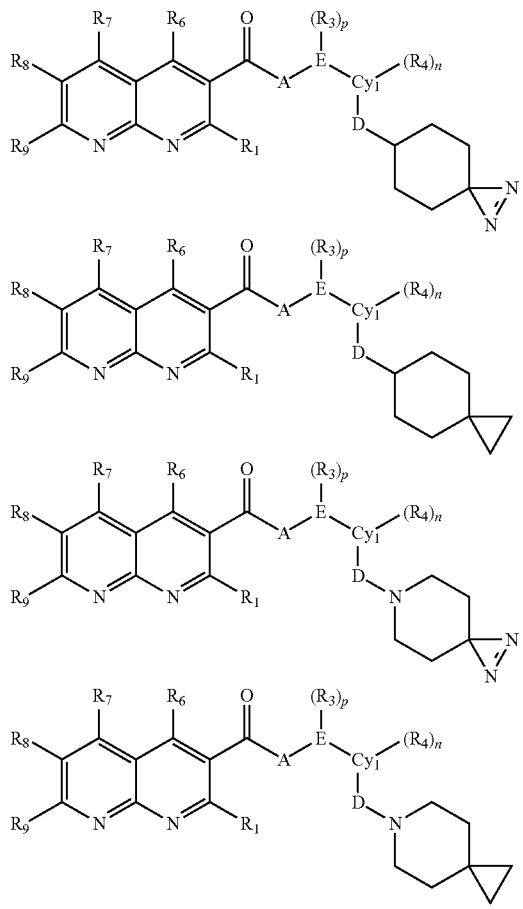

According to one embodiment R6, R7, and/or R8 may be, independently of each other, selected from H, methyl, halogen, OMe, cyano and N-piperidinyl. Furthermore, R6, R7 and/or R8 may be, independently of each other, selected from H, methyl, OMe and cyano, such as H or methyl. Especially, R6, R7 and/or R8 may be H According to one embodiment, R9 may be selected from halogen, C1-C3 alkyl, such as Me, C1-3 fluoroalkyl, such as CF3. Preferably, R9 is H.

According to one embodiment R6 and/or R7, may be, independently of each other, selected from H, halogen, C1-C3 alkyl, such as Me, NH2, NH(C1-C3 alkyl), such as NHMe, C1-3 fluoroalkyl, such as CF3, OC1-C3 alkyl, such as OMe, OC1-3 fluoroalkyl, such as OCF3, N(C4-5 alkylene), such as N-piperidinyl, N(C1-C3 alkyl)₂, in which the C0-3 alkyl may be the same or different, such as NMe2, and cyano.

According to one embodiment R7, may be is H or methyl, such as being H.

In one embodiment, R1 is methyl, R6 to R9 are H, A is NH or O, the integer "p" is 0 (zero) or 1. R3, if present, is Me, Cy1 is pyridyl or phenyl, the integer "n" is 1 or 2 and one R4 is

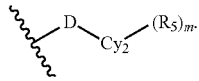

Furthermore, although various selections, within the interval given for each of the different groups of formula (I), have been described individually above as various possible embodiments, any combination of these selections is also possible.

Accordingly, other embodiments of the invention relates to a compound according to formula (I), wherein at least two different groups, such as 2, 3, 4, 5, or further different groups, of formula (I) are to be selected from the various selections, within the interval given for each of the different groups of formula (I), disclosed herein.

In one embodiment, compounds according to formula (I) may be selected from the group consisting of 2-Methyl-N-(2-(trifluoromethyl)benzyl)-1,8-naphthyridine-3-carboxamide
2-Methyl-N-(4-(trifluoromethyl)benzyl)-1,8-naphthyridine-3-carboxamide
N-(4-tert-butylbenzyl)-2-methyl-1,8-naphthyridine-3-carboxamide
2-Methyl-N-((2-phenylthiazol-4-yl)methyl)-1,8-naphthyridine-3-carboxamide
2-Methyl-N-(1-(3-(trifluoromethyl)phenyl)propyl)-1,8-naphthyridine-3-carboxamide
2-Methyl-N-(3-(trifluoromethyl)phenethyl)-1,8-naphthyridine-3-carboxamide
N-(4-Benzoylbenzyl)-2-methyl-1,8-naphthyridine-3-carboxamide
2-Methyl-N-((3-phenylisoxazol-5-yl)methyl)-1,8-naphthyridine-3-carboxamide
2-Methyl-N-(4-(methylsulfonyl)benzyl)-1,8-naphthyridine-3-carboxamide
N-(4-Chlorobenzyl)-2-methyl-1,8-naphthyridine-3-carboxamide
N-(4-Chlorophenethyl)-2-methyl-1,8-naphthyridine-3-carboxamide
N-(4-Fluorobenzyl)-2-methyl-1,8-naphthyridine-3-carboxamide
N-(3-Chlorobenzyl)-2-methyl-1,8-naphthyridine-3-carboxamide
2-Methyl-N-(3-(trifluoromethyl)benzyl)-1,8-naphthyridine-3-carboxamide
2-Methyl-N-((6-phenylpyridin-3-yl)methyl)-1,8-naphthyridine-3-carboxamide
2-Methyl-N-(1-(3-(trifluoromethyl)phenyl)ethyl)-1,8-naphthyridine-3-carboxamide
N-(4-Chloro-3-(trifluoromethyl)benzyl)-2-methyl-1,8-naphthyridine-3-carboxamide
N-(3,5-bis(Trifluoromethyl)benzyl)-2-methyl-1,8-naphthyridine-3-carboxamide
N-(Biphenyl-4-ylmethyl)-2-methyl-1,8-naphthyridine-3-carboxamide
N-(Biphenyl-3-ylmethyl)-2-methyl-1,8-naphthyridine-3-carboxamide
(S)-2-Methyl-N-(1-(3-(trifluoromethyl)phenyl)ethyl)-1,8-naphthyridine-3-carboxamide
N-(3-Chlorobenzyl)-2-(trifluoromethyl)-1,8-naphthyridine-3-carboxamide
(R)-2-Methyl-N-(1-(3-(trifluoromethyl)phenyl)ethyl)-1,8-naphthyridine-3-carboxamide
N-(3-Methoxybenzyl)-2-methyl-1,8-naphthyridine-3-carboxamide N-(3-Bromobenzyl)-2-methyl-1,8-naphthyridine-3-carboxamide N-(4-Bromobenzyl)-2-methyl-1,8-naphthyridine-3-carboxamide N-(4-fluorobenzyl)-2-(trifluoromethyl)-1,8-naphthyridine-3-carboxamide (S)—N-(1-(4-bromophenyl)ethyl)-2-methyl-1,8-naphthyridine-3-carboxamide (R)—N-(1-(4-bromophenyl)ethyl)-2-methyl-1,8-naphthyridine-3-carboxamide 2-Methyl-N-(4-(methylthio)benzyl)-1,8-naphthyridine-3-carboxamide N-(1-(4-tert-butylphenyl)ethyl)-2-methyl-1,8-naphthyridine-3-carboxamide (S)—N-(1-(4-tert-butylphenyl)ethyl)-2-methyl-1,8-naphthyridine-3-carboxamide (R)—N-(1-(4-tert-butylphenyl)-2-hydroxyethyl)-2-methyl-1,8-naphthyridine-3-carboxamide N-(4-isopropylbenzyl)-2-methyl-1,8-naphthyridine-3-carboxamide 2-Methyl-N-(3-(phenylcarbamoyl)benzyl)-1,8-naphthyridine-3-carboxamide 2-Methyl-N-(4-(pyridin-4-yl)benzyl)-1,8-naphthyridine-3-carboxamide 2-Methyl-N-(4-(pyridin-3-yl)benzyl)-1,8-naphthyridine-3-carboxamide N-((4'-Methoxybiphenyl-4-yl)methyl)-2-methyl-1,8-naphthyridine-3-carboxamide 2-Methyl-N-((2'-(trifluoromethyl)biphenyl-3-yl)methyl)-1,8-naphthyridine-3-carboxamide 2-Methyl-N-(3-(pyridin-3-yl)benzyl)-1,8-naphthyridine-3-carboxamide 2-Methyl-N-(3-(pyridin-4-yl)benzyl)-1,8-naphthyridine-3-carboxamide N-((4'-Methoxybiphenyl-3-yl)methyl)-2-methyl-1,8-naphthyridine-3-carboxamide 2-Methyl-N-((2'-(trifluoromethyl)biphenyl-4-yl)methyl)-1,8-naphthyridine-3-carboxamide (S)-2-methyl-N-(1-(4-(pyridin-3-yl)phenyl)ethyl)-1,8-naphthyridine-3-carboxamide (R)-2-methyl-N-(1-(4-(pyridin-3-yl)phenyl)ethyl)-1,8-naphthyridine-3-carboxamide (S)—N-(1-(4-Cyclohexenylphenyl)ethyl)-2-methyl-1,8-naphthyridine-3-carboxamide N-(4-(3,6-Dihydro-2H-pyran-4-yl)-3-(trifluoromethyl)benzyl)-2-methyl-1,8-naphthyridine-3-carboxamide (S)-2-methyl-N-(1-(4-(piperidin-1-yl)phenyl)ethyl)-1,8-naphthyridine-3-carboxamide N-(4-(3,6-Dihydro-2H-pyran-4-yl)-3-(trifluoromethyl)benzyl)-2-methyl-1,8-naphthyridine-3-carboxamide N-(4-Cyclohexenyl-3-(trifluoromethyl)benzyl)-2-methyl-1,8-naphthyridine-3-carboxamide N-(4-cyclohexylbenzyl)-2-methyl-1,8-naphthyridine-3-carboxamide 2-Methyl-N-((4-phenylfuran-2-yl)methyl)-1,8-naphthyridine-3-carboxamide 2-Methyl-N-(4-(pyrrolidin-1-yl)benzyl)-1,8-naphthyridine-3-carboxamide 2-Methyl-N-(4-(4-methylphenylsulfonamido)-3-(trifluoromethyl)benzyl)-1,8-naphthyridine-3-carboxamide N-(4-(1H-Imidazol-1-yl)-3-(trifluoromethyl)benzyl)-2-methyl-1,8-naphthyridine-3-carboxamide N-(4-(2-(Dimethylamino)ethoxy)-3-(trifluoromethyl)benzyl)-2-methyl-1,8-naphthyridine-3-carboxamide 2-Methyl-N-(4-(pyridin-3-ylmethoxy)-3-(trifluoromethyl)benzyl)-1,8-naphthyridine-3-carboxamide 2-Methyl-N-(4-(piperidin-1-yl)-3-(trifluoromethyl)benzyl)-1,8-naphthyridine-3-carboxamide 2-Methyl-N-(4-morpholino-3-(trifluoromethyl)benzyl)-1,8-naphthyridine-3-carboxamide N-(4-Isopropoxy-3-(trifluoromethyl)benzyl)-2-methyl-1,8-naphthyridine-3-carboxamide N-(4-Benzamido-3-(trifluoromethyl)benzyl)-2-methyl-1,8-naphthyridine-3-carboxamide 2-Methyl-N-(4-(4-methylpiperazin-1-yl)-3-(trifluoromethyl)benzyl)-1,8-naphthyridine-3-carboxamide 2-Methyl-N-(4-(tetrahydro-2H-pyran-4-yloxy)-3-(trifluoromethyl)benzyl)-1,8-naphthyridine-3-carboxamide N-(4-(Dimethylamino)-3-(trifluoromethyl)benzyl)-2-methyl-1,8-naphthyridine-3-carboxamide 2-Methyl-N-(4-(methylsulfonyl)-3-(trifluoromethyl)benzyl)-1,8-naphthyridine-3-carboxamide N-(4-cyclopentylbenzyl)-2-methyl-1,8-naphthyridine-3-carboxamide (S)-2-Methyl-N-(4-(3-methylmorpholino)benzyl)-1,8-naphthyridine-3-carboxamide (R)-2-methyl-N-(4-(3-methylmorpholino)benzyl)-1,8-naphthyridine-3-carboxamide N-(4-(4-Hydroxypiperidin-1-yl)-3-(trifluoromethyl)benzyl)-2-methyl-1,8-naphthyridine-3-carboxamide 2-Methyl-N-(4-(1,1,1-trifluoropropan-2-yloxy)benzyl)-1,8-naphthyridine-3-carboxamide 2-Methyl-N-(4-(2-methylpiperidin-1-yl)benzyl)-1,8-naphthyridine-3-carboxamide N-(4-(2-(Hydroxymethyl)piperidin-1-yl)benzyl)-2-methyl-1,8-naphthyridine-3-carboxamide N-(4-(4-Acetylpiperazin-1-yl)-3-(trifluoromethyl)benzyl)-2-methyl-1,8-naphthyridine-3-carboxamide N-(4-(4,4-Dimethylpiperidin-1-yl)benzyl)-2-methyl-1,8-naphthyridine-3-carboxamide N-(4-(4,4-dimethylpiperidin-1-yl)-3-fluorobenzyl)-2-methyl-1,8-naphthyridine-3-carboxamide N-(3-cyano-4-(4,4-dimethylpiperidin-1-yl)benzyl)-2-methyl-1,8-naphthyridine-3-carboxamide N-(4-(Cyclopentyloxy)benzyl)-2-methyl-1,8-naphthyridine-3-carboxamide N-(3-fluoro-4-(4-methoxy-4-methylpiperidin-1-yl)benzyl)-2-methyl-1,8-naphthyridine-3-carboxamide 2-Methyl-N-(4-thiomorpholinobenzyl)-1,8-naphthyridine-3-carboxamide N-(4-(8-oxa-3-azabicyclo[3.2.1]octan-3-yl)-3-fluorobenzyl)-2-methyl-1,8-naphthyridine-3-carboxamide N-(4-(2,6-dimethylmorpholino)-3-fluorobenzyl)-2-methyl-1,8-naphthyridine-3-carboxamide N-(3-fluoro-4-(1,4-dioxa-8-azaspiro[4.5]decan-8-yl)benzyl)-2-methyl-1,8-naphthyridine-3-carboxamide N-(4-(4,4-difluoropiperidin-1-yl)-3-fluorobenzyl)-2-methyl-1,8-naphthyridine-3-carboxamide 2-Methyl-N-(4-(1,1-dioxothiomorpholino)benzyl)-1,8-naphthyridine-3-carboxamide 2-Methyl-N-(4-(pyridin-3-yl)-3-(trifluoromethyl)benzyl)-1,8-naphthyridine-3-carboxamide N-((6-tert-Butylpyridin-3-yl)methyl)-2-methyl-1,8-naphthyridine-3-carboxamide 2-methyl-N-((5-(piperidin-1-yl)pyridin-2-yl)methyl)-1,8-naphthyridine-3-carboxamide 2-methyl-N-(4-(tetrahydro-2H-pyran-4-yl)benzyl)-1,8-naphthyridine-3-carboxamide N-(4-(1-hydroxycyclohexyl)benzyl)-2-methyl-1,8-naphthyridine-3-carboxamide 2-Methoxy-N-(3-(trifluoromethyl)benzyl)-1,8-naphthyridine-3-carboxamide 2-(Methylamino)-N-(3-(trifluoromethyl)benzyl)-1,8-naphthyridine-3-carboxamide
2-Amino-N-(3-(trifluoromethyl)benzyl)-1,8-naphthyridine-3-carboxamide.
2-Methyl-N-(1-(4-(3-(trifluoromethyl)-3H-diazirin-3-yl)phenyl)ethyl)-1,8-naphthyridine-3-carboxamide
N-(4-(1,2-diazaspiro[2.5]oct-1-en-6-yl)benzyl)-2-methyl-1,8-naphthyridine-3-carboxamide
N-(4-(1,4-Dioxaspiro[4.5]decan-8-yl)benzyl)-2-methyl-1,8-naphthyridine-3-carboxamide
2-Methyl-N-(4-(4-oxocyclohexyl)benzyl)-1,8-naphthyridine-3-carboxamide
N-(1-(4'-methoxybiphenyl-4-yl)ethyl)-2-methyl-1,8-naphthyridine-3-carboxamide
3-(Trifluoromethyl)benzyl 2-methyl-1,8-naphthyridine-3-carboxylate
(6-Phenylpyridin-3-yl)methyl 2-methyl-1,8-naphthyridine-3-carboxylate
(5-Phenylisoxazol-3-yl)methyl 2-methyl-1,8-naphthyridine-3-carboxylate
(2-Phenylthiazol-4-yl)methyl 2-methyl-1,8-naphthyridine-3-carboxylate
(6-tert-Butylpyridin-3-yl)methyl 2-methyl-1,8-naphthyridine-3-carboxylate
Biphenyl-3-ylmethyl 2-methyl-1,8-naphthyridine-3-carboxylate
(6-Cyclohexylpyridin-3-yl)methyl 2-methyl-1,8-naphthyridine-3-carboxylate
(5)-1-(4-morpholino-3-(trifluoromethyl)phenyl)ethyl 2-methyl-1,8-naphthyridine-3-carboxylate
2-Methyl-4-(piperidin-1-yl)-N-(3-(trifluoromethyl)benzyl)-1,8-naphthyridine-3-carboxamide
2-Methyl-4-oxo-N-(3-(trifluoromethyl)benzyl)-1,4-dihydro-1,8-naphthyridine-3-carboxamide
4-Methoxy-2-methyl-N-(3-(trifluoromethyl)benzyl)-1,8-naphthyridine-3-carboxamide
N-(4-tert-butylbenzyl)-2,7-dimethyl-1,8-naphthyridine-3-carboxamide
N-(4-tert-butylbenzyl)-2,6-dimethyl-1,8-naphthyridine-3-carboxamide
N-(4-tert-butylbenzyl)-2,5-dimethyl-1,8-naphthyridine-3-carboxamide
6-Bromo-N-(4-tert-butylbenzyl)-2-methyl-1,8-naphthyridine-3-carboxamide
6-amino-N-(4-tert-butylbenzyl)-2-methyl-1,8-naphthyridine-3-carboxamide
N-(4-tert-butylbenzyl)-6-iodo-2-methyl-1,8-naphthyridine-3-carboxamide
N-(4-tert-Butylbenzyl)-6-hydroxy-2-methyl-1,8-naphthyridine-3-carboxamide
N-(4-tert-Butylbenzyl)-6-cyano-2-methyl-1,8-naphthyridine-3-carboxamide
N-(4-tert-butylbenzyl)-2,4-dimethyl-1,8-naphthyridine-3-carboxamide
5-Methoxy-2-methyl-N-(3-(trifluoromethyl)benzyl)-1,8-naphthyridine-3-carboxamide
5-(Dimethylamino)-2-methyl-N-(3-(trifluoromethyl)benzyl)-1,8-naphthyridine-3-carboxamide
2-Methyl-5-morpholino-N-(3-(trifluoromethyl)benzyl)-1,8-naphthyridine-3-carboxamide
6-Chloro-2-methyl-N-(3-(trifluoromethyl)benzyl)-1,8-naphthyridine-3-carboxamide
N-((6-tert-Butyl-2-chloropyridin-3-yl)methyl)-2-methyl-1,8-naphthyridine-3-carboxamide
N-((2-chloro-6-cyclopentylpyridin-3-yl)methyl)-2-methyl-1,8-naphthyridine-3-carboxamide
N-((6-tert-Butyl-2-methoxypyridin-3-yl)methyl)-2-methyl-1,8-naphthyridine-3-carboxamide
N-(4-Azido-3-iodobenzyl)-2-methyl-1,8-naphthyridine-3-carboxamide
N-(4-tert-butyl-2-hydroxybenzyl)-2-methyl-1,8-naphthyridine-3-carboxamide and be present as a free base, an acid in its non-charged protonated form, a pharmaceutically addition acceptable salt, solvate, solvate of a salt thereof, a pure stereoisomer, a racemic, diastereomeric or scalemic mixture, a corresponding tautomeric form resulting from a hydrogen shift between two hetero-atoms, such as 1,3-shift in any direction between O and N or between N and N, and/or the corresponding tautomeric form resulting from a keto-enol tautomerization.

In one embodiment, compounds according to formula (I) may be selected from the group consisting of
2-methyl-N-(4-(trifluoromethyl)benzyl)-1,8-naphthyridine-3-carboxamide
N-(4-tert-butylbenzyl)-2-methyl-1,8-naphthyridine-3-carboxamide
2-Methyl-N-((2-phenylthiazol-4-yl)methyl)-1,8-naphthyridine-3-carboxamide
2-Methyl-N-((3-phenylisoxazol-5-yl)methyl)-1,8-naphthyridine-3-carboxamide
2-Methyl-N-(3-(trifluoromethyl)benzyl)-1,8-naphthyridine-3-carboxamide
2-Methyl-N-((6-phenylpyridin-3-yl)methyl)-1,8-naphthyridine-3-carboxamide
2-Methyl-N-(1-(3-(trifluoromethyl)phenyl)ethyl)-1,8-naphthyridine-3-carboxamide
N-(4-Chloro-3-(trifluoromethyl)benzyl)-2-methyl-1,8-naphthyridine-3-carboxamide
N-(Biphenyl-4-ylmethyl)-2-methyl-1,8-naphthyridine-3-carboxamide
(S)-2-Methyl-N-(1-(3-(trifluoromethyl)phenyl)ethyl)-1,8-naphthyridine-3-carboxamide
(S)—N-(1-(4-bromophenyl)ethyl)-2-methyl-1,8-naphthyridine-3-carboxamide
2-Methyl-N-(4-(pyridin-4-yl)benzyl)-1,8-naphthyridine-3-carboxamide
2-Methyl-N-(4-(pyridin-3-yl)benzyl)-1,8-naphthyridine-3-carboxamide
2-Methyl-N-((2'-(trifluoromethyl)biphenyl-4-yl)methyl)-1,8-naphthyridine-3-carboxamide
(S)-2-methyl-N-(1-(4-(pyridin-3-yl)phenyl)ethyl)-1,8-naphthyridine-3-carboxamide
(S)—N-(1-(4-Cyclohexenylphenyl)ethyl)-2-methyl-1,8-naphthyridine-3-carboxamide
N-(4-(3,6-Dihydro-2H-pyran-4-yl)-3-(trifluoromethyl)benzyl)-2-methyl-1,8-naphthyridine-3-carboxamide
N-(4-(3,6-Dihydro-2H-pyran-4-yl)-3-(trifluoromethyl)benzyl)-2-methyl-1,8-naphthyridine-3-carboxamide
N-(4-Cyclohexenyl-3-(trifluoromethyl)benzyl)-2-methyl-1,8-naphthyridine-3-carboxamide
2-Methyl-N-((4-phenylfuran-2-yl)methyl)-1,8-naphthyridine-3-carboxamide
2-Methyl-N-(4-(pyrrolidin-1-yl)benzyl)-1,8-naphthyridine-3-carboxamide
2-Methyl-N-(4-(piperidin-1-yl)-3-(trifluoromethyl)benzyl)-1,8-naphthyridine-3-carboxamide
2-Methyl-N-(4-morpholino-3-(trifluoromethyl)benzyl)-1,8-naphthyridine-3-carboxamide
N-(4-Isopropoxy-3-(trifluoromethyl)benzyl)-2-methyl-1,8-naphthyridine-3-carboxamide
2-Methyl-N-(4-(tetrahydro-2H-pyran-4-yloxy)-3-(trifluoromethyl)benzyl)-1,8-naphthyridine-3-carboxamide N-(4-(Dimethylamino)-3-(trifluoromethyl)benzyl)-2-methyl-1,8-naphthyridine-3-carboxamide
N-(4-cyclopentylbenzyl)-2-methyl-1,8-naphthyridine-3-carboxamide
(S)-2-Methyl-N-(4-(3-methylmorpholino)benzyl)-1,8-naphthyridine-3-carboxamide
(R)-2-methyl-N-(4-(3-methylmorpholino)benzyl)-1,8-naphthyridine-3-carboxamide
2-Methyl-N-(4-(1,1,1-trifluoropropan-2-yloxy)benzyl)-1,8-naphthyridine-3-carboxamide
2-Methyl-N-(4-(2-methylpiperidin-1-yl)benzyl)-1,8-naphthyridine-3-carboxamide
2-Methyl-N-(4-(pyridin-3-yl)-3-(trifluoromethyl)benzyl)-1,8-naphthyridine-3-carboxamide
N-((6-tert-Butylpyridin-3-yl)methyl)-2-methyl-1,8-naphthyridine-3-carboxamide
2-methyl-N-(4-(tetrahydro-2H-pyran-4-yl)benzyl)-1,8-naphthyridine-3-carboxamide
N-(4-(1,2-diazaspiro[2.5]oct-1-en-6-yl)benzyl)-2-methyl-1,8-naphthyridine-3-carboxamide
3-(Trifluoromethyl)benzyl 2-methyl-1,8-naphthyridine-3-carboxylate
(6-Phenylpyridin-3-yl)methyl 2-methyl-1,8-naphthyridine-3-carboxylate
(5-Phenylisoxazol-3-yl)methyl 2-methyl-1,8-naphthyridine-3-carboxylate
(2-Phenylthiazol-4-yl)methyl 2-methyl-1,8-naphthyridine-3-carboxylate
N-(4-tert-butylbenzyl)-2,7-dimethyl-1,8-naphthyridine-3-carboxamide
N-(4-tert-butylbenzyl)-2,6-dimethyl-1,8-naphthyridine-3-carboxamide
6-amino-N-(4-tert-butylbenzyl)-2-methyl-1,8-naphthyridine-3-carboxamide
N-((6-tert-Butyl-2-chloropyridin-3-yl)methyl)-2-methyl-1,8-naphthyridine-3-carboxamide
N-((2-chloro-6-cyclopentylpyridin-3-yl)methyl)-2-methyl-1,8-naphthyridine-3-carboxamide
N-((6-tert-Butyl-2-methoxypyridin-3-yl)methyl)-2-methyl-1,8-naphthyridine-3-carboxamide
N-(4-(4,4-Dimethylpiperidin-1-yl)benzyl)-2-methyl-1,8-naphthyridine-3-carboxamide
N-(4-(Cyclopentyloxy)benzyl)-2-methyl-1,8-naphthyridine-3-carboxamide
2-Methyl-N-(4-thiomorpholinobenzyl)-1,8-naphthyridine-3-carboxamide
N-(4-(4,4-dimethylpiperidin-1-yl)-3-fluorobenzyl)-2-methyl-1,8-naphthyridine-3-carboxamide
N-(3-cyano-4-(4,4-dimethylpiperidin-1-yl)benzyl)-2-methyl-1,8-naphthyridine-3-carboxamide
N-(4-tert-butyl-2-hydroxybenzyl)-2-methyl-1,8-naphthyridine-3-carboxamide
N-(4-cyclohexylbenzyl)-2-methyl-1,8-naphthyridine-3-carboxamide
N-(4-(8-oxa-3-azabicyclo[3.2.1]octan-3-yl)-3-fluorobenzyl)-2-methyl-1,8-naphthyridine-3-carboxamide
N-(4-(2,6-dimethylmorpholino)-3-fluorobenzyl)-2-methyl-1,8-naphthyridine-3-carboxamide
N-(3-fluoro-4-(1,4-dioxa-8-azaspiro[4.5]decan-8-yl)benzyl)-2-methyl-1,8-naphthyridine-3-carboxamide
N-(4-(4,4-difluoropiperidin-1-yl)-3-fluorobenzyl)-2-methyl-1,8-naphthyridine-3-carboxamide
2-Methyl-N-(4-(1,1-dioxothiomorpholino)benzyl)-1,8-naphthyridine-3-carboxamide
and be present as a free base, an acid in its non-charged protonated form, a pharmaceutically addition acceptable salt, solvate, solvate of a salt thereof, a pure stereoisomer, a racemic, diastereomeric or scalemic mixture, a corresponding tautomeric form resulting from a hydrogen shift between two hetero-atoms, such as 1,3-shift in any direction between O and N or between N and N, and/or the corresponding tautomeric form resulting from a keto-enol tautomerization.

Another embodiment relates to a pharmaceutical composition, such as medicament, comprising a compound according to the various embodiments disclosed herein or a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide and a pharmaceutically acceptable excipient.

Further, such a pharmaceutical composition may comprise an anti-asthmatic. Such an anti-asthmatic may be selected from anti-asthmatics wherein the principal mechanism of action of the anti-asthmatic is selected from the group consisting of β2-agonist, and anticholinergicum, or wherein the anti-asthmatic is a corticosteroid. Various examples of such anti-asthmatics are well known to the one skilled in the art.

Examples of β2-agonists comprises adrenaline, albuterol, amiterol, bambuterol, bitolterol, buphenine, broxaterol, carbuterol, cimaterol, clenbuterol, clorprenaline, colterol, denopamine, dioxethedrine, dioxifedrine, dopexamine, doxaminol, dobutamine, etanterol, ephedrine, epinephrine, adrenaline, eprozinol, etafedrine, ethylnorepinephrine, fenoterol, berotec, dosberotec, partusisten, flerobuterol, formoterol, eformoterol, R,R-formoterol, hexoprenaline, ibopamine, isoeharine, ibuterol, imoxiterol, isoxsuprine, ibuterol, isoprenolol, isoproterenol, levalbuterol, R-form of albuterol, levosalbutamol, levisoprenaline, l-form of isoprenaline, mabuterol, meluadrine, mesuprine, metaterol, metaproterenol, methoxyphenamine, nardeterol, oxyfedrine, orciprenalin, picumeterol, pirbuterol, prenalterol, procaterol, protokylol, quinprenaline, reproterol, rimiterol, ritodrine, salbutamol, albuterol, salmeterol, soterenol, sulphonterol, ta-2005, terbutaline, tretoquinol, tulobuterol, xamoterol, zilpaterol, ar-c68397aa, 4-hydroxy-7-[2-[2-[3-phenylethoxypropane-1-sulfonyl]ethylamino]ethyl]-3h-benzothiazol-2-one hydrochloride, chf-1035, rac-5,6-diiso-butyryloxy-2-methylamino-1,2,3,4-tetrahydronaphthalene hydrochloride, hoku-81, 1-(2-chloro-4-hydroxyphenyl)-2-tert-butylamino-ethanol, ibuterol, 1-(3,5-dihydroxyphenyl)-2-(tert-butylamino)ethanol diisobutyrate ester, meluadrine, 4-(2-tert-butylamino-1-hydroxyethyl)-3-chlorophenol, ta-2005, 8-hydroxy-5-[(1r)-1-hydroxy-2-[n-[(1r)-2-(p-methoxyphenyl)-1-methylethyl]-amino]ethyl]carbostyril hydrochloride, tiaramide, 5-chloro-3-[4-(2-hydroxyethyl)-1-piperazinyl]carbonyl-methyl-2-benzothiazolinone, trimetoquinol, (1,2,3,4-tetrahydro-1-((3,4,5-trimethoxyphenyl)methyl)-6,7-isoquinolinediol), desformoterol, ((r,r) or (s,s)-3-amino-4-hydroxy-.alpha.-(((2-(4-methoxy-phenyl)-1-methylethyl)amino)methyl)-benzenemethanol, 4-hydroxy-7-[2-{[2-{[3-(2-phenylethoxy)propyl]sulphonyl}-ethyl]-amino}-ethyl]-2(3h)-benzothiazolone, 1-(2-fluoro-4-hydroxyphenyl)-2-[4-(1-benzimidazolyl)-2-methyl-2-butylamino]-ethanol, 1-[3-(4-methoxybenzyl-amino)-4-hydroxyphenyl]-2-[4-(1-benzimidazolyl)-2-methyl-2-butylamino]ethanol, 1-[2h-5-hydroxy-3-oxo-4h-1,4-benzoxazin-8-yl]-2-[3-(4-n,n-dimethyl-aminophenyl)-2-methyl-2-propylamino]ethanol, 1-[2h-5-hydroxy-3-oxo-4h-1,4-benzoxazin-8-yl]-2-[3-(4- methoxyphenyl)-2-methyl-2-propylamino]ethanol, 1-[2h-5-hydroxy-3-oxo-4h-1,4-benzoxazin-8-yl]-2-[3-(4-n-butyloxy-phenyl)-2-methyl-2-propylamino]ethanol, 1-[2h-5-hydroxy-3-oxo-4h-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylamino-butyl)-2h-1,4-benzoxazin-3-(4h)-one, 1-(4-amino-3-chloro-5-trifluoromethylphenyl)-2-tert.-butylamino)ethanol, indacaterol, carmoterol, and 1-(4-ethoxycarbonylamino-3-cyano-5-fluorophenyl)-2-(tert.-butylamino)ethanol.

A pharmaceutical composition comprising a compound according to the various embodiments disclosed herein or a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide may also comprise a β2-agonists selected from the group consisting of fenoterol, terbutalin, formoterol, salbutamol, salmeterol, bambuterol, bitolterol, carbuterol, clenbuterol, hexoprenaline, procaterol, ibuterol, pirbuterol, tulobuterol, reproterol, sulfonterol, indacaterol, carmoterol and arformoterol.

Examples of anticholinergicum comprises aclidinium bromide, adiphenine, alverine, ambutonium bromide, aminopentamide, amixetrine, amprotropine phosphate, anisotropine methylbromide, apoatropine, atropine, atropine N-oxide, benactyzine, benapryzine, benzetimide, benzilonium, benzilonium bromide, benztropine mesylate, bevonium methyl sulfate, biperiden, butropium bromide, buzepide, camylofine, caramiphen, chlorbenzoxamine, chlorphenoxamine, cimetropium bromide, clidinium bromide, cyclodrine, cyclonium, cyclopentolate, cycrimine, darifenacin, deptropine, dexetimide, dibutoline sulfate, dicyclomine, diethazine, difemerine, dihexyverine, diphemanil methylsulfate, dipiproverine, diponium, emepronium, emepronium bromide, endobenzyline, ethopropazine, ethybenztropine, ethylbenzhydramine, etomidoline, eucatropine, fenpiverinium bromide, fentonium, fentonium bromide, flavoxate, flutropium, flutropium bromide, glycopyrrolate, heteronium, hexocyclium methyl sulfate, homatropine, hyocyamine, hyoscyamine, ipratropium, ipratropium bromide, isopropamide, isopropamide iodide, levomepate, mecloxamine, mepenzo late, mepenzo late bromide, metcaraphen, methantheline, methantheline bromide, methixene, methscopolamin bromide, n-(1,2-diphenylethyl)nicotinamide, n-butylscopolammonium bromide, octamylamine, oxitropium bromide, oxybutynin, oxyphencyclimine, oxyphenonium, oxyphenonium bromide, pentapiperide, penthienate, penthienate bromide, phencarbamide, phenglutarimide, pipenzolate, pipenzo late bromide, piperdolate, piperidolate, piperilate, poldine methylsulfate, pridinol, prifinium, procyclidine, profinium bromide, propantheline, propantheline bromide, propenzolate, propiverine, propyromazine, scopolamine, scopolamine n-oxide, stilonium, stramonium, sultroponium, telenzepine, thihexinol, thiphenamil, tiemonium, tiemonium iodide, timepidium, timepidium bromide, tiotropium bromide, tiquizium, tiquizium bromide, tolterodine, tridihexethyl iodide, trihexyphenidyl hydrochloride, tropacine, tropenzile, tropicamide, trospium, trospium chloride, valethamate, valethamate bromide, and xenylropium.

A pharmaceutical composition comprising a compound according to the various embodiments disclosed herein or a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide may also comprise a anticholinergicum selected from the group consisting of tiotropium bromide, ipratropium bromide, glycopyrrolate and aclidinium bromide.

Examples of corticosteroid comprises 21-acetoxy-pregnenolone, alclometasone, algestone, amcinonide, beclomethasone, betamethasone, betamethasone valerate, budesonide, chloroprednisone, ciclesonide, clobetasol, clobetasol propionate, clobetasone, clobetasone butyrate, clocortolone, cloprednol, corticosterone, cortisone, cortivazol, deflazacort, desonide, desoximethasone, dexamethasone, diflorasone, diflucortolone, difluprednate, enoxolone, fluazacort, flucloronide, flumethasone, flumethasone pivalate, flunisolide, fluocinolone acetonide, fluorocinolone acetonide, fluorocortolone hexanoate, diflucortolone valerate, fluocinonide, fluocortine, butyl fluocortolone, fluorometholone, fluperolone acetate, fluprednidene acetate, fluprednisonole, flurandrenolide, fluticasone propionate, formocortal, halcinonide, halobetasol propionate, halometason, halopredone acetate, hydrocortamate, hydrocortisone, hydrocortisone acetate, hydrocortisone butyrate, hydrocortisone phosphate, hydrocortisone 21-sodium succinate, hydrocortisone tebutate, loteprednol etabonate, mazipredone, medrysone, meprednisone, methylprednisolone, momethasone furoate, paramethasone, prednicarbate, prednisolone, prednisolone, 21-diethylaminoacetate, prednisolone sodium phosphate, prednisolone sodium succinate, prednisolone sodium 21-m-sulfobenzoate, prednisolone sodium 21-stearoylglycolate, prednisolone tebutate, prednisolone 21-trimethylacetate, prednisone, prednival, prednylidene, prednylidene 21-diethylaminoacetate, rimexolone, tixocortol, triamcinolone, triamcinolone acetonoide, triamcinolone benetonide, and triamcinolone hexacetonide.

A pharmaceutical composition comprising a compound according to the various embodiments disclosed herein or a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide may also comprise a corticosteroid selected from the group consisting of budesonide, beclomethasone, ciclesonide, fluticasone propionate and momethasone furoate.

According to another embodiment a compound or a pharmaceutical composition as disclosed herein or a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide may be used in therapy.

A compound or a pharmaceutical composition as disclosed herein or a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide may be used to prevent and/or treat bronchoconstriction.

Furthermore, a compound or a pharmaceutical composition as disclosed herein or a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide may be used in the prevention and/or treatment of a disease or condition characterized by bronchoconstriction of the respiratory apparatus.

Diseases or conditions characterized by bronchoconstriction may be selected from the group consisting of asthma, chronic obstructive pulmonary disease, chronic bronchitis, emphysema, bronchiectasis, cystic fibrosis, bronchiolitis and bronchopulmonary dysplasia.

Another embodiment relates to a method of prevention and/or treatment of bronchoconstriction, comprising administering to a mammal, including man in need of such prevention and/or treatment, a therapeutically effective amount of compound as disclosed herein, a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide or a pharmaceutical composition comprising a therapeutically effective amount of a compound as disclosed herein.

Another embodiment relates to a method of prevention and/or treatment of a disease or condition characterized by bronchoconstriction of the respiratory apparatus, comprising administering to a mammal, including man in need of such prevention and/or treatment, a therapeutically effective amount of compound as disclosed herein, a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide or a pharmaceutical composition comprising a therapeutically effective amount of a compound as disclosed herein.

Further, such treatment and/or prevention may comprise the simultaneous or consecutive administration of at least one anti-asthmatic. If administered simultaneous or consecutive the administered dose of the anti-asthmatic may be 1 to 10 times less than the established therapeutically effective dose when administered alone for prevention or treatment of the same disease or condition. Further, if administered simultaneous or consecutive the administered dose of a compound as disclosed herein may be 1 to 10 times less than the established therapeutically effective dose when administered alone for prevention or treatment of the same disease or condition. When an anti-asthmatic used in such a method as disclosed above it may be selected from anti-asthmatics wherein the principal mechanism of action of the anti-asthmatic is selected from the group consisting of β2-agonist, anticholinergicum and calcium antagonist, or wherein the anti-asthmatic is a corticosteroid. Various examples of such anti-asthmatics are well known to the one skilled in the art. Furthermore, various examples of anti-asthmatics to be used in methods disclosed herein are given above.

According to another embodiment, a compound or a pharmaceutical composition, as disclosed herein, or a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide may be used in the prevention and/or treatment of a disease or condition characterized by systemic or respiratory vasoconstriction.

Similarly, a compound or a pharmaceutical composition as disclosed herein or a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide may be used in a method of prevention and/or treatment of a disease or condition characterized by systemic or respiratory vasoconstriction. Such a method comprises administering to a mammal, including man in need of such prevention and/or treatment, a therapeutically effective amount of a compound as disclosed herein, a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide or a pharmaceutical composition comprising a therapeutically effective amount of a compound as disclosed herein.

According to another embodiment, a compound or a pharmaceutical composition, as disclosed herein, or a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide may be used in the prevention and/or treatment of a disease or condition related to smooth muscle dysfunction including hypertension, pulmonary hypertension, incontinence and overactive bladder, irritable bowel syndrome, pre-term labor, vasospasm, subarachnoid hemmorages and erectile dysfunction.

Similarly, a compound or a pharmaceutical composition as disclosed herein may be used in a method of prevention and/or treatment of a disease or condition related to smooth muscle dysfunction including hypertension, pulmonary hypertension, incontinence and overactive bladder, irritable bowel syndrome, pre-term labor, vasospasm, subarachnoid hemorrhages and erectile dysfunction. Such a method comprises administering to a mammal, including man in need of such prevention and/or treatment, a therapeutically effective amount of a compound as disclosed herein or a pharmaceutical composition comprising a therapeutically effective amount of a compound as disclosed herein.

When used herein, "prevent/preventing" should not be construed to mean that a condition and/or a disease never might occur again after use of a compound or pharmaceutical composition according to embodiments disclosed herein to achieve prevention. Further, the term should neither be construed to mean that a condition not might occur, at least to some extent, after such use to prevent said condition. Rather, "prevent/preventing" is intended to mean that the condition to be prevented, if occurring despite such use, will be less severe than without such use.

According to one embodiment treatment does also encompass pre-treatment, i.e. prophylactic treatment.

The usefulness of the compounds, as defined in the preceding embodiments, in treating, pretreating, revoking, mitigating, alleviating and/or preventing a condition of the respiratory apparatus characterized by bronchoconstriction, were evaluated in a complex and relevant in vitro model.

The model was in accordance with the in vitro model disclosed in US 2006-0040254 A1 and Skogvall, S., Berglund, M., Dalence-Guzmán, M. F., Svensson, K., Jönsson, P., Persson, C. G. A and Sterner, O., Pulmonary Pharmacology and Therapeutics, vol 20:3, 2007, p. 273-280.

In short, lung tissue was obtained from patients undergoing lobectomia or pulmectomia due to lung carcinoma. From the bronchus of this tissue were rectangular oblong preparations obtained. The contraction induced by inflammatory mediators, such as Leukotriene D4, histamine, prostaglandin D2 or acetylcholine, in the presence and absence of the compound to be evaluated, were compared.

The compounds synthesized as described below were all tested at 10 µM and shown to reduce the contraction evoked by 10 nM Leukotriene D4 in the in vitro model referred to above.

According to one embodiment, preferred compounds according to any of the preceding embodiments are those reducing the contraction evoked by 10 nM Leukotriene D4 when tested at 1 µM in the in vitro model referred to above.

A pharmaceutical composition, e.g. a medicament, as has been described herein above may further comprise pharmaceutically acceptable excipients, such as carriers, diluents, stabilisers and/or.

"Pharmaceutically acceptable" means an excipient that, at the dosage and concentrations employed, does not cause any unwanted effects in the patients to whom it is administered. Such pharmaceutically acceptable excipients are well-known in the art.

A pharmaceutical composition according embodiments herein may be administered to a patient in a pharmaceutically effective dose. By "pharmaceutically effective dose" is meant a dose that is sufficient to produce the desired effects in relation to the condition for which it is administered. The exact dose may be dependent on the activity of the compound, manner of administration, nature and severity of the disorder and/or disease and the general conditions, such as age and body weight of the patient.

According to one embodiment, a pharmaceutical composition according to embodiments herein may be administered alone or in combination with other therapeutic agents, such as anti-asthmatics. These agents may be incorporated as part of the same pharmaceutical composition or may be administered separately. It is well known in the art that a combination of mechanistically unrelated therapeutic agents in the same medicament may have beneficial effects in the treatment of conditions or diseases characterized by bronchoconstriction, as described in, for example, M. F. Fitzgerald and J. C. Fox, Drug Discovery Today, 2007, 12 (11/12), p. 472-478.

In one embodiment of the invention such other therapeutic agents to be administered in combination with a pharmaceutical composition according to embodiments herein are selected from therapeutic agents known to the one skilled in the art to prevent bronchoconstriction or revoke, fully or partly, any present bronchoconstriction. Examples of such agents are, but not limited to, β2-agonists, anticholinergics, and other agents suitable for the treatment of asthma and/or COPD and related diseases and/or disorders. Preferred agents in this aspect are β2-agonists and anticholinergics, such as fenoterol, terbutalin, formoterol, salbutamol, salmeterol, bambuterol, bitolterol, carbuterol, clenbuterol, hexoprenaline, procaterol, ibuterol, pirbuterol, tulobuterol, reproterol, sulfonterol, indacaterol, carmoterol, arformoterol tiotropium bromide, ipratropium bromide, glycopyrrolate and aclidinium bromide.

Furthermore such other therapeutic agents to be administered in combination with pharmaceutical composition according to embodiments herein may also comprise therapeutic agents known to the one skilled in the art to be useful to treat, revoke, mitigate, alleviate or prevent inflammation associated with diseases and disorders of respiratory tract. Examples of such agents are corticosteroids, such as budesonide, beclomethasone, ciclesonide, fluticasone propionate and momethasone furoate.

When a compound according to embodiments disclosed herein is combined with at least another therapeutic agent, such as an anti-asthmatic, in a pharmaceutical composition, such as a medicament, a therapeutically effective dose of said pharmaceutical composition may comprise 1 to 10 times less than the respective established therapeutically effective dose of the components, i.e. a compound according to the invention and the therapeutic agent, when administered alone for prevention or treatment of the same disease or condition of each.

Accordingly, by combining a compound according to embodiments disclosed herein with another therapeutic agent, such as an anti-asthmatic, it may be possible to achieve synergistic effects compared to if only a compound according to the present invention, or the other therapeutic agent, were administrated alone. Furthermore, it may be possible to improve both the underlying cause, e.g. the inflammation, and the clinical signs, e.g. airflow obstruction and exacerbations.

A method to treat, revoke, mitigate, alleviate or prevent bronchoconstriction in a mammal, such as a human being, in need thereof, by the administration of a compound or pharmaceutical composition, such as a medicament, according to embodiments disclosed herein may also include the simultaneous or consecutive administration a therapeutic agent, such as an anti-asthmatic. In such a method the therapeutically effective dose of said compound, medicament or pharmaceutical composition and said therapeutic agent may comprise 1 to 10 times less than the respective established therapeutically effective dose when administered alone for prevention or treatment of the same disease or condition. The advantageous of such co-administration are discussed above.

A pharmaceutical composition according to embodiments disclosed herein may be administered through different routes such as, but not limited to, intravenously, intraperitonealy, intramuscularly, intranasaleously, subcutaneously, sublingually, rectally, orally or through inhalation or insufflation.

Particular suitable formulations of pharmaceutical compositions as disclosed herein are formulations suitable to be taken orally or to be administrated through inhalation or insufflation.

Administration by inhalation or insufflation will allow a high proportion of the delivered dose to reach the site of action, that is, the bronchi and the lung in general. Furthermore the systemic effects may be lower if the medicament is administrated through inhalation or insufflation compared to other administration routes.

Inhalation may be by the oral or the nasal route. Conventional pulmonary applicators may be employed, such as pressurized spray containers comprising suitable propellants for aerosols and powder spray devices for preparations in form of fine powders. Pharmaceutical compositions suitable for administration by the inhalation or insufflation route are known in the art. The compound may be dissolved in a suitable vehicle or employed as a fine powder, such as a micronized powder of a medium particle size from about 2 μm to about 20 μm. An indicated daily dose for administration by inhalation may be 10 times and lower than the corresponding oral dose. Satisfactory doses, preferably metered by using a device capable of metering, or by single doses of predetermined size, may easily be determined by experimentation.

Compounds according to embodiments disclosed herein may also be useful in treatment or prevention of hypertension. In the treatment of conditions or diseases characterized by hypertension, by employment of the compounds of the present invention, oral administration is the preferred route of administration.

In addition to their use in therapeutic medicine, compounds according to formula (I) may also be useful as pharmacological tools in the development and standardisation of in vitro and in vivo test systems for the evaluation of other compounds with similar activity.

Furthermore, compounds of formula (I) may be used as molecular probes to identify and/or locate the target of their action, such as a target within the airways, as well as employed as a diagnostic tool for diagnosis of a disease or condition in vivo, ex vivo or in vitro, or as synthetic precursors to such probes. Molecular probes of formula (I) may include reactive, labeled, i.e. compounds of formula (I) wherein one or several of the composing atoms have been enriched with a radioactive or by other means detectable isotope, and fluorescent compounds as well known to the one skilled in the art.

Furthermore, compounds according to formula (I) do also include compounds wherein one or several atoms have been substituted with heavier isotopes, such as substitution of hydrogen for deuterium, carbon-12 for carbon-13 or carbon-14, and/or nitrogen-14 for nitrogen-15.

All references disclosed herein are hereby incorporated in their entirety by reference.

Although the present invention has been described above with reference to specific illustrative embodiments, it is not intended to be limited to the specific form set forth herein. Any combination of the above mentioned embodiments should be appreciated as being within the scope of the invention. Rather, the invention is limited only by the accompanying claims and other embodiments than the specific above are equally possible within the scope of these appended claims.

In the claims, the term "comprises/comprising" does not exclude the presence of other species or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality.

Methods of Preparation

Another embodiment of the present invention relates to a process for preparing a compound according to formula (I) as a free base, acid, or salts thereof. Further, additionally embodiments relate to synthetic intermediates, which are useful in the synthesis of a compound of formula (I) as a free base, acid, or salts thereof. Specific and generic examples of such intermediates are given below. Further, such intermediates may include compounds according to formula (I), which may be used to produce another compound according to formula (I).

Throughout the following description of such processes it is to be understood that, where appropriate, suitable protecting groups will be attached to, and subsequently removed from, the various reactants and intermediates in a manner that will be readily understood by one skilled in the art of organic synthesis. Conventional procedures for using such protecting groups, as well as examples of suitable protecting groups, are well known within the art. Further such procedures and groups are described in the literature, such as in "Protective Groups in Organic Synthesis", 3rd ed., T. W. Green, P. G. M. Wuts, Wiley-Interscience, New York (1999).

It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis.

Examples of transformations are given below, and it is to be understood that the described transformations are not limited only to the generic groups or substituents for which the transformations are exemplified.

References and descriptions on other suitable transformations are for example given in "Comprehensive Organic Transformations—A Guide to Functional Group Preparations", 2nd ed., R. C. Larock, Wiley-VCH, New York (1999). References and descriptions of other suitable reactions are described in textbooks of organic chemistry well known to the one skilled in the art, such as "March's Advanced Organic Chemistry", 5th ed., M. B. Smith, J. March, John Wiley & Sons (2001) or, "Organic Synthesis", 2nd ed., M. B. Smith, McGraw-Hill, (2002).

Techniques for purification of intermediates and final products include for example, straight and reversed phase chromatography on column or rotating plate, size exclusion chromatography, recrystallisation, distillation and liquid-liquid or solid-liquid extraction, which will be readily understood by the one skilled in the art.

The terms "room temperature" and "ambient temperature" shall mean, unless otherwise specified, a temperature between 16 and 25° C. The term "reflux" shall mean, unless otherwise stated, in reference to an employed solvent using a temperature at or slightly above the boiling point of the named solvent. It is understood that microwaves can be used for the heating of reaction mixtures.

The terms "flash chromatography" or "flash column chromatography" shall mean preparative chromatography on silica using an organic solvent, or mixtures thereof, as mobile phase.

In the various schemes given below, generic groups, such as R-groups, have the same representation as given above herein, if not specifically defined.

Methods of Preparation of Final Compounds of Formula I by Coupling of Intermediates II and III (Scheme 1)

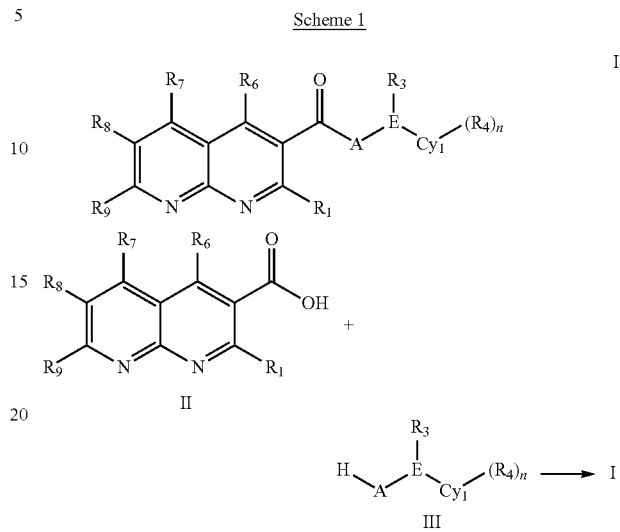

Formation of compounds of formula I, may be accomplished by coupling of II and III under standard amide or ester coupling conditions, such as in the presence of N-(3-dimethylaminopropyl)-N'-ethyl-carbodiimide hydrochloride, 1-hydroxybenzotriazole hydrate and triethyl amine, or for example, via initial conversion of the acid II into the corresponding acid chloride, followed by coupling III according to standard protocols.

Methods of Preparation of Final Compounds of Formula I by Coupling of Intermediates II and III (Scheme 2)

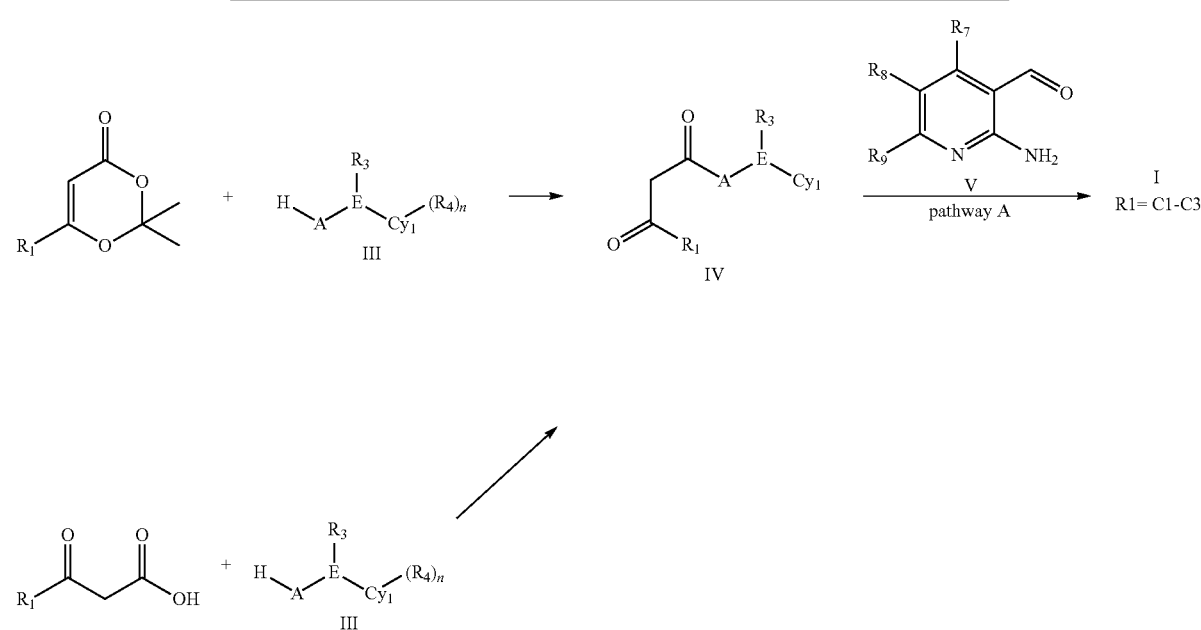

Scheme 2. Examples of non-limiting methods for the preparation of final compounds of formula I, by assembly of the 1,8-naphthyridine ring, including pathways A, B and C.

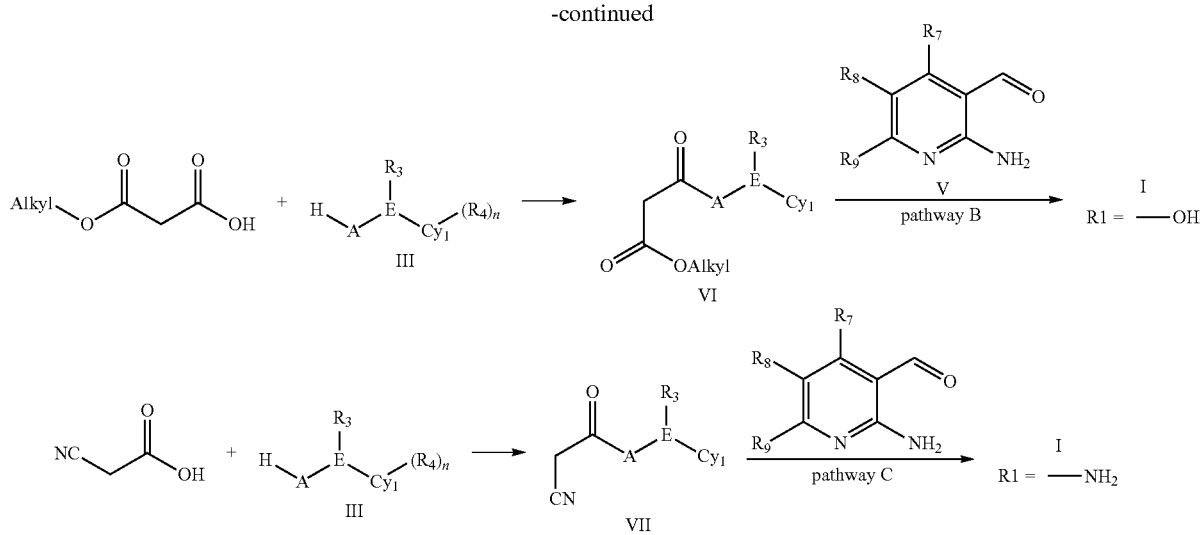

The synthesis according to pathway A involves the condensation of a suitably substituted 2-amino-3-pyridine carboxaldehyde (V) with a 1, 3 keto ester IV in the presence of a suitable base to obtain final compounds where R1=—C1-C3. Analogously final compounds where R1=—OH or —NH$_2$ according to formula I, can be prepared following pathways B and C through condensation 2-amino-3-pyridine carboxaldehyde with 1,3 dicarbonyl compounds of formula VI (depicted "alkyl" is preferably short alkyls such as methyl) and 2-cyanoacetates of formula VII respectively.

Methods of Preparation of Final Compounds of Formula I by Reacting Intermediates VII with Nucleophiles (Scheme 3)

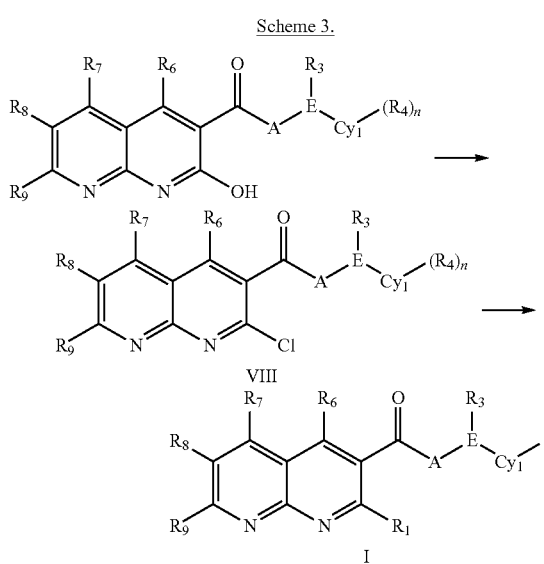

Compounds according to formula I were R1=OH can be treated with e.g. POCl3 while heating to obtain the 2-chloro naphtyridine intermediate VIII. The 2-chloro can readily be displaced by alcohols and amines by heating in a solvent such as DMF or DMSO in the presence of a suitable base to obtain final products of formula I were R1=—OR, —NHC0-C3 or —N(C0-C3)2.

Methods of Preparation of Final Compounds of Formula I by Coupling of Intermediates VIII (Scheme 4)

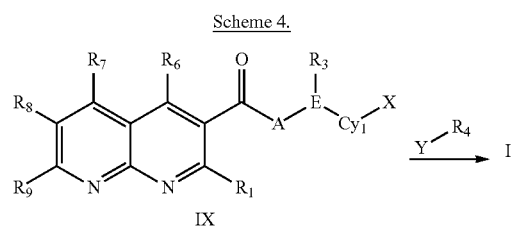

Formation of compounds of formula I, may be accomplished by coupling of intermediate IX, where depicted X is preferably, but not limited to, halogens such as Br or I but can also be triflates or mesylates, with intermediate X where depicted Y is B(OH)$_2$, B(OR)$_2$, SnR$_3$, ZnCl, SiR$_3$ in the presence of a suitable transitions metal catalyst, for example Pd(Ph$_3$)$_4$.

Methods of Preparation of Intermediates of Formula III (Scheme 5)

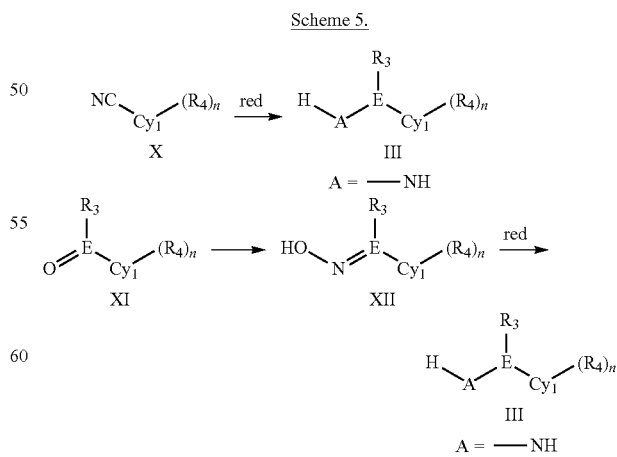

Intermediates of formula III where A is —NH, E=—Cl and R3=H may be prepared from readily available aromatic nitriles X through reduction using for example LiAlH$_4$, NaBH$_4$ and NiCl$_2$, hydrogen gas and a suitable catalyst and Ra/Ni depending on the nature of R4 and Cy1. Alternatively amines can be prepared from the corresponding ketones or aldehydes (formula XI). Readily available carbonyl compounds XI can be converted to oximes XII by condensing with hydroxyamine which then can be reduced to the desired amine III using for example LiAlH$_4$ or hydrogen gas with a suitable catalyst.

Intermediates of formula III where A is —OH may be prepared from readily available carboxylic acids or esters through reduction using for example LiAlH$_4$ or BH$_3$ depending on the nature of R4 and Cy1 of formula I.

Methods of Preparation of Enantiomerically Enriched Intermediates of Formula III (Scheme 6)

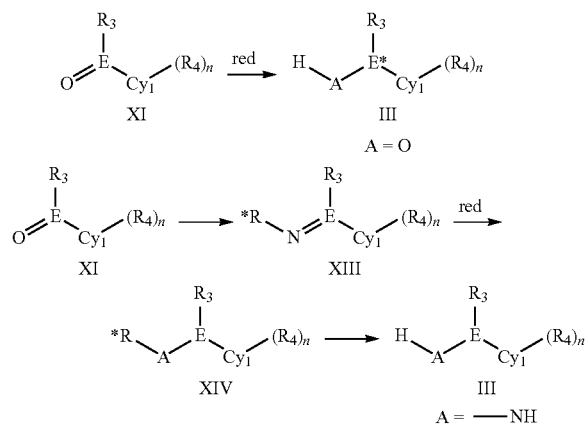

Racemic mixtures of III where R3 is not H can be separated into the corresponding enantiomers through chiral separation using chiral chromatography using a suitable chiral stationary phase. Enantiomerically enriched amines corresponding to formula III maybe be prepared treating a racemic mixture of III with a chiral acid and then separating the diastereomeric salts through for example recrystallization. Furthermore racemic mixtures of III can be derivatized with a chiral auxiliary followed by separation of the formed diastereomers through recrystallization or chromatography. The enantiomerically enriched compound can then be obtained by cleaving the auxiliary group. Kinetic resolution using a suitable lipase and acetyl donor can also provide III in an enantiomerically enriched form. Asymmetric synthetic methods can also produce intermediate III directly in an enantiomerically enriched form. Chiral alcohols III where A=O can be prepared from ketones XI through an enantioselective reduction using oxazaborolidine catalysts, chiral boranes or chiral transition metal catalysts under phase transfer or normal hydrogenation conditions. Chiral amines III where A=—NH can be prepared from chiral imines XIII obtained from the condensation of the corresponding ketones XI and a chiral amine, for example (S)-1-phenylethanamine, followed by a diastereoeselective reduction using a hydride reducing agent for example NaBH$_4$. The chiral amine III where A=NH can finally be obtained through cleavage of the N—R bond of XIII through for example hydrogenolysis using palladium and hydrogen gas.

Methods of Preparation of Intermediates of Formula X (Scheme 7)

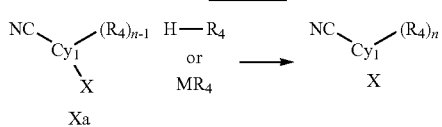

Utilizing aromatic nucleophilic substitution, nitriles of formula X may be prepared from commercially available nitriles of formula Xa where X is a suitable leaving group such as a halogen. Nitrile Xa is then reacted with nucleophilic reagent R4, either as a neutral compound HR4 or as a salt MR4 where M is a cation such as sodium or potassium. The reaction may be performed in polar protic (such as water or ethanol) or polar aprotic solvents (such as DMF, THF or DMSO) or mixtures thereof. Depending on the reactivity of starting material Xa, as well as the reactivity of reagent R4, the reaction may be performed at ambient or elevated temperature.

The salt MR4 may be generated prior to the reaction by treating neutral compound HR4 with an appropriate base such as sodium metal or sodium hydride. The generation of salt MR4 is normally performed in polar aprotic solvent such as DMF, THF or DMSO.

Methods of Preparation of Intermediates of Formula V (Scheme 8)

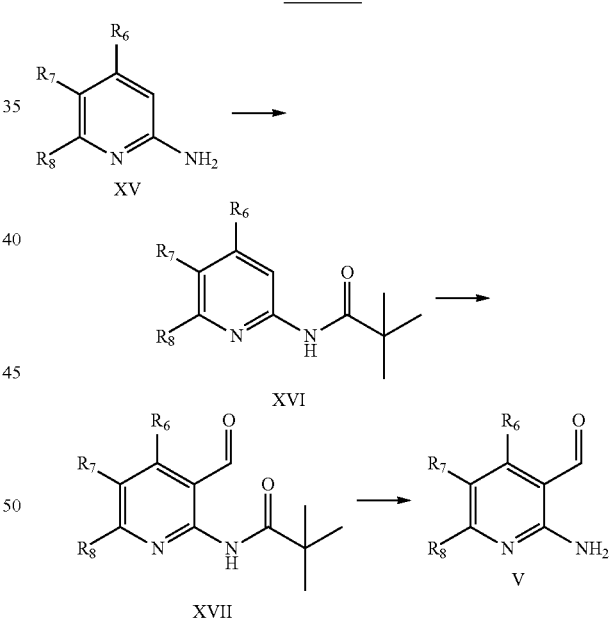

Suitably substituted 2-amino 3-pyridine carboxaldehydes according to formula V can be prepared from the corresponding and readily available 2-amino pyridines XV through a sequence of pivaloylation, lithiation and formylation. First, amino pyridines according to formula XV are treated with pivaloyl chloride in the presence of a suitable base. The pivaloyl group then acts as a directing group in the following lithiation step. Compounds according to formula XVI are treated with an alkyl lithium reagent and the lithiated intermediate is quenched with DMF and following hydrolysis products according to formula XVII are obtained. Final removal of the pivaloyl group in e.g. HCl/water affords V.

COMPOUND EXAMPLES

Abbreviations

DMF N,N'-Dimethylformamide
EDC 1-Ethyl-3-(3-dimethylaminopropyl)carbodiimide
HOBt N-Hydroxybenzotriazole
THF Tetrahydrofurane
DMSO Dimethylsulfoxide
Dppf Bis-(Diphenylphosphino)ferrocene
sat Saturated aqueous solution
Boc t-Butoxycarbonyl
TFA Trifluoroacetic acid
DMAP 4-Dimethylaminopyridine
DIPEA N,N-Diisopropylethylamine
h hour
r.t. room temperature
RC Remaining contraction
equiv equivalents
quant quantitative
aq aqueous
Ph phenyl
tol toluene
pyr pyridine
dba dibenzylideneacetone
XPhos 2-dicyclohexylphosphino-2',4',6'-triisopropylbiphenyl
BINAP 2,2'-bis(diphenylphosphino)-1,1'-binaphthyl
CDI carbonyldiimidazole
DME 1,2 dimethoxy ethane
Pet. petroleum
CBS Corey-Bakshi-Shibata
pTsOH Para-toluene sulfonic acid Preparation of Intermediates Below follows non-limiting examples on the synthesis of intermediates useful for the preparation of compounds of formula I.

Preparation of Final Compounds

Below follows non-limiting examples on the synthesis of final compounds of formula I.

General Methods

All materials were obtained from commercial sources and were used without further purification unless otherwise noted. THF was distilled from sodium and benzophenone. NMR spectra (in $CDCl_3$, $CD_3OD$ or DMSO-d6) were recorded on a Bruker DRX 400 or on a Bruker Ultrashield 400 spectrometer at 400 MHz. All chemical shifts are in ppm on the delta-scale (δ) relative to TMS using the residual $CHCl_3$ peak in $CDCl_3$, or the residual $CD_2HOD$ peak in $CD_3OD$, or the residual $CD_3SOCD_2H$ peak in $(CD_3)_2SO$ as internal standard (7.26, 3.31 or 2.50 ppm respectively relative to TMS) and the fine splitting of the signals as appearing in the recordings (s: singlet, d: doublet, t: triplet, q: quartet, m: multiplet, br: broad signal). Flash chromatography was performed using 60 Å 35-70 μm Davisil silica gel. TLC analyses were made on Silica Gel 60 F254 (Merck) plates and visualised under a 254/365 nm UV-lamp.

Scheme 9

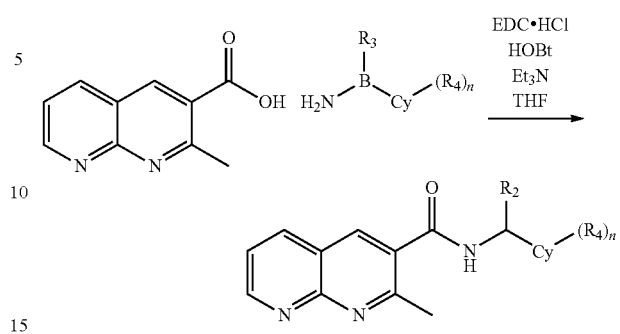

General Procedure for the Synthesis of 1,8-naphthyridines-3-carboxamides by Amide Coupling (Scheme 9)

2-Methyl-1,8-naphthyridine (1.0 eq.), N-(3-dimethylaminopropyl)-N'-ethyl-carbodiimide hydrochloride (1.1 eq.), 1-hydroxybenzotriazole hydrate (0.5 eq.) and $Et_3N$ (1.0 eq.) were suspended in anhydrous THF. The mixture was stirred at room temperature for 30 min. The corresponding amine (1.1 eq.) was added to the mixture and stirring continued for 18 h. Water was added to the mixture and the product extracted with EtOAc, dried over $MgSO_4$ and concentrated. The crude product was purified by flash chromatography (solvent system, yield and analytical data given for each compound).

Example 1

2-Methyl-N-(2-(trifluoromethyl)benzyl)-1,8-naphthyridine-3-carboxamide

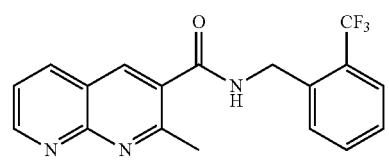 [SMILES: Cc1nc2ncccc2cc1C(=O)NCc1ccccc1C(F)(F)F]

($CH_2Cl_2$/MeOH 98:2→97:3)
Yield: 71%
$^1$H NMR ($CD_3OD$) δ 9.07 (m, 1H), 8.49-8.46 (m, 2H), 7.76-7.62 (m, 4H), 7.50 (m, 1H), 4.84 (s, 2H), 2.84 (s, 3H).

Example 2

2-Methyl-N-(4-(trifluoromethyl)benzyl)-1,8-naphthyridine-3-carboxamide

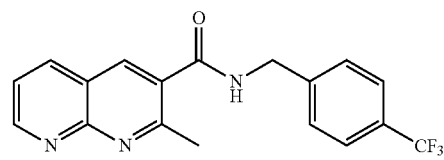 [SMILES: Cc1nc2ncccc2cc1C(=O)NCc1ccc(C(F)(F)F)cc1]

($CH_2Cl_2$/MeOH 98:2→96:4)
Yield: 37%
$^1$H NMR ($CD_3OD$) δ 9.05 (m, 1H), 8.46-8.44 (m, 2H), 7.70-7.61 (m, 4H), 4.70 (s, 2H), 2.81 (s, 3H).

Example 3

N-(4-tert-butylbenzyl)-2-methyl-1,8-naphthyridine-3-carboxamide

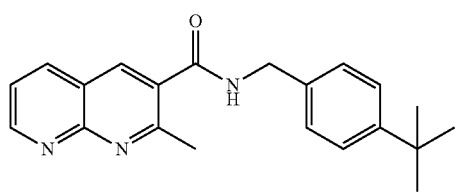 [SMILES: Cc1nc2ncccc2cc1C(=O)NCc1ccc(C(C)(C)C)cc1]

(CH$_2$Cl$_2$/MeOH 95:5)
Yield: 82%
$^1$H NMR (CDCl$_3$) δ 9.05 (m, 1H), 8.11 (s, 1H), 8.10 (m, 1H), 7.48-7.41 (m. 2H), 7.36 (d 2H), 6.43 (m, 1H), 4.68 (d, 2H), 2.91 (s, 3H), 1.34 (s, 9H).

Example 4

2-Methyl-N-((2-phenylthiazol-4-yl)methyl)-1,8-naphthyridine-3-carboxamide

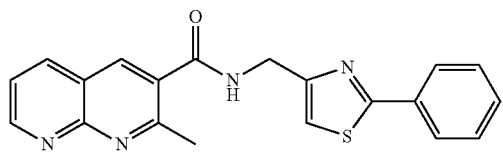 [SMILES: Cc1nc2ncccc2cc1C(=O)NCc1csc(-c2ccccc2)n1]

(CH$_2$Cl$_2$/MeOH 95:5)
Yield: 82%
$^1$H NMR (CDCl$_3$) δ 9.04 (m, 1H), 8.11 (s, 1H), 8.10 (m, 1H), 7.77 (bd, 1H), 7.61-7.29 (m, 7H), 6.53 (bt, 1H), 4.76 (d, 2H), 2.90 (s, 3H).

Example 5

2-Methyl-N-(1-(3-(trifluoromethyl)phenyl)propyl)-1,8-naphthyridine-3-carboxamide

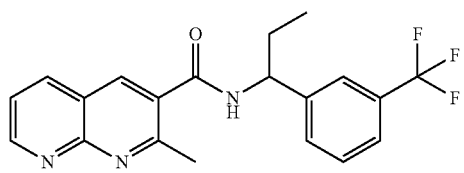 [SMILES: CCC(NC(=O)c1cc2cccnc2nc1C)c1cccc(C(F)(F)F)c1]

(CH$_2$Cl$_2$/MeOH 95:5)
Yield: 38%
$^1$H NMR (CDCl$_3$) δ 9.04 (m, 1H), 7.93 (m, 1H), 7.83 (s, 1H), 7.77 (bs, 1H), 7.71 (bd, 1H), 7.62-7.51 (m, 2H), 7.41 (m, 1H), 7.08 (d, 1H), 5.21 (m, 1H), 2.79 (s, 3H), 2.14-1.99 (m, 2H), 1.11 (t, 3H).

Example 6

2-Methyl-N-(3-(trifluoromethyl)phenethyl)-1,8-naphthyridine-3-carboxamide

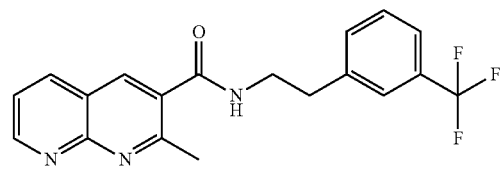 [SMILES: Cc1nc2ncccc2cc1C(=O)NCCc1cccc(C(F)(F)F)c1]

(CH$_2$Cl$_2$/MeOH 95:5)
Yield: 74%
$^1$H NMR (CDCl$_3$) δ 8.92 (m, 1H), 7.95 (m, 1H), 7.82 (s, 1H), 7.61-7.46 (m, 4H), 7.39 (m, 1H), 6.58 (bt, 1H), 3.84 (m, 2H), 3.12 (t, 2H), 2.78 (s, 3H).

Example 7

N-(4-Benzoylbenzyl)-2-methyl-1,8-naphthyridine-3-carboxamide

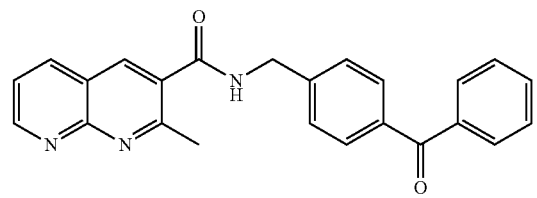 [SMILES: Cc1nc2ncccc2cc1C(=O)NCc1ccc(C(=O)c2ccccc2)cc1]

(CH$_2$Cl$_2$/MeOH 90:10)
Yield: 64%
$^1$H NMR (CD$_3$OD) δ 9.07 (m, 1H), 8.49 (s, 1H), 8.47 (m, 1H), 7.85-7.75 (m, 4H), 7.69-7.58 (m, 4H), 7.57-7.50 (m, 2H), 4.74 (s, 2H), 2.84 (s, 3H).

Example 8

2-Methyl-N-((3-phenylisoxazol-5-yl)methyl)-1,8-naphthyridine-3-carboxamide

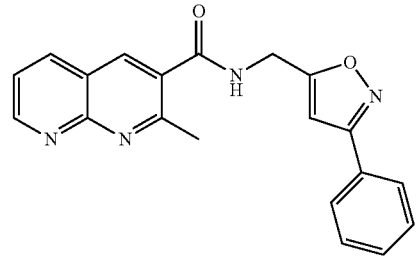 [SMILES: Cc1nc2ncccc2cc1C(=O)NCc1cc(-c2ccccc2)no1]

(CH$_2$Cl$_2$/MeOH 90:10)
Yield: 71%
$^1$H NMR (CD$_3$OD) δ 9.07 (m, 1H), 8.51 (s, 1H), 8.48 (m, 1H), 7.89-7.82 (m, 2H), 7.65 (m, 1H), 7.53-7.46 (m, 3H), 6.88 (s, 1H), 4.83 (s, 2H), 2.85 (s, 3H).

Example 9

2-Methyl-N-(4-(methylsulfonyl)benzyl)-1,8-naphthyridine-3-carboxamide

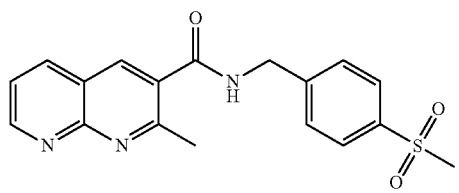 [SMILES: Cc1nc2ncccc2cc1C(=O)NCc1ccc(S(C)(=O)=O)cc1]

(CH$_2$Cl$_2$/MeOH 92:8)

Yield: 55%

$^1$H NMR (CD$_3$OD) δ 9.07 (m, 1H), 8.49 (s, 1H), 8.47 (m, 1H), 7.99 (d, 1H), 7.70 (d, 1H), 7.65 (m, 1H), 4.74 (s, 2H), 3.14 (s, 3H), 2.83 (s, 3H).

Example 10

N-(4-Chlorobenzyl)-2-methyl-1,8-naphthyridine-3-carboxamide

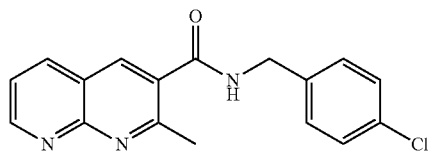 [SMILES: Cc1nc2ncccc2cc1C(=O)NCc1ccc(Cl)cc1]

(CH$_2$Cl$_2$/MeOH 97:3)

Yield: 16%

$^1$H NMR (CD$_3$OD) δ 9.06 (m, 1H), 8.46 (m, 1H), 8.43 (s, 1H), 7.64 (m, 1H), 7.45-7.37 (m, 4H), 4.60 (s, 2H), 2.81 (s, 3H).

Example 11

N-(4-Chlorophenethyl)-2-methyl-1,8-naphthyridine-3-carboxamide

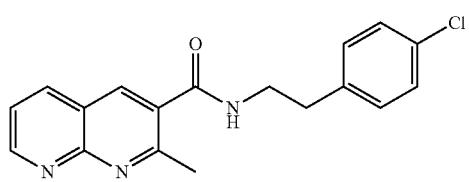 [SMILES: Cc1nc2ncccc2cc1C(=O)NCCc1ccc(Cl)cc1]

(CH$_2$Cl$_2$/MeOH 96:4)

Yield: 39%

$^1$H NMR (CD$_3$OD) δ 9.05 (m, 1H), 8.43 (m, 1H), 8.27 (s, 1H), 7.63 (m, 1H), 7.35-7.29 (m, 4H), 3.69 (t, 2H), 2.97 (t, 2H), 2.71 (s, 3H).

Example 12

N-(4-Fluorobenzyl)-2-methyl-1,8-naphthyridine-3-carboxamide

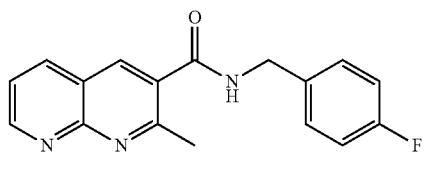 [SMILES: Cc1nc2ncccc2cc1C(=O)NCc1ccc(F)cc1]

(CH$_2$Cl$_2$/MeOH 96:4)

Yield: 35%

$^1$H NMR (CD$_3$OD) δ 9.05 (m, 1H), 8.45 (m, 1H), 8.41 (s, 1H), 7.63 (m, 1H), 7.48-7.43 (m, 2H), 7.14-7.08 (m, 2H), 4.60 (s, 2H), 2.80 (s, 3H).

Example 13

N-(3-Chlorobenzyl)-2-methyl-1,8-naphthyridine-3-carboxamide

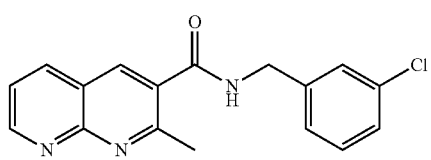 [SMILES: Cc1nc2ncccc2cc1C(=O)NCc1cccc(Cl)c1]

(CH$_2$Cl$_2$/MeOH 96:4)

Yield: 27%

$^1$H NMR (CD$_3$OD) δ 9.06 (m, 1H), 8.46 (m, 1H), 8.43 (s, 1H), 7.63 (m, 1H), 7.46 (bs, 1H), 7.35-7.29 (m, 3H), 4.61 (s, 2H), 2.81 (s, 3H).

Example 14

2-Methyl-N-(3-(trifluoromethyl)benzyl)-1,8-naphthyridine-3-carboxamide

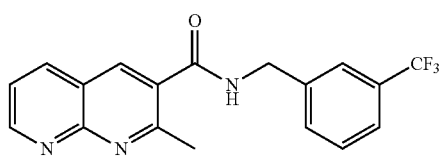 [SMILES: Cc1nc2ncccc2cc1C(=O)NCc1cccc(C(F)(F)F)c1]

(CH$_2$Cl$_2$/MeOH 96:4)

Yield: 44%

$^1$H NMR (CD$_3$OD) δ 9.06 (m, 1H), 8.46 (m, 1H), 8.44 (s, 1H), 7.80-7.50 (m, 5H), 4.70 (s, 2H), 2.81 (s, 3H).

Example 15

2-Methyl-N-((6-phenylpyridin-3-yl)methyl)-1,8-naphthyridine-3-carboxamide

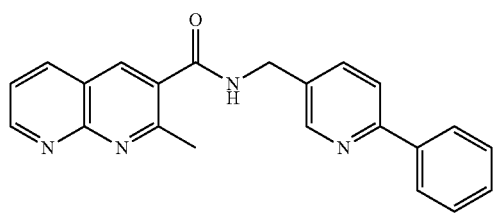 [SMILES: Cc1nc2ncccc2cc1C(=O)NCc1ccc(-c2ccccc2)nc1]

(CH$_2$Cl$_2$/MeOH 10:1)
Yield: 64%
$^1$H NMR (CDCl$_3$) δ 8.81 (m, 1H), 8.62 (d, 1H), 8.06 (bt, 1H), 7.92 (m, 3H), 7.85 (m, 1H), 7.79 (m, 1H), 7.65 (d, 1H), 7.45 (m, 2H), 7.29 (m, 1H), 4.68 (d, 2H), 2.73 (s, 3H).

Example 16

2-Methyl-N-(1-(3-(trifluoromethyl)phenyl)ethyl)-1,8-naphthyridine-3-carboxamide

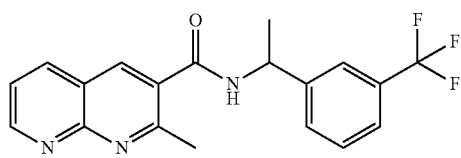 [SMILES: Cc1nc2ncccc2cc1C(=O)NC(C)c1cccc(C(F)(F)F)c1]

(CH$_2$Cl$_2$/MeOH 20:1)
Yield: 54%
$^1$H NMR CDCl$_3$) δ 8.83 (m, 1H), 8.20 (d, 1H), 7.85 (s, 1H), 7.75 (d, 1H), 7.63 (m, 1H), 7.55 (m, 3H), 7.24 (m, 1H), 5.37 (m, 1H), 2.65 (s, 3H), 1.70 (d, 3H).

Example 17

N-(4-Chloro-3-(trifluoromethyl)benzyl)-2-methyl-1,8-naphthyridine-3-carboxamide

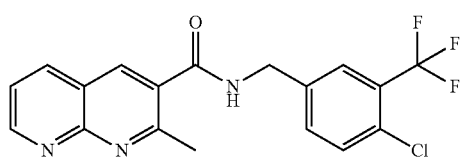 [SMILES: Cc1nc2ncccc2cc1C(=O)NCc1ccc(Cl)c(C(F)(F)F)c1]

(CH$_2$Cl$_2$/MeOH 40:1)
Yield: 45%
$^1$H NMR (CD$_3$OD) δ 9.06 (m, 1H), 8.47 (d, 1H), 8.44 (s, 1H), 7.85 (s, 1H), 7.65 (m, 3H), 4.66 (s, 2H), 2.80 (s, 3H).

Example 18

N-(3,5-bis(Trifluoromethyl)benzyl)-2-methyl-1,8-naphthyridine-3-carboxamide

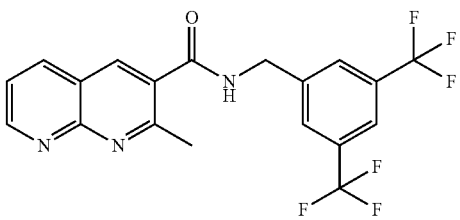 [SMILES: Cc1nc2ncccc2cc1C(=O)NCc1cc(C(F)(F)F)cc(C(F)(F)F)c1]

(CH$_2$Cl$_2$/MeOH 40:1)
Yield: 81%
$^1$H NMR (CDCl$_3$) δ 8.99 (m, 1H), 8.00 (m, 1H), 7.99 (s, 1H), 7.96 (s, 2H), 7.85 (s, 1H), 7.71 (m, 1H), 7.42 (m, 1H), 4.86 (d, 2H), 2.80 (s, 3H).

Example 19

N-(Biphenyl-4-ylmethyl)-2-methyl-1,8-naphthyridine-3-carboxamide

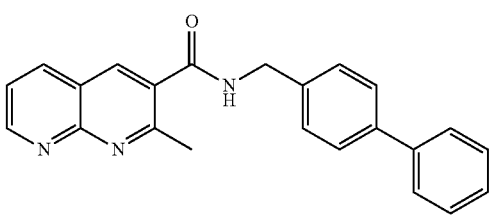 [SMILES: Cc1nc2ncccc2cc1C(=O)NCc1ccc(-c2ccccc2)cc1]

(CH$_2$Cl$_2$/MeOH 40:1)
Yield: 76%
$^1$H NMR (CD$_3$OD) δ 9.05 (m, 1H), 8.44 (m, 1H), 8.43 (s, 1H), 7.63 (m, 5H), 7.52 (m, 2H), 7.45 (m, 2H), 7.32 (m, 1H), 4.66 (s, 2H), 2.83 (s, 3H).

Example 20

N-(Biphenyl-3-ylmethyl)-2-methyl-1,8-naphthyridine-3-carboxamide

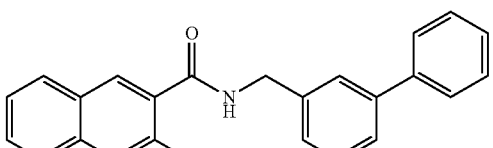

(CH$_2$Cl$_2$/MeOH 20:1)
Yield: 61%
$^1$H NMR (CDCl$_3$) δ 9.07 (m, 1H), 8.14 (s, 1H), 8.11 (m, 1H), 7.60 (m, 4H), 7.36-7.47 (m, 6H), 6.47 (m, 1H), 4.79 (d, 2H), 2.93 (s, 3H).

Example 21

(S)-2-Methyl-N-(1-(3-(trifluoromethyl)phenyl)ethyl)-1,8-naphthyridine-3-carboxamide

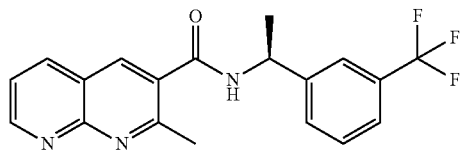 [SMILES: Cc1nc2ncccc2cc1C(=O)N[C@@H](C)c1cccc(C(F)(F)F)c1]

(CH$_2$Cl$_2$/MeOH 30:1)

Yield: 63%

$^1$H NMR (CDCl$_3$) δ 8.98 (m, 1H), 7.85 (m, 1H), 7.82 (s, 1H), 7.75 (m, 2H), 7.44-7.62 (m, 3H), 7.36 (m, 1H), 5.44 (m, 1H), 2.76 (s, 3H), 1.73 (d, 3H).

Example 22

N-(3-Chlorobenzyl)-2-(trifluoromethyl)-1,8-naphthyridine-3-carboxamide

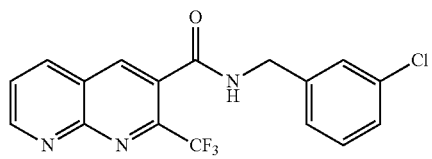

Precipitated from EtOAc

Yield: 52%

$^1$H NMR (CD$_3$OD) δ 9.24 (m, 1H), 8.75 (s, 1H), 8.65 (m, 1H), 7.85 (m, 1H), 7.47 (bs, 1H), 7.40-7.25 (m, 3H), 4.62 (s, 2H).

Example 23

(R)-2-Methyl-N-(1-(3-(trifluoromethyl)phenyl)ethyl)-1,8-naphthyridine-3-carboxamide

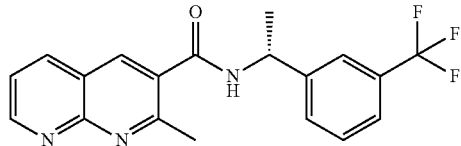

(CH$_2$Cl$_2$/MeOH 30:1)

Yield: 64%

$^1$H NMR (CDCl$_3$) δ 8.85 (m, 1H), 8.22 (d, 1H), 7.85 (s, 1H), 7.74 (m, 1H); 7.51 (m, 3H), 7.25 (m 1H), 5.38 (m, 1H), 2.66 (s, 3H), 1.72 (d, 3H).

Example 24

N-(3-Methoxybenzyl)-2-methyl-1,8-naphthyridine-3-carboxamide

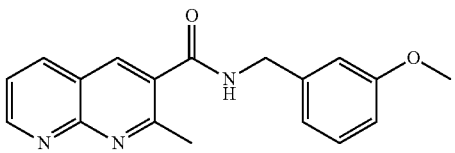 [SMILES: COc1cccc(CNC(=O)c2cc3cccnc3nc2C)c1]

(CH$_2$Cl$_2$/MeOH 30:1)

Yield: 35%

$^1$H NMR (CD$_3$OD) δ 9.02 (m, 1H), 8.41 (m, 1H), 8.38 (s, 1H), 7.59 (m, 1H), 7.27 (m, 1H), 6.98 (m, 2H), 6.94 (m, 1H), 4.57 (s, 2H), 3.79 (s, 3H).

Example 25

N-(3-Bromobenzyl)-2-methyl-1,8-naphthyridine-3-carboxamide

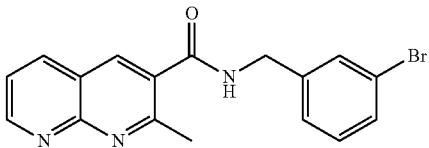 [SMILES: Cc1nc2ncccc2cc1C(=O)NCc1cccc(Br)c1]

(CH$_2$Cl$_2$/MeOH 95:5)

Yield: 26%

$^1$H NMR (CDCl$_3$) δ 8.98 (m, 1H), 8.00 (m, 1H), 7.99 (s, 1H), 7.60 (bs, 1H), 7.48-7.36 (m, 3H), 7.27 (m, 1H), 7.08 (t, 1H), 4.69 (d, 2H), 2.84 (s, 3H).

Example 26

N-(4-Bromobenzyl)-2-methyl-1,8-naphthyridine-3-carboxamide

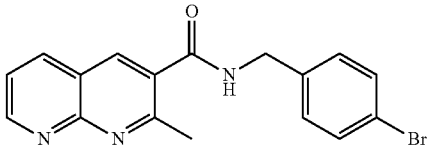 [SMILES: Cc1nc2ncccc2cc1C(=O)NCc1ccc(Br)cc1]

(CH$_2$Cl$_2$/MeOH 20:1)

Yield: 22%

$^1$H NMR (CD$_3$OD) δ 9.06 (m, 1H), 8.46 (m, 1H), 8.43 (s, 1H), 7.64 (m, 1H), 7.55 (m, 2H), 7.38 (m, 2H), 4.59 (s, 2H), 2.81 (s, 3H).

Example 27

N-(4-fluorobenzyl)-2-(trifluoromethyl)-1,8-naphthyridine-3-carboxamide

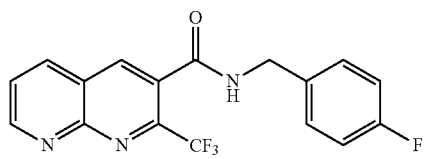 [SMILES: O=C(NCc1ccc(F)cc1)c1cc2cccnc2nc1C(F)(F)F]

(CH$_2$Cl$_2$/MeOH 97:3)
Yield: 71%
$^1$H NMR (CD$_3$OD) δ 9.24 (m, 1H), 8.74 (s, 1H), 8.64 (m, 1H), 7.85 (m, 1H), 7.86-7.43 (m, 2H), 7.13-7.07 (m, 2H), 4.60 (s, 2H).

Example 28

(S)—N-(1-(4-bromophenyl)ethyl)-2-methyl-1,8-naphthyridine-3-carboxamide

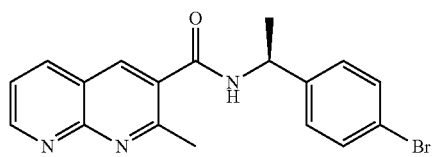 [SMILES: Cc1nc2ncccc2cc1C(=O)N[C@@H](C)c1ccc(Br)cc1]

Yield: 77%
Crystallized from EtOAc, Pet ether
$^1$H NMR (CD$_3$OD) δ 9.06 (m, 1H), 8.47 (m, 1H), 8.41 (s, 1H), 7.65 (m, 1H), 7.54 (d, 1H), 7.39 (d, 1H), 5.24 (m, 1H), 2.76 (s, 3H), 1.57 (d, 2H).

Example 29

(R)—N-(1-(4-bromophenyl)ethyl)-2-methyl-1,8-naphthyridine-3-carboxamide

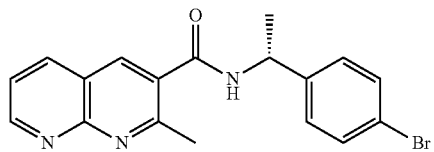 [SMILES: Cc1nc2ncccc2cc1C(=O)N[C@H](C)c1ccc(Br)cc1]

(CH$_2$Cl$_2$/MeOH 20:1)
Yield: 68%
$^1$H NMR (CDCl$_3$) δ 9.02 (m, 1H), 7.96 (m, 1H), 7.88 (m, 1H), 7.53 (m, 2H), 7.40 (m, 3H), 6.91 (m, 1H), 5.34 (m, 1H), 2.79 (m, 1H), 1.68 (d, 3H).

Example 30

2-Methyl-N-(4-(methylthio)benzyl)-1,8-naphthyridine-3-carboxamide

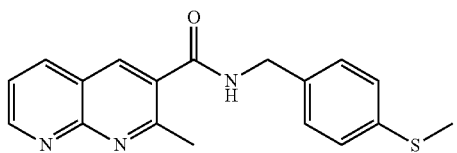 [SMILES: CSc1ccc(CNC(=O)c2cc3cccnc3nc2C)cc1]

(CH$_2$Cl$_2$/MeOH 30:1)
Yield: 40%
$^1$H NMR (CDCl$_3$) δ 9.00 (m, 1H), 8.05 (m, 2H), 7.42 (m, 1H), 7.34 (m, 2H), 7.26 (m, 2H), 4.65 (d, 2H), 2.86 (s, 3H), 2.50 (s, 3H).

Example 31

N-(1-(4-tert-butylphenyl)ethyl)-2-methyl-1,8-naphthyridine-3-carboxamide

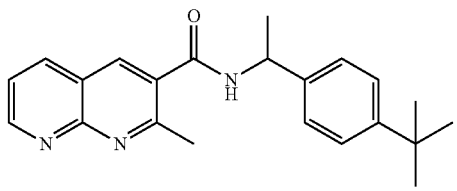 [SMILES: Cc1nc2ncccc2cc1C(=O)NC(C)c1ccc(C(C)(C)C)cc1]

(CH$_2$Cl$_2$/MeOH 96:4)
Yield: 83%
$^1$H NMR (CDCl$_3$) δ 9.04 (m, 1H), 8.09 (m, 1H), 8.07 (s, 1H), 7.43 (m, 5H), 6.59 (d, 1H), 5.38 (m, 1H), 2.86 (s, 3H), 1.68 (d, 3H), 1.34 (s, 9H).

Example 32

(S)—N-(1-(4-tert-butylphenyl)ethyl)-2-methyl-1,8-naphthyridine-3-carboxamide

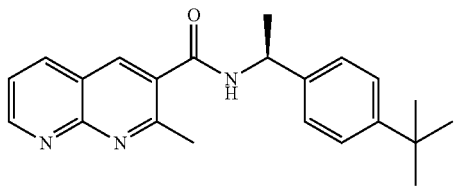 [SMILES: Cc1nc2ncccc2cc1C(=O)N[C@@H](C)c1ccc(C(C)(C)C)cc1]

(CH$_2$Cl$_2$/MeOH 96:4)
Yield: 92%
$^1$H NMR (CDCl$_3$) δ 9.04 (m, 1H), 8.09 (m, 1H), 8.07 (s, 1H), 7.43 (m, 5H), 6.59 (d, 1H), 5.38 (m, 1H), 2.86 (s, 3H), 1.68 (d, 3H), 1.34 (s, 9H).

Example 33

(R)—N-(1-(4-tert-butylphenyl)-2-hydroxyethyl)-2-methyl-1,8-naphthyridine-3-carboxamide

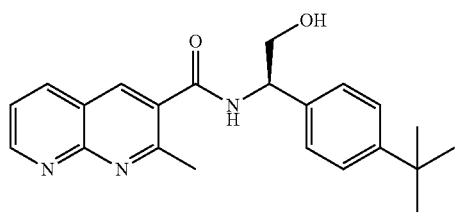 [SMILES: Cc1nc2ncccc2cc1C(=O)N[C@@H](CO)c1ccc(C(C)(C)C)cc1]

(CH$_2$Cl$_2$/MeOH 30:1)
Yield: 53%
$^1$H NMR (CDCl$_3$) δ 8.97 (m, 1H), 8.44 (d, 1H), 7.61 (m, 1H), 7.52 (m, 2H), 7.48 (m, 2H), 7.45 (s, 1H), 7.32 (m, 1H), 5.36 (m, 1H), 4.12 (m, 2H), 2.74 (s, 3H), 1.35 (s, 9H).

Example 34

N-(4-isopropylbenzyl)-2-methyl-1,8-naphthyridine-3-carboxamide

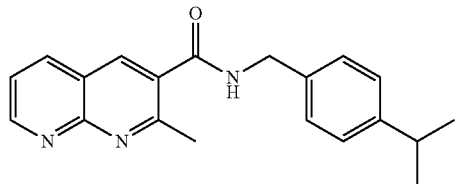 [SMILES: Cc1nc2ncccc2cc1C(=O)NCc1ccc(C(C)C)cc1]

(CH$_2$Cl$_2$/MeOH 95:5)
Yield: 30%
$^1$H NMR (CDCl$_3$) δ 9.00 (m, 1H), 8.09 (s, 1H), 8.07 (m, 1H), 7.43 (m, 1H), 7.36 (d, 2H), 7.26 (d, 2H), 6.70 (t, 1H), 4.66 (d, 2H), 2.93 (m, 1H), 2.87 (s, 3H), 1.26 (d, 6H).

Methyl 3-((2-methyl-1,8-naphthyridine-3-carboxamido)methyl)benzoate

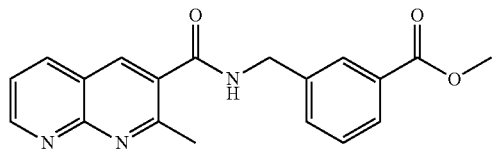 [SMILES: COC(=O)c1cccc(CNC(=O)c2cc3cccnc3nc2C)c1]

(CH$_2$Cl$_2$/MeOH 20:1)
Yield: 61%
$^1$H NMR (CDCl$_3$) δ 8.98 (m, 1H), 8.06 (m, 2H), 8.01 (m, 1H), 7.98 (m, 1H); 7.65 (m, 1H), 7.47 (m 1H), 7.41 (m, 1H), 7.16 (m, 1H), 4.76 (d, 2H), 3.92 (s, 3H), 2.86 (s, 3H).

Example 35

2-Methyl-N-(3-(phenylcarbamoyl)benzyl)-1,8-naphthyridine-3-carboxamide

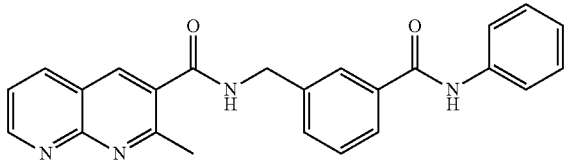 [SMILES: Cc1nc2ncccc2cc1C(=O)NCc1cccc(C(=O)Nc2ccccc2)c1]

62 mg (1.48 mmol) LiOH was added to a solution of 330 mg (0.98 mmol) methyl 3-((2-methyl-1,8-naphthyridine-3-carboxamido)methyl)benzoate in 10 ml THF/water (1:1). The solution was stirred at r.t. for 6 h and then diluted with water. THF was removed under reduced pressure and the aqueous solution was washed with EtOAc. The aqueous phases was acidified with 1M HCl and extracted with EtOAc and CH$_2$Cl$_2$. The combined organic phases were dried (MgSO$_4$) and concentrated to give 80 mg of a crude residue. The crude product was dissolved in 2.5 ml CH$_2$Cl$_2$ and 42 μl (0.49 mmol) oxalylchloride was added followed by a drop of DMF. The mixture was stirred at r.t. for 3 h and then concentrated to dryness under reduced pressure. 2.5 ml CH$_2$Cl$_2$ was added to the crude acid chloride. 174 μl (1.25 mmol) Et$_3$N followed by 45 μl (0.49 mmol) aniline. The resulting mixture was stirred over night at r.t. The reaction mixture was diluted with CH$_2$Cl$_2$ and washed with water, NaHCO$_3$ (sat) and brine, dried (MgSO$_4$) and concentrated. Flashchromatography (SiO$_2$, CH$_2$Cl$_2$/MeOH 20:1) gave 50 mg (13%, 2 steps) of the title compound as an off-white solid.

$^1$H NMR (400 MHz, DMSO-d6) δ 10.30 (s, 1H), 9.28 (m, 1H), 9.08 (m, 1H), 8.50 (m, 1H), 8.32 (m, 1H), 7.97 (s, 1H), 7.88 (m, 1H), 7.78 (m, 2H), 7.63 (m, 1H), 7.55 (m, 1H), 7.35 (m, 2H), 7.10 (m, 1H9, 4.62 (d, 2H), 2.75 (s, 3H).

Scheme 10

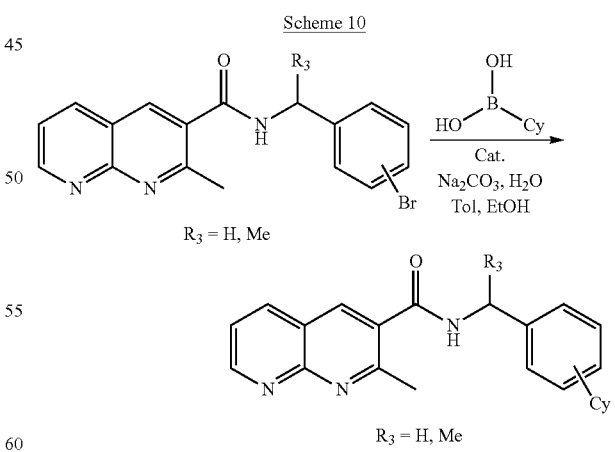

General Procedure A for the Coupling of Aryl Bromides with Boronic Acids (Scheme 10)

N$_2$ was bubbled through a solution of N-(4-bromobenzyl)-2-methyl-1,8-naphthyridine-3-carboxamide (1.0 eq.), the corresponding boronic acid (1.5 eq.) and Na$_2$CO$_3$ (3.0 eq.) in a mixture of toluene/EtOH/water 1:1:0.5. Pd(II)dppfCl$_2$ (0.03 eq.) were added and the reaction mixture was heated at 90° C. for 12 h. The reaction mixture was cooled to r.t., diluted with EtOAc and washed with water, NaHCO$_3$ (sat) and brine. The organic phase was dried (MgSO$_4$) and concentrated. Purification was done by flash chromatography The following substances were synthesized following the general procedure A for the coupling of aryl bromides with the corresponding boronic acid. The solvent system used for the purification, the yield and analytical data is given for each compound.

Example 36

2-Methyl-N-(4-(pyridin-4-yl)benzyl)-1,8-naphthyridine-3-carboxamide

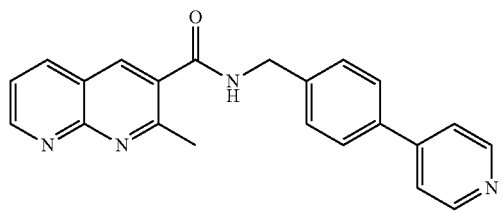 [SMILES: Cc1nc2ncccc2cc1C(=O)NCc1ccc(-c2ccncc2)cc1]

(CH$_2$Cl$_2$/MeOH 10:1)

Yield: 29%

$^1$H NMR (CDCl$_3$) δ 8.85 (m, 1H), 8.58 (m, 2H), 7.93 (s, 1H), 7.88 (m, 1H), 7.82 (m, 1H), 7.61 (d, 2H), 7.53 (d, 2H), 7.46 (m, 2H), 7.31 (m, 1H), 4.74 (d, 2H), 2.78 (s, 1H).

Example 37

2-Methyl-N-(4-(pyridin-3-yl)benzyl)-1,8-naphthyridine-3-carboxamide

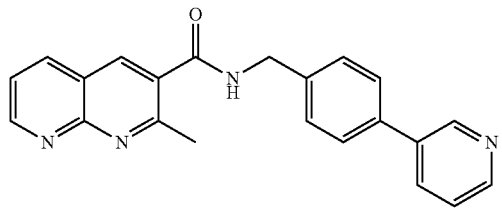 [SMILES: Cc1nc2ncccc2cc1C(=O)NCc1ccc(-c2cccnc2)cc1]

(CH$_2$Cl$_2$/MeOH 10:1)

Yield: 26%

$^1$H NMR (CDCl$_3$) δ 8.85 (m, 1H), 8.62 (m, 1H), 8.42 (s, 1H), 8.00 (m, 1H), 7.98 (s, 1H), 7.90 (m, 1H), 7.82 (m, 2H), 7.30 (m, 2H), 4.73 (d, 2H), 2.79 (2, 3H).

Example 38

N-((4'-Methoxybiphenyl-4-yl)methyl)-2-methyl-1,8-naphthyridine-3-carboxamide

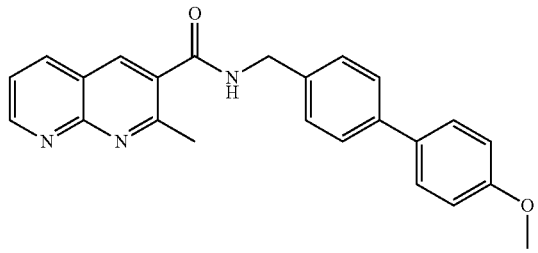 [SMILES: COc1ccc(-c2ccc(CNC(=O)c3cc4cccnc4nc3C)cc2)cc1]

(CH$_2$Cl$_2$/MeOH 20:1)

Yield: 10%

$^1$H NMR (CDCl$_3$) δ 9.02 (m, 1H), 8.10 (s, 1H), 8.06 (m, 1H), 7.53-7.58 (m, 4H), 7.38-7.47 (m, 3H), 6.99 (m, 2H), 6.79 (m, 1H), 4.72 (d, 2H), 3.86 (s, 3H), 2.89 (s, 3H).

General Procedure B for the Coupling of Aryl Bromides with Boronic Acids (See Scheme 10 Above).

In a screw cap pressure tube, N-(3-bromobenzyl)-2-methyl-1,8-naphthyridine-3-carboxamide or N-(4-bromobenzyl)-2-methyl-1,8-naphthyridine-3-carboxamide (1.0 eq.) and the corresponding boronic acid (1.4 eq.) were suspended in a mixture of toluene:EtOH (4:1). Na$_2$CO$_3$ (sat) (0.2 ml/mmol aryl bromide) was added. N$_2$ was bubbled through the mixture for 5 minutes. Pd(PPh$_3$)$_4$ was added. The tube was sealed and the mixture heated to reflux for 20 h. The mixture was allowed to cool. H$_2$O was added and the product extracted with EtOAc. The combined organic extracts were dried (MgSO$_4$), filtered and concentrated. The crude product was purified by flash chromatography.

The following substances were synthesized following the general procedure B for the coupling of aryl bromides with the corresponding boronic acid. The solvent system used for the purification, the yield and analytical data is given for each compound.

Example 39

2-Methyl-N-((2'-(trifluoromethyl)biphenyl-3-yl)methyl)-1,8-naphthyridine-3-carboxamide

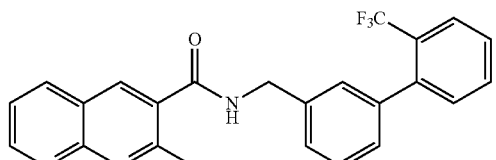

(CH$_2$Cl$_2$/MeOH 95:5)

Yield: 82%

$^1$H NMR (CDCl$_3$) δ 9.04 (m, 1H), 8.11 (s, 1H), 8.10 (m, 1H), 7.77 (bd, 1H), 7.61-7.29 (m, 7H), 6.53 (bt, 1H), 4.76 (d, 2H), 2.90 (s, 3H).

Example 40

2-Methyl-N-(3-(pyridin-3-yl)benzyl)-1,8-naphthyridine-3-carboxamide

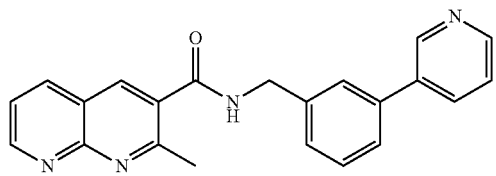 [SMILES: Cc1nc2ncccc2cc1C(=O)NCc1cccc(-c2cccnc2)c1]

(CH$_2$Cl$_2$/MeOH 95:5→90:10)
Yield: 58%
$^1$H NMR (CDCl$_3$) δ 9.05 (m, 1H), 8.78 (d, 1H), 8.58 (m, 1H), 8.17 (bs, 1H), 8.10 (m, 1H), 7.91-7.87 (m, 1H), 7.62 (s, 1H), 7.56-7.48 (m, 3H), 7.45 (m, 1H), 7.38 (m, 1H), 6.85 (bt, 1H), 4.80 (d, 2H), 2.98 (s, 3H).

Example 41

2-Methyl-N-(3-(pyridin-4-yl)benzyl)-1,8-naphthyridine-3-carboxamide

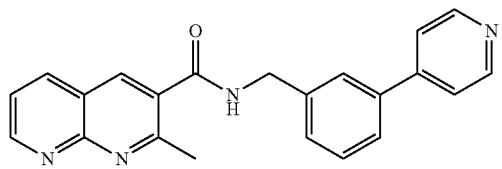 [SMILES: Cc1nc2ncccc2cc1C(=O)NCc1cccc(-c2ccncc2)c1]

(CH$_2$Cl$_2$/MeOH 96:4→90:10)
Yield: 61%
$^1$H NMR (CDCl$_3$) δ 9.08 (m, 1H), 8.685-8.66 (m, 2H), 8.14 (s, 1H), 8.11 (m, 1H), 7.70 (bs, 1H), 7.62 (m, 1H), 7.55-7.51 (m, 4H), 7.46 (m, 1H), 6.62 (bt, 1H), 4.80 (d, J=6.0 Hz, 2H), 2.91 (s, 3H).

Example 42

N-((4'-Methoxybiphenyl-3-yl)methyl)-2-methyl-1,8-naphthyridine-3-carboxamide

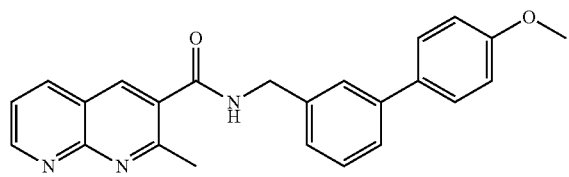 [SMILES: COc1ccc(-c2cccc(CNC(=O)c3cc4cccnc4nc3C)c2)cc1]

(CH$_2$Cl$_2$/MeOH 95:5)
Yield: 83%
$^1$H NMR (CDCl$_3$) δ 9.02 (m, 1H), 8.10 (s, 1H), 8.07 (m, 1H), 7.59 (bs, 1H), 7.55-7.51 (m, 3H), 7.47-7.35 (m, 3H), 6.99 (d, 2H), 6.65 (bt, 1H), 4.76 (d, 2H), 3.86 (s, 3h), 2.90 (s, 3H).

Example 43

2-Methyl-N-((2'-(trifluoromethyl)biphenyl-4-yl)methyl)-1,8-naphthyridine-3-carboxamide

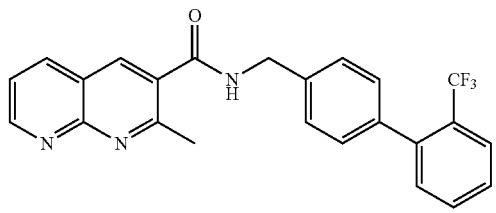 [SMILES: Cc1nc2ncccc2cc1C(=O)NCc1ccc(-c2ccccc2C(F)(F)F)cc1]

(CH$_2$Cl$_2$/MeOH 95:5)
Yield: 80%
$^1$H NMR (CDCl$_3$) δ 8.97 (m, 1H), 8.07 (s, 1H), 8.06 (m, 1H), 7.77 (bd, 1H), 7.61-7.45 (m, 4H), 7.43 (m, 1H), 7.40-7.31 (m, 3H), 6.84 (m, 1H), 4.78 (d, 2H), 2.89 (s, 3H).

Example 44

(S)-2-Methyl-N-(1-(4-(pyridin-3-yl)phenyl)ethyl)-1,8-naphthyridine-3-carboxamide

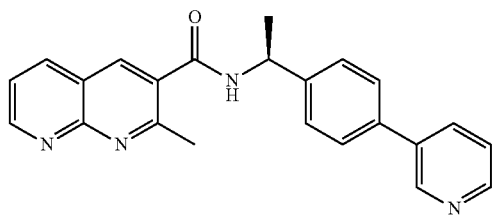 [SMILES: Cc1nc2ncccc2cc1C(=O)N[C@@H](C)c1ccc(-c2cccnc2)cc1]

(CH$_2$Cl$_2$/MeOH 95:5)
Yield: 36%
$^1$H NMR (CD$_3$OD) δ 9.07 (m, 1H), 8.83 (d, 1H), 8.56-8.40 (m, 3H), 8.12 (m, 1H), 7.80-7.50 (m, 6H), 5.34 (m, 1H), 1.79 (s, 3H), 1.64 (d, 2H).

Example 45

(R)-2-Methyl-N-(1-(4-(pyridin-3-yl)phenyl)ethyl)-1,8-naphthyridine-3-carboxamide

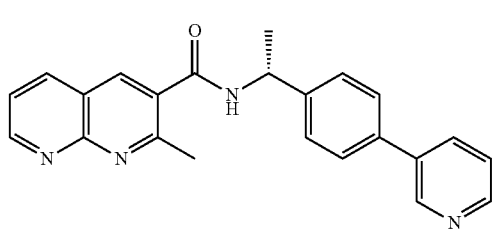 [SMILES: Cc1nc2ncccc2cc1C(=O)N[C@H](C)c1ccc(-c2cccnc2)cc1]

(CH$_2$Cl$_2$/MeOH 20:1)
Yield: 64%
$^1$H NMR (CDCl$_3$) δ 8.76 (bs, 1H), 8.58 (bs, m), 8.52 (d, 1H), 8.36 (bs, 1H), 7.75 (m, 1H), 7.67 (m, 2H), 7.54 (d, 2H), 7.42 (d, 2H), 7.22 (m, 1H), 7.15 (m, 1H), 5.30 (m, 1H), 2.64 (s, 3H), 1.62 (d, 3H).

Example 46

(S)—N-(1-(4-Cyclohexenylphenyl)ethyl)-2-methyl-1,8-naphthyridine-3-carboxamide

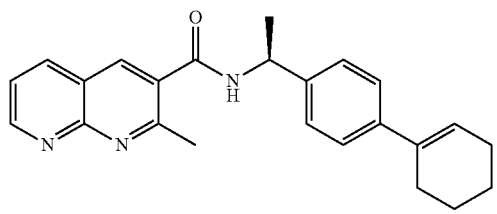 [SMILES: Cc1nc2ncccc2cc1C(=O)N[C@@H](C)c1ccc(C2=CCCCC2)cc1]

(CH$_2$Cl$_2$/MeOH 96:4)
Yield: 94%.
$^1$H NMR (CD$_3$OD) δ 9.06 (m, 1H), 8.47 (dd, 1H), 8.39 (s, 1H), 8.09 (s, 1H), 7.64 (dd, 1H), 7.40 (d, 2H), 7.39 (d, 2H), 6.13 (m, 1H), 5.26 (m, 1H), 2.76 (s, 3H), 2.42 (m, 2H), 2.22 (m, 2H), 1.81 (m, 2H), 1.69 (m, 2H), 1.58 (d, 3H).

Example 47

N-(4-(3,6-Dihydro-2H-pyran-4-yl)-3-(trifluoromethyl)benzyl)-2-methyl-1,8-naphthyridine-3-carboxamide

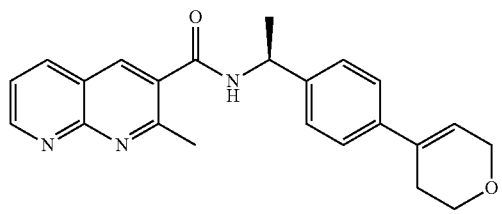 [SMILES: Cc1nc2ncccc2cc1C(=O)N[C@@H](C)c1ccc(C2=CCOCC2)cc1]

In a screw cap pressure tube, (S)—N-(1-(4-bromophenyl)ethyl)-2-methyl-1,8-naphthyridine-3-carboxamide (50 mg, 0.14 mmol) and 2-(3,6-dihydro-2H-pyran-4-yl)-4,4,5,5-tetramethyl-1,3,2-dioxaborolane (28.4 mg, 0.14 mmol) were dissolved in dimethoxyethane. Na$_2$CO$_3$ (2 M aq. sln, 0.5 ml) and LiCl (17.2 mg, 0.41 mmol) were added. N$_2$ was bubbled through the mixture for 5 minutes. Pd(PPh$_3$)$_4$ (3.1 mg, 0.003 mmol) was added. The tube was sealed and the mixture heated to reflux for 20 h. The mixture was allowed to cool. H$_2$O was added and the product extracted with EtOAc. The combined organic extracts were dried (MgSO$_4$), filtered and concentrated. The crude product was purified by flash chromatography; Pet. Ether, EtOAc (4:1) affording 29 mg (55%) of the title compound.

$^1$H NMR (CDCl$_3$) δ 9.11 (dd, 1H), 8.12 (m, 2H), 7.47 (m, 5H), 6.27 (d, 1H), 6.16 (m, 1H), 5.40 (m, 1H), 4.34 (dd, 2H), 3.95 (t, 2H), 2.88 (s, 3H), 2.53 (m, 2H), 1.68 (d, 3H).

Example 48

(S)-2-Methyl-N-(1-(4-(piperidin-1-yl)phenyl)ethyl)-1,8-naphthyridine-3-carboxamide

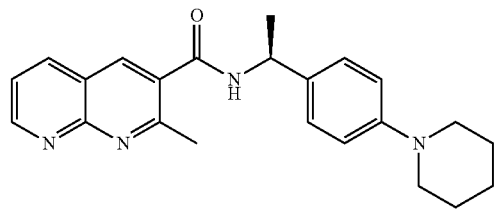 [SMILES: Cc1nc2ncccc2cc1C(=O)N[C@@H](C)c1ccc(N2CCCCC2)cc1]

A mixture of 174 mg (0.47 mmol) (S)—N-(1-(4-bromophenyl)ethyl)-2-methyl-1,8-naphthyridine-3-carboxamide, 11 mg (0.012 mmol) Pd$_2$dba$_3$ and 23 mg (0.048 mmol) XPhos in 3.5 ml DME was stirred an degassed at room temperature for 5 min in a thick walled sealable tube. 250 mg (1.18 mmol) K$_3$PO$_4$ and 52 µl (0.52 mmol) piperidine were added. The tube was sealed and heated at 80° C. over night. The reaction mixture was cooled to room temperature and filtered through a pad of silica with CH$_2$Cl$_2$/MeOH 9:1. The filtrate was concentrated and purified with flash chromatography (SiO$_2$, CH$_2$Cl$_2$/MeOH 30:1) to give 54 mg (31%) of the title compound.

$^1$H NMR (CDCl$_3$) δ 8.85 (m, 1H), 7.79 (m, 1H), 7.70 (s, 1H), 7.34 (d, 2H), 7.26 (m, 1H), 6.91 (d, 2H), 5.26 (m, 1H), 3.14, (m, 4H), 2.70 (s, 3H), 1.64 (d, 3H), 1.55 (m, 2H).

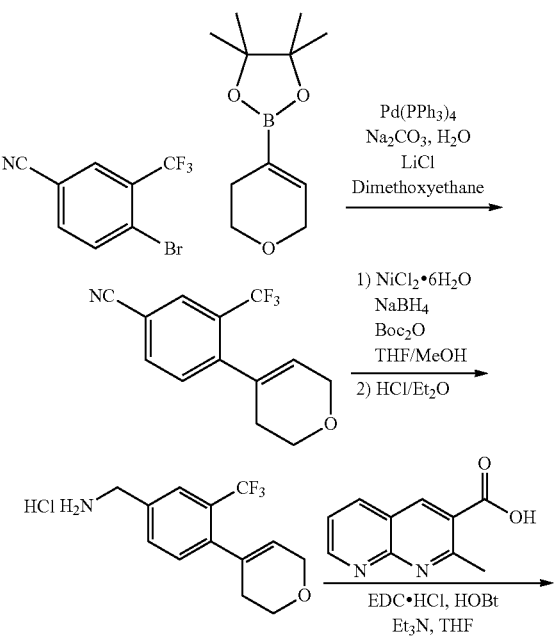

Scheme 11

-continued

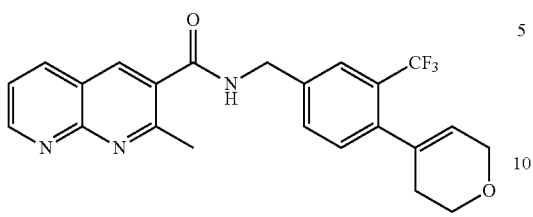

4-(3,6-Dihydro-2H-pyran-4-yl)-3-(trifluoromethyl)benzonitrile

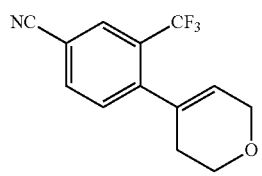 [SMILES: N#Cc1ccc(C2=CCOCC2)c(C(F)(F)F)c1]

In a screw cap pressure tube, 4-fluoro-3-(trifluoromethyl)-benzonitrile (425 mg, 1.70 mmol) and 2-(3,6-dihydro-2H-pyran-4-yl)-4,4,5,5-tetramethyl-1,3,2-dioxaborolane (357.1 mg, 1.70 mmol) were dissolved in dimethoxyethane. $Na_2CO_3$ (2 M aq. sln, 2.5 ml) and LiCl (216.4 mg, 5.1 mmol) were added. $N_2$ was bubbled through the mixture for 5 minutes. Pd(PPh$_3$)$_4$ (39.3 mg, 0.03 mmol) was added. The tube was sealed and the mixture heated to reflux for 20 h. The mixture was allowed to cool. $H_2O$ was added and the product extracted with EtOAc. The combined organic extracts were dried (MgSO$_4$), filtered and concentrated. The crude product was purified by flash chromatography; Pet. Ether, EtOAc (4:1) affording 254 mg (59%) the title compound.

$^1$H NMR (CDCl$_3$) δ 7.97 (d, 1H), 7.80 (dd, 1H), 7.40 (d, 1H), 5.72 (m, 1H), 4.29 (dd, 2H), 3.92 (t, 2H), 2.36 (m, 2H).

(4-(3,6-Dihydro-2H-pyran-4-yl)-3-(trifluoromethyl)phenyl)methanamine hydrochloride

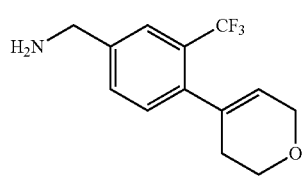 [SMILES: NCc1ccc(C2=CCOCC2)c(C(F)(F)F)c1]

This compound was synthesized in 94% yield following the General procedure F for the reduction of benzonitriles to benzylamines, see below.

$^1$H NMR (CD$_3$OD) δ 7.84 (d, 1H), 7.69 (dd, 1H), 7.42 (d, 1H), 5.67 (m, 1H), 4.25 (dd, 2H), 4.21 (s, 2H), 3.91 (t, 2H), 2.35 (m, 2H).

Example 49

N-(4-(3,6-Dihydro-2H-pyran-4-yl)-3-(trifluoromethyl)benzyl)-2-methyl-1,8-naphthyridine-3-carboxamide

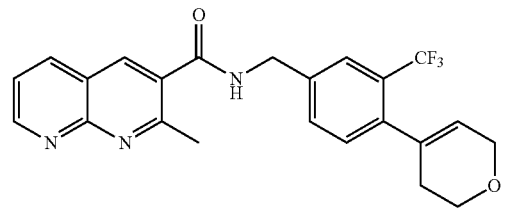 [SMILES: Cc1nc2ncccc2cc1C(=O)NCc1ccc(C2=CCOCC2)c(C(F)(F)F)c1]

This substance was synthesized following the general amide coupling procedure. Purification was done by flash chromatography (CH$_2$Cl$_2$/MeOH 95:5→94:6) to give the title substance in 55% yield.

$^1$H NMR (CDCl$_3$) δ 9.00 (dd, 1H), 8.02 (m, 2H), 7.72 (d, 1H), 6.61 (dd, 1H), 7.42 (dd, 1H), 7.28 (d, 1H), 7.16 (t, 1H), 5.66 (m, 1H), 4.76 (d, 2H), 4.28 (dd, 2H), 3.92 (t, 2H), 2.85 (s, 3H), 2.36 (m, 2H).

Scheme 12

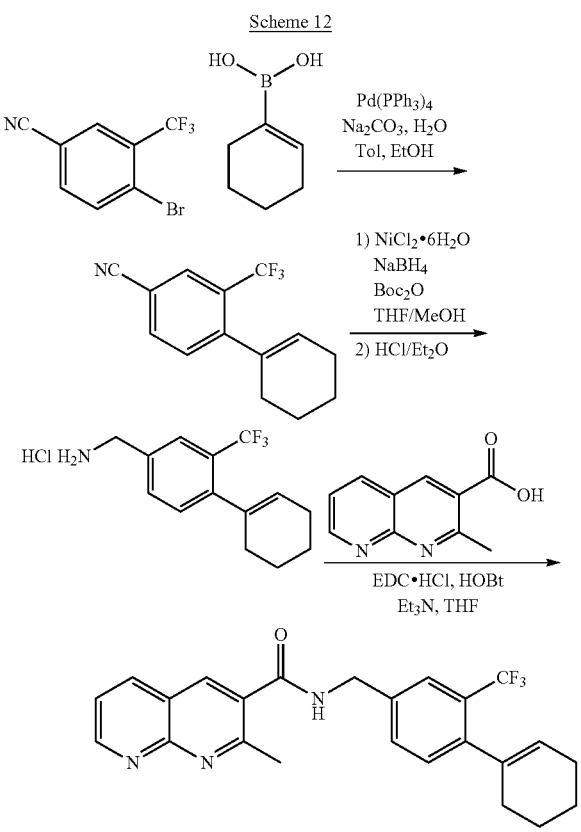

4-Cyclohexenyl-3-(trifluoromethyl)benzonitrile

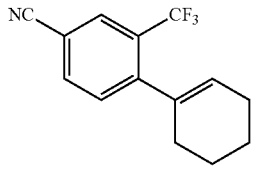 [SMILES: N#Cc1ccc(C2=CCCCC2)c(C(F)(F)F)c1]

This compound was synthesised following the General procedure B for the coupling of aryl bromides with boronic acids. Purification was done by flash chromatography (Pet. Ether, EtOAc 95:5→90:10) to give the title compound in 80% yield.

$^1$H NMR (CDCl$_3$) δ 7.93 (d, 1H), 7.76 (dd, 1H), 7.36 (d, 1H), 5.63 (m, 1H), 2.18 (m, 4H), 1.78 (m, 2H), 1.70 (m, 2H).

(4-Cyclohexenyl-3-(trifluoromethyl)phenyl)methanamine hydrochloride

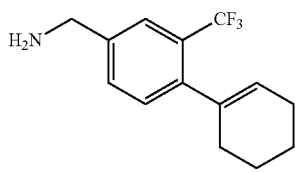 [SMILES: NCc1ccc(C2=CCCCC2)c(C(F)(F)F)c1]

This compound was synthesized following the General procedure F for the reduction of benzonitriles to benzylamines, see below. to give the title compound in quantitative yield.

$^1$H NMR (CD$_3$OD) δ 7.79 (d, 1H), 7.64 (dd, 1H), 7.35 (d, 1H), 5.57 (m, 1H), 4.19 (s, 2H), 2.18 (m, 4H), 1.75 (m, 4H).

Example 50

N-(4-Cyclohexenyl-3-(trifluoromethyl)benzyl)-2-methyl-1,8-naphthyridine-3-carboxamide

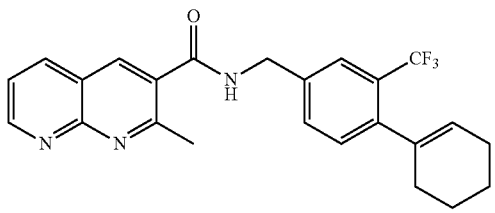 [SMILES: Cc1nc2ncccc2cc1C(=O)NCc1ccc(C2=CCCCC2)c(C(F)(F)F)c1]

This substance was synthesized following the General amide coupling procedure, see below. Purification was done by flash chromatography (CH$_2$Cl$_2$/MeOH 95:5→94:6) to give the title substance in 59% yield.

$^1$H NMR (CDCl$_3$) δ 9.01 (dd, 1H), 8.05 (m, 2H), 7.67 (d, 1H), 7.55 (dd, 1H), 7.43 (dd, 1H), 7.25 (d, 1H), 6.99 (t, 1H), 5.59 (m, 1H), 4.74 (d, 2H), 2.86 (s, 3H), 2.20 (m, 2H), 2.15 (m, 2H), 1.76 (m, 2H), 1.70 (m, 2H).

Scheme 13

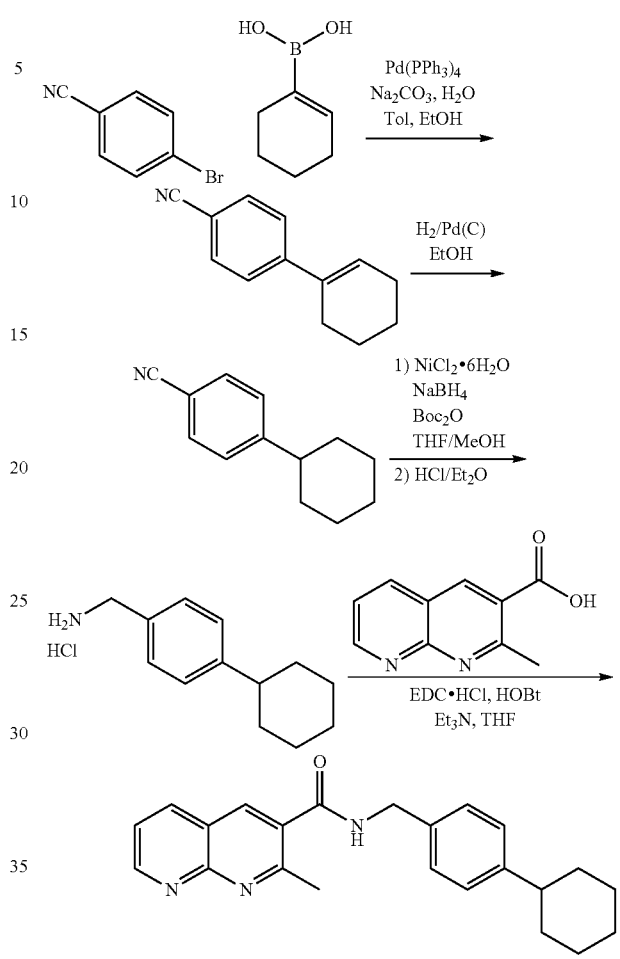

4-Cyclohexenylbenzonitrile

This compound was synthesized following the general procedure B for the coupling of aryl bromides with boronic acids. Purification was done by flash column chromatography; Pet. Ether, EtOAc (97:3→95:5) affording the title compound in 83% yield.

$^1$H NMR (CDCl$_3$) δ 7.59 (d, 2H), 7.46 (d, 2H), 6.27 (m, 1H), 2.39 (m, 2H), 2.26 (m, 2H), 1.80 (m, 2H), 1.69 (m, 2H).

4-Cyclohexylbenzonitrile

4-Cyclohexenylbenzonitrile (404 mg, 2.2 mmol) was dissolved in 15 ml EtOH and 40 mg 10% Pd/C was added. The reaction mixture was stirred under H$_2$ at 3.0 atm. over night at room temperature. The mixture was filtered through celite with EtOAc washing. The filtrate was concentrated and the crude product 350 mg (86%) was used directly in the next step.

$^1$H NMR (CDCl$_3$) δ 7.58 (d, 2H), 7.30 (d, 2H), 2.55 (m, 1H), 1.83 (m, 4H), 1.39 (m, 4H), 0.89 (m, 2H).

(4-Cyclohexylphenyl)methanamine hydrochloride

This compound was synthesized following the General procedure F for the reduction of benzonitriles to benzylamines, to give the title compound in quantitative yield.

$^1$H NMR (CD$_3$OD) δ 7.15 (m, 4H), 4.17 (s, 2H), 2.54 (m, 1H), 1.78 (m, 4H), 1.39 (m, 4H), 0.91 (m, 2H)

Example 51

N-(4-Cyclohexylbenzyl)-2-methyl-1,8-naphthyridine-3-carboxamide

This substance was synthesized following the general amide coupling procedure. Purification was done by flash chromatography (CH$_2$Cl$_2$/MeOH 95:5) to give the title substance in 44% yield.
$^1$H NMR (CDCl$_3$) δ 9.04 (dd, 1H), 8.14 (s, 1H), 8.12 (dd, 1H), 7.46 (dd, 1H), 7.34 (d, 2H), 7.24 (d, 2H), 6.54 (t, 1H), 4.67 (d, 2H), 2.90 (s, 3H), 1.85 (m, 4H), 1.35 (m, 6H).

Scheme 14

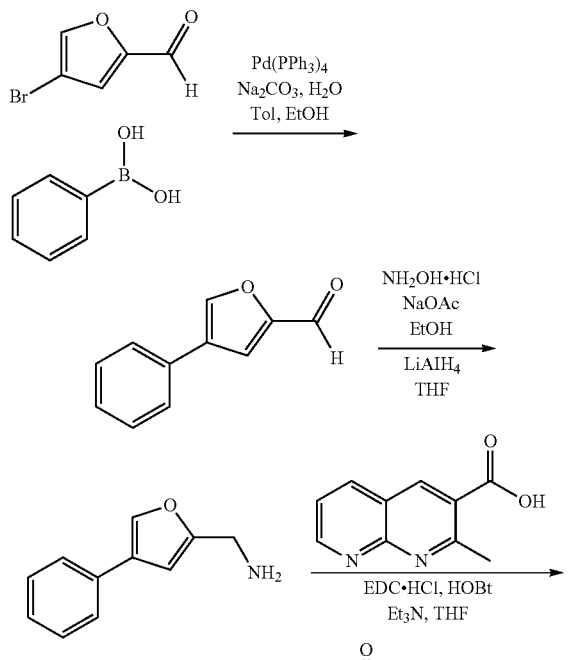

4-Phenylfuran-2-carbaldehyde

In a screw cap pressure tube, 4-bromofuran-2-carbaldehyde (504 mg, 2.88 mmol) and phenyl boronic acid (491.7, 4.03 mmol) were suspended in a mixture of toluene:EtOH (4:1). Na$_2$CO$_3$ (sat) (6.0 ml) was added. N$_2$ was bubbled through the mixture for 5 minutes. Pd(PPh$_3$)$_4$ (166.4 mg, 0.05 mmol) was added. The tube was sealed and the mixture heated to reflux for 4.0 h. The mixture was allowed to cool. H$_2$O was added and the product extracted with EtOAc. The combined organic extracts were dried (MgSO$_4$), filtered and concentrated. The crude product was purified by flash chromatography (Pet. Ether/EtOAc 90/10→85/15) to afford the title substance in 97% yield.

$^1$H NMR (CDCl$_3$) δ 9.72 (s, 1H), 7.97 (s, 1H), 7.55-7.50 (m, 3H), 7.47-7.41 (m, 2H), 7.39-7.33 (m, 1H).

(4-Phenylfuran-2-yl)methanamine

To a solution of 4-Phenylfuran-2-carbaldehyde (470 mg, 2.73 mmol) in EtOH hydroxylamine hydrochloride (227.6 mg, 3.28 mmol) and sodium acetate (268.6 mg, 3.28 mmol) were added. The mixture was heated to reflux and stirred for 30 minutes. The mixture was diluted with EtOAc, washed with H$_2$O, dried (MgSO$_4$), filtered and concentrated to dryness. The residue was then dissolved in anhydrous THF (20.0 ml) under N$_2$. LiAlH$_4$ (1.0 M in THF) (3.2 ml) was slowly added to the solution. The mixture was stirred at r.t. for 24 h. Then it was carefully poured into MeOH (50 ml), the solvent was removed and the residue purified by flash chromatography (CH$_2$Cl$_2$/MeOH 90/10→85/15) to afford the title substance in 21% yield.

$^1$H NMR (CD$_3$OD) δ 8.81 (d, 1H), 7.55-7.49 (m, 2H), 7.34 (t, 2H), 7.29-7.25 (m, 1H), 6.63 (d, 1H), 3.82 (s, 2H).

Example 52

2-Methyl-N-((4-phenylfuran-2-yl)methyl)-1,8-naphthyridine-3-carboxamide (4-Phenylfuran-2-yl)methanamine and 2-methyl-1,8-naphtiridine-3-carboxylic acid were coupled following the general amide coupling procedure (see above). The crude product was purified by flash chromatography (CH$_2$Cl$_2$/MeOH 95:5) to afford the title substance in 87% yield.

$^1$H NMR (CDCl$_3$) δ 9.08 (m, 1H), 6.70 (s, 1H), 8.11 (m, 1H), 7.70 (d, 1H), 7.52-7.34 (m, 5H), 7.32-7.25 (m, 1H), 6.70 (s, 1H), 6.63 (t, 1H), 4.75 (d, 2H), 2.90 (s, 3H).

Scheme 15

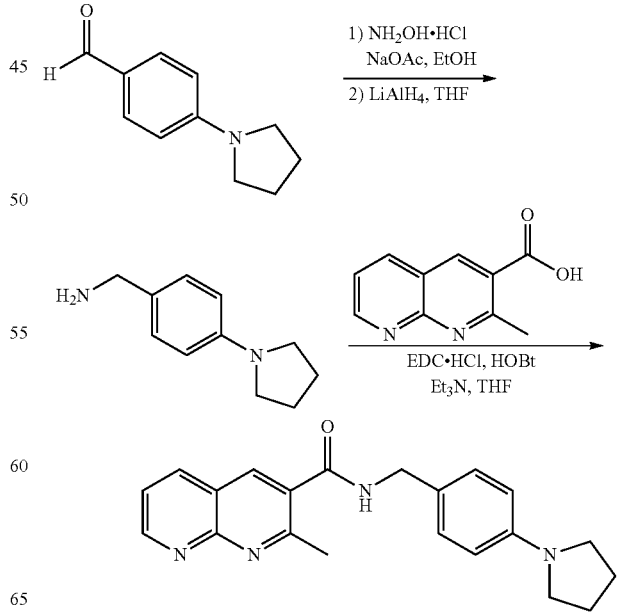

Example 53

2-Methyl-N-(4-(pyrrolidin-1-yl)benzyl)-1,8-naphthyridine-3-carboxamide

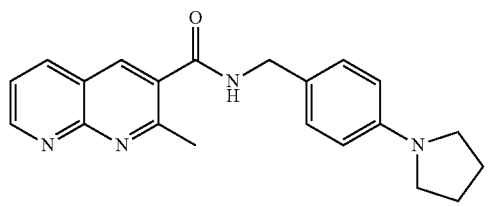 [SMILES: Cc1nc2ncccc2cc1C(=O)NCc1ccc(N2CCCC2)cc1]

To a solution of 4-(1-pirrolidino)-benzaldehyde (833 mg, 4.75 mmol) in EtOH (25 ml) hydroxylamine hydrochloride (396.4 mg, 5.70 mmol) and sodium acetate (467.8 mg, 5.70 mmol) were added. The mixture was heated to reflux and stirred for 1.0 hour. The mixture was diluted with EtOAc, washed with $H_2O$, dried ($MgSO_4$), filtered and concentrated to dryness. The residue was then dissolved in anhydrous THF (20.0 ml) under $N_2$. $LiAlH_4$ (1.0 M in THF) (5.7 ml) was slowly added to the solution. The mixture was stirred at r.t. for 24 h. Then it was carefully poured into MeOH (60 ml), the solvent was removed and the residue was suspended in MeOH and filtered. The filtrate was concentrated under reduced pressure yielding 4-(1-Pyrrolidino)-benzylamine which was coupled to 2-Methyl-1,8-naphthyridine following the general amide coupling procedure. Purification was done by flash chromatography ($CH_2Cl_2$/MeOH 95:5) to give the title substance in 29% yield.

$^1$H NMR (CDCl$_3$) δ 9.08 (m, 1H), 8.11 (m, 2H), 7.46 (m, 1H), 7.27 (d, 2H), 6.60 (d, 2H), 6.24 (bs, 1H), 4.58 (d, 2H), 3.30 (m, 4H), 2.92 (s, 3H), 2.03 (m, 4H).

Scheme 16-Nucleophilic aromatic substitution of 4-fluoro-3-(trifluoromethyl)-benzonitrile, reduction of benzonitriles to benzylamines and coupling of benzylamines and 2-Methyl-1,8-naphthyridine

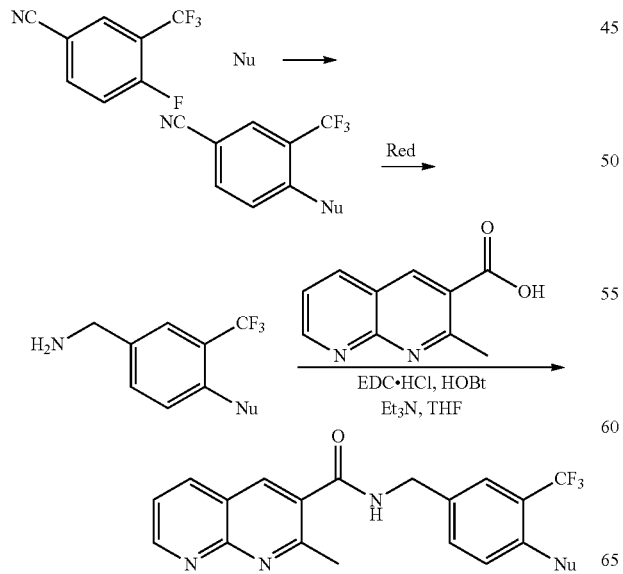

General Procedure C for the Nucleophilic Aromatic Substitution of 4-fluoro-3-(trifluoromethyl)-benzonitrile (Scheme 16).

NaH (2.2 eq.) was suspended in DMF under $N_2$. The suspension was cooled using an ice-bath. 2.0 equiv. of the corresponding nucleophile (Nu in scheme 16) was slowly added. The mixture was stirred for 20 min. 4-Fluoro-3-(trifluoromethyl)benzonitrile (1.0 eq.) was then added to the mixture and the stirring continued for between 1.0 and 18.0 hours. Then the mixture was poured into $NH_4Cl$ (sat). The resulting precipitate was collected by filtration, washed with water and dried under reduced pressure.

The following substances were synthesized following general procedure C for the nucleophilic aromatic substitution of 4-fluoro-3-(trifluoromethyl)-benzonitrile. The solvent system used for the purification, the yield and analytical data is given for each compound.

4-(2-(Dimethylamino)ethoxy)-3-(trifluoromethyl)benzonitrile

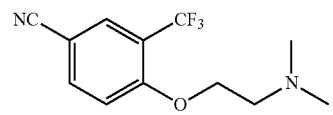 [SMILES: CN(C)CCOc1ccc(C#N)cc1C(F)(F)F]

Yield: quant.
$^1$H NMR (CDCl$_3$) δ 7.85 (d, 1H), 7.78 (m, 1H), 7.08 (d, 1H), 4.23 (t, 2H), 2.81 (t, 2H), 2.34 (s, 6H).

4-(Pyridin-3-ylmethoxy)-3-(trifluoromethyl)benzonitrile

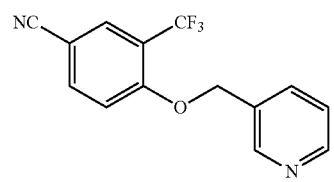 [SMILES: N#Cc1ccc(OCc2cccnc2)c(C(F)(F)F)c1]

Yield: quant.
$^1$H NMR (CDCl$_3$) δ 8.69 (bd, 1H), 8.64 (m, 1H), 7.92 (bs, 1H), 7.84-7.78 (m, 2H), 7.38 (m, 1H), 7.16 (d, 1H), 5.28 (s, 2H).

4-Isopropoxy-3-(trifluoromethyl)benzonitrile

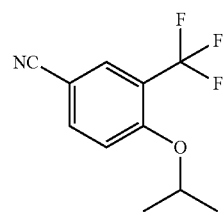 [SMILES: CC(C)Oc1ccc(C#N)cc1C(F)(F)F]

Yield: 84%
$R_f$=0.46 (Petroleum ether/EtOAc 1:1).

N-(4-Cyano-2-(trifluoromethyl)phenyl)-4-methyl-benzenesulfonamide

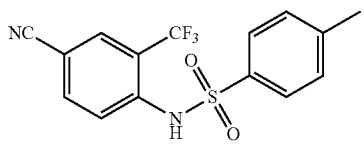 [SMILES: Cc1ccc(S(=O)(=O)Nc2ccc(C#N)cc2C(F)(F)F)cc1]

Yield: 37%

Flash chromatography: Petroleum ether/EtOAc (3:1)

N-(4-Cyano-2-(trifluoromethyl)phenyl)benzamide

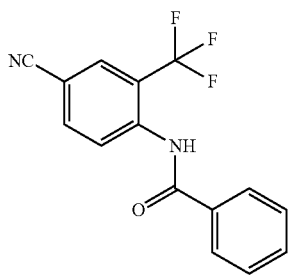 [SMILES: N#Cc1ccc(NC(=O)c2ccccc2)c(C(F)(F)F)c1]

Yield: 69%

$R_f$=0.69 (Petroleum ether/EtOAc 1:1).

4-(Tetrahydro-2H-pyran-4-yloxy)-3-(trifluoromethyl)benzonitrile

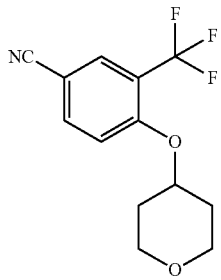 [SMILES: N#Cc1ccc(OC2CCOCC2)c(C(F)(F)F)c1]

Yield: 95%

$R_f$=0.3 (Petroleum ether/EtOAc 1:1).

4-(4-Acetylpiperazin-1-yl)-3-(trifluoromethyl)benzonitrile

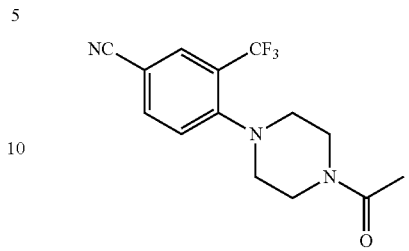

Yield: 27%

Flash chromatography: (EtOAc→EtOAc/MeOH 98:2)

$^1$H NMR (CDCl$_3$) δ 7.95 (d, 1H), 7.81 (dd, 1H), 7.32 (d, 1H), 3.79 (t, 2H), 3.63 (t, 2H), 3.02 (m, 4H), 2.15 (s, 3H).

4-(1,1,1-Trifluoropropan-2-yloxy)benzonitrile

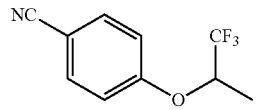

Sodium hydride (297 mg, 12.4 mmol) was suspended in DMF (3 ml) at 0° C. 1,1,1-trifluoropropan-2-ol (500 µl, 5.52 mmol) was added slowly and the reaction was stirred for 15 minutes at 0° C. before addition of 4-fluorobenzonitrile (500 mg, 4.13 mmol). The mixture was allowed to reach room temperature and was then stirred at 50° C. for 20 hours. The reaction was cooled, diluted with water (75 ml) and extracted with EtOAc (4*20 ml). Combined organics were washed with water (20 ml), dried over MgSO$_4$ and evaporated. The product was purified by flash chromatography using pet.ether/EtOAc (8:1) as eluent to give 690 mg (78%) of the title compound as a clear liquid.

$^1$H NMR (CDCl$_3$) δ 7.62 (d, 2H), 7.02 (d, 2H), 4.76 (m, 1H), 1.53 (d, 3H).

General Procedure D for the Nucleophilic Aromatic Substitution of 4-fluoro-3-(trifluoromethyl)-benzonitrile (see Scheme 16 Above).

K$_2$CO$_3$ (2.0 eq.) and 2.0 equiv. of the corresponding nucleophile (Nu in scheme 16) were added to a solution of 4-fluoro-3-(trifluoromethyl)benzonitrile (1.0 eq.) in DMSO. The mixture was heated at 90° C. overnight. The mixture was cooled to r.t. and the solids were removed by filtration. Water was added to the filtrate and the product was precipitated, collected by filtration, washed with water and dried under vacuum.

The following substances were synthesized following general procedure D for the nucleophilic aromatic substitution of 4-fluoro-3-(trifluoromethyl)-benzonitrile. The solvent system used for the purification, the yield and analytical data is given for each compound.

4-Morpholino-3-(trifluoromethyl)benzonitrile

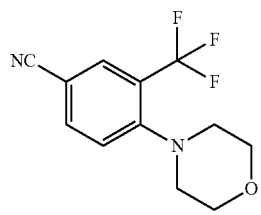 [SMILES: N#Cc1ccc(N2CCOCC2)c(C(F)(F)F)c1]

Yield: 80%

$^1$H NMR (CDCl$_3$) δ 7.92 (d, 1H), 7.79 (m, 1H), 7.33 (d, 1H), 3.86 (m, 4H), 3.95 (m, 4H)

4-(1H-Imidazol-1-yl)-3-(trifluoromethyl)benzonitrile

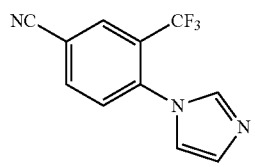 [SMILES: N#Cc1ccc(-n2ccnc2)c(C(F)(F)F)c1]

Yield: 64%

$^1$H NMR (CDCl$_3$): δ 8.14 (s, 1H), 7.99 (d, 1H), 7.65 (s, 1H), 7.56 (d, 1H), 7.24 (s, 1H), 7.15 (s, 1H).

4-(4-Methylpiperazin-1-yl)-3-(trifluoromethyl)benzonitrile

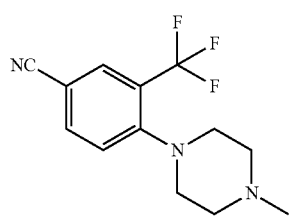 [SMILES: CN1CCN(c2ccc(C#N)cc2C(F)(F)F)CC1]

Yield: 59%

R$_f$=0.07 (CH$_2$Cl$_2$/MeOH 20:1)

$^1$H NMR (CDCl$_3$) δ 7.90 (d, 1H), 7.75 (m, 1H), 7.31 (d, 1H), 3.09 (m, 4H), 2.59 (m, 4H), 2.37 (s, 3H).

4-(Piperidin-1-yl)-3-(trifluoromethyl)benzonitrile

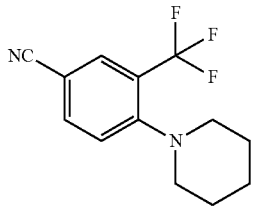 [SMILES: N#Cc1ccc(N2CCCCC2)c(C(F)(F)F)c1]

Yield: 80%

$^1$H NMR (CDCl$_3$) δ 7.87 (d, 1H), 7.71 (m, 1H), 7.25 (d, 1H), 3.01 (m, 4H), 1.73 (m, 4H), 1.60 (m, 2H).

4-(Methylsulfonyl)-3-(trifluoromethyl)benzonitrile

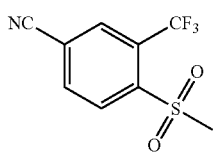 [SMILES: CS(=O)(=O)c1ccc(C#N)cc1C(F)(F)F]

4-Fluoro-3-(trifluoromethyl)benzonitrile (400 mg, 2.12 mmol) was suspended together with sodium methanesulfinate (216 mg, 2.12 mmol) in DMSO (2 ml) and stirred at 80° C. for 22 hours. The reaction was then cooled, diluted with 25 ml H$_2$O and filtered. Filtered solids were evaporated from toluene to give 536 mg of the title substance (quant).

$^1$H NMR (CDCl$_3$) δ 8.49 (d, 1H), 8.20 (s, 1H), 8.10 (d, 1H), 3.24 (s, 3H).

4-(Dimethylamino)-3-(trifluoromethyl)benzonitrile

4-Fluoro-3-(trifluoromethyl)benzonitrile (240 mg, 1.27 mmol) was dissolved in DMSO (1 ml) together with dimethylamine (1 ml, 40% aq). The mixture was stirred at r.t. for 18 hours followed by 4 hours at 50° C. The reaction was cooled, diluted with EtOAc (10 ml), washed with H$_2$O (2*20 ml), dried over MgSO$_4$ and evaporated to give 253 mg (93%) of the title substance as a greenish oil.

¹H NMR (CDCl₃) δ 7.83 (d, 1H), 7.62 (m, 1H), 7.08 (d, 1H), 2.96 (s, 6H).

(S)-4-(3-Methylmorpholino)benzonitrile

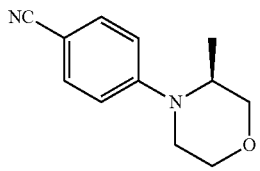

4-Fluorobenzonitrile (359 mg, 2.97 mmol), (S)-3-methylmorpholine (150 mg, 1.48 mmol) and K₂CO₃ were suspended in DMSO (1.5 ml). The mixture was stirred for 70 hours at 110° C. in a closed high-pressure flask. The reaction was cooled, diluted with water (50 ml) and extracted with EtOAc (3*20 ml). Combined organics were washed with water (20 ml), dried over MgSO₄ and evaporated. The product was purified by flash chromatography using pet.ether/EtOAc (3:1) as eluent to give 130 mg (43%) of the title compound as pale solids.

¹H NMR (CDCl₃) δ 7.50 (d, 2H), 6.80 (d, 2H), 4.03 (dd, 1H), 3.92 (m, 1H), 3.80 (s, 2H), 3.65 (t, 1H), 3.31 (m, 1H), 3.20 (m, 1H), 1.19 (d, 3H).

(R)-4-(3-methylmorpholino)benzonitrile

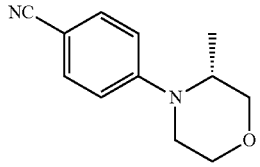

(Pet. Ether/EtOAc 3:1)
Yield: 19%
¹H NMR (CDCl₃) δ identical to (S)-4-(3-methylmorpholino)benzonitrile.

4-(4-Oxopiperidin-1-yl)-3-(trifluoromethyl)benzonitrile

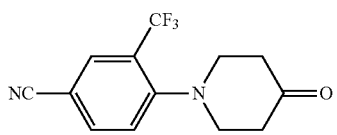

Yield: 24%
¹H NMR (CDCl₃) δ 7.97 (s, 1H), 7.83 (d, 1H), 7.39 (d, 1H), 3.35 (t, 4H), 2.66 (s, 4H).

4-(2-Methylpiperidin-1-yl)benzonitrile

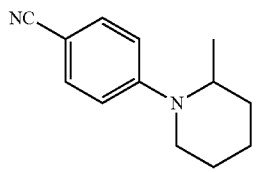

(Pet. Ether/EtOAc 6:1→4:1)
Yield: 36%
¹H NMR (CDCl₃) δ 7.46 (d, 2H), 6.81 (d, 2H), 4.22 (m, 1H), 3.56 (m, 1H), 2.98 (m, 1H), 1.80 (m, 2H), 1.65 (m, 4H), 1.11 (d, 3H).

4-(2-(Hydroxymethyl)piperidin-1-yl)benzonitrile

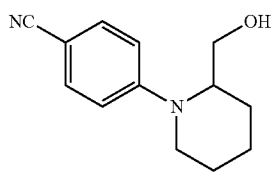 [SMILES: N#Cc1ccc(N2CCCCC2CO)cc1]

In a screw cap pressure tube, 4-fluorobenzonitrile (354.0 mg, 3.15 mmol), piperidin-2-ylmethanol (363.4 mg, 3.15 mmol) and NaHCO₃ were suspended in DMF (2.0 ml). The tube was sealed and the mixture heated to 120° C. for 3 days. The mixture was allowed to cool. H₂O was added and the product extracted with EtOAc. The combined organic extracts were washed with H₂O, dried (MgSO₄), filtered and concentrated. The crude product was purified by flash chromatography (CH₂Cl₂/MeOH 98:2→96:4) affording 63 mg (9%) of the title compound.

¹H NMR (CDCl₃) δ 7.46 (d, 2H), 6.91 (d, 2H), 4.12 (m, 1H), 3.89 (m, 1H), 3.69 (m, 2H), 3.10 (m, 1H), 1.72 (m, 6H).

4-(4,4-Dimethylpiperidin-1-yl)benzonitrile

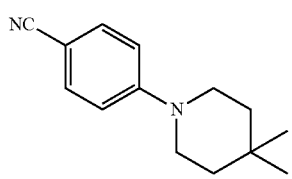 [SMILES: CC1(C)CCN(c2ccc(C#N)cc2)CC1]

(pet.ether/EtOAc 5:1→3:1)
Yield: 54%
¹H NMR (CDCl₃) δ 7.37 (d, 2H), 6.78 (d, 2H), 3.25 (m, 4H), 1.42 (m, 4H), 0.94 (s, 6H).

4-(4,4-Dimethylpiperidin-1-yl)-3-fluorobenzonitrile

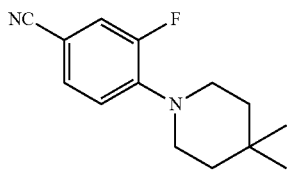 [SMILES: CC1(C)CCN(c2ccc(C#N)cc2F)CC1]

(Pet. Ether/EtOAc 9:1)
Yield: 46%
$^1$H NMR (CDCl$_3$) δ 7.34 (m, 1H), 7.26 (m, 1H), 6.94 (m, 1H), 3.18 (m, 4H), 1.54 (m, 4H), 1.01 (s, 6H).

3-bromo-4-(4,4-dimethylpiperidin-1-yl)benzonitrile

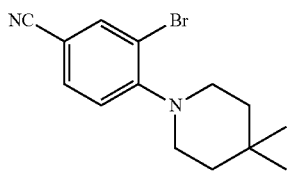 [SMILES: CC1(C)CCN(c2ccc(C#N)cc2Br)CC1]

(Pet. Ether/EtOAc 95:5)
Yield: 59%
$^1$H NMR (CDCl$_3$) δ 7.80 (d, 1H), 7.53 (m, 1H), 7.06 (d, 1H), 3.08 (m, 4H), 1.57 (m, 4H), 1.02 (s, 6H).

4-(Cyclopentyloxy)benzonitrile

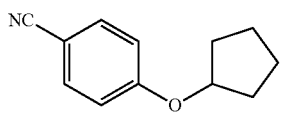 [SMILES: N#Cc1ccc(OC2CCCC2)cc1]

(pet.ether/EtOAc 7:1)
Yield: 64%
$^1$H NMR (CDCl$_3$) δ 7.55 (d, 2H), 6.90 (d, 2H), 4.80 (m, 1H), 1.97-1.70 (br m, 6H), 1.64 (m, 2H).

3-fluoro-4-(4-methoxy-4-methylpiperidin-1-yl)benzonitrile

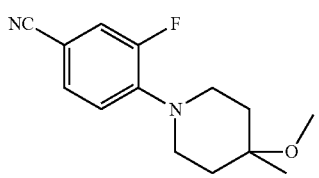 [SMILES: COC1(C)CCN(c2ccc(C#N)cc2F)CC1]

Yield: 62%
$^1$H NMR (CDCl$_3$) δ 7.51 (m, 1H), 7.37 (m, 1H), 7.28 (m, 1H), 3.32 (m, 2H), 3.23 (s, 3H), 3.20 (m, 2H), 1.90 (m, 2H), 1.77 (m, 2H), 1.23 (s, 3H).

4-Thiomorpholinobenzonitrile

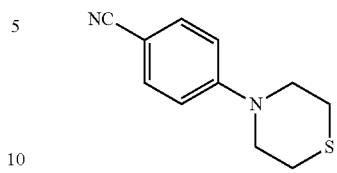

4-fluorobenzonitrile (500 mg, 4.13 mmol) and thiomorpholine (1.18 ml, 12.4 mmol) was dissolved in acetonitrile (2 ml) and stirred at 100° C. for 40 hours. The reaction was cooled, evaporated and purified by flash chromatography using pet.ether/EtOAc (4:1) as eluent to give 450 mg (53%) of the title compound as pale solids.
$^1$H NMR (CDCl$_3$) δ 7.50 (d, 2H), 6.82 (d, 2H), 3.77 (t, 4H), 2.70 (t, 4H).

4-(8-Oxa-3-azabicyclo[3.2.1]octan-3-yl)-3-fluorobenzonitrile

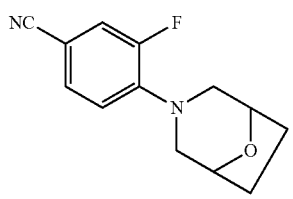 [SMILES: N#Cc1ccc(N2CC3CCC(C2)O3)c(F)c1]

(Pet. Ether, EtOAc (4:1→3:1))
Yield: 75%
$^1$H NMR (CDCl$_3$) δ 7.35 (dd, 1H), 7.27 (dd, 1H), 6.84 (m, 1H), 4.44 (s, 2H), 3.28 (d, 2H), 3.14 (d, 2H), 2.01 (m, 4H).

4-(2,6-Dimethylmorpholino)-3-fluorobenzonitrile

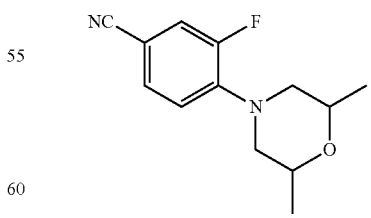

(Pet. Ether, EtOAc (5:1)
Yield: 64%
$^1$H NMR (CDCl$_3$) δ 7.37 (m, 1H), 7.29 (dd, 1H), 6.92 (t, 1H), 3.85 (m, 2H), 3.41 (d, 2H), 2.55 (t, 2H), 1.24 (d, 6H).

3-Fluoro-4-(1,4-dioxa-8-azaspiro[4.5]decan-8-yl)benzonitrile

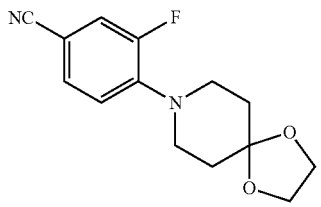 [SMILES: N#Cc1ccc(N2CCC3(CC2)OCCO3)c(F)c1]

(Pet. Ether, EtOAc (2:1)
Yield: 95%
$^1$H NMR (CDCl$_3$) δ 7.35 (m, 1H), 7.28 (dd, 1H), 6.97 (t, 1H), 4.01 (s, 4H), 3.33 (t, 4H), 1.88 (t, 4H).

4-(4,4-Difluoropiperidin-1-yl)-3-fluorobenzonitrile

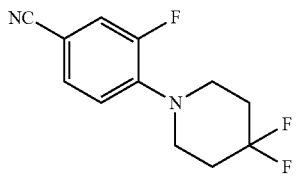 [SMILES: N#Cc1ccc(N2CCC(F)(F)CC2)c(F)c1]

(Pet. Ether, EtOAc (5:1)
Yield: 80% $^1$H NMR (CDCl$_3$) δ 7.38 (m, 1H), 7.31 (dd, 1H), 6.96 (t, 1H), 3.34 (t, 4H), 2.16 (m, 4H).

4-(1,1-Dioxothiomorpholino)benzonitrile

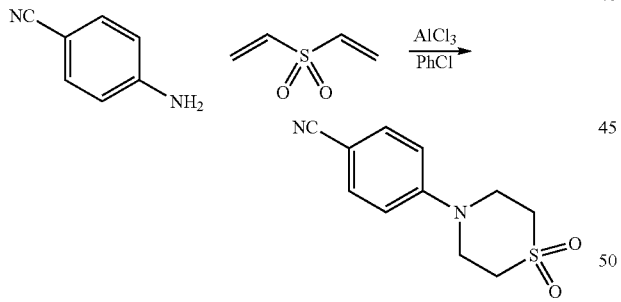

Aluminium trichloride (1.13 g, 8.46 mmol) was suspended in chlorobenzene (50 ml) at 0° C. Divinyl sulfone (850 µl, 8.46 mmol) was added followed by 4-aminobenzonitrile (1.0 g, 8.46 mmol). The mixture was allowed to reach room temperature and was then stirred at 130° C. for 90 hours. The reaction was cooled and diluted with CH$_2$Cl$_2$ (200 ml), water (150 ml) and MeOH (50 ml) before filtration. Filtered liquid was separated and the aqueous phase was extracted with CH$_2$Cl$_2$ (50 ml). Combined organics were dried over MgSO$_4$ and evaporated. The crude product was purified by flash chromatography using pet.ether/EtOAc (1:1→0:1) as eluent to give 610 mg (30%) of the title compound as pale solids.

$^1$H NMR (CDCl$_3$) δ 7.57 (d, 2H), 6.92 (d, 2H), 3.99 (t, 4H), 3.10 (t, 4H).

General Procedure E for the Reduction of Benzonitriles to Benzylamines (c.f. Scheme 16).

The corresponding benzonitrile (1.0 eq.) was dissolved in anhydrous THF and cooled to 0° C. NaBH$_4$ (3.0 eq.) was added to this solution followed by slow addition of BF$_3$*THF (4.0 eq.). The resulting mixture was stirred 15 minutes at 0° C., then 1 h at room temperature and finally refluxed for 15 h. The reaction was then cooled to room temperature and quenched with MeOH followed by aqueous HCl (6M). The mixture was refluxed for 3 h, cooled and the pH was adjusted to 10 by addition of NaOH (50% aq). Organic solvents were evaporated and the aqueous residue was extracted with chloroform. Combined organic extracts were dried over MgSO$_4$, filtered and evaporated to give the corresponding benzylamines.

The following substances were synthesized following the general procedure E for the reduction of benzonitriles to benzylamines. The yield and analytical data is given for each compound.

(4-(1H-Imidazol-1-yl)-3-(trifluoromethyl)phenyl)methanamine

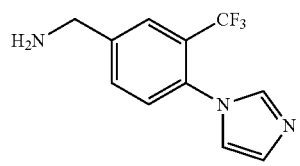 [SMILES: NCc1ccc(-n2ccnc2)c(C(F)(F)F)c1]

Yield: 89%
$^1$H NMR (CDCl$_3$) δ 7.77 (s, 1H), 7.61 (d, 1H), 7.56 (s, 1H), 7.31 (d, 1H), 7.13 (s, 1H), 7.06 (s, 1H), 4.00 (s, 2H).

N-(4-(Aminomethyl)-2-(trifluoromethyl)phenyl)-4-methylbenzenesulfonamide

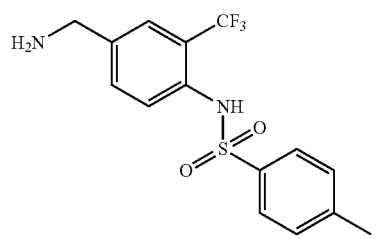 [SMILES: Cc1ccc(S(=O)(=O)Nc2ccc(CN)cc2C(F)(F)F)cc1]

Yield: 90%
$^1$H NMR (CDCl$_3$) δ 7.78 (d, 1H), 7.64 (d, 2H), 7.47 (br, 2H), 7.25-7.15 (m, 3H), 3.87 (s, 2H), 2.37 (s, 3H).

2-(4-(Aminomethyl)-2-(trifluoromethyl)phenoxy)-N,N-dimethylethanamine

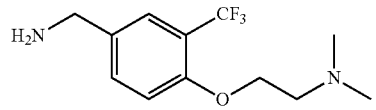 [SMILES: CN(C)CCOc1ccc(CN)cc1C(F)(F)F]

Yield: 90%
$^1$H NMR (CD$_3$OD) δ 7.81 (d, 1H), 7.76 (m, 1H), 7.36 (d, 1H), 4.55 (t, 2H), 4.16 (s, 2H), 3.66 (t, 2H), 3.02 (s, 6H).

(4-(Pyridin-3-ylmethoxy)-3-(trifluoromethyl)phenyl)methanamine

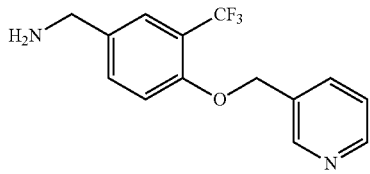 [SMILES: NCc1ccc(OCc2cccnc2)c(C(F)(F)F)c1]

Yield: 90%

$^1$H NMR (CD$_3$OD) δ 8.95 (s, 1H), 8.87 (d, 1H), 8.73 (d, 1H), 8.17 (m, 1H), 7.83 (d, 1H), 7.77 (m, 1H), 7.46 (d, 1H), 5.55 (s, 2H), 4.17 (s, 2H).

4-(Aminomethyl)-N,N-dimethyl-2-(trifluoromethyl)aniline

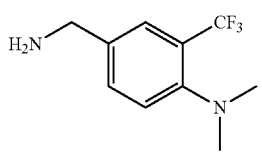

Yield: 93%

$^1$H NMR (CDCl$_3$) δ 7.53 (d, 1H), 7.44 (m, 1H), 7.31 (d, 1H), 3.85 (s, 2H), 2.70 (s, 6H).

General Procedure F for the Reduction of Benzonitriles to Benzylamines, c.f. Scheme 16.

The corresponding benzonitrile (1.0 eq.), NiCl$_2$.6H$_2$0 (1.0 eq.) and Boc$_2$O (2.0 eq.) were dissolved in THF/MeOH (3:1). The solution was cooled to 0° C. and NaBH$_4$ was slowly added. The mixture was stirred at r.t. overnight. The solvents were removed under reduced pressure. The residue was suspended in EtOAc and Na$_2$CO$_3$ (sat) and then filtered. The organic layer was separated, dried (MgSO$_4$), filtered and concentrated to give the corresponding Boc-protected amine.

The corresponding Boc-protected amine in 10 ml 1:1 TFA/CH$_2$Cl$_2$ was stirred at r.t. for 2 h. Solid NaHCO$_3$ was added until pH>10. The mixture was extracted with three portions of CHCl$_3$. The combined organic fractions were dried (MgSO$_4$) and concentrated under reduced pressure.

Alternatively the corresponding Boc-protected amine was dissolved in diethyl ether and treated with HCl (2.0M in diethyl ether) for 2-12 h. The hydrochloride salt of the resulting benzyl amine was collected by filtration, washed with diethyl ether and dried under vacuum. The amine was then used without further purification.

The following Boc-protected amines and the corresponding free amines were synthesized following the general procedure F for the reduction of benzonitriles to benzylamines. The yield and analytical data is given for each compound.

tert-Butyl 4-benzamido-3-(trifluoromethyl)benzylcarbamate

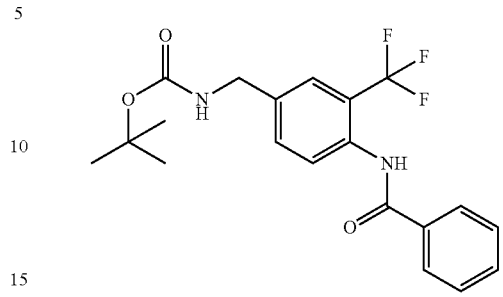

Yield: 89%

$^1$H NMR (CDCl$_3$) δ 8.40 (d, 1H), 8.22 (bs, 1H), 7.88 (m, 2H), 7.58 (m, 4H), 4.93 (bs, 1H), 4.36 (m, 2H), 1.48 (s, 9H).

N-(4-(Aminomethyl)-2-(trifluoromethyl)phenyl)benzamide

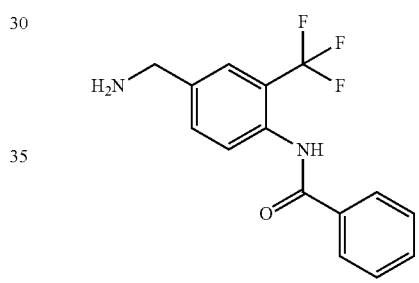

Yield: 40%

$^1$H NMR (CDCl$_3$) δ 8.37 (d, 1H), 8.22 (s, 1H), 7.88 (m, 2H), 7.65 (s, 1H), 7.58 (m, 4H), 3.95 (s, 2H).

tert-Butyl 4-(4-methylpiperazin-1-yl)-3-(trifluoromethyl)benzylcarbamate

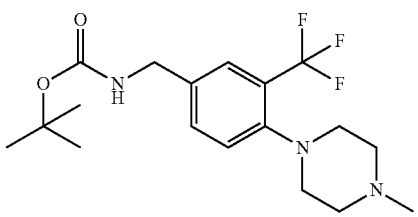 [SMILES: CN1CCN(c2ccc(CNC(=O)OC(C)(C)C)cc2C(F)(F)F)CC1]

Yield: 78%

$^1$H NMR (CDCl$_3$) δ 7.52 (s, 1H), 7.43 (d, 1H), 7.33 (d, 1H), 4.94 (bs, 1H), 4.31 (m, 2H), 2.94 (m, 4H), 2.56 (m, 4H), 2.36 (s, 3H), 1.46 (s, 9H).

79

(4-(4-Methylpiperazin-1-yl)-3-(trifluoromethyl)phenyl)methanamine

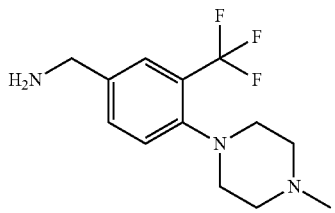 [SMILES: CN1CCN(c2ccc(CN)cc2C(F)(F)F)CC1]

Yield: 90%

¹H NMR (CDCl₃) δ 7.57 (m, 1H), 7.46 (d, 1H), 7.34 (d, 1H), 3.88 (s, 2H), 2.96 (m, 4H), 2.60 (bs, 4H), 2.38 (s, 3H).

tert-Butyl 4-(tetrahydro-2H-pyran-4-yloxy)-3-(trifluoromethyl)benzylcarbamate

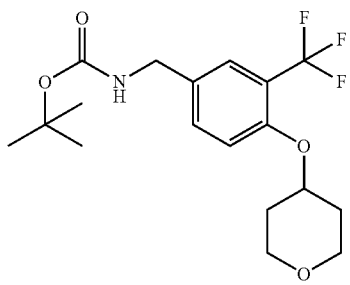 [SMILES: CC(C)(C)OC(=O)NCc1ccc(OC2CCOCC2)c(C(F)(F)F)c1]

Yield: 91%

R_f=0.4 (Petroleum ether/EtOAc 1:1).

(4-(Tetrahydro-2H-pyran-4-yloxy)-3-(trifluoromethyl)phenyl)methanamine

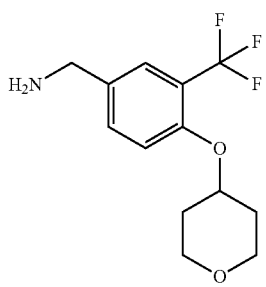 [SMILES: NCc1ccc(OC2CCOCC2)c(C(F)(F)F)c1]

Yield: 68%

¹H NMR (CDCl₃) δ 7.54 (s, 1H), 7.43 (m, 1H), 6.95 (m, 1H), 3.97 (m, 2H), 3.85 (s, 2H), 3.62 (m, 2H), 2.01 (m, 2H), 1.86 (m, 2H).

80 tert-Butyl 4-(piperidin-1-yl)-3-(trifluoromethyl)

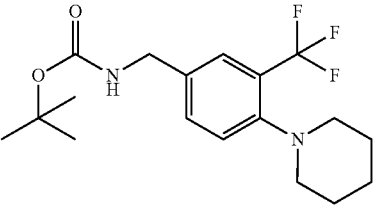 [SMILES: CC(C)(C)OC(=O)NCc1ccc(N2CCCCC2)c(C(F)(F)F)c1]

Yield: 91%

R_f=0.56 (Petroleum ether/EtOAc 4:1).

(4-(Piperidin-1-yl)-3-(trifluoromethyl)phenyl)methanamine

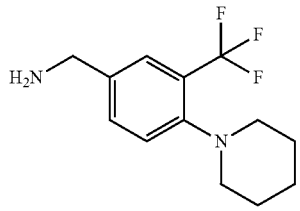 [SMILES: NCc1ccc(N2CCCCC2)c(C(F)(F)F)c1]

Yield: 100%

¹H NMR (CDCl₃) δ 7.57 (m, 1H), 7.46 (m, 1H), 7.30 (m, 1H), 2.84 (m, 2H), 1.69 (m, 6H), 1.56 (m, 4H).

tert-Butyl 4-(methylsulfonyl)-3-(trifluoromethyl)benzylcarbamate

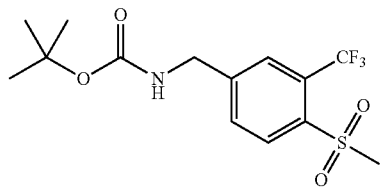 [SMILES: CC(C)(C)OC(=O)NCc1ccc(S(C)(=O)=O)c(C(F)(F)F)c1]

Yield: 93%

¹H NMR (CDCl₃) δ 8.16 (d, 1H), 7.76 (s, 1H), 7.63 (d, 1H), 5.39 (br s, 1H), 4.42 (d, 2H), 3.13 (s, 3H), 1.44 (s, 9H).

4-(Methylsulfonyl)-3-(trifluoromethyl)benzylamine hydrochloride

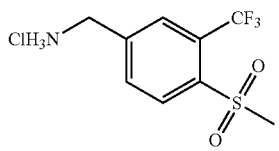

tert-Butyl 4-(methylsulfonyl)-3-(trifluoromethyl)benzylcarbamate (420 mg, 1.18 mmol) was dissolved in CH$_2$Cl$_2$ (12 ml) and HCl in Et$_2$O (3 ml, 2M) were added. Resulting mixture was stirred at room temperature overnight followed by evaporation to give 4-(methylsulfonyl)-3-(trifluoromethyl)benzylamine hydrochloride as white solids. This material was used in subsequent reactions without further purification.

(4-cyclopentylphenyl)methanamine hydrochloride

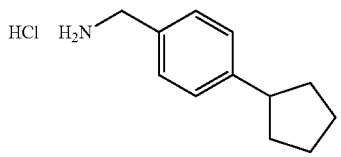 [SMILES: Cl ; NCc1ccc(C2CCCC2)cc1]

226 mg (6.0 mmol) NaBH$_4$ was added slowly to a solution of 146 mg (0.85 mmol) 4-cyclopentylbenzonitrile, 202 mg (0.85 mmol) NiCl$_2$ hexahydrate and 371 mg (1.7 mmol) di-tert-butyl dicarbonate in 8 ml THF and 5 ml MeOH. The reaction mixture was stirred at room temperature for 7 h and then concentrated to dryness. The residue was dissolved in EtOAc and NaHCO$_3$(sat.) and filtered through celite. The celite was washed with EtOAc and the phases were separated. The organic phase was dried (MgSO$_4$) and concentrated. Flash chromatography (SiO$_2$, petroleum ether/EtOAc 95:5) afforded 37 mg of the Boc-protected amine. The product was dissolved in 2 ml 2M HCl in diethylether and stirred at room temperature for 4 h. The solvent was decanted and the precipitate washed with diethylether. Gave 20 mg (11%) as a white solid.

$^1$H NMR (400 MHz, CD$_3$OD) δ 7.37 (d, 2H), 7.32 (d, 2H), 4.08 (s, 2H), 3.03 (m, 1H), 2.07 (m, 2H), 1.83 (m, 2H), 1.72 (m, 2H), 1.58 (m, 2H).

(S)-tert-Butyl 4-(3-methylmorpholino)benzylcarbamate

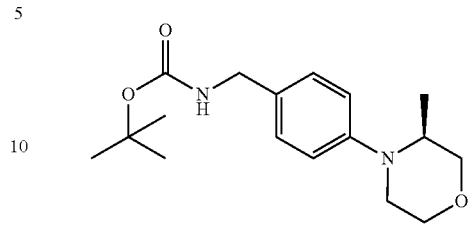

Yield: 79%
$^1$H NMR (CDCl$_3$) δ 7.18 (d, 2H), 6.85 (d, 2H), 4.85 (br, 1H), 4.22 (d, 2H), 3.95 (m, 1H), 3.84 (m, 1H), 3.70 (m, 3H), 3.10 (m, 2H), 1.45 (s, 9H), 1.05 (d, 3H).

tert-Butyl 4-(4-hydroxypiperidin-1-yl)-3-(trifluoromethyl)benzylcarbamate

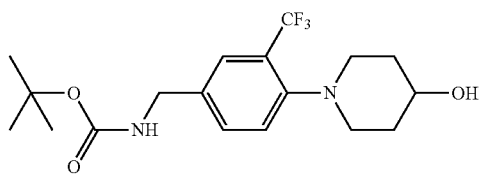 [SMILES: CC(C)(C)OC(=O)NCc1ccc(N2CCC(O)CC2)c(C(F)(F)F)c1]

Yield: 48%
$^1$H NMR (CDCl$_3$) δ 7.51 (s, 1H), 7.42 (d, 1H), 7.28 (d, 1H), 4.95 (br, 1H), 4.30 (d, 2H), 3.83 (m, 1H), 3.06 (m, 2H), 2.75 (m, 2H), 1.98 (m, 2H), 1.73 (m, 2H), 1.47 (s, 9H).

tert-Butyl 4-(1,1,1-trifluoropropan-2-yloxy)benzylcarbamate

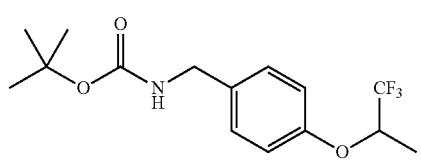 [SMILES: CC(Oc1ccc(CNC(=O)OC(C)(C)C)cc1)C(F)(F)F]

Yield: 74%
$^1$H NMR (CDCl$_3$) δ 7.23 (d, 2H), 6.92 (d, 2H), 4.84 (br, 1H), 4.61 (m, 1H), 4.26 (d, 2H), 1.49 (d, 3H), 1.46 (s, 9H).

(4-(2-Methylpiperidin-1-yl)phenyl)methanamine hydrochloride

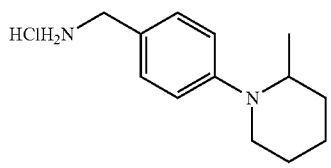

Yield: quant.
$^1$H NMR (CD$_3$OD) δ 7.84 (d, 2H), 7.74 (d, 2H), 4.23 (s, 2H), 3.90 (m, 1H), 3.66 (m, 2H), 1.98 (m, 6H), 1.08 (d, 3H).

83

(1-(4-(Aminomethyl)phenyl)piperidin-2-yl)methanol hydrochloride

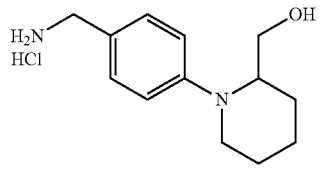 [SMILES: Cl ; NCc1ccc(N2CCCCC2CO)cc1]

Yield: quant.
$^1$H NMR (CD$_3$OD) δ 7.83 (d, 2H), 7.72 (d, 2H), 4.23 (s, 2H), 3.79 (m, 2H), 3.54 (m, 1H), 3.43 (m, 1H), 3.23 (m, 1H), 2.19 (m, 1H), 2.03 (m, 4H), 1.87 (m, 1H).

1-(4-(4-(Aminomethyl)phenyl)-2-(trifluoromethyl)piperazin-1-yl)ethanone hydrochloride

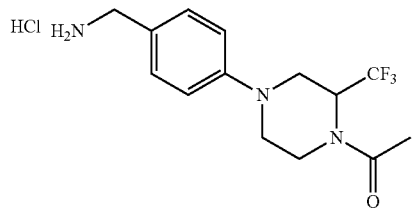 [SMILES: Cl ; CC(=O)N1CCN(c2ccc(CN)cc2)CC1C(F)(F)F]

Yield: 100%
$^1$H NMR (CD$_3$OD) δ 7.82 (d, 1H), 7.72 (dd, 1H), 7.57 (d, 1H), 4.19 (s, 2H), 3.72 (t, 2H), 3.68 (t, 2H), 2.97 (t, 2H), 2.91 (t, 2H), 2.15 (s, 3H).

tert-Butyl 4-(4,4-dimethylpiperidin-1-yl)benzylcarbamate

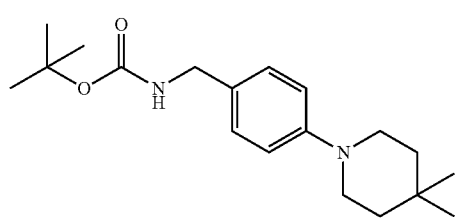 [SMILES: CC1(C)CCN(c2ccc(CNC(=O)OC(C)(C)C)cc2)CC1]

(pet.ether/EtOAc 6:1)
Yield: 79%
$^1$H NMR (CDCl$_3$) δ 7.17 (d, 2H), 6.91 (d, 2H) 4.77 (br, 1H), 4.23 (d, 2H), 3.15 (m, 4H), 1.52 (m, 4H), 0.98 (s, 6H).

84

(4-(4,4-Dimethylpiperidin-1-yl)-3-fluorophenyl)methanamine hydrochloride

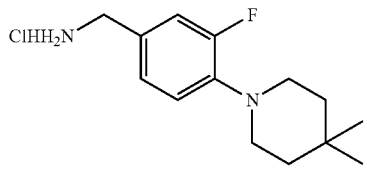

Yield: 100%
$^1$H NMR (CD$_3$OD) δ 7.34 (m, 1H), 7.26 (m, 1H), 6.94 (m, 1H), 4.20 (s, 2H), 3.18 (m, 4H), 1.54 (m, 4H), 1.01 (s, 6H).

tert-Butyl 3-bromo-4-(4,4-dimethylpiperidin-1-yl)benzylcarbamate

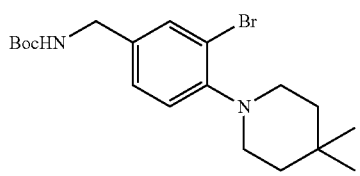 [SMILES: CC1(C)CCN(c2ccc(CNC(=O)OC(C)(C)C)cc2Br)CC1]

(Pet. Ether/EtOAc 95:5)
Yield: 51%
$^1$H NMR (CDCl$_3$) δ 7.48 (d, 1H), 7.18 (m, 1H), 7.03 (d, 1H), 4.81 (bs, 1H), 4.23 (d, 2H), 2.95 (m, 4H), 1.55 (m, 4H), 1.47 (s, 9H), 1.01 (s, 6H).

tert-Butyl 3-cyano-4-(4,4-dimethylpiperidin-1-yl)benzylcarbamate

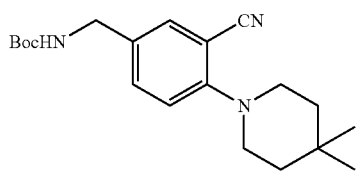 [SMILES: CC1(C)CCN(c2ccc(CNC(=O)OC(C)(C)C)cc2C#N)CC1]

In a screw cap pressure tube were tert-butyl 3-bromo-4-(4,4-dimethylpiperidin-1-yl)benzylcarbamate (105 mg, 0.26 mmol) and CuCN (47.3 mg, 0.53 mmol) suspended in DMF (1.0 ml). N$_2$ was bubbled through the suspension for 5 min. The tube was sealed and the mixture heated to 140° C. overnight. The mixture was allowed to cool and then it was poured over ice-water. FeCl$_3$ (94.3 mg, 0.58 mmol) was added and the product extracted with EtOAc. The combined organic extracts were dried (MgSO$_4$), filtered and concentrated. The crude product was purified by flash chromatography (Pet. Ether/EtOAc 4:1) affording 40 mg (45%) of the title compound.

¹H NMR (CDCl₃) δ 7.43 (d, 1H), 7.37 (m, 1H), 6.97 (d, 1H), 4.94 (bs, 1H), 4.22 (d, 2H), 3.15 (m, 4H), 1.57 (m, 4H), 1.45 (s, 9H), 1.00 (s, 6H).

5-(Aminomethyl)-2-(4,4-dimethylpiperidin-1-yl)benzonitrile hydrochloride

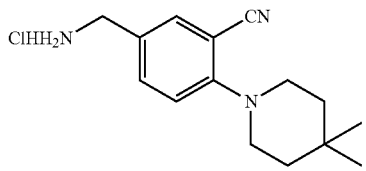

tert-Butyl 3-cyano-4-(4,4-dimethylpiperidin-1-yl)benzylcarbamate (250 mg, 0.73 mmol) was dissolved in Et₂O (10 ml). HCl (2.0 M in Et₂O)(10 ml) was added to the solution. The mixture was stirred for 36 h. The solvents were removed and the residue was used without further purification.

¹H NMR (CD₃OD) δ 7.52 (d, 1H), 7.48 (m, 1H), 7.21 (m, 1H), 4.16 (s, 2H), 3.22 (m, 4H), 1.62 (m, 4H), 1.04 (s, 6H).

tert-Butyl 4-(cyclopentyloxy)benzylcarbamate

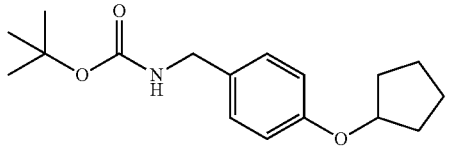 [SMILES: CC(C)(C)OC(=O)NCc1ccc(OC2CCCC2)cc1]

Yield: 89%

¹H NMR (CDCl₃) δ 7.17 (d, 2H), 6.83 (d, 2H), 4.79 (br, 1H), 4.74 (m, 1H), 4.23 (d, 2H), 1.92-1.78 (br m, 6H), 1.63 (m, 2H), 1.47 (s, 9H).

(3-fluoro-4-(4-methoxy-4-methylpiperidin-1-yl)phenyl)methanamine hydrochloride

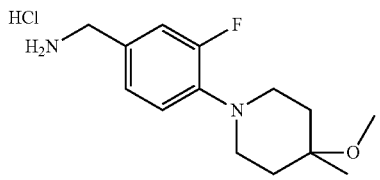 [SMILES: Cl ; COC1(C)CCN(c2ccc(CN)cc2F)CC1]

Yield: 55%

¹H NMR (CD₃OD) δ 7.92 (m, 1H), 7.49 (m, 1H), 7.32 (m, 1H), 4.22 (s, 2H), 3.36 (s, 3H), 3.30 (m, 4H), 2.15 (m, 4H), 1.30 (s, 3H).

tert-Butyl 4-thiomorpholinobenzylcarbamate

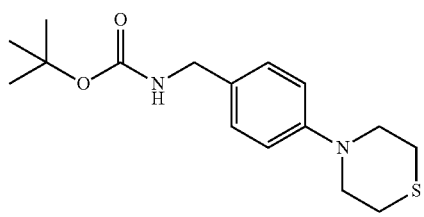 [SMILES: CC(C)(C)OC(=O)NCc1ccc(N2CCSCC2)cc1]

Yield: 95%

¹H NMR (CDCl₃) δ 7.17 (d, 2H), 6.84 (d, 2H), 4.89 (br, 1H), 4.21 (d, 2H), 3.50 (t, 4H), 2.72 (t, 4H), 1.45 (s, 9H).

(4-(8-Oxa-3-azabicyclo[3.2.1]octan-3-yl)-3-fluorophenyl)methanamine hydrochloride

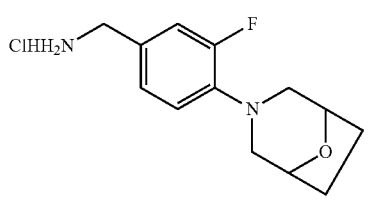

Yield: Crude used without further purification.

¹H NMR (CD₃OD) δ 7.18 (m, 3H), 7.00 (m, 1H), 4.40 (s, 2H), 4.03 (s, 2H), 3.19 (d, 2H), 3.00 (d, 2H), 2.06 (m, 2H), 1.95 (m, 2H).

(4-(2,6-Dimethylmorpholino)-3-fluorophenyl)methanamine hydrochloride

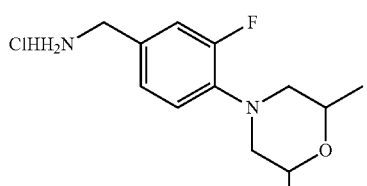

Yield: Crude used without further purification.

¹H NMR (CD₃OD) δ 7.24 (m, 2H), 7.15 (t, 1H), 4.07 (s, 2H), 3.88 (m, 2H), 3.36 (t, 2H), 2.51 (t, 2H), 1.20 (d, 6H).

(3-Fluoro-4-(1,4-dioxa-8-azaspiro[4.5]decan-8-yl)phenyl)methanamine hydrochloride

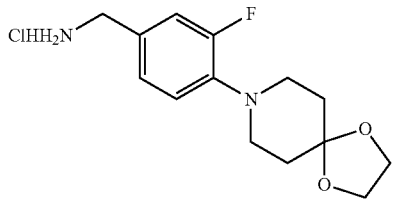

Yield: Crude used without further purification.
$^1$H NMR (CD$_3$OD) δ 7.36 (m, 3H), 4.27 (s, 2H), 4.05 (s, 4H), 3.84 (t, 4H), 2.21 (t, 4H).

(4-(4,4-Difluoropiperidin-1-yl)-3-fluorophenyl)methanamine hydrochloride

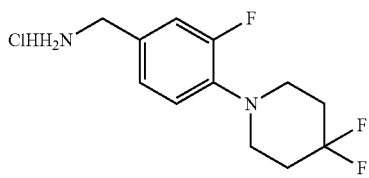

Yield: Crude used without further purification.
$^1$H NMR (CD$_3$OD) δ 7.21 (m, 2H), 7.14 (t, 1H), 4.07 (s, 2H), 3.22 (m, 2H), 2.14 (m, 2H).

tert-Butyl 4-(1,1-dioxothiomorpholino)benzylcarbamate

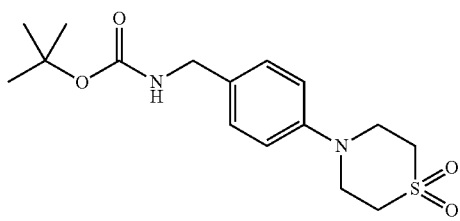 [SMILES: CC(C)(C)OC(=O)NCc1ccc(N2CCS(=O)(=O)CC2)cc1]

(pet.ether/EtOAc 1:1)
Yield: 49%
$^1$H NMR (CDCl$_3$) δ 7.22 (d, 2H), 6.90 (d, 2H) 4.82 (br, 1H), 4.24 (d, 2H), 3.84 (t, 4H), 3.11 (t, 4H), 1.46 (s, 9H).

General Procedure G for the Reduction of Benzonitriles to Benzylamines, c.f. Scheme 16.

TFA (2.5 eq.) in THF was added slowly to a mixture of NaBH$_4$ (2.5 eq.) in THF at 0° C. under N$_2$. Stirring was continued for 10 min at 0° C. and then at r.t. for 20 min. The solution was again cooled to 0° C. and the corresponding benzonitrile (1.0 eq.) in THF was added slowly. The resulting reaction mixture was stirred at r.t. for 5 h. Cooled to 0° C. and 4 ml MeOH was added slowly. The reaction mixture was concentrated to dryness under reduced pressure. The residue was dissolved in CH$_2$Cl$_2$ and washed with water. The organic phase was extracted with 1M HCl. The acidic aqueous phase was made basic with solid NaHCO$_3$ and then extracted with CH$_2$Cl$_2$ three times. The organic phase was dried (MgSO$_4$) and concentrated under reduced pressure to give the corresponding benzylamine.

The following benzylamines were synthesized following the general procedure G for the reduction of benzonitriles to benzylamines. The yield and analytical data is given for each compound.

(4-Morpholino-3-(trifluoromethyl)phenyl)methanamine

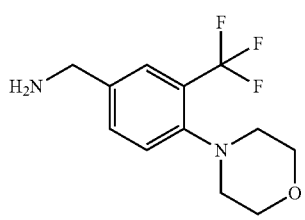 [SMILES: NCc1ccc(N2CCOCC2)c(C(F)(F)F)c1]

Yield: 45%
$^1$H NMR (CDCl$_3$) δ 7.59 (m, 1H), 7.49 (d, 1H), 7.34 (d, 1H), 3.89 (s, 2H), 3.83 (m, 4H), 2.91 (m, 4H).

(4-Isopropoxy-3-(trifluoromethyl)phenyl)methanamine

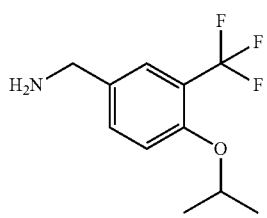 [SMILES: CC(C)Oc1ccc(CN)cc1C(F)(F)F]

Yield: 44%
$^1$H NMR (CDCl$_3$) δ 7.50 (m, 1H), 7.40 (d, 1H), 6.97 (d, 1H), 4.63 (m, 1H), 3.83 (s, 2H), 1.35 (d, 6H).

The following substances were synthesized following the general procedure for the synthesis of 1,8-naphthyridines-3-carboxamides by amide coupling (see above scheme 9), by use of 2-Methyl-1,8-naphthyridine and the corresponding benzyl amine. The solvent system used for the purification, the yield and analytical data is given for each compound.

Example 54

2-Methyl-N-(4-(4-methylphenylsulfonamido)-3-(trifluoromethyl)benzyl)-1,8-naphthyridine-3-carboxamide

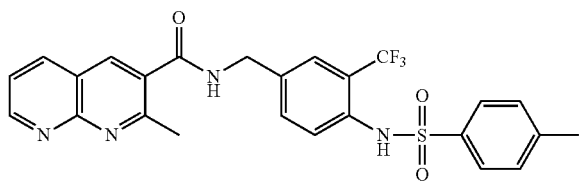 [SMILES: Cc1ccc(S(=O)(=O)Nc2ccc(CNC(=O)c3cc4cccnc4nc3C)cc2C(F)(F)F)cc1]

(CH$_2$Cl$_2$/MeOH 15:1)
Yield: 54%
$^1$H NMR (CDCl$_3$) δ 8.80 (m, 1H), 8.12 (m, 1H), 7.97 (s, 1H), 7.87 (m, 1H), 7.65 (d, 1H), 7.60 (d, 2H), 7.53 (m, 2H), 7.31 (m, 1H), 7.19 (d, 2H), 4.65 (d, 2H), 2.68 (s, 3H), 2.35 (s, 3H).

Example 55

N-(4-(1H-Imidazol-1-yl)-3-(trifluoromethyl)benzyl)-2-methyl-1,8-naphthyridine-3-carboxamide

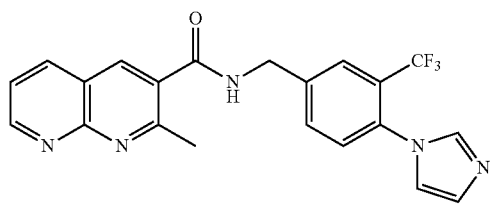 [SMILES: Cc1nc2ncccc2cc1C(=O)NCc1ccc(-n2ccnc2)c(C(F)(F)F)c1]

(CH$_2$Cl$_2$/MeOH 10:1)
Yield: 62%
$^1$H NMR (CD$_3$OD) δ 9.03 (m, 1H), 8.46 (s, 1H), 8.43 (m, 1H), 7.98 (s, 1H), 7.88 (d, 1H), 7.83 (s, 1H), 7.62 (m, 1H), 7.56 (d, 1H), 7.32 (s, 1H), 7.15 (s, 1H), 4.78 (s, 2H), 2.81 (s, 3H).

Example 56

N-(4-(2-(Dimethylamino)ethoxy)-3-(trifluoromethyl)benzyl)-2-methyl-1,8-naphthyridine-3-carboxamide

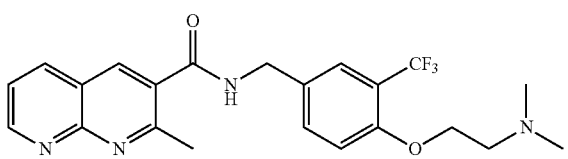 [SMILES: Cc1nc2ncccc2cc1C(=O)NCc1ccc(OCCN(C)C)c(C(F)(F)F)c1]

Sephadex LH20 (CHCl$_3$/MeOH 1:1)
Yield: 59%
$^1$H NMR (CD$_3$OD) δ 9.06 (m, 1H), 8.46 (m, 1H), 8.41 (s, 1H), 7.72-7.60 (m, 3H), 7.22 (d, 1H), 4.60 (s, 2H), 4.28 (t, 2H), 2.97 (t, 2H), 2.80 (s, 3H), 2.48 (s, 6H).

Example 57

2-Methyl-N-(4-(pyridin-3-ylmethoxy)-3-(trifluoromethyl)benzyl)-1,8-naphthyridine-3-carboxamide

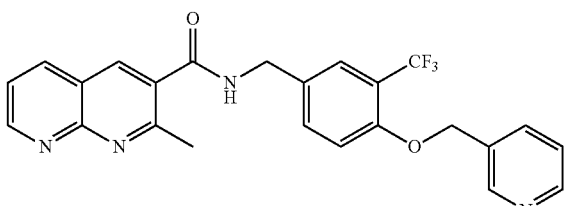

(CH$_2$Cl$_2$/MeOH 90:10)
Yield: 60%
$^1$H NMR (CD$_3$OD) δ 9.06 (m, 1H), 8.67 (d, 1H), 8.52 (m, 1H), 8.46 (m, 1H), 8.42 (s, 1H), 8.00-7.94 (m, 1H), 7.73 (d, 1H), 7.70-7.65 (m, 1H), 7.64 (m, 1H), 7.49 (m, 1H), 7.33 (d, 1H), 5.32 (s, 2H), 4.61 (s, 2H), 2.80 (s, 3H).

Example 58

2-Methyl-N-(4-(piperidin-1-yl)-3-(trifluoromethyl)benzyl)-1,8-naphthyridine-3-carboxamide

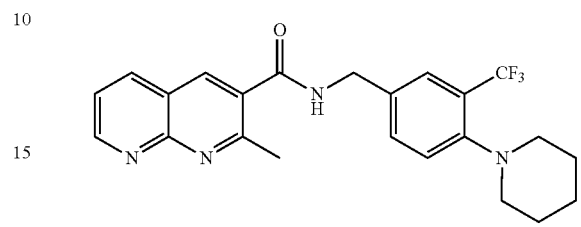

(CH$_2$Cl$_2$/MeOH 95:5)
Yield: 70%
$^1$H NMR (CDCl$_3$) δ 8.99 (m, 1H), 8.02 (s, 1H), 8.02 (m, 1H), 7.65 (d, 1H), 7.57 (m, 1H), 7.42 (m, 1H), 7.35 (d, 1H), 6.95 (m, 1H), 4.70 (d, 2H), 2.95-2.55 (m, 7H), 1.75-1.62 (m, 4H), 1.60-1.50 (m, 2H).

Example 59

2-Methyl-N-(4-morpholino-3-(trifluoromethyl)benzyl)-1,8-naphthyridine-3-carboxamide

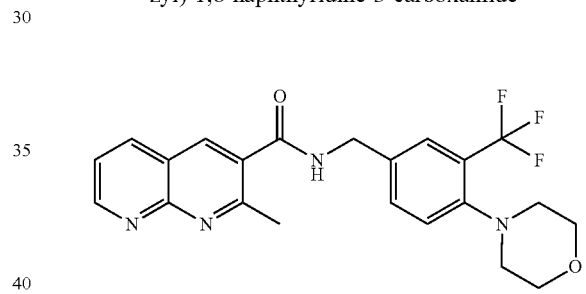

(CH$_2$Cl$_2$/MeOH 30:1)
Yield: 37%
$^1$H NMR (CDCl$_3$) δ 9.07 (m, 1H), 8.11 (s, 1H), 8.10 (m, 1H), 7.68 (m, 1H), 7.62 (m, 1H), 7.47 (m, 1H), 7.40 (d, 1H), 4.72 (d, 2H), 3.85 (m, 4H), 2.94 (m, 4H), 2.89 (s, 3H).

Example 60

N-(4-Isopropoxy-3-(trifluoromethyl)benzyl)-2-methyl-1,8-naphthyridine-3-carboxamide

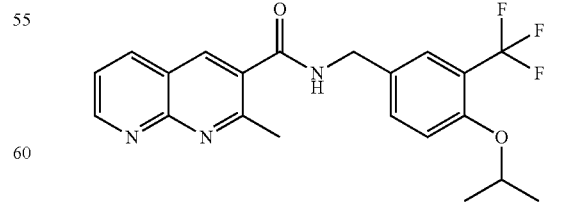

(CH$_2$Cl$_2$/MeOH 20:1)
Yield: 25%
$^1$H NMR (CDCl$_3$) δ 9.04 (m, 1H), 8.08 (m, 1H), 8.07 (s, 1H), 7.60 (m, 1H), 7.55 (m, 1H), 7.44 (m, 1H), 7.02 (d, 1H), 6.66 (m, 1H), 4.66 (d, 2H), 4.65 (m, 1H), 2.88 (s, 3H), 1.38 (d, 6H).

Example 61

N-(4-Benzamido-3-(trifluoromethyl)benzyl)-2-methyl-1,8-naphthyridine-3-carboxamide

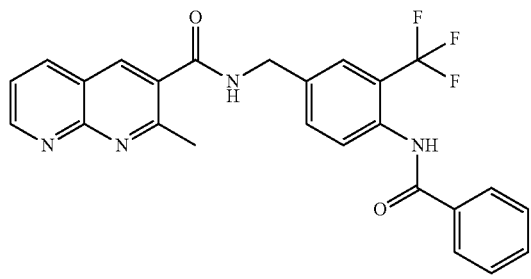 [SMILES: Cc1nc2ncccc2cc1C(=O)NCc1ccc(NC(=O)c2ccccc2)c(C(F)(F)F)c1]

(CH$_2$Cl$_2$/MeOH 20:1)
Yield: 29%
$^1$H NMR (CDCl$_3$) δ 8.96 (m, 1H), 8.28 (d, 1H), 8.21 (s, 1H), 8.14 (s, 1H), 8.03 (m, 1H), 7.83 (m, 2H), 7.75 (m, 1H), 7.60 (m, 3H), 7.52 (m, 2H), 7.41 (m, 1H), 4.73 (d, 2H), 2.86 (s, 3H).

Example 62

2-methyl-N-(4-(4-methylpiperazin-1-yl)-3-(trifluoromethyl)benzyl)-1,8-naphthyridine-3-carboxamide

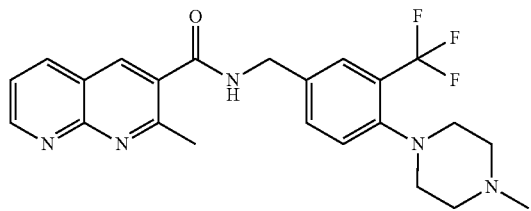 [SMILES: Cc1nc2ncccc2cc1C(=O)NCc1ccc(N2CCN(C)CC2)c(C(F)(F)F)c1]

(CH$_2$Cl$_2$/MeOH 10:1)
Yield: 35%
$^1$H NMR (CDCl$_3$) δ 9.03 (m, 1H), 8.06 (s, 1H), 8.05 (m, 1H), 7.67 (m, 1H), 7.59 (m, 1H), 7.44 (m, 1H), 7.40 (m, 1H), 6.84 (m, 1H), 4.71 (d, 2H), 2.97 (m, 4H), 2.87 (s, 3H), 2.60 (bs, 4H), 2.38 (s, 3H).

Example 63

2-Methyl-N-(4-(tetrahydro-2H-pyran-4-yloxy)-3-(trifluoromethyl)benzyl)-1,8-naphthyridine-3-carboxamide

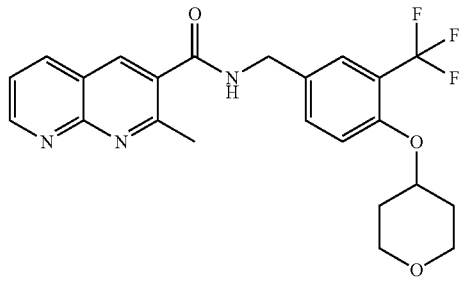 [SMILES: Cc1nc2ncccc2cc1C(=O)NCc1ccc(OC2CCOCC2)c(C(F)(F)F)c1]

(CH$_2$Cl$_2$/MeOH 20:1)
Yield: 26%
$^1$H NMR (CDCl$_3$) δ 8.88 (m, 1H), 7.90 (m, 2H), 7.63 (m, 1H), 7.54 (m, 2H), 7.34 (m, 1H), 6.98 (d, 1H), 4.67 (m, 3H), 3.94 (m, 2H), 3.63 (m, 2H), 2.76 (s, 1H), 2.01 (m, 2H), 1.84 (m, 2H).

Example 64

N-(4-(Dimethylamino)-3-(trifluoromethyl)benzyl)-2-methyl-1,8-naphthyridine-3-carboxamide

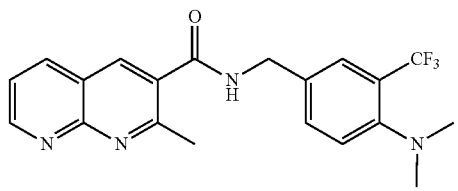 [SMILES: Cc1nc2ncccc2cc1C(=O)NCc1ccc(N(C)C)c(C(F)(F)F)c1]

(CH$_2$Cl$_2$/MeOH 15:1)
Yield: 69%
$^1$H NMR (CDCl$_3$) δ 8.84 (m, 1H), 7.89 (s, 1H), 7.86 (m, 1H), 7.68 (m, 1H), 7.64 (d, 1H), 7.56 (m, 1H), 7.31 (m, 2H), 4.68 (d, 2H), 2.74 (s, 3H), 2.73 (s, 6H).

Example 65

2-Methyl-N-(4-(methylsulfonyl)-3-(trifluoromethyl)benzyl)-1,8-naphthyridine-3-carboxamide

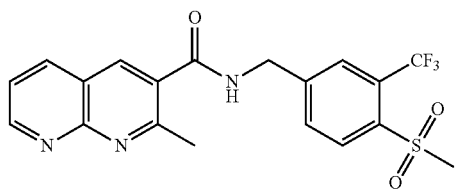 [SMILES: Cc1nc2ncccc2cc1C(=O)NCc1ccc(S(C)(=O)=O)c(C(F)(F)F)c1]

(CH$_2$Cl$_2$/CH$_3$OH) 10:1
Yield: 65%
$^1$H NMR (CDCl$_3$) δ 8.81 (m, 1H), 8.75 (m, 1H), 8.26 (s, 1H), 8.00 (m, 1H), 7.97 (m, 1H), 7.81 (brs, 1H), 7.68 (m, 1H), 7.34 (m, 1H), 4.78 (d, 2H), 3.09 (s, 3H), 2.27 (s, 3H).

Example 66

N-(4-cyclopentylbenzyl)-2-methyl-1,8-naphthyridine-3-carboxamide

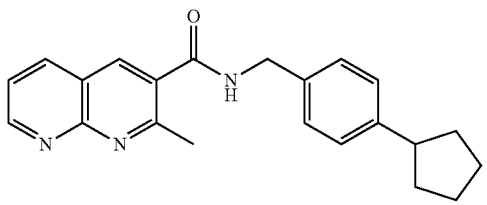 [SMILES: Cc1nc2ncccc2cc1C(=O)NCc1ccc(C2CCCC2)cc1]

(CH$_2$Cl$_2$/MeOH 30:1)
Yield: 80%
$^1$H NMR (400 MHz, CDCl$_3$) δ 8.85 (m, 1H), 7.95 (m, 1H), 7.94 (m, 1H), 7.34 (m, 1H), 7.33 (d, 2H), 7.25 (d, 2H), 7.13 (m, 1H), 4.64 (d, 2H), 3.01 (m, 1H), 2.70 (s, 3H), 2.08 (m, 2H), 1.79 (m, 2H), 1.72 (m, 2H), 1.58 (m, 2H).

Example 67

(S)-2-Methyl-N-(4-(3-methylmorpholino)benzyl)-1,8-naphthyridine-3-carboxamide

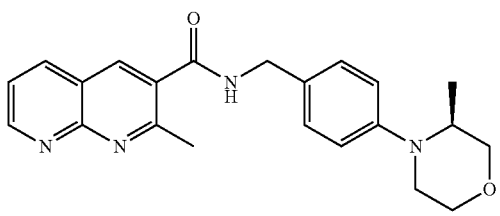 [SMILES: Cc1nc2ncccc2cc1C(=O)NCc1ccc(N2CCOC[C@@H]2C)cc1]

(CH$_2$Cl$_2$/CH$_3$OH 16:1)
Yield: 56%
$^1$H NMR (CDCl$_3$) δ 8.82 (m, 1H), 7.88 (m, 2H) 7.30 (m, 3H), 6.85 (d, 2H), 4.58 (d, 2H), 3.95 (m, 1H), 3.82 (m, 1H), 3.71 (m, 3H), 3.09 (m, 2H), 2.75 (s, 3H), 1.05 (d, 3H).

Example 68

(R)-2-methyl-N-(4-(3-methylmorpholino)benzyl)-1,8-naphthyridine-3-carboxamide

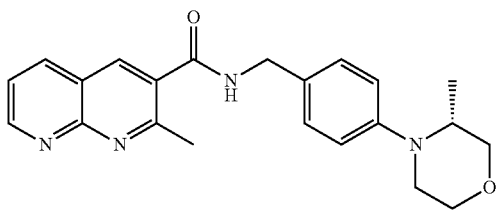 [SMILES: Cc1nc2ncccc2cc1C(=O)NCc1ccc(N2CCOC[C@H]2C)cc1]

(CH$_2$Cl$_2$/MeOH 20:1)
Yield: 54%
$^1$H NMR (CDCl$_3$) δ 8.88 (m, 1H), 7.94 (m, 2H), 7.33 (m, 3H), 7.01 (m, 1H), 6.87 (d, 2H), 4.60 (d, 2H), 3.98 (m, 1H), 3.80 (m, 1H), 3.71 (m, 3H), 3.11 (m, 2H), 2.79 (s, 1H), 1.07 (d, 3H).

Example 69

N-(4-(4-Hydroxypiperidin-1-yl)-3-(trifluoromethyl)benzyl)-2-methyl-1,8-naphthyridine-3-carboxamide

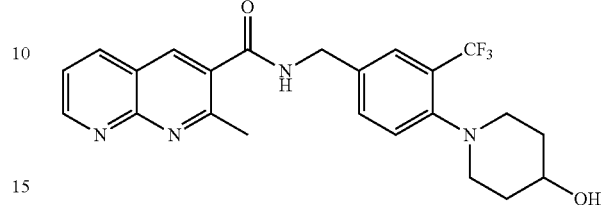

(CH$_2$Cl$_2$/CH$_3$OH 16:1→10:1)
Yield: 56%
$^1$H NMR (CDCl$_3$) δ 9.00 (m, 1H), 8.01 (m, 2H) 7.67 (s, 1H), 7.59 (d, 1H), 7.41 (m, 1H), 7.36 (d, 1H), 4.71 (d, 2H), 3.86 (m, 1H), 3.08 (m, 2H), 2.81 (m, 5H), 2.01 (m, 2H), 1.74 (m, 2H).

Example 70

2-Methyl-N-(4-(1,1,1-trifluoropropan-2-yloxy)benzyl)-1,8-naphthyridine-3-carboxamide

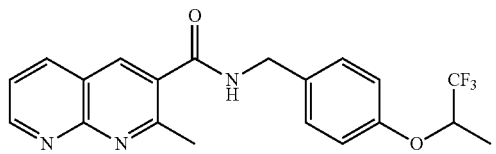 [SMILES: Cc1nc2ncccc2cc1C(=O)NCc1ccc(OC(C)C(F)(F)F)cc1]

(CH$_2$Cl$_2$/CH$_3$OH 16:1)
Yield: 69%
$^1$H NMR (CDCl$_3$) δ 8.84 (m, 1H), 7.90 (m, 2H) 7.35 (m, 3H), 6.95 (d, 2H), 4.64 (m, 3H), 2.76 (s, 3H), 1.50 (d, 3H).

Example 71

2-Methyl-N-(4-(2-methylpiperidin-1-yl)benzyl)-1,8-naphthyridine-3-carboxamide

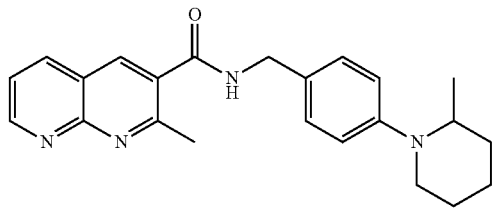 [SMILES: Cc1nc2ncccc2cc1C(=O)NCc1ccc(N2CCCCC2C)cc1]

(CH$_2$Cl$_2$/MeOH 94:6)
Yield: 42%
$^1$H NMR (CDCl$_3$) δ 9.08 (dd, 1H), 8.12 (m, 2H), 7.46 (dd, 1H), 7.28 (d, 2H), 6.93 (d, 2H), 6.25 (bs, 1H), 4.60 (d, 2H), 3.98 (m, 1H), 3.26 (m, 1H), 2.91 (m, 4H), 1.88 (m, 1H), 1.77 (m, 1H), 1.61 (m, 4H), 1.01 (d, 3H).

Example 72

N-(4-(2-(Hydroxymethyl)piperidin-1-yl)benzyl)-2-methyl-1,8-naphthyridine-3-carboxamide

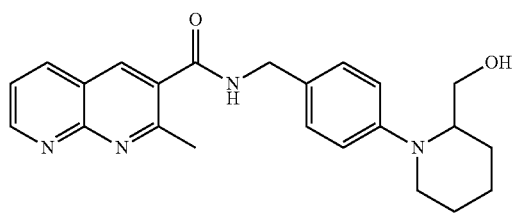 [SMILES: Cc1nc2ncccc2cc1C(=O)NCc1ccc(N2CCCCC2CO)cc1]

(CH$_2$Cl$_2$/MeOH 95:5)
Yield: 12%
$^1$H NMR (CDCl$_3$) δ 8.98 (dd, 1H), 8.03 (m, 2H), 7.40 (dd, 1H), 7.25 (d, 2H), 6.97 (d, 2H), 6.80 (bs, 1H), 4.57 (d, 2H), 3.82 (m, 2H), 3.61 (m, 1H), 3.40 (m, 1H), 3.09 (m, 1H), 2.82 (s, 3H), 1.74 (m, 6H).

Example 73

N-(4-(4-Acetylpiperazin-1-yl)-3-(trifluoromethyl)benzyl)-2-methyl-1,8-naphthyridine-3-carboxamide

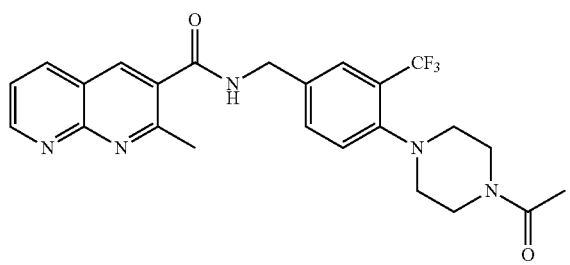 [SMILES: CC(=O)N1CCN(c2ccc(CNC(=O)c3cc4cccnc4nc3C)cc2C(F)(F)F)CC1]

(CH$_2$Cl$_2$/MeOH 95:5→90:10)
Yield: 52%
$^1$H NMR (CDCl$_3$) δ 9.09 (dd, 1H), 8.18 (m, 2H), 7.70 (d, 1H), 7.63 (dd, 1H), 7.50 (dd, 1H), 7.34 (d, 1H), 6.91 (bs, 1H), 4.73 (d, 2H), 3.75 (t, 2H), 3.61 (t, 2H), 2.90 (m, 7H), 2.14 (s, 3H)

Example 74

N-(4-(4,4-Dimethylpiperidin-1-yl)benzyl)-2-methyl-1,8-naphthyridine-3-carboxamide

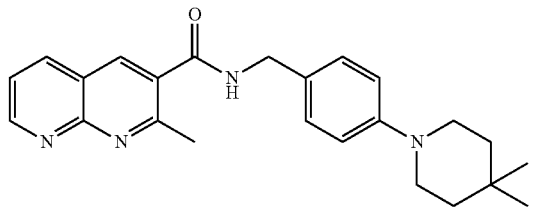 [SMILES: Cc1nc2ncccc2cc1C(=O)NCc1ccc(N2CCC(C)(C)CC2)cc1]

(CH$_2$Cl$_2$/CH$_3$OH 15:1)
Yield: 58%
$^1$H NMR (CDCl$_3$) δ 8.89 (m, 1H), 7.95 (m, 2H) 7.35 (m, 1H), 7.27 (d, 2H), 6.99 (br, 1H), 6.92 (d, 2H), 4.58 (d, 2H), 3.16 (m, 4H), 2.79 (s, 3H), 1.52 (m, 4H), 0.98 (s, 6H).

Example 75

N-(4-(4,4-dimethylpiperidin-1-yl)-3-fluorobenzyl)-2-methyl-1,8-naphthyridine-3-carboxamide

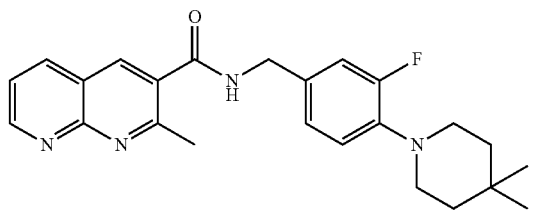 [SMILES: Cc1nc2ncccc2cc1C(=O)NCc1ccc(N2CCC(C)(C)CC2)c(F)c1]

(CH$_2$Cl$_2$/MeOH 95:5)
Yield: 34%
$^1$H NMR (CDCl$_3$) δ 8.81 (m, 1H), 7.88 (s, 1H), 7.85 (m, 1H), 7.69 (m, 1H), 7.30 (m, 1H), 7.06 (m, 2H), 6.91 (t, 1H), 4.57 (d, 2H), 2.99 (m, 4H), 2.73 (s, 3H), 1.53 (m, 4H), 0.98 (s, 6H).

Example 76

N-(3-cyano-4-(4,4-dimethylpiperidin-1-yl)benzyl)-2-methyl-1,8-naphthyridine-3-carboxamide

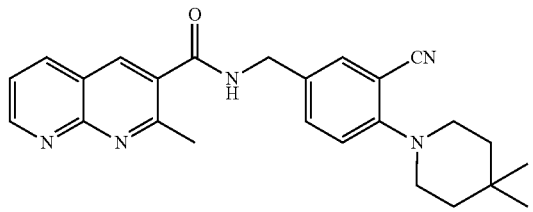

(CH$_2$Cl$_2$/MeOH 95:5)
Yield: 20%
$^1$H NMR (CDCl$_3$) δ 8.96 (m, 1H), 8.08 (s, 1H), 8.01 (m, 1H), 7.55 (m, 3H), 7.41 (m, 1H), 7.00 (d, 1H), 4.61 (d, 2H), 3.17 (m, 4H), 2.82 (s, 3H), 1.58 (m, 4H), 1.01 (s, 6H).

Example 77

N-(4-(Cyclopentyloxy)benzyl)-2-methyl-1,8-naphthyridine-3-carboxamide

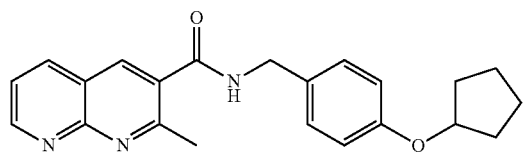 [SMILES: Cc1nc2ncccc2cc1C(=O)NCc1ccc(OC2CCCC2)cc1]

(CH$_2$Cl$_2$/CH$_3$OH 16:1)
Yield: 60%
$^1$H NMR (CDCl$_3$) δ 8.87 (m, 1H), 7.94 (m, 2H) 7.34 (m, 1H), 7.29 (d, 2H), 7.12 (br, 1H), 6.85 (d, 2H), 4.75 (m, 1H), 4.59 (d, 2H), 2.78 (s, 3H), 1.95-1.73 (m, 6H), 1.62 (m, 2H).

Example 78

N-(3-fluoro-4-(4-methoxy-4-methylpiperidin-1-yl)benzyl)-2-methyl-1,8-naphthyridine-3-carboxamide

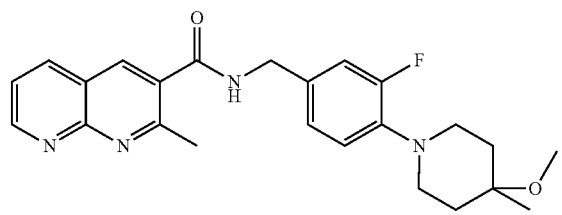 [SMILES: COC1(C)CCN(c2ccc(CNC(=O)c3cc4cccnc4nc3C)cc2F)CC1]

(CH$_2$Cl$_2$/MeOH 30:1)+Sephadex LH20 (CHCl$_3$/MeOH 1:1)
Yield: 20%
$^1$H NMR (CDCl$_3$) δ 8.91 (m, 1H), 7.95 (m, 2H), 7.36 (m, 1H), 7.24 (m, 1H), 7.10 (m, 1H), 7.09 (s, 1H), 6.69 (m, 1H), 4.60 (d, 2H), 3.21 (s, 3H), 3.12 (m, 2H), 3.03 (m, 2H), 2.80 (s, 3H), 1.88 (m, 2H), 1.72 (m, 2H), 1.20 (s, 3H).

Example 79

2-Methyl-N-(4-thiomorpholinobenzyl)-1,8-naphthyridine-3-carboxamide

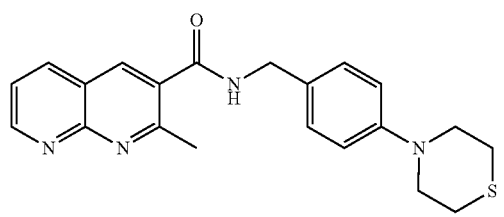 [SMILES: Cc1nc2ncccc2cc1C(=O)NCc1ccc(N2CCSCC2)cc1]

(CH$_2$Cl$_2$/CH$_3$OH 15:1)
Yield: 30%
$^1$H NMR (CDCl$_3$) δ 8.98 (m, 1H), 8.02 (m, 2H) 7.40 (m, 1H), 7.30 (d, 2H), 6.89 (d, 2H), 6.69 (br, 1H), 4.61 (d, 2H), 3.56 (t, 4H), 2.85 (s, 3H), 2.74 (t, 4H).

Example 80

N-(4-(8-oxa-3-azabicyclo[3.2.1]octan-3-yl)-3-fluorobenzyl)-2-methyl-1,8-naphthyridine-3-carboxamide

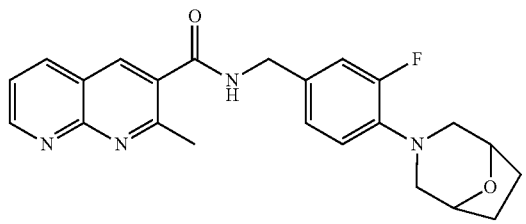 [SMILES: Cc1nc2ncccc2cc1C(=O)NCc1ccc(N2CC3CCC(C2)O3)c(F)c1]

(CH$_2$Cl$_2$/MeOH (97:3→95:5)
Yield: 49%
$^1$H NMR (CDCl$_3$) δ 9.05 (dd, 1H), 8.20 (s, 1H), 8.17 (dd, 1H), 7.49 (dd, 1H), 7.11 (d, 2H), 6.98 (bs, 1H), 6.86 (t, 1H), 4.61 (d, 2H), 4.41 (s, 2H), 3.15 (d, 2H), 3.05 (d, 2H), 2.89 (s, 3H), 2.10 (m, 2H), 1.97 (m, 2H).

Example 81

N-(4-(2,6-dimethylmorpholino)-3-fluorobenzyl)-2-methyl-1,8-naphthyridine-3-carboxamide

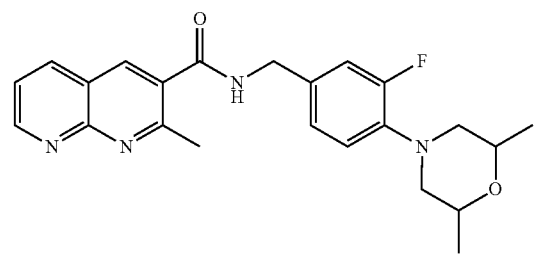 [SMILES: Cc1nc2ncccc2cc1C(=O)NCc1ccc(N2CC(C)OC(C)C2)c(F)c1]

(CH$_2$Cl$_2$/MeOH (95:5)
Yield: 56%
$^1$H NMR (CDCl$_3$) δ 9.05 (dd, 1H), 8.19 (s, 1H), 8.16 (dd, 1H), 7.49 (dd, 1H), 7.15 (m, 2H), 7.95 (m, 2H), 4.63 (d, 2H), 4.41 (s, 2H), 3.89 (m, 2H), 3.28 (d, 2H), 2.87 (s, 3H), 2.46 (t, 2H), 1.24 (d, 6H).

Example 82

N-(3-fluoro-4-(1,4-dioxa-8-azaspiro[4.5]decan-8-yl)benzyl)-2-methyl-1,8-naphthyridine-3-carboxamide

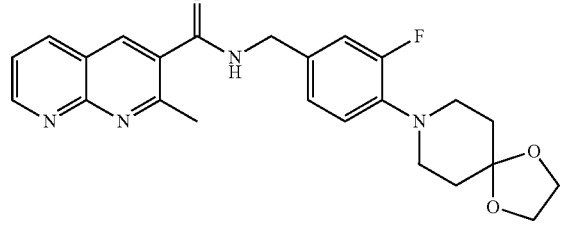

(CH$_2$Cl$_2$/MeOH (95:5)
Yield: 42%

¹H NMR (CDCl₃) δ 9.05 (dd, 1H), 8.15 (s, 1H), 8.13 (dd, 1H), 7.47 (dd, 1H), 7.12 (m, 3H), 6.82 (bs, 1H), 4.62 (d, 2H), 4.01 (s, 4H), 3.22 (m, 4H), 2.89 (s, 3H), 1.93 (m, 4H).

Example 83

N-(4-(4,4-difluoropiperidin-1-yl)-3-fluorobenzyl)-2-methyl-1,8-naphthyridine-3-carboxamide

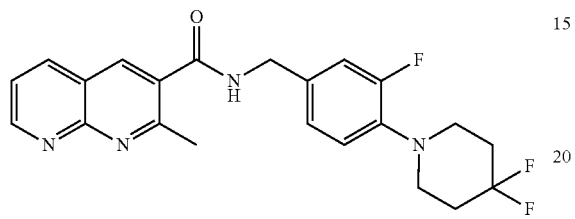

Crude was washed with EtOAc

Yield: 75%

¹H NMR (CDCl₃) δ 9.05 (dd, 1H), 8.13 (s, 1H), 8.11 (dd, 1H), 7.47 (dd, 1H), 7.15 (m, 2H), 6.98 (t, 1H), 6.84 (bs, 1H), 4.64 (d, 2H), 3.21 (m, 4H), 2.88 (s, 3H), 2.17 (m, 4H).

Example 84

2-Methyl-N-(4-(1,1-dioxothiomorpholino)benzyl)-1,8-naphthyridine-3-carboxamide

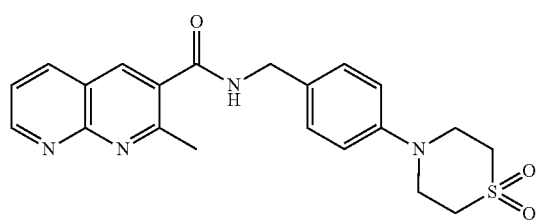 [SMILES: Cc1nc2ncccc2cc1C(=O)NCc1ccc(N2CCS(=O)(=O)CC2)cc1]

(CH₂Cl₂/CH₃OH 16:1)

Yield: 29%

¹H NMR (CDCl₃) δ 9.03 (d, 1H), 8.09 (m, 2H), 7.45 (m, 1H), 7.37 (d, 2H), 6.93 (d, 2H), 6.81 (br, 1H), 4.63 (d, 2H), 3.86 (t, 4H), 3.10 (t, 4H), 2.87 (s, 3H).

Scheme 17

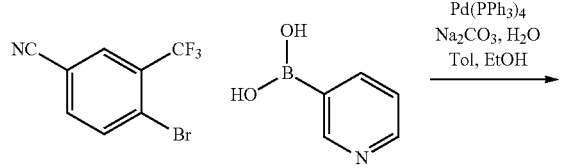

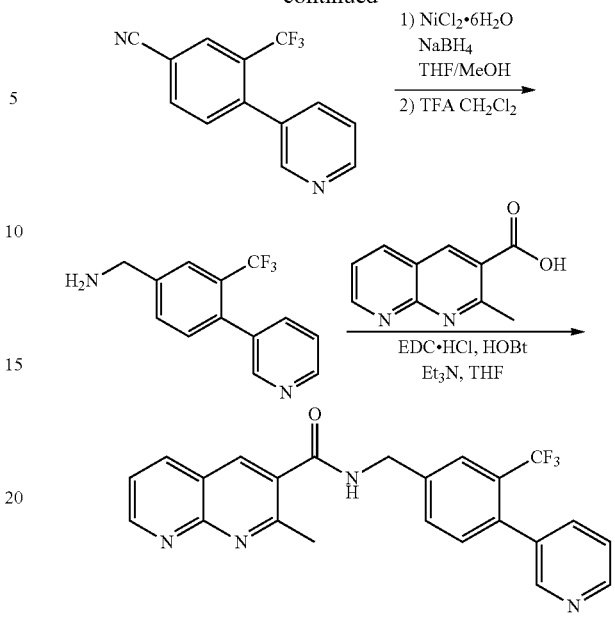

4-(Pyridin-3-yl)-3-(trifluoromethyl)benzonitrile

The title substance was synthesized using the general procedure B for the coupling of aryl bromides with boronic acids. Purification was done using flash column chromatography (Pet. Ether/EtOAc 1:1→100% EtOAc) to give the title substance in 85% yield.

¹H NMR (CDCl₃) δ 8.72 (m, 1H), 8.58 (bs, 1H), 8.10 (bs, 1H), 7.92 (m, 1H), 7.68-7.66 (m, 1H), 7.51 (d, 1H), 7.43-7.39 (m, 1H).

(4-(Pyridin-3-yl)-3-(trifluoromethyl)phenyl)methanamine

The title substance was synthesized using the general procedure F, (see above and scheme 16), for the reduction of benzonitriles to benzylamines and used without further purification.

¹H NMR (CD₃OD) δ 8.67 (m, 1H), 8.54 (bs, 1H), 8.00 (bs, 1H), 7.94-7.89 (m, 1H), 7.84-7.80 (m, 1H), 7.64-7.59 (m, 1H), 7.54 (d, 1H), 7.81 (s, 2H).

Example 85

2-Methyl-N-(4-(pyridin-3-yl)-3-(trifluoromethyl)benzyl)-1,8-naphthyridine-3-carboxamide The title substance was synthesized following the general amide coupling procedure, c.f. scheme 13. Purification was done by flash chromatography (CH₂Cl₂/MeOH 95:5→90:10) to give the title substance in 44% yield.

¹H NMR (CDCl₃) δ 8.05 (m, 1H), 8.57 (m, 1H), 8.44 (bs, 1H), 8.11 (s, 1H), 8.06 (m, 1H), 7.86 (bs, 1H), 7.73-7.70 (m, 1H), 7.69-7.64 (m, 1H), 7.46 (m, 1H), 7.40-7.27 (m, 3H), 4.85 (d, 2H), 2.90 (s, 3H).

Scheme 18

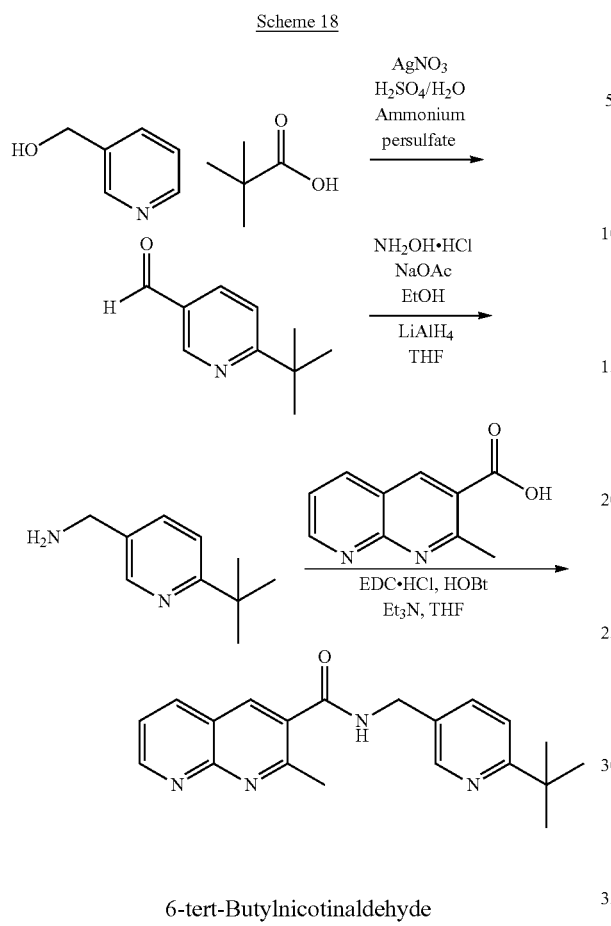

6-tert-Butylnicotinaldehyde

3-Pyridinemethanol (2.2 g, 20.2 mmol), pivalic acid (10.3 g, 100.8 mmol) and silver nitrate (0.68, 4.0 mmol) were suspended in 10% aqueous $H_2SO_4$ (20 ml). Ammonium persulfate (9.2 g, 40.3 mmol) in $H_2O$ (40 ml) was added to the mixture. The mixture was stirred at r.t. for 2.0 h. $NH_4OH$ was added until pH=9. The product was extracted with EtOAc. The combined organic extracts were washed with water, dried ($MgSO_4$), filtered and concentrated. Purification was done by flash chromatography (Pet. Ether/EtOAc 70:30) to give the title substance in 43% yield.

$^1$H NMR (CDCl$_3$) δ 10.08 (s, 1H), 9.01 (bs, 1H), 8.10 (m, 1H), 7.51 (d, J=8.4 Hz, 1H), 1.40 (s, 9H).

(6-tert-Butylpyridin-3-yl)methanamine

To a solution of 6-tert-butylnicotinaldehyde (683 mg, 4.18 mmol) in EtOH hydroxylamine hydrochloride (249.0 g, 5.02 mmol) and sodium acetate (412.0 mg, 5.02 mmol) were added. The mixture was heated to reflux and stirred for 1.0 h. The mixture was diluted with EtOAc, washed with $H_2O$, dried ($MgSO_4$), filtered and concentrated to dryness. The residue was then dissolved in anhydrous THF under $N_2$. LiAlH$_4$ (1.0 M in THF) (5.0 ml) was slowly added to the solution. The mixture was stirred at r.t. for 24 h. Then it was carefully poured into MeOH (70 ml), the solvent was removed and the residue was extracted with MeOH. The solvent was removed yielding 480 mg of the title substance (70%).

$^1$H NMR (CD$_3$OD) δ 8.57 (d, 1H), 7.89 (m, 1H), 7.34 (d, 1H), 4.15 (s, 2H), 1.37 (s, 9H).

Example 86

N-((6-tert-Butylpyridin-3-yl)methyl)-2-methyl-1,8-naphthyridine-3-carboxamide

The title substance was synthesized using the general amide coupling procedure, (see above and c.f. scheme 9). Purification was done by flash chromatography ($CH_2Cl_2$/MeOH 95:5→90:10) to give the title substance in 36% yield.

$^1$H NMR (CDCl$_3$) δ 9.06 (m, 1H), 8.61 (d, 1H), 8.12 (s, 1H), 8.10 (m, 1H), 7.72 (m, 1H), 7.46 (m, 1H), 7.34 (d, 1H), 6.60 (m, 1H), 4.71 (d, 2H), 2.90 (s, 3H), 1.38 (s, 9H).

Scheme 19

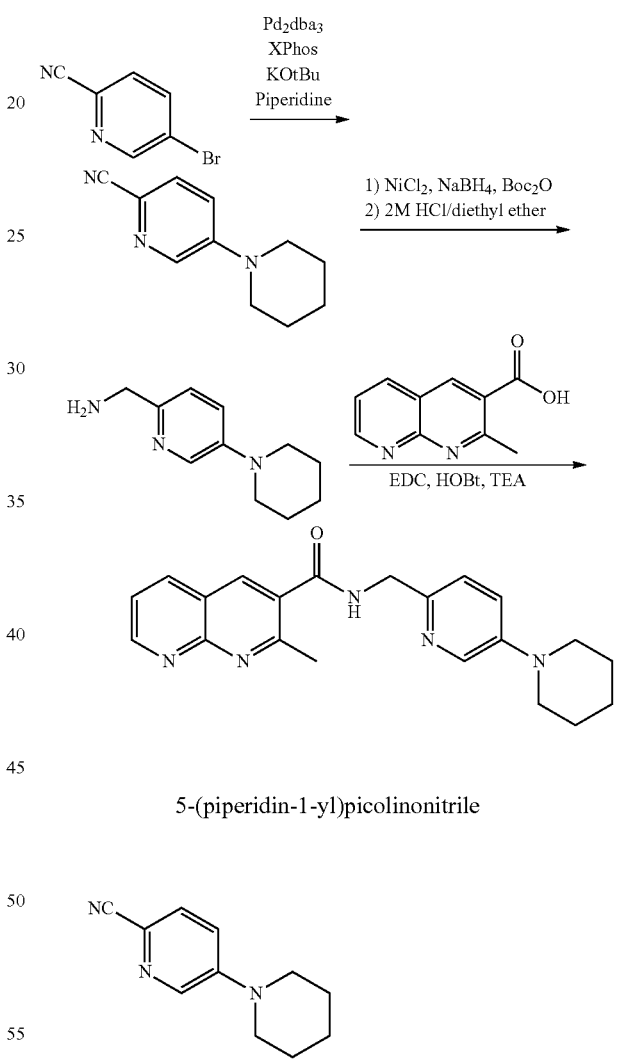

5-(piperidin-1-yl)picolinonitrile

A solution of 500 mg (2.73 mmol) 5-bromopicolinonitrile, 63 mg (0.07 mmol) Pd$_2$dba$_3$ and 130 mg (0.27 mmol) 2-dicyclohexylphosphino-2',4',6'-triisopropylbiphenyl in 20 ml DME was stirred and degassed with $N_2$ for 10 min. 1.45 g (6.83 mmol) K$_3$PO$_4$ and 297 µl (3.0 mmol) piperidine were added. The mixture was heated at 80° C. under $N_2$ over night. The mixture was cooled to r.t. and filtered through a plug of SiO$_2$ with $CH_2Cl_2$/MeOH 9:1. The filtrate was concentrated and purified by flash chromatography (SiO$_2$, Pet. ether/EtOAc 4:1→1:1) to afford 323 mg (63%, yellow oil).

$^1$H NMR (CDCl$_3$) δ 8.28 (d, 1H), 7.47 (d, 1H), 7.05 (m, 1H), 3.37 (m, 4H), 1.69 (m, 6H).

Example 87

2-methyl-N-((5-(piperidin-1-yl)pyridin-2-yl)methyl)-1,8-naphthyridine-3-carboxamide

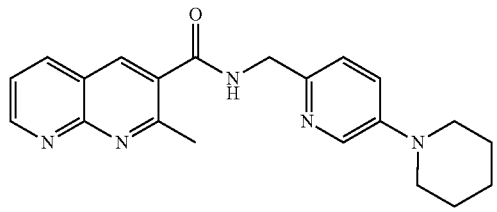 [SMILES: Cc1nc2ncccc2cc1C(=O)NCc1ccc(N2CCCCC2)cn1]

323 mg (1.73 mmol) 5-(piperidin-1-yl)picolinonitrile was reduced according to the general procedure with NiCl$_2$ and NaBH$_4$. The intermediate Boc-protected amine was treated with 2M HCl in diethyl ether to remove the Boc group. The crude was collected by filtration to yield 242 mg (61%) of the title compound as a grey white solid. Used without further purification. The obtained (5-bromopyridin-2-yl)methanamine hydrochloride salt was coupled with 2-methyl-1,8-naphthyridine-3-carboxylic acid according to standard procedures to afford the final product.

(CH$_2$Cl$_2$/MeOH 20:1)
Yield: 14%
$^1$H NMR (CDCl$_3$) δ 9.12 (m, 1H), 8.27 (s, 1H), 8.19 (s, 1H), 8.18 (m, 1H), 7.48 (m, 1H), 7.39 (m, 1H), 7.25 (m, 1H), 4.71 (d, 2H), 3.19 (m, 4H), 2.94 (s, 3H), 1.71 (m, 4H), 1.61 (m, 2H).

Scheme 20

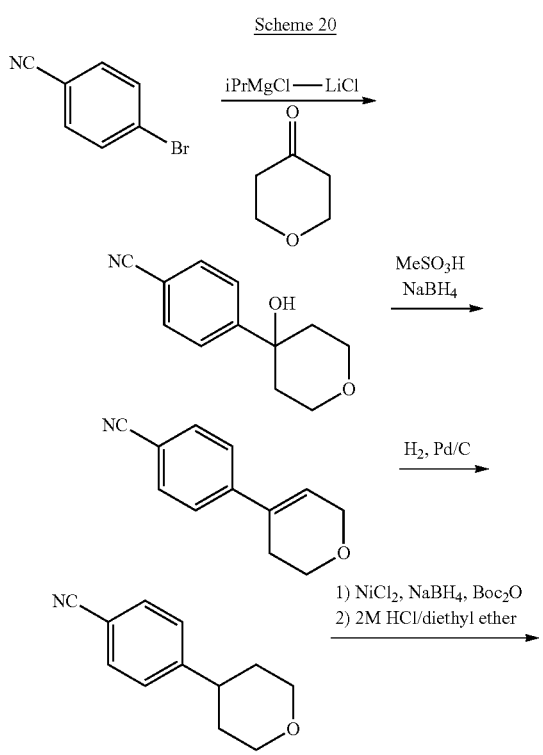

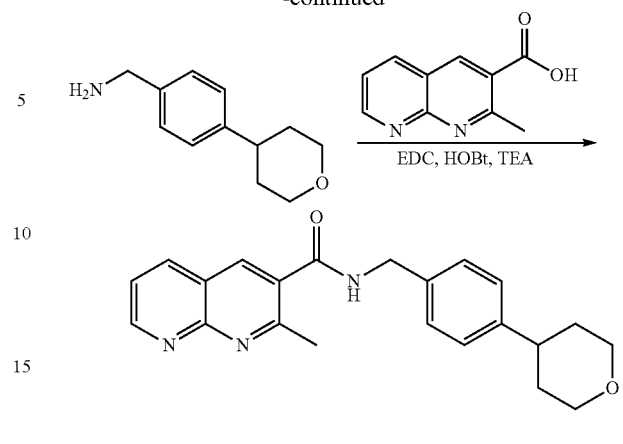

4-(4-hydroxytetrahydro-2H-pyran-4-yl)benzonitrile

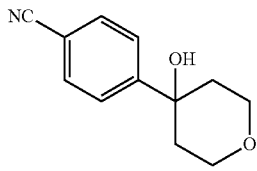

11.2 ml (7.50 mmol) of a 0.67 M iPrMgCl.LiCl solution in THF [Prepared by adding 5 ml (10 mmol) iPrMgCl (2.0 M in THF) to a solution of 424 mg (10 mmol) LiCl in 5 ml THF at r.t. followed by stirring for 1 h] was added to a solution of 1.24 g (6.81 mmol) 4-bromo benzonitrile in 10 ml THF at 0° C. Stirred at r.t. for 2 h. 691 μl (7.49 mmol) dihydro-2H-pyran-4(3H)-one was added and stirring continued for 45 min. NH$_4$Cl (sat) was added and the mixture was extracted twice with diethyl ether. The organic phase was dried (MgSO$_4$) and concentrated. Flash chromatography (Pet. ether/EtOAc 2:1→1:1) gave 654 mg (47%).

$^1$H NMR (CDCl$_3$) δ 7.68 (d, 2H), 7.63 (d, 2H), 3.93 (m, 14H), 2.18 (m, 2H), 1.64 (m, 2H).

4-(3,6-dihydro-2H-pyran-4-yl)benzonitrile

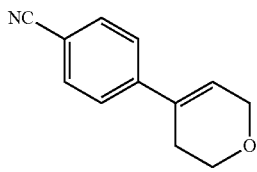 [SMILES: N#Cc1ccc(C2=CCOCC2)cc1]

12.65 ml (195 mmol) MeSO$_3$H in 10 ml CH$_2$Cl$_2$ was slowly added to a mixture of 611 mg (3.0 mmol) 4-(4-hydroxytetrahydro-2H-pyran-4-yl)benzonitrile and 1.13 g (30 mmol) NaBH$_4$ in 15 ml CH$_2$Cl$_2$ at 0° C. Stirred for 1 h. 2M NaOH was added until pH>10. The mixture was extracted with CH$_2$Cl$_2$. The organic phase was dried (MgSO$_4$) and concentrated. The crude product (450 mg, 81%) was used directly in the next step.

$^1$H NMR (CDCl$_3$) δ 7.64 (m, 2H), 7.47 (m, 2H), 6.28 (m, 1H), 4.35 (m, 2H), 3.95 (m, 2H), 2.52 (m, 2H).

4-(tetrahydro-2H-pyran-4-yl)benzonitrile

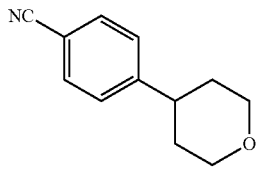

450 mg (2.43 mmol) 4-(3,6-dihydro-2H-pyran-4-yl)benzonitrile was dissolved in 15 ml EtOH and 50 mg 10% Pd/C was added. The reaction mixture was stirred under H$_2$ (4 bar) over night at room temperature. The mixture was filtered through celite with EtOAc washing. The filtrate was concentrated and the crude product 340 mg (75% yield) was used directly in the next step.
$^1$H NMR (CD$_3$OD$_3$) δ 7.67 (d, 2H), 7.45 (d, 2H), n 4.05 (m, 2H), 3.57 (m, 2H), 2.91 (m, 1H), 1.78 (m, 4H).

(4-(tetrahydro-2H-pyran-4-yl)phenyl)methanamine

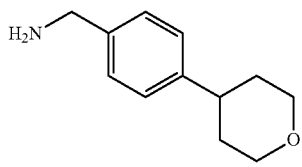 [SMILES: NCc1ccc(C2CCOCC2)cc1]

340 mg (1.82 mmol) 4-(tetrahydro-2H-pyran-4-yl)benzonitrile was reduced according to the general procedure with NiCl$_2$ and NaBH$_4$. The intermediate Boc-protected amine was treated with 2M HCl in diethyl ether to remove the Boc group. The crude was treated with aqueous NaHCO$_3$ and extracted with CH$_2$Cl$_2$ to afford after drying and evaporation 234 mg (67%) of the title compound as an oil.
$^1$H NMR (CDCl$_3$) δ 7.19-7.28 (m, 4H), 4.30 (d, 2H), 4.08 (m, 2H), 3.54 (m, 2H), 2.75 (m, 1H), 1.81 (m, 4H).

Example 88

2-methyl-N-(4-(tetrahydro-2H-pyran-4-yl)benzyl)-1,8-naphthyridine-3-carboxamide

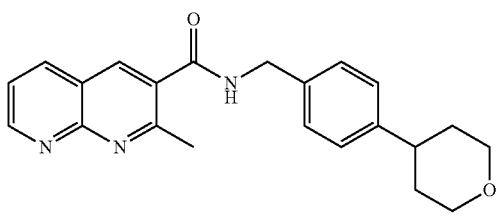 [SMILES: Cc1nc2ncccc2cc1C(=O)NCc1ccc(C2CCOCC2)cc1]

(CH$_2$Cl$_2$/MeOH 20:1)
Yield: 17%
$^1$H NMR (CDCl$_3$) δ 9.05 (m, 1H), 8.18 (s, 1H), 8.14 (m, 1H), 7.47 (m, 1H), 7.39 (d, 2H), 7.26 (d, 2H), 6.69 (m, 1H), 4.69 (d, 2H), 4.09 (m, 2H), 3.47 (m, 2H), 2.90 (s, 1H), 2.79 (m, 1H), 1.76-1.88 (m, 4H).

Scheme 21

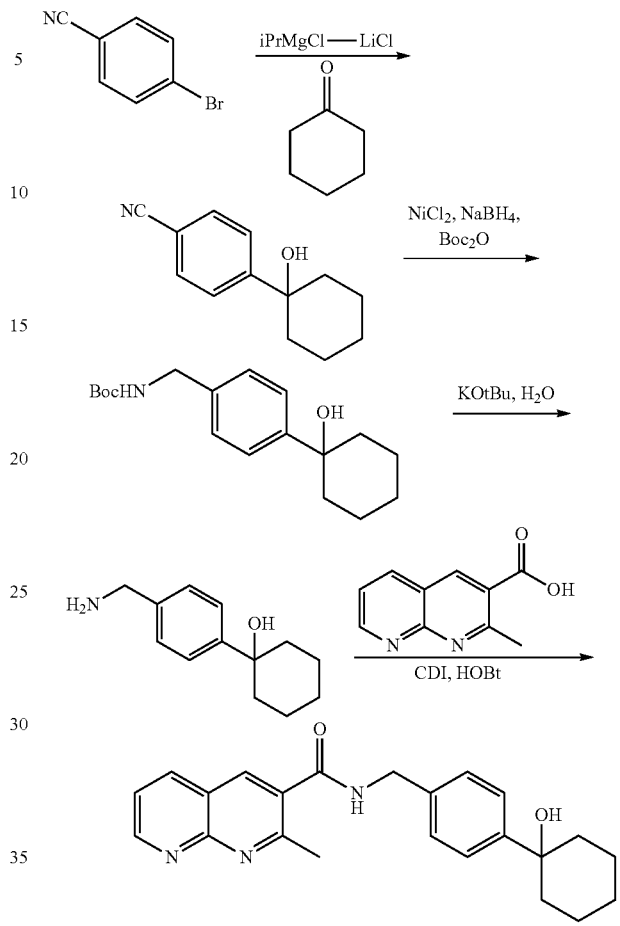

4-(1-hydroxycyclohexyl)benzonitrile

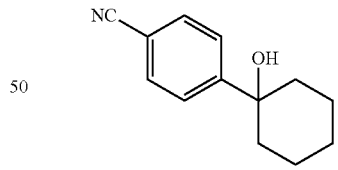

4.4 ml (2.95 mmol) of a 0.67 M iPrMgCl.LiCl solution [Prepared by adding 5 ml (10 mmol) iPrMgCl (2.0 M in THF) to a solution of 424 mg (10 mmol) LiCl in 5 ml THF at r.t. followed by stirring for 1 h] was added to a solution of 530 mg (2.96 mmol) 4-bromo benzonitrile in 5 ml THF at 0° C. Stirred at r.t. for 2 h. 311 µl (3.26 mmol) cyclohexanone was added and stirring continued for 45 min. NH$_4$Cl (sat) was added and the mixture was extracted twice with diethyl ether. The organic phase was dried (MgSO4) and concentrated. Flash chromatography (Pet. ether/EtOAc 5:1) gave 270 mg (45%).
$^1$H NMR (CDCl$_3$) δ 7.63 (s, 4H), 1-67-1.82 (m, 10H).

tert-butyl 4-(1-hydroxycyclohexyl)benzylcarbamate

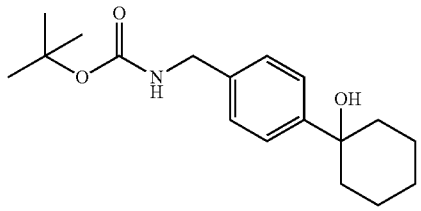 [SMILES: CC(C)(C)OC(=O)NCc1ccc(C2(O)CCCCC2)cc1]

4-(1-hydroxycyclohexyl)benzonitrile was reduced with NiCl$_2$ and NaBH$_4$ in the presence of Boc$_2$O according to the standard procedure.
Yield: 95%
$^1$H NMR (CDCl$_3$) δ 7.48 (m, 1H), 7.27 (m, 2H), 4.32 (d, 2H), 1.71-1.84 (m, 6H), 1.62-1.67 (m, 4H), 1.44 (s, 9H).

1-(4-(aminomethyl)phenyl)cyclohexanol

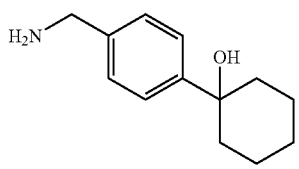 [SMILES: NCc1ccc(C2(O)CCCCC2)cc1]

355 mg (3.16 mmol) KOtBu and 14 μl (0.79 mmol) H$_2$O were added to a solution of 386 mg (0.79 mmol) tert-butyl 4-(1-hydroxycyclohexyl)benzylcarbamate in 3.9 ml THF. Refluxed for 2 h. Cooled to r.t. The reaction was quenched with NH$_4$Cl (sat.) and the pH was adjusted to 10-11 with 2 M NaOH. The mixture was extracted 3 times with EtOAc. The organic phase was dried (MgSO$_4$) and concentrated. Gave 164 mg (quant. yield). Used directly in the next step.
$^1$H NMR (CDCl$_3$) δ 7.46 (d, 2H), 7.29 (d, 2H), 3.87 (s, 2H), 1.75-1.77 (m, 6H), 1.65 (m, 4H).

Example 89

N-(4-(1-hydroxycyclohexyl)benzyl)-2-methyl-1,8-naphthyridine-3-carboxamide

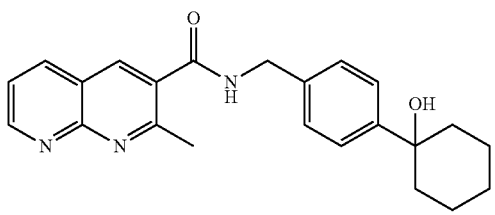 [SMILES: Cc1nc2ncccc2cc1C(=O)NCc1ccc(C2(O)CCCCC2)cc1]

144 mg (0.76 mmol) 2-methyl-1,8-naphthyridine-3-carboxylic acid and 136 mg (0.84 mmol) CDI were refluxed in 5 ml EtOAc for 2 h. The solution was cooled to r.t. and 157 mg (0.76 mmol) 1-(4-(aminomethyl)phenyl)cyclohexanol followed by 5 ml CH$_2$Cl$_2$ was added. The mixture was stirred for 2 days at r.t. Concentrated to dryness and purified by flash chromatography (SiO2, CH$_2$Cl$_2$/MeOH 20:1→10:1) to afford 50 mg (13%) of the title compound.
$^1$H NMR (CDCl$_3$) δ 8.92 (m, 1H), 8.03 (s, 1H), 8.00 (m, 1H), 7.47 (m, 2H), 7.37 (m, 1H), 7.36 (m, 2H), 7.11 (t, 1H), 4.65 (d, 2H), 2.80 (s, 3H), 1.69-1.82 (m, 8H), 1.62-1.66 (m, 2H).

Scheme 22

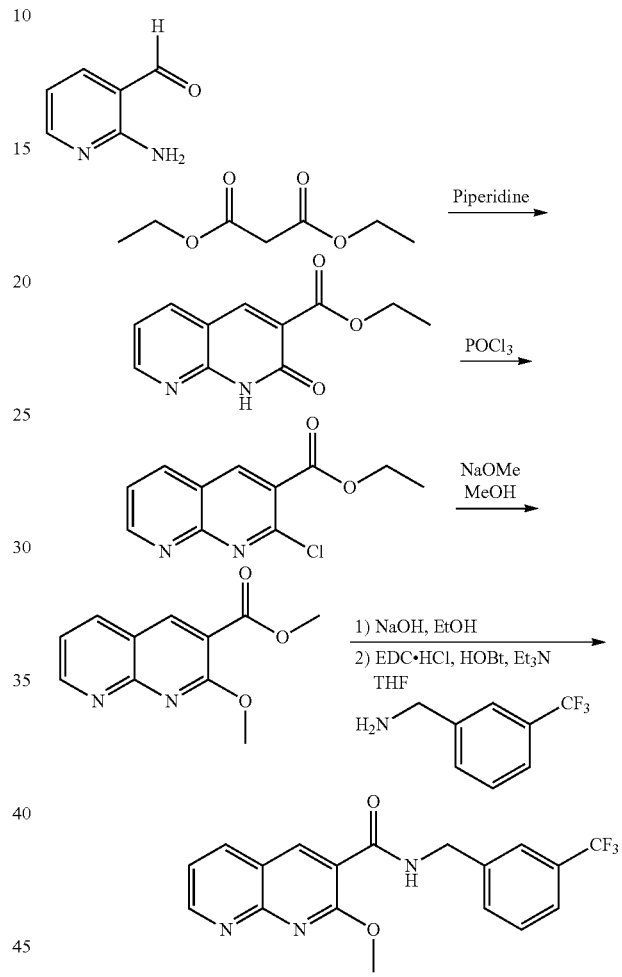

Ethyl 2-oxo-1,2-dihydro-1,8-naphthyridine-3-carboxylate

2-Amino-3-pyridine carboxaldehyde (1.0 g, 8.19 mmol) was suspended in diethylmalonate (6.2 ml, 41.0 mmol) in a screw cap pressure tube. Piperidine (1.6 ml, 16.4 mmol) was added and the tube was sealed. The mixture was heated to 120° C. for 3.0 hours. The mixture was allowed to cool. The precipitate formed was filtered and washed with Et$_2$O to yield 1.62 g (91%) of the title compound.
$^1$H NMR (CD$_3$OD) δ 8.64 (m, 1H), 8.62 (s, 1H), 8.22 (m, 1H), 7.32 (m, 1H), 4.38 (m, 2H), 1.40 (t, 3H).

Ethyl 2-chloro-1,8-naphthyridine-3-carboxylate

Ethyl 2-oxo-1,2-dihydro-1,8-naphthyridine-3-carboxylate (405.0 mg, 1.86 mmol) was suspended in POCl$_3$ (4.5 ml) under N$_2$. The mixture was heated to reflux for 1.5 h, and then it was allowed to cool down and carefully poured over an ice-water mixture. The mixture was neutralized with solid NaOH and the product extracted with EtOAc. The combined organic extracts were dried (MgSO₄), filtered and concentrated. Purification was done by flash chromatography (CH₂Cl₂/MeOH 97:3→95:5) to give 242.6 mg (55%) of the title compound.

¹H NMR (CDCl₃) δ 9.21 (m, 1H), 8.70 (s, 1H), 8.30 (m, 1H), 7.60 (m, 1H), 4.50 (m, 2H), 1.47 (t, 3H).

Methyl 2-methoxy-1,8-naphthyridine-3-carboxylate

Ethyl 2-chloro-1,8-naphthyridine-3-carboxylate (104.0 mg, 0.44 mmol) was dissolved in anhydrous MeOH under N₂. NaOMe (33.2 mg, 0.62 mmol) was added as a solution in MeOH. The mixture was refluxed for 15 h, and then it was allowed to cool. NH₄Cl (sat) was added and the product extracted with EtOAc. The combined organic extracts were dried (MgSO₄), filtered and concentrated to yield 102.0 mg (quant) of the title compound.

¹H NMR (CDCl₃) δ 9.05 (m, 1H), 8.66 (s, 1H), 8.19 (m, 1H), 7.43 (m, 1H), 4.27 (s, 3H), 3.99 (s, 3H).

Example 90

2-Methoxy-N-(3-(trifluoromethyl)benzyl)-1,8-naphthyridine-3-carboxamide

Methyl 2-methoxy-1,8-naphthyridine-3-carboxylate (87.0 mg, 0.40 mmol) was dissolved in MeOH. NaOH (1.2 ml, 1M aqueous solution) was added to the solution and the mixture stirred at room temperature for 18 h. The organic solvent was removed under reduced pressure. The remaining aqueous residue was treated with HCl (1M aqueous solution) until slightly acidic and the product extracted with EtOAc. The combined organic phases were dried over MgSO₄, filtered and concentrated yielding 2-methoxy-1,8-naphthyridine-3-carboxylic acid which was coupled without further purification to 3-(trifluoromethyl)benzylamine using the general amide coupling procedure. The crude product was purified by flash chromatography, CH₂Cl₂/MeOH 96:4, yielding 124 mg (86%) of the title compound.

¹H NMR (CDCl₃) δ 9.10 (s, 1H), 9.06 (m, 1H), 8.41 (m, 1H), 8.29 (m, 1H), 7.65 (bs, 1H), 7.61-7.56 (m, 2H), 7.53-7.45 (m, 2H), 4.80 (d, 2H), 4.32 (s, 3H).

Scheme 23

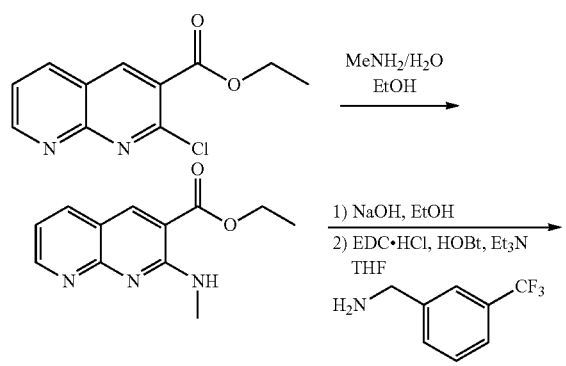

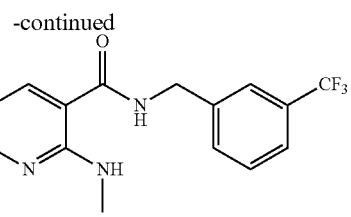

Ethyl 2-(methylamino)-1,8-naphthyridine-3-carboxylate

Ethyl 2-chloro-1,8-naphthyridine-3-carboxylate (100 mg, 0.42 eq.) was dissolved in EtOH. MeNH₂ (71.8 µl, 11.84 M aqueous solution) was added to the solution. The mixture was stirred at r.t. for 18 h. The solvents were removed under reduced pressure. The residue was dissolved in EtOAc and washed with water (×2). The organic extract was dried (MgSO₄), filtered and concentrated to yield 60.2 mg (62%) of the title compound.

¹H NMR (CDCl₃) δ 8.90 (m, 1H), 8.63 (s, 1H), 8.18 (bs, 1H), 7.98 (ddm, 1H), 7.15 (m, 1H), 7.98 (m, 2H), 3.24 (d, 3H), 1.45 (t, 3H).

2-(methylamino)-1,8-naphthyridine-3-carboxylic acid

Ethyl 2-(methylamino)-1,8-naphthyridine-3-carboxylate (58 mg, 0.25 mmol) was dissolved in EtOH. NaOH (0.75 ml, 1M aqueous solution) was added to the solution and the mixture stirred at 40° C. for 5.0 h. The organic solvent was removed under vacuo. The remaining aqueous residue was treated with HCl (1M aqueous solution) until slightly acidic and the product extracted with EtOAc. The combined organic phases were dried over MgSO₄, filtered and concentrated yielding 50.0 mg (quant) of the title compound.

¹H NMR (CD₃OD) δ 9.00 (s, 1H), 8.84 (m, 1H), 7.75 m, 1H), 7.59 (m, 1H), 3.24 (s, 3H).

Example 91

2-(Methylamino)-N-(3-(trifluoromethyl)benzyl)-1,8-naphthyridine-3-carboxamide 2-(Methylamino)-1,8-naphthyridine-3-carboxylic acid was coupled to 3-(trifluoromethyl)benzylamine using the general amide coupling procedure. The crude product was purified by flash chromatography, CH₂Cl₂/MeOH 95:5, yielding 62.4 mg (69%) of the title compound.

¹H NMR (CD₃OD) δ 8.72 (m, 1H), 8.34 (s, 1H), 8.14 (m, 1H), 7.70-7.65 (m, 2H), 7.60-7.53 (m, 2H), 7.24 (m, 1H), 4.66 (s, 2H), 3.12 (s, 3H).

Scheme 24

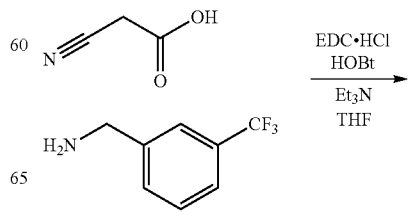

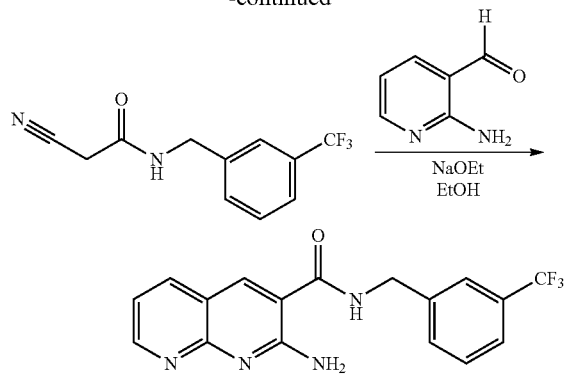

2-Cyano-N-(3-(trifluoromethyl)benzyl)acetamide

Cyanoacetic acid (297.0 mg, 3.5 mmol), N-(3-dimethylaminopropyl)-N'-ethyl-carbodiimide hydrochloride (1.34 g, 7.0 mmol), 1-hydroxybenzotriazole hydrate (641.0 mg, 4.2 mmol) and DIPEA (1.8 g, 14.0 mmol) and 3-(trifluoromethyl)benzylamine (611.0 mg, 3.5 mmol) were suspended in THF. The mixture was heated to 60° for 18 h. Water was added to the mixture and the product extracted with EtOAc, dried over $MgSO_4$ and concentrated. The crude product was purified by flash chromatography, $CH_2Cl_2$/MeOH 98:2, yielding 430.0 mg (51%) of the title compound.

$^1$H NMR ($CDCl_3$) δ 7.60 (m, 4H), 6.52 (bs, 1H), 4.55 (d, 3H), 3.46 (s, 3H).

Example 92

2-Amino-N-(3-(trifluoromethyl)benzyl)-1,8-naphthyridine-3-carboxamide

To a solution of NaOEt prepared by dissolving Na (50 mg, 1.47 mmol) in EtOH (2.5 ml), was added 2-cyano-N-(3-(trifluoromethyl)benzyl)acetamide (297.5 mg, 1.23 mmol) and 2-amino-3-pyridine-carboxaldehyde (150.0 mg, 1.23 mmol). The mixture was refluxed for 30 minutes. The solvent was removed under reduced pressure and the residue chromatographed $CH_2Cl_2$/MeOH 95:5→92:8, yielding 244.5 mg (57%) of the title compound.

$^1$H NMR ($CDCl_3$) δ 8.79 (m, 1H), 8.23 (s, 1H), 7.85 (m, 1H), 7.62-7.47 (m, 4H), 7.29 (bt, 1H), 7.12 (m, 1H), 6.66 (bs, 2H), 4.68 (d, 2H).

Scheme 25

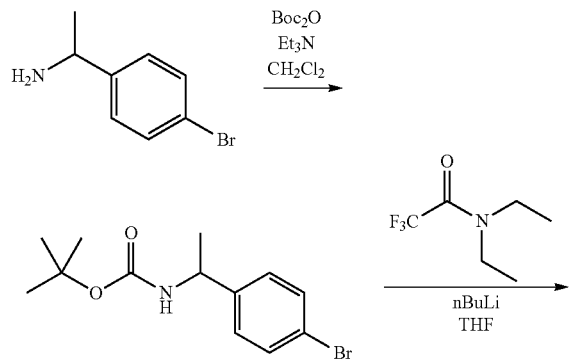

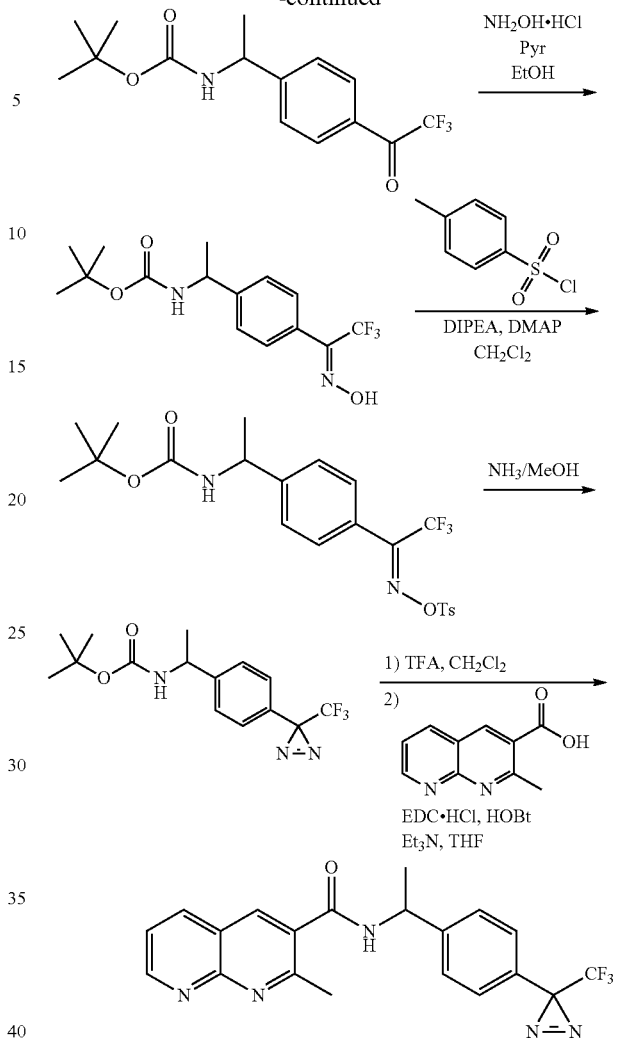

tert-Butyl 1-(4-bromophenyl)ethylcarbamate 1-(4-Bromophenyl)ethanamine (3.58 ml, 25 mmol) and $Et_3N$ (4.39 ml, 31.25 mmol) was dissolved in $CH_2Cl_2$ and cooled to 0° C. To this was added $(Boc)_2O$ (6.0 g, 27.5 mmol) and the resulting solution was stirred 5 minutes at 0° C. for 5 and then 3 h at room temperature. The reaction was washed with HCl (50 ml, 1M) followed by $NaHCO_3$ (sat) (2*50 ml). The organic phase was dried over $MgSO_4$, filtered and evaporated. The residue was purified by precipitation from MeOH/$H_2O$ (10:1) to give 6.35 g (85%) of the title compound as a white powder.

$^1$H NMR ($CDCl_3$) δ 7.45 (d, 2H), 7.18 (d, 2H), 4.83-4.70 (br, 2H), 1.46-1.32 (br, 12H).

tert-Butyl 1-(4-(2,2,2-trifluoroacetyl)phenyl)ethylcarbamate tert-Butyl 1-(4-bromophenyl)ethylcarbamate (6.35 g, 21.2 mmol) was dissolved in dry THF (100 ml) and cooled to −78° C. under an atmosphere of nitrogen. n-Butyllithium (21 ml, 52.9 mmol, 2.5M in hexanes) was added dropwise under 10 minutes and the reaction was stirred at −78° C. for 3 hours. A solution of diethyl trifluoroacetamide (5.0 g, 29.6 mmol) in 10 ml dry THF was added dropwise and the reaction was stirred 1.5 hours at −78° C. Reaction was quenched with NH₄Cl (sat) (50 ml) and H₂O (50 ml) and allowed to reach room temperature. The aqueous phase was separated and extracted with EtOAc (100 ml). The combined organics were washed with NH₄Cl (sat) (2*100 ml), H₂O (100 ml), dried over MgSO₄, filtered and evaporated. Unreacted starting material was removed by precipitation from MeOH/H₂O (9/1). The mother liquor was evaporated and the residue purified by flash chromatography using Pet. Ether/EtOAc (7:1→5:1) as eluent to give 3.09 g (46%) of the title compound as white solids.

¹H NMR (CDCl₃) δ 8.03 (d, 2H), 7.47 (d, 2H), 5.10-4.70 (br, 2H), 1.49-1.33 (br, 12H).

tert-Butyl 1-(4-(2,2,2-trifluoro-1-(hydroxyimino)ethyl)phenyl)ethylcarbamate tert-Butyl 1-(4-(2,2,2-trifluoroacetyl)phenyl)ethylcarbamate (1.02 g, 3.21 mmol) was mixed with NH₂OH*HCl (223 mg, 3.21 mmol) in pyridine (25 ml) and EtOH (12 ml). The mixture was stirred at 80° C. for 16 hours and then evaporated. The residue was dissolved in EtOAc (60 ml), washed with H₂O (2*40 ml), dried over MgSO₄, filtered and evaporated. The product was purified by flash chromatography using CH₂Cl₂/MeOH (20:0→20:1) as eluent to give 640 mg (60%) of the title compound as pale solids.

¹H NMR (CDCl₃) δ 7.51-7.26 (br m, 4H), 5.10-4.70 (br, 2H), 1.49-1.33 (br, 12H).

tert-Butyl 1-(4-(2,2,2-trifluoro-1-(tosyloxyimino)ethyl)phenyl)ethylcarbamate tert-Butyl 1-(4-(2,2,2-trifluoro-1-(hydroxyimino)ethyl)phenyl)ethylcarbamate (640 mg, 1.93 mmol) was dissolved in CH₂Cl₂ (15 ml) together with DIPEA (367 µl, 2.11 mmol) and DMAP (23 mg, 0.19 mmol). The mixture was cooled to 0° C. before slow, portionwise addition of 4-toluenesulfonyl chloride (367 mg, 1.93 mmol). The reaction was allowed to reach room temperature over 2 h, washed with H₂O (4*15 ml), dried over MgSO₄, filtered and evaporated. The product was purified by flash chromatography using Pet. Ether/EtOAc (3:1) as eluent to give 817 mg (87%) of the title compound as pale solids.

¹H NMR (CDCl₃) δ 7.88 (m, 2H), 7.43-7.31 (br m, 6H), 4.99-4.70 (br, 2H), 2.46 (d, 3H), 1.49-1.33 (br, 12H).

tert-Butyl 1-(4-(3-(trifluoromethyl)-3H-diazirin-3-yl)phenyl)ethylcarbamate tert-Butyl 1-(4-(2,2,2-trifluoro-1-(tosyloxyimino)ethyl)phenyl)ethylcarbamate (400 mg, 0.82 mmol) was dissolved in CH₂Cl₂ (5 ml). Ammonia in MeOH (7 ml, 7M) was added and the resulting mixture was stirred at room temperature for 7 days. The reaction was then diluted with water (50 ml) and extracted with CH₂Cl₂ (2*25 ml). Combined organics were dried over MgSO₄, filtered and evaporated. The product was purified by flash chromatography using Pet. Ether/EtOAc (3:1) as eluent to give 125 mg (46%) of the title compound as white solids.

¹H NMR (CDCl₃) δ 7.33 (d, 2H), 7.16 (d, 2H), 4.89-4.73 (br, 2H), 1.45-1.37 (br, 12H).

Example 93

2-Methyl-N-(1-(4-(3-(trifluoromethyl)-3H-diazirin-3-yl)phenyl)ethyl)-1,8-naphthyridine-3-carboxamide tert-Butyl 1-(4-(3-(trifluoromethyl)-3H-diazirin-3-yl)phenyl)ethylcarbamate (125 mg, 0.38 mmol) was dissolved in CH₂Cl₂ (4 ml). TFA (1 ml, 13 mmol) was added and the mixture stirred at r.t. for 1.0 h. The solvents were removed and the residue was coupled without further purification to 2-methyl-1,8-naphthyridine using the general amide coupling procedure. The product was purified by flash chromatography using CH₂Cl₂/MeOH (10:1) as eluent to give 120 mg (79%) of the title compound as white solids (79%).

¹H NMR (CDCl₃) δ 8.85 (m, 1H), 7.98 (d, 1H), 7.69 (m, 1H), 7.60 (m, 3H), 7.27 (m, 1H), 7.21 (d, 2H), 5.32 (m, 1H), 2.65 (s, 3H), 1.66 (d, 1H).

Scheme 26

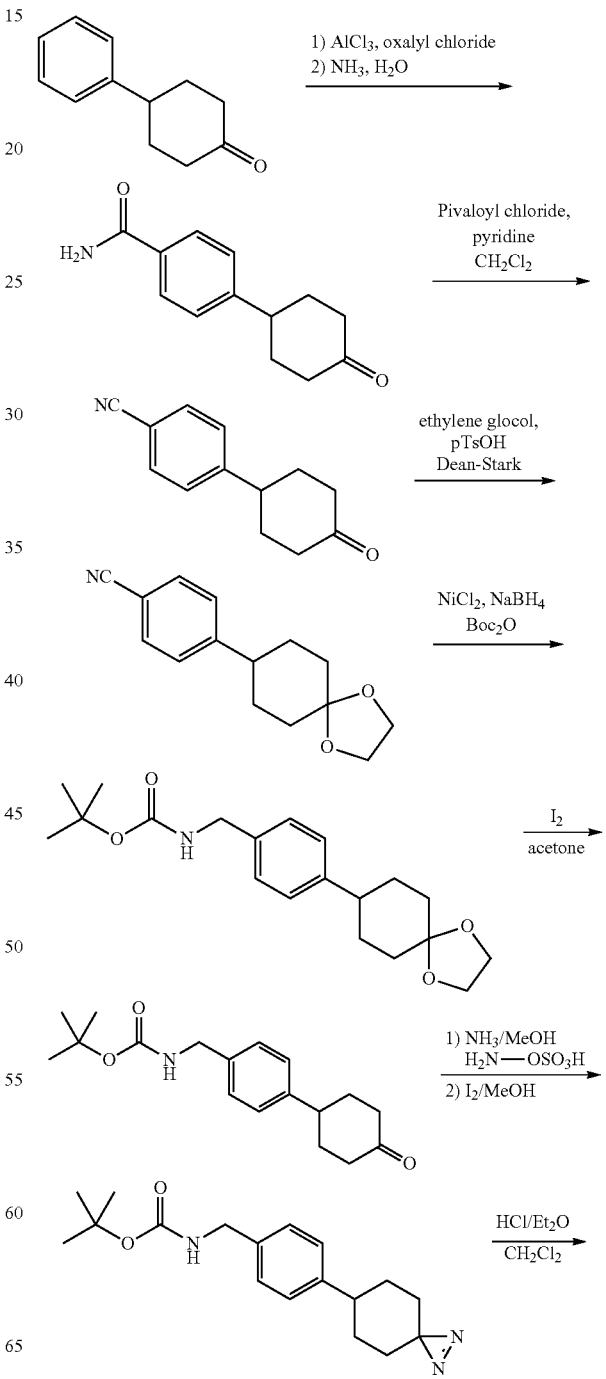

-continued

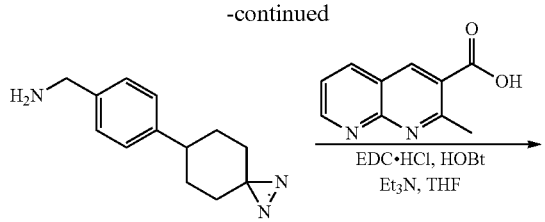

4-(4-oxocyclohexyl)benzamide

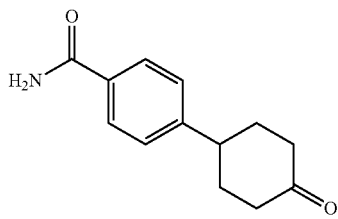 [SMILES: NC(=O)c1ccc(C2CCC(=O)CC2)cc1]

14.24 g (107 mmol) AlCl₃ was added portionwise to a solution of 6.98 g (40 mmol) 4-phenylcyclohexanone and 4.51 ml (53.3 mmol) oxalylchloride in 200 ml CH₂Cl₂ at 0° C. Stirred at 0° C. for 1 h and at r.t. for 2 h. Cooled to 0° C. and aqueous NH₃ was added carefully until pH>10. The mixture was diluted with CH₂Cl₂ and water. The mixture was filtered to remove solids. The phases were separated. The organic phase was dried (MgSO₄) and concentrated. Gave 4.8 g (55%) of the title compound. Used in the next step without further purification.

¹H NMR (CDCl₃) δ 7.78 (d, 2H), 7.34 (d, 2H), 3.10 (m, 1H), 2.53 (m, 4H), 2.25 (m, 2H), 2.01 (m, 2H).

4-(4-oxocyclohexyl)benzonitrile

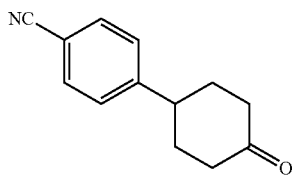 [SMILES: N#Cc1ccc(C2CCC(=O)CC2)cc1]

2.14 ml (26.5 mmol) pyridine was added to a solution of 3.0 ml (24.3 mmol) pivaloylchloride and 4.8 g (22.1 mmol) 4-(4-oxocyclohexyl)benzamide in 50 ml CH₂Cl₂ at r.t. The reaction mixture was stirred over night. Diluted with 50 ml CH₂Cl₂ and washed three times with water. The organic phase was dried (MgSO₄) and concentrated. Flash chromatography (SiO₂, Pet. ether/EtOAc 1:1→1:4) gave 700 mg (16%).

¹H NMR (CDCl₃) δ 7.61 (d, 2H), 7.36 (d, 2H), 3.09 (m, 1H), 2.51 (m, 4H), 2.25 (m, 2H), 1.96 (m, 2H).

tert-butyl 4-(1,4-dioxaspiro[4.5]decan-8-yl)benzylcarbamate

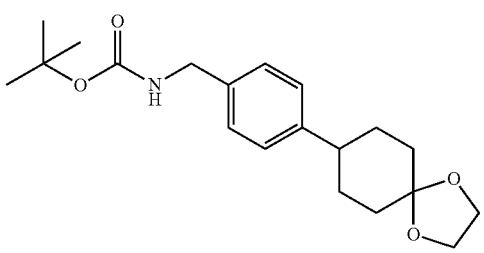 [SMILES: CC(C)(C)OC(=O)NCc1ccc(C2CCC3(CC2)OCCO3)cc1]

A solution of 700 mg (3.5 mmol) 4-(4-oxocyclohexyl)benzonitrile, 67 mg (0.35 mmol) p-TsOH and 395 μl (7.03 mmol) ethylene glycol was refluxed with a Dean-Stark trap for 2 h. The mixture was cooled to r.t. and concentrated to dryness. Used directly in the next step without further purification. The crude product was reduced and Boc-protected according to the general procedure F to yield 935 mg (77%) of the title product.

¹H NMR (CDCl₃) δ 7.20 (m, 4H), 4.29 (d, 2H), 3.99 (s, 4H), 2.54 (m, 1H), 1.86 (m, 4H), 1.65 (m, 4H), 1.46 (s, 9H).

tert-butyl 4-(4-oxocyclohexyl)benzylcarbamate

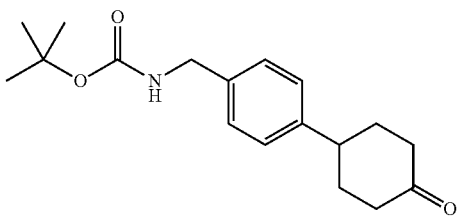 [SMILES: CC(C)(C)OC(=O)NCc1ccc(C2CCC(=O)CC2)cc1]

tert-butyl 4-(1,4-dioxaspiro[4.5]decan-8-yl)benzylcarbamate (935 mg, 2.6 mmol) was dissolved in acetone (15 ml) together with iodine (68 mg, 0.26 mmol). The mixture was stirred at reflux temperature for 4 hours and at room temperature for 72 hours. The mixture was partially evaporated and then diluted with CH₂Cl₂ (50 ml). The organic phase was washed with NaHSO₃ (50 ml, sat aq), water (50 ml) and brine (50 ml) followed by drying over MgSO₄ and evaporation. The product was purified by flash chromatography using pet.ether/EtOAc (3:1) as eluent to give 475 mg (60%) of the title compound as clear syrup.

$^1$H NMR (CDCl$_3$) δ 7.20 (m, 4H), 4.29 (d, 2H), 3.99 (s, 4H), 2.54 (m, 1H), 1.86 (m, 4H), 1.65 (m, 4H), 1.46 (s, 9H).

Example 94

N-(4-(1,2-diazaspiro[2.5]oct-1-en-6-yl)benzyl)-2-methyl-1,8-naphthyridine-3-carboxamide

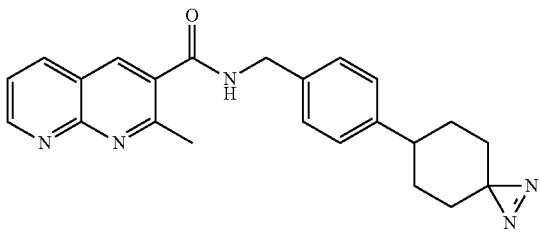 [SMILES: Cc1nc2ncccc2cc1C(=O)NCc1ccc(C2CCC3(CC2)N=N3)cc1]

The title substance was synthesized following the general deprotection and amide coupling procedure. Purification was done by flash chromatography (CH$_2$Cl$_2$/MeOH 16:1) to give the title substance in 79% yield.

$^1$H NMR (CDCl$_3$) δ 8.87 (m, 1H), 7.94 (m, 2H), 7.35 (m, 3H), 7.22 (m, 2H), 4.68 (d, 2H), 2.79 (s, 3H), 2.65 (m, 1H), 2.03 (m, 2H), 1.85 (m, 4H), 0.64 (d, 2H).

Example 95

N-(4-(1,4-Dioxaspiro[4.5]decan-8-yl)benzyl)-2-methyl-1,8-naphthyridine-3-carboxamide

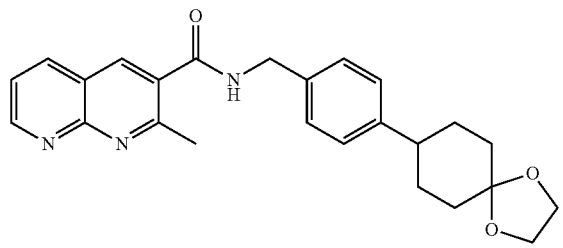 [SMILES: Cc1nc2ncccc2cc1C(=O)NCc1ccc(C2CCC3(CC2)OCCO3)cc1]

tert-Butyl 4-(1,4-dioxaspiro[4.5]decan-8-yl)benzylcarbamate (120 mg, 0.35 mmol) was dissolved in CH$_2$Cl$_2$ (10 ml) and 2M HCl in Et$_2$O (1.0 ml, 2 mmol) was added. The reaction was stirred at room temperature for 16 hours before evaporation to give 85 mg (86%) of the title compound as pale solids. The obtained crude (4-(1,4-dioxaspiro[4.5]decan-8-yl)phenyl)methanamine hydrochloride was used directly without further purification. The title substance was synthesized following the general deprotection and amide coupling procedure. Purification was done by flash chromatography (CH$_2$Cl$_2$/MeOH 16:1) to give the title substance in 49% yield.

$^1$H NMR (CDCl$_3$) δ 8.86 (m, 1H), 7.95 (m, 2H) 7.34 (m, 3H), 7.26 (d, 2H), 7.13 (br, 1H), 4.64 (d, 2H), 3.97 (m, 4H), 2.78 (s, 3H), 2.57 (m, 1H), 1.87-1.65 (br m, 8H).

Example 96

2-Methyl-N-(4-(4-oxocyclohexyl)benzyl)-1,8-naphthyridine-3-carboxamide

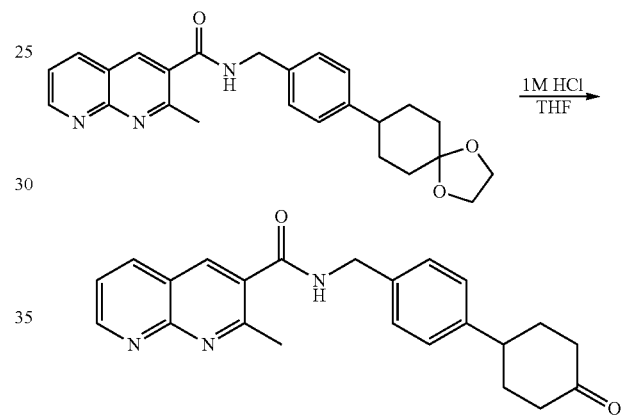

N-(4-(1,4-Dioxaspiro[4.5]decan-8-yl)benzyl)-2-methyl-1,8-naphthyridine-3-carboxamide (35.9 mg, 0.086 mmol) was dissolved in THF (1 ml). Aqueous HCl (1 ml, 1M) was added and the reaction was stirred at room temp for 18 hours. Reaction was then diluted with NaHCO$_3$ (10 ml, sat aq) and extracted with EtOAc (2*15 ml). Combined organics were dried over MgSO$_4$ and evaporated to give 25 mg (88%) of title compound as a pale mass.

$^1$H NMR (CDCl$_3$) δ 8.96 (m, 1H), 8.02 (m, 2H) 7.40 (m, 3H), 7.27 (d, 2H), 6.99 (br, 1H), 4.68 (d, 2H), 3.05 (m, 1H), 2.82 (m, 4H), 2.23 (m, 2H), 1.91 (m, 2H).

Scheme 27

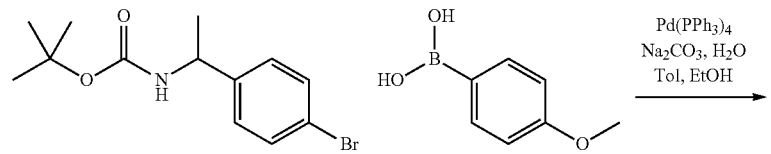

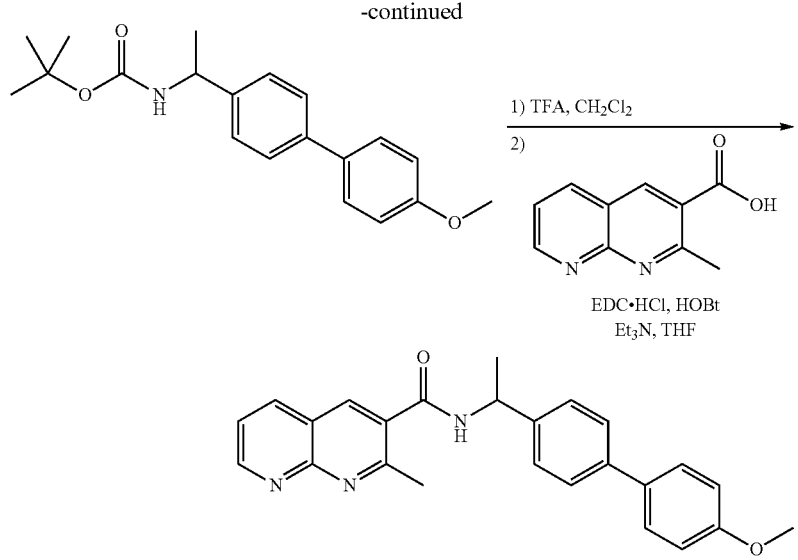

tert-Butyl
1-(4'-methoxybiphenyl-4-yl)ethylcarbamate

The title compound was synthesized from tert-Butyl 1-(4-bromophenyl)ethylcarbamate and phenyl boronic acid, following the general procedure for the coupling of aryl bromides with boronic acids (see above and c.f. scheme 27). Purification was done by flash column chromatography using Pet. ether/EtOAc 5:1→100% EtOAc as eluent. The fractions containing product were further purified by size exclusion chromatography Sephadex LH20, CHCl$_3$/MeOH 1:1 yielding the title compound (68%).

$^1$H NMR (CDCl$_3$) δ 7.52 (d, 4H), 7.35 (d, 2H), 6.98 (d, 2H), 4.83 (bs, 2H), 3.86 (s, 3H), 1.49 (d, 3H), 1.44 (s, 9H).

Example 97

N-(1-(4'-methoxybiphenyl-4-yl)ethyl)-2-methyl-1,8-naphthyridine-3-carboxamide tert-Butyl 1-(4'-methoxybiphenyl-4-yl)ethylcarbamate was dissolved in CH$_2$Cl$_2$. TFA was added to the solution and the mixture was stirred at r.t. for 30 min. The solvents were removed and the residue was coupled without further purification to 2-Methyl-1,8-naphthyridine using the general amide coupling procedure. Purification was done by flash chromatography, CH$_2$Cl$_2$/MeOH 95/5, yielding the title compound (44%).

$^1$H NMR (CDCl$_3$) δ 9.11 (m, 1H), 8.14 (m, 1H), 8.13 (s, 1H), 7.65-7.45 (m, 7H), 6.99 (d, 2H), 6.29 (d, 1H), 5.50-5.40 (m, 1H), 3.87 (s, 3H), 2.90 (s, 3H), 1.71 (d, 3H).

Scheme 28

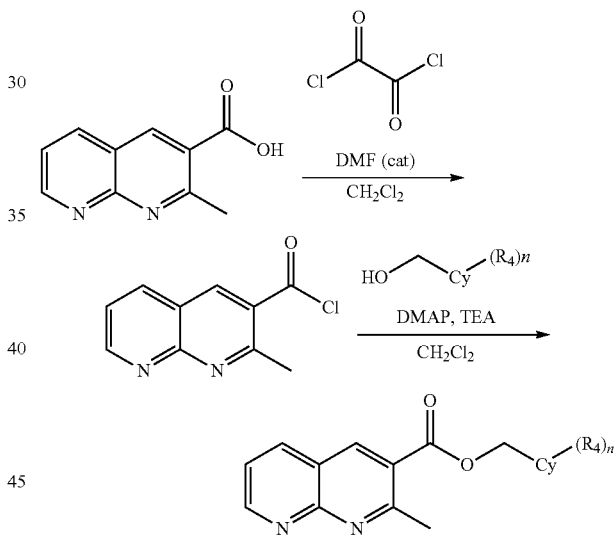

General Procedure for the Synthesis of 1,8-naphthyridines-3-carboxylates (Scheme 28).

Oxalylchloride (2.0 eq.) followed by a drop (approx. 0.05 ml) of DMF was added to a slurry of 2-methyl-1,8-naphthyridine-3-carboxylic acid (1.0 eq.) in CH$_2$Cl$_2$. The mixture was stirred at r.t. for 3 h., concentrated to dryness under reduced pressure and resuspended in CH$_2$Cl$_2$. DMAP (0.01 eq.), Et$_3$N (3.0 eq.) and the corresponding alcohol (1.1 eq.) were added. The resulting solution was stirred under N$_2$ at r.t. overnight. The reaction mixture was diluted with water and the phases were separated. The aqueous phase was extracted with CH$_2$Cl$_2$. The organic phases were combined, washed with water, NaHCO$_3$ and brine, dried (MgSO$_4$) and concentrated. The crude product was purified by flash chromatography.

The following compound were synthesized, by coupling the corresponding alcohol with 2-methyl-1,8-naphthyridine- 3-carboxylic acid. The solvent system used for the purification, the yield and analytical data are given for each compound.

Example 98

3-(Trifluoromethyl)benzyl 2-methyl-1,8-naphthyridine-3-carboxylate

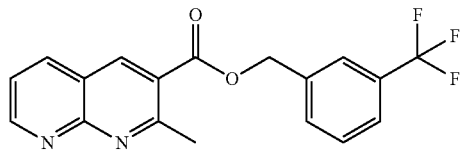 [SMILES: Cc1nc2ncccc2cc1C(=O)OCc1cccc(C(F)(F)F)c1]

(CH$_2$Cl$_2$/MeOH 40:1)
Yield: 33%
$^1$H NMR (CDCl$_3$) δ 9.17 (m, 1H), 8.80 (s, 1H), 8.25 (m, 1H), 7.75 (s, 1H), 7.67 (m, 2H), 7.56 (m, 1H), 7.51 (m, 1H), 5.48 (s, 2H), 3.07 (s, 3H).

Example 99

(6-Phenylpyridin-3-yl)methyl 2-methyl-1,8-naphthyridine-3-carboxylate

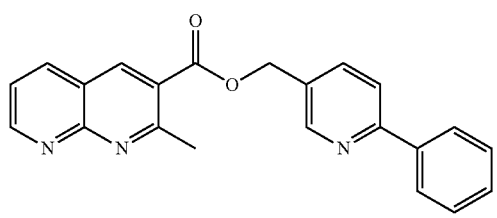 [SMILES: Cc1nc2ncccc2cc1C(=O)OCc1ccc(-c2ccccc2)nc1]

(CH$_2$Cl$_2$/MeOH 20:1)
Yield: 29%
$^1$H NMR (CDCl$_3$) δ 9.18 (m, 1H), 8.85 (m, 1H), 8.80 (s, 1H), 8.24 (m, 1H), 8.03 (m, 2H), 7.90 (m, 1H), 7.81 (m, 1H), 7.47 (m, 4H), 4.49 (s, 1H), 3.09 (s, 1H).

Example 100

(5-Phenylisoxazol-3-yl)methyl 2-methyl-1,8-naphthyridine-3-carboxylate

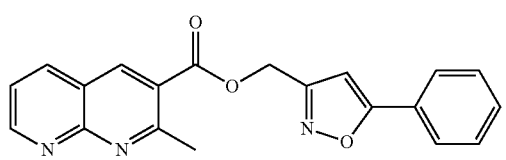 [SMILES: Cc1nc2ncccc2cc1C(=O)OCc1cc(-c2ccccc2)on1]

(EtOAc/Petroleum Ether 4:1)
Yield: 52%
$^1$H NMR (CDCl$_3$) δ 9.19 (m, 1H), 8.86 (s, 1H), 8.26 (m, 1H), 7.81 (m, 2H), 7.50 (m, 4H), 6.68 (m, 1H), 5.55 (s, 2H), 3.11 (s, 3H).

Example 101

(2-Phenylthiazol-4-yl)methyl 2-methyl-1,8-naphthyridine-3-carboxylate

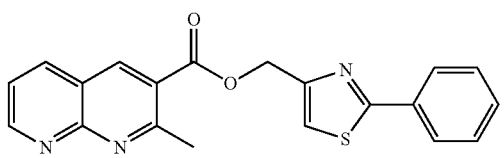 [SMILES: Cc1nc2ncccc2cc1C(=O)OCc1csc(-c2ccccc2)n1]

(EtOAc/Petroleum Ether 4:1)
Yield: 55%
$^1$H NMR (CDCl$_3$) δ 9.17 (m, 1H), 8.85 (s, 1H), 8.24 (m, 1H), 7.98 (m, 2H), 7.47 (m, 5H), 5.59 (s, 2H), 3.10 (s, 3H).

Scheme 29

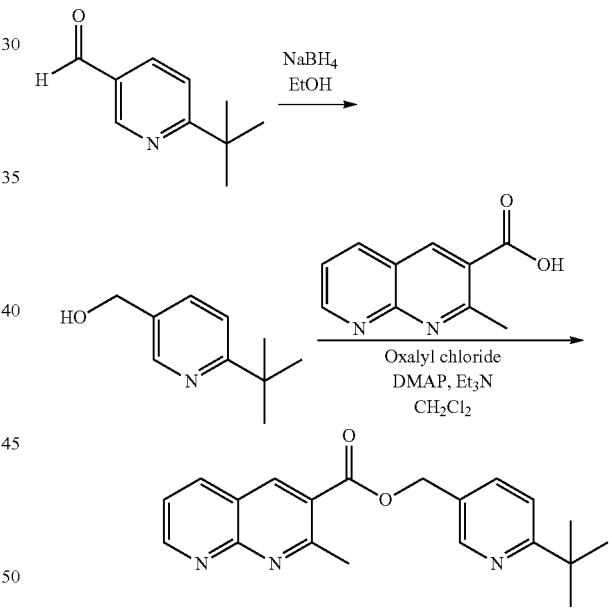

(6-tert-Butylpyridin-3-yl)methanol 6-tert-Butylnicotinaldehyde (363.0 mg, 2.22 mmol) was dissolved in EtOH (20 ml). NaBH$_4$ (193.5 mg, 5.12 mmol) was added. The mixture was stirred at r.t. for 1.0 h. The solvent was removed under reduced pressure. The residue was suspended in aqueous Na$_2$CO$_3$ and the product extracted with EtOAc. The combined organic extracts were dried (MgSO$_4$), filtered and concentrated yielding 311.5 mg the title compound as a colourless oil (85%).

$^1$H NMR (CDCl$_3$) δ 8.50 (d, 1H), 7.65 (m, 1H), 7.34 (d, 1H), 4.68 (s, 2H), 1.36 (s, 9H).

Example 102

(6-tert-Butylpyridin-3-yl)methyl 2-methyl-1,8-naphthyridine-3-carboxylate

The title substance was synthesized following the general procedure for the synthesis of 1,8-naphthyridines-3-carboxylates. Purification by flash chromatography (EtOAc/Pet. ether 4:1) gave the title compound as an orange solid (53%).

$^1$H NMR (CDCl$_3$) δ 9.17 (m, 1H), 8.79 (s, 1H), 8.72 (d, 1H), 8.24 (m, 1H), 7.75 (m, 1H), 7.51 (m, 1H), 7.41 (d, 1H), 5.42 (s, 2H), 3.08 (s, 3H), 1.40 (s, 9H).

Scheme 30

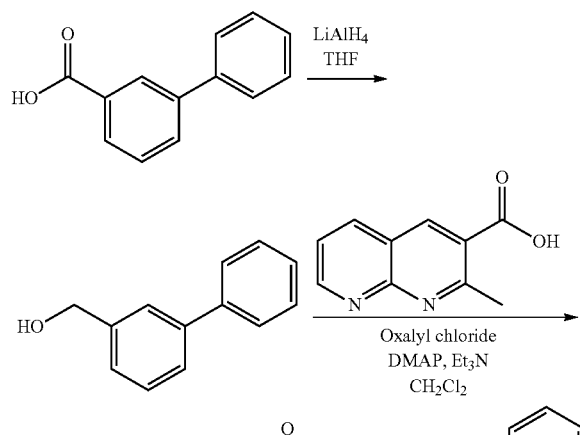

Biphenyl-3-ylmethanol

Biphenyl-3-carboxylic acid (217.0 mg, 1.09 mmol) in THF was added to LiAlH$_4$ (1.0 M in THF) (1.64 ml) at 0° C. under N$_2$ during 15 min. The mixture was then stirred at r.t. for 2.5 h. H$_2$O was carefully added to the mixture at 0° C. NaOH (1.0 M) was added. The product was extracted with EtOAc. The combined organic extracts were dried (MgSO$_4$), filtered and concentrated yielding the title compound as a yellow oil (95%).

$^1$H NMR (CD$_3$OD) δ 7.61-7.59 (m, 3H), 7.52-7.49 (m, 1H), 7.45-7.38 (m, 3H), 7.35-7.30 (m, 2H), 4.67 (s, 2H).

Example 103

Biphenyl-3-ylmethyl 2-methyl-1,8-naphthyridine-3-carboxylate

The title substance was synthesized following the general procedure for the synthesis of 1,8-naphthyridines-3-carboxylates. Purification was done by flash chromatography (CH$_2$Cl$_2$/MeOH 20:1) gave 20 mg (11%) of the title compound as a red white solid.

$^1$H NMR (CDCl$_3$) δ 9.16 (m, 1H), 8.80 (s, 1H), 8.22 (m, 1H), 7.71 (s, 1H), 7.61 (m, 3H), 7.49 (m, 5H), 7.38 (m, 1H), 5.50 (s, 2H), 3.09 (s, 3H).

6-Cyclohexylnicotinaldehyde

This compound was synthesized in 6% yield from 3-pyridine methanol and cyclohexane carboxylic acid using the same procedure as for 6-tert-butylnicotinaldehyde.

$^1$H NMR (CDCl$_3$) δ 10.34 (s, 1H), 8.93 (s, 1H), 8.69 (d, 1H), 7.37 (d, 1H), 3.58 (m, 1H), 1.85 (m, 4H), 1.45 (m, 4H), 1.35 (m, 2H).

Example 104

(6-Cyclohexylpyridin-3-yl)methyl 2-methyl-1,8-naphthyridine-3-carboxylate

6-Cyclohexylnicotinaldehyde (85.0 mg, 0.45 mmol) was dissolved in EtOH (5 ml). NaBH$_4$ (39.1 mg, 1.03 mmol) was added. The mixture was stirred at r.t. for 1.0 h. The solvent was removed under reduced pressure. The residue was suspended in aqueous Na$_2$CO$_3$ and the product extracted with EtOAc. The combined organic extracts were dried (MgSO$_4$), filtered and concentrated. This crude mixture was used directly to synthesized the title compound in 45% yield following the General procedure for the synthesis of 1,8-naphthyridines-3-carboxylates. Purification was done by flash chromatography (CH$_2$Cl$_2$/MeOH 97:3).

$^1$H NMR (CDCl$_3$) δ 9.16 (m, 1H), 8.75 (s, 1H), 8.67 (s, 1H), 8.55 (d, 1H), 8.21 (m, 1H), 7.51 (dd, 1H), 7.27 (d, 1H), 5.51 (s, 2H), 3.07 (s, 3H), 2.86 (m, 1H), 1.85 (m, 4H), 1.40 (m, 6H).

Scheme 31

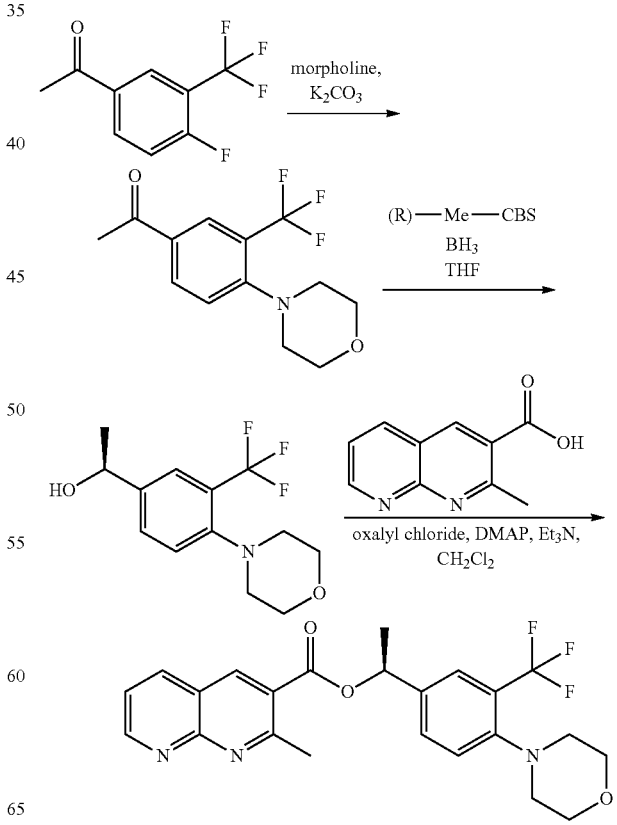

1-(4-morpholino-3-(trifluoromethyl)phenyl)ethanone

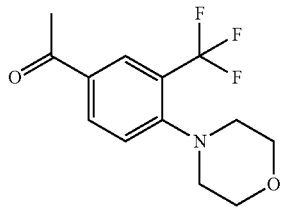 [SMILES: CC(=O)c1ccc(N2CCOCC2)c(C(F)(F)F)c1]

1-(4-Fluoro-3-(trifluoromethyl)phenyl)ethanone (510.0 mg, 2.5 mmol) and morpholine (724.2 mg, 8.31 mmol) were placed in a screw cap pressure tube. The tube was sealed and the mixture heated to 100° C. for 20 hours. The mixture was allowed to cool. H$_2$O was added and the product extracted with EtOAc. The combined organic extracts were washed with water, dried (MgSO$_4$), filtered and concentrated. Purification was done by flash chromatography (Pet. Ether/EtOAc 4:1→3:2) to give 541.0 mg (84%) of the title substance $^1$H NMR (CDCl$_3$) δ 8.23 (d, 1H), 8.11 (dd, 1H), 7.33 (d, 1H), 3.86 (t, 4H), 3.05 (t, 4H), 2.61 (s, 3H).

(S)-1-(4-morpholino-3-(trifluoromethyl)phenyl)ethanol

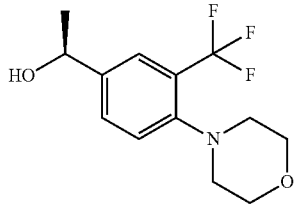 [SMILES: C[C@H](O)c1ccc(N2CCOCC2)c(C(F)(F)F)c1]

2.0 ml (2.0 mmol) BH$_3$.THF (1.0 M in THF) was slowly added to a solution of 11 mg (0.4 mmol) (R)-2-Methyl-CBS-oxazaborolidine in 0.4 ml THF at 0° C. under an atmosphere of N$_2$. After stirring for 10 min a solution of 547 mg (2.0 mmol) 1-(4-morpholino-3-(trifluoromethyl)phenyl)ethanone in 2.0 ml THF was added. Stirred at 0° C. for 2 h. Quenched with 1 ml MeOH and 0.1 ml HCl (conc.). Stirred for 10 min. Diluted with water and extracted twice with diethyl ether. The organic phase was washed with brine, dried (MgSO4) and concentrated. Flash chromatography (SiO2, Pet. Ether/EtOAc 3:1→2:1) gave 453 mg (82%) as a yellow oil.

$^1$H NMR (CDCl$_3$) δ 7.65 (s, 1H), 7.55 (m, 1H), 7.35 (d, 1H), 4.93 (m, 1H), 3.83 (m, 4H), 2.91 (m, 4H), 1.50 (d, 3H).

Example 105

(S)-1-(4-morpholino-3-(trifluoromethyl)phenyl)ethyl 2-methyl-1,8-naphthyridine-3-carboxylate

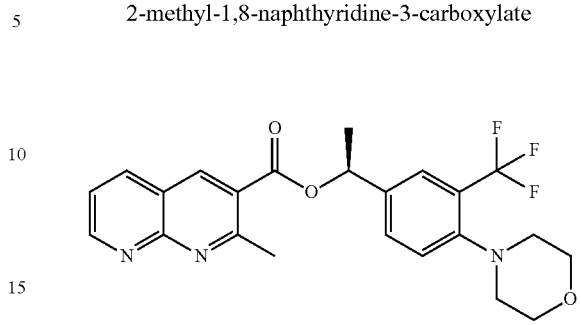

The title substance was synthesized following the general procedure for the synthesis of 1,8-naphthyridines-3-carboxylates. Purification by flash chromatography (CH$_2$Cl$_2$/MeOH 30:1) gave the title compound as an orange solid (53%).

$^1$H NMR (CDCl$_3$) δ 9.18 (m, 1H), 8.78 (s, 1H), 8.27 (d, 1H), 7.74 (m, 1H), 7.65 (m, 1H), 7.53 (m, 1H), 7.39 (d, 1H), 6.19 (m, 1H), 3.84 (m, 4H), 3.06 (s, 3H), 2.94 (m, 4H), 1.75 (d, 3H).

Scheme 32

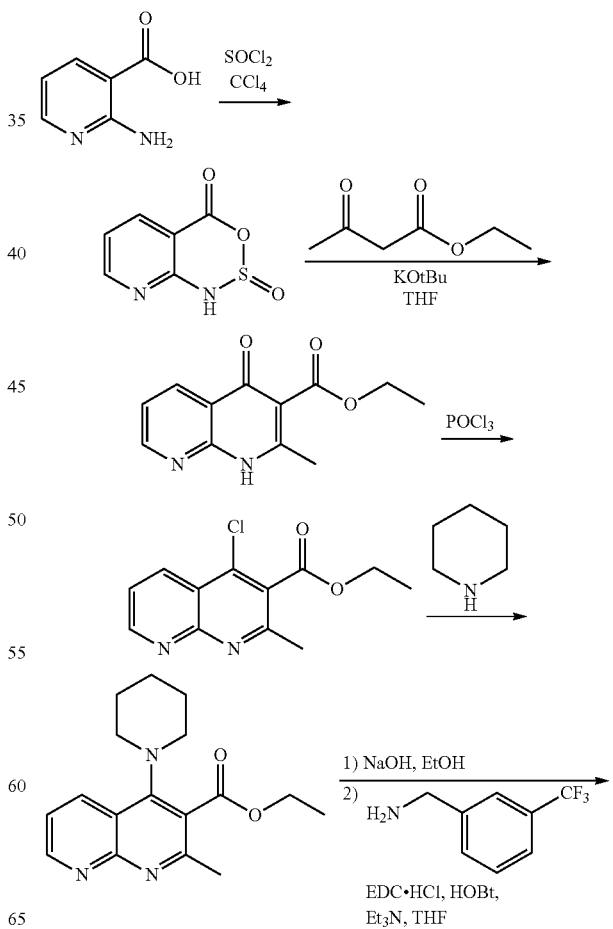

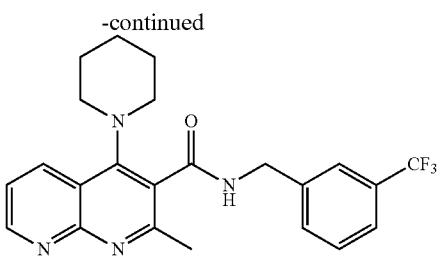

Azathiosatoic Anhydride

To a dispersion of 2-aminonicotinic acid (1.5 g, 10.9 mmol) in CCl$_4$ (15 ml), thionyl chloride (1.6 ml, 21.7 mmol) was added. The mixture was stirred for 2 h. under reflux. Then it was cooled and concentrated under reduced pressure yielding the title compound which was used without further purification.

Ethyl 2-methyl-4-oxo-1,4-dihydro-1,8-naphthyridine-3-carboxylate

To a solution of potassium tert-butoxide (2.4 g, 21.7 mmol) in anhydrous THF (100 ml) ethyl acetoacetate (2.75 ml, 21.7 mmol) was added dropwise. After the mixture was stirred at r.t. for 30 min, azathiosatoic anhydride (2.0 g, 10.9 mmol) was added and stirring continued for 24 h. H$_2$O (20 ml) was added, the solvents were removed under reduced pressure. The crude was purified by flash chromatography (CH$_2$Cl$_2$/MeOH 98:2→90:10) giving 441 mg (17%) of the title compound.

$^1$H NMR (CDCl$_3$) δ 8.71 (m, 1H), 8.67 (m, 1H), 7.37 (m, 1H), 4.42 (m, 2H), 2.62 (s, 3H), 1.41 (t, 2H).

Ethyl 4-chloro-2-methyl-1,8-naphthyridine-3-carboxylate

Ethyl 2-methyl-4-oxo-1,4-dihydro-1,8-naphthyridine-3-carboxylate (5.18 mg, 2.23 mmol) was dissolved in POCl$_3$. The mixture was heated to 100° C. for 1.0 h. The mixture was allowed to cool and then it was carefully poured into ice-water (250 ml). The mixture was neutralized with solid NaOH. The product was extracted with EtOAc. The combined organic extracts were dried (MgSO$_4$), filtered and concentrated. Purification was done by flash chromatography (CH$_2$Cl$_2$/MeOH 97:3→96:4) giving 531 mg (95%) of the title compound.

$^1$H NMR (CDCl$_3$) δ 9.17 (m, 1H), 8.60 (m, 1H), 7.60 (m, 1H), 4.54 (m, 2H), 2.81 (s, 3H), 1.46 (t, 2H).

Ethyl 2-methyl-4-(piperidin-1-yl)-1,8-naphthyridine-3-carboxylate

In a screw cap pressure tube ethyl 4-chloro-2-methyl-1,8-naphthyridine-3-carboxylate (250 mg, 1.0 mmol) was suspended in piperidine (2.0 ml, 20 mmol). The tube was sealed and the mixture heated to 80° C. for 1.0 h. The mixture was then adsorbed on silica and chromatographed (CH$_2$Cl$_2$/MeOH 98:2→97:3) giving 189.4 mg (63%) of the title compound.

$^1$H NMR (CDCl$_3$) δ 8.98 (m, 1H), 8.39 (m, 1H), 7.38 (m, 1H), 4.44 (m, 2H), 3.25-3.15 (m, 4H), 2.69 (s, 3H), 1.85-1.62 (m, 6H), 1.42 (t, 2H).

Example 106

2-Methyl-4-(piperidin-1-yl)-N-(3-(trifluoromethyl)benzyl)-1,8-naphthyridine-3-carboxamide Ethyl 2-methyl-4-(piperidin-1-yl)-1,8-naphthyridine-3-carboxylate (120.0 mg, 0.4 mmol) was dissolved in EtOH. NaOH (4.0 ml of a 1.0 M aq. solution) was added and the mixture refluxed for 3.0 days. The mixture was cooled, acidified with aq. HCl (1.0 M) and concentrated to dryness. The residue was suspended in anhydrous THF, N-(3-dimethylaminopropyl)-N'-ethyl-carbodiimide hydrochloride (84.34 mg, 0.44 mmol), 1-hydroxybenzotriazole hydrate (30.74 mg, 0.2 mmol.) and Et$_3$N (54.8 µl, 0.4 mmol) were added. The mixture was stirred at room temperature for 30 min. 3-(trifluoromethyl)benzyl amine (57.33 µl, 0.4 mmol) was added to the mixture and stirring continued for 18 h. H$_2$O was added to the mixture and the product extracted with EtOAc, dried over MgSO$_4$ and concentrated. Purification was done by flash chromatography (CH$_2$Cl$_2$/MeOH 98:2→96:4) giving 20.0 mg (12%) of the title compound.

$^1$H NMR (CD$_3$OD) δ 8.91 (m, 1H), 8.51 (m, 1H), 7.82 (bs, 1H), 7.76-7.57 (m, 3H), 7.52 (m, 1H), 4.68 (s, 2H), 3.20-3.05 (m, 4H), 2.60 (s, 3H), 1.75-1.45 (m, 6H).

3-Oxo-N-(3-(trifluoromethyl)benzyl)butanamide

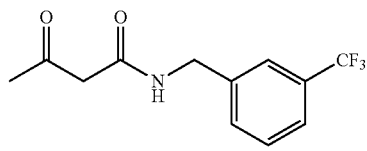 [SMILES: CC(=O)CC(=O)NCc1cccc(C(F)(F)F)c1]

3-(Trifluoromethyl)benzylamine (2.0 ml, 13.95 mmol) was mixed with 2,2,6-trimethyl-4H-1,3-dioxin-4-one (2.0 ml, 15.12 mmol), The mixture was stirred at 150° C. for 2 hours followed by 60 hours at 50° C. The reaction was cooled, diluted with EtOAc (50 ml), washed with 1M HCl (40 ml), NaHCO$_3$ (2*40 ml, sat aq), dried over MgSO$_4$ and evaporated. The crude product was purified by precipitation from toluene/pet.ether to give 2.57 g (71%) of 3-oxo-N-(3-(trifluoromethyl)benzyl)butanamide as pale solids.

$^1$H NMR (CDCl$_3$) δ 7.50 (m, 4H), 4.53 (d, J=6.0 Hz, 2H), 3.51 (s, 3H), 2.29 (s, 3H).

Scheme 33

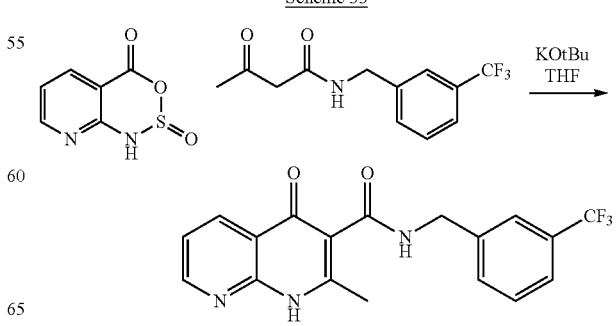

Example 107

2-Methyl-4-oxo-N-(3-(trifluoromethyl)benzyl)-1,4-dihydro-1,8-naphthyridine-3-carboxamide Potassium tert-butoxide (519.5 mg, 4.63 mmol) was dissolved in anhydrous THF (10.0 ml). 3-Oxo-N-(3-(trifluoromethyl)benzyl)butanamide (1.0 g, 3.86 mmol) was slowly added as a solution in THF (3.0 ml). The mixture was stirred at r.t. for 1.0 h. and then azathiosatoic anhydride (710.5 mg, 3.86 mmol) was added. The suspension was stirred for 2.0 days. HCl (1.0 M aq.) (10 ml) was added and the product extracted with EtOAc. The combined organic extracts were dried over MgSO$_4$ and concentrated. Purification was done by flash chromatography (CH$_2$Cl$_2$/MeOH 98:2→97:3) giving 313.0 mg (22%) of the title compound.

$^1$H NMR (CDCl$_3$) δ 10.67 (bs, 1H), 9.65 (bs, 1H), 8.75-8.69 (m, 2H), 7.65-7.41 (m, 5H), 4.71 (d, 2H), 3.05 (s, 3H).

Scheme 34

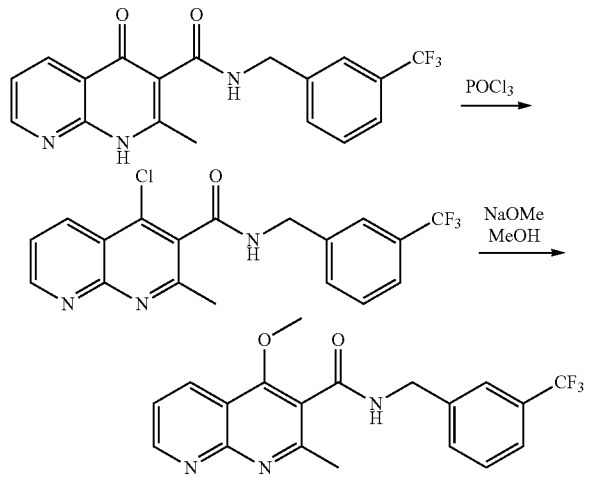

4-Chloro-2-methyl-N-(3-(trifluoromethyl)benzyl)-1,8-naphthyridine-3-carboxamide This substance was synthesized from 2-Methyl-4-oxo-N-(3-(trifluoromethyl)benzyl)-1,4-dihydro-1,8-naphthyridine-3-carboxamide (130.0 mg, 0.36 mmol) following the same procedure used for ethyl 4-chloro-2-methyl-1,8-naphthyridine-3-carboxylate. Purification was done by flash chromatography (EtOAc/MeOH 100:0→96:4) giving 80.0 mg (59%) of the title compound.

$^1$H NMR (CDCl$_3$) δ 8.62 (m, 1H), 8.53 (t, 1H), 8.06 (m, 1H), 7.89 (bs, 1H), 7.73 (d, 1H), 7.62 (d, 1H), 7.54 (m, 1H), 7.33 (m, 1H), 4.88 (d, 1H), 2.77 (s, 3H).

Example 108

4-Methoxy-2-methyl-N-(3-(trifluoromethyl)benzyl)-1,8-naphthyridine-3-carboxamide 4-Chloro-2-methyl-N-(3-(trifluoromethyl)benzyl)-1,8-naphthyridine-3-carboxamide (60.0 mg, 0.16 mmol) was dissolved in anhydrous MeOH (1.0 ml). NaOMe was added and the mixture refluxed for 15 h. The mixture was allowed to cool. NH$_4$Cl (5.0 ml (sat)) was added and the product extracted with EtOAc. The combined organic extracts were dried over MgSO$_4$ and concentrated. Purification was done by flash chromatography (EtOAc/MeOH 98:2) giving 12.0 mg (20%) of the title compound.

$^1$H NMR (CDCl$_3$) δ 8.85 (t, 1H), 8.69 (m, 1H), 7.96-7.89 (m, 2H), 7.78 (d, 1H), 7.61 (d, 1H), 7.54 (m, 1H), 7.19 (m, 1H), 4.87 (d, 1H), 3.88 (s, 3H), 2.62 (s, 3H).

N-(4-tert-Butylbenzyl)-3-oxobutanamide

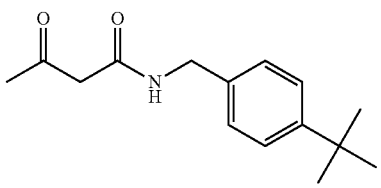 [SMILES: CC(=O)CC(=O)NCc1ccc(C(C)(C)C)cc1]

2,2,6-Trimethyl-4H-1,3-dioxin-4-one (1.6 ml, 12.09 mmol) and (4-tert-butylphenyl)methanamine (2.0 ml, 11.36 mmol) were dissolved in toluene (2 ml) and heated at 130° C. for 28 hours. Reaction was cooled to room temperature and diluted with EtOAc (40 ml). The organic phase was washed with HCl (2*30 ml, 1M) and NaHCO$_3$ (2*30 ml, sat aq), dried over MgSO$_4$ and evaporated. The crude product was purified by precipitation from toluene/pet.ether to give 1.57 g (56%) of N-(4-tert-butylbenzyl)-3-oxobutanamide as a pale powder.

$^1$H NMR (CDCl$_3$): δ 7.37 (d, 2H), 7.23 (d, 2H), 4.45 (d, 2H), 3.47 (s, 2H), 2.29 (s, 3H), 1.32 (s, 9H).

Example 109

N-(4-tert-butylbenzyl)-2,7-dimethyl-1,8-naphthyridine-3-carboxamide

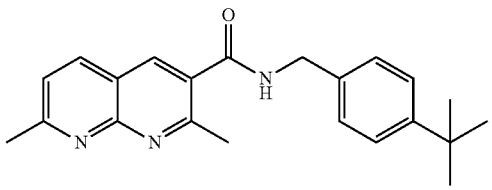 [SMILES: Cc1ccc2cc(C(=O)NCc3ccc(C(C)(C)C)cc3)c(C)nc2n1]

A solution of 200 mg (1.47 mmol) 2-amino-6-methylnicotinaldehyde, 400 mg (1.62 mmol) N-(4-tert-butylbenzyl)-3-oxobutanamide and 15 (0.15 mmol) piperidine in 3 ml EtOH was refluxed for 36 h. The reaction mixture was concentrated under reduced pressure. Flash chromatography (CH$_2$Cl$_2$/MeOH 20:1) afforded 258 mg (51%) of the title compound as a yellow-brown amorphous solid.

$^1$H NMR (400 MHz, CDCl$_3$) δ 8.10 (s, 1H), 7.99 (d, 1H), 7.42 (d, 2H), 7.36 (s, 1H), 7.34 (d, 2H), 6.28 (m, 1H), 4.67 (d, 2H), 2.91 (s, 3H), 2.79 (s, 3H), 1.34 (s, 9H).

Example 110

N-(4-tert-butylbenzyl)-2,6-dimethyl-1,8-naphthyridine-3-carboxamide

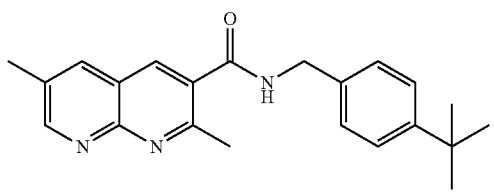 [SMILES: Cc1cnc2nc(C)c(C(=O)NCc3ccc(C(C)(C)C)cc3)cc2c1]

Prepared as above. Yield 46%.

$^1$H NMR (400 MHz, CDCl$_3$) δ 8.49 (s, 1H), 7.71 (s, 2H), 7.49 (s, 1H), 7.34 (d, 2H), 7.29 (d, 2H), 4.58 (d, 2H), 2.62 (s, 3H), 2.33 (s, 3H), 1.29 (s, 9H).

Example 111

N-(4-tert-butylbenzyl)-2,5-dimethyl-1,8-naphthyridine-3-carboxamide

In a screw cap pressure tube were N-(4-tert-butylbenzyl)-3-oxobutanamide (94.5 mg, 0.38 mmol), 2-amino-4-methylnicotinaldehyde (52.0 mg, 0.38 mmol) and piperidine (151.0 µl, 1.53 mmol) suspended in EtOH (0.5 ml). The tube was sealed and the mixture heated to 120° C. for 1.5 h. The mixture was allowed to cool. EtOAc was added and the mixture washed with H$_2$O, dried (MgSO$_4$), filtered and concentrated. The crude product was purified by flash chromatography CH$_2$Cl$_2$/MeOH 96/4 yielding 61.5 mg of the title compound (47%).

$^1$H NMR (CDCl$_3$) δ 8.92 (d, 1H), 8.31 (s, 1H), 7.43 (d, 2H), 7.36 (d, 2H), 7.28 (d, 1H), 6.33 (t, 1H), 4.70 (d, 2H), 2.90 (s, 3H), 2.68 (s, 3H), 1.35 (s, 9H).

Example 112

6-Bromo-N-(4-tert-butylbenzyl)-2-methyl-1,8-naphthyridine-3-carboxamide

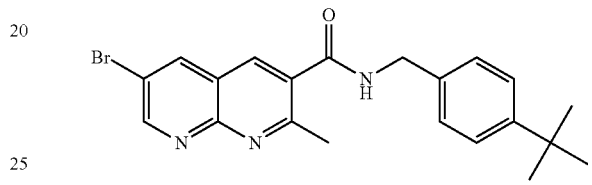

2-Amino-5-bromonicotinaldehyde (0.50 g, 2.49 mmol) and N-(4-tert-butylbenzyl)-3-oxobutanamide (0.62 g, 2.49 mmol) were suspended in piperidine (1.0 ml) and EtOH (1.0 ml) in a high-pressure vial. The mixture was heated at 120° C. for 4.5 hours and then cooled to room temperature. The reaction was diluted with water (40 ml) and extracted with CH$_2$Cl$_2$ (3*30 ml). Combined organics were washed with water (30 ml), dried over MgSO$_4$ and evaporated. The crude product was purified by flash chromatography using CH$_2$Cl$_2$/CH$_3$OH (20:1) as eluent to give 0.56 g (54%) of 6-bromo-N-(4-tert-butylbenzyl)-2-methyl-1,8-naphthyridine-3-carboxamide as yellow solids.

$^1$H NMR (CDCl$_3$) δ 8.71 (d, 1H), 7.94 (d, 1H), 7.76 (s, 1H), 7.59 (m, 1H), 7.36 (d, 2H), 7.28 (d, 2H), 4.57 (d, 2H), 2.64 (s, 3H), 1.31 (s, 9H).

Scheme 35

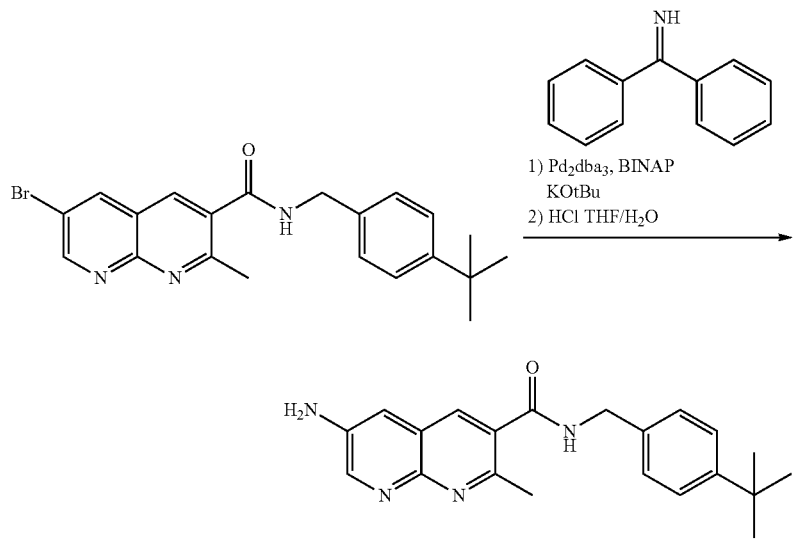

Example 113

6-amino-N-(4-tert-butylbenzyl)-2-methyl-1,8-naphthyridine-3-carboxamide

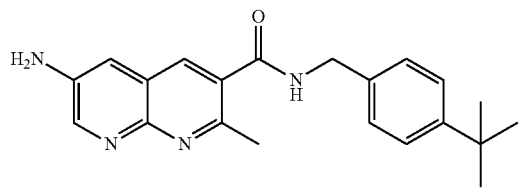 [SMILES: Cc1nc2ncc(N)cc2cc1C(=O)NCc1ccc(C(C)(C)C)cc1]

9.2 mg (0.01 mmol) Pd2 dba3 and 19 mg (0.03 mmol) BINAP were added to a degassed mixture of 205 mg (0.5 mmol) 6-bromo-N-(4-tert-butylbenzyl)-2-methyl-1,8-naphthyridine-3-carboxamide, 100 ml (0.6 mmol) diphenylmethanimine and 79 mg (0.7 mmol) KOtBu in 2 ml toluene. The flask was sealed with a septa and heated at 80° C. over night. The reaction mixture was diluted with EtOAc and filtered through celite and SiO2 with EtOAc. The filtrate was concentrated and treated with THF and 1.0 M HCl for 2 h. The solution was diluted with 0.5 M Hcl and washed with EtOAc/ Pet. ether 1:1. The aqueous phase was neutralized with 1 M NaOH and extracted twice with $CH_2Cl_2$. The organic phase was dried (MgSO4) and concentrated. Flash chromatography (CH2Cl2/MeOH 10:1) gave 4.6 mg of the title compound.

$^1$H NMR ($CDCl_3$) δ 8.56 (s, 1H), 7.84 (s, 1H), 7.42 (d, 2H), 7.34 (d, 2H), 7.05 (s, 1H), 6.44 (s, 1H), 4.65 (d, 2H), 2.79 (s, 3H), 1.33 (s, 9H).

2-Amino-5-iodonicotinaldehyde

2-Aminonicotinaldehyde (515 mg, 4.22 mmol), periodic acid (144.1 mg, 0.63 mmol) and iodine (460.2 mg, 0.43 mmol) were dissolved in a mixture of acetic acid (12.0 ml), $H_2O$ (0.6 ml) and $H_2SO_4$ (0.1 ml). The mixture was heated to 80° C. for 4 h. Then it was poured into $Na_2S_2O_3$ (10% aq. solution), neutralized with NaOH (2N aq. solution) and extracted with EtOAc. The combined organic extracts were dried ($MgSO_4$), filtered and concentrated. The crude product was purified by flash chromatography; Pet. Ether, EtOAc (4:1→1:1) affording 842 mg (80%) the title compound.

$^1$H NMR ($CDCl_3$) δ 9.81 (s, 1H), 8.41 (d, 1H), 8.04 (d, 1H), 6.80 (bs, 2H).

Example 114

N-(4-tert-butylbenzyl)-6-iodo-2-methyl-1,8-naphthyridine-3-carboxamide

In a screw cap pressure tube were N-(4-tert-butylbenzyl)-3-oxobutanamide (104.2 mg, 0.42 mmol) and 2-amino-5-iodonicotinaldehyde (95.0 mg, 0.38 mmol) suspended in piperidine (151.0 μl, 1.53 mmol). The tube was sealed and the mixture heated to 120° C. for 2 h. The mixture was allowed to cool, diluted with MeOH, adsorbed in silica and purified by flash chromatography ($CH_2Cl_2$/MeOH 99:1→97:3) yielding 110 mg of the title compound (63%).

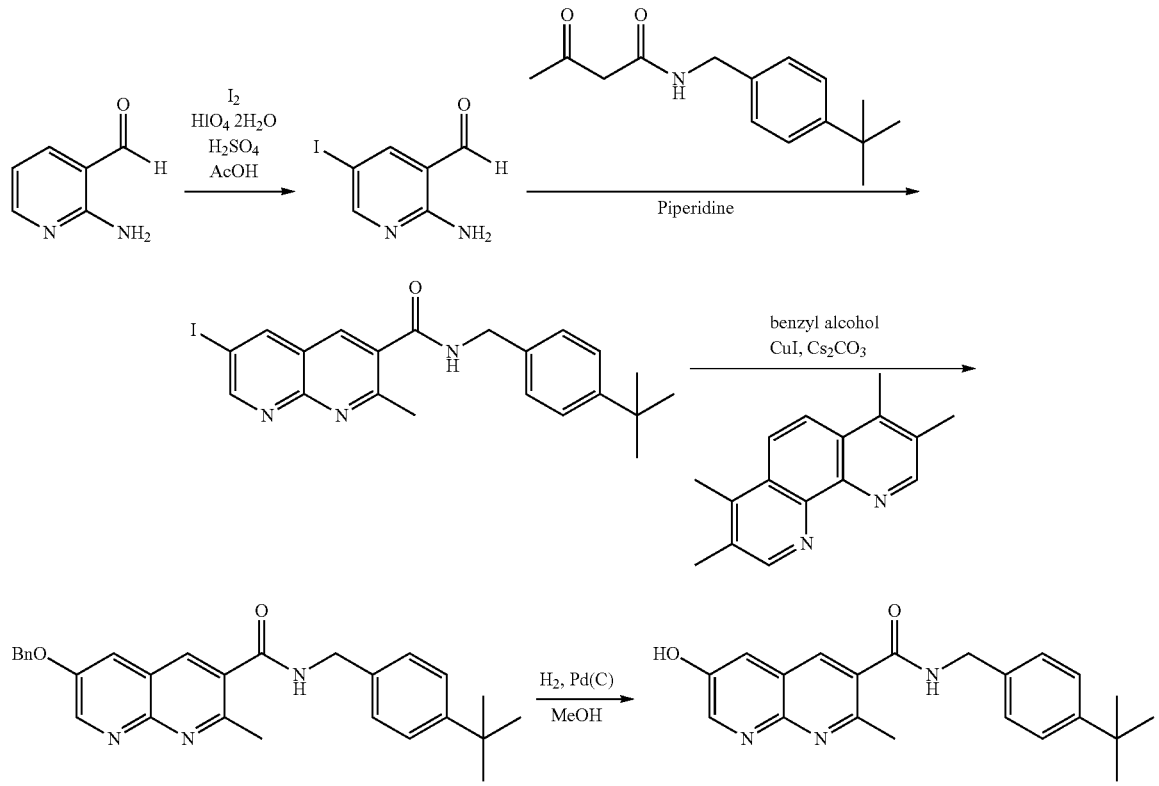

Scheme 36

$^1$H NMR (CDCl$_3$) δ 9.17 (d, 1H), 8.46 (d, 1H), 8.03 (s, 1H), 7.43 (d, 2H), 7.35 (d, 2H), 6.44 (bt, 1H), 4.67 (d, 2H), 2.88 (s, 3H), 1.34 (s, 9H).

6-(benzyloxy)-N-(4-tert-butylbenzyl)-2-methyl-1,8-naphthyridine-3-carboxamide

In a screw cap pressure tube were N-(4-tert-butylbenzyl)-6-iodo-2-methyl-1,8-naphthyridine-3-carboxamide (135 mg, 0.30 mmol), Cs$_2$CO$_3$ (191.5 mg, 0.6 mmol), CuI (5.6 mg, 0.03 mmol) and 3,4,7,8-tetramethyl-1,10-phenantroline (14.0 mg, 0.06 mmol)) suspended in benzyl alcohol (4.5 ml). N$_2$ was bubbled through the suspension for 5 min. The tube was sealed and the mixture heated to 120° C. overnight. The mixture was allowed to cool. CH$_2$Cl$_2$ was added and the mixture washed with H$_2$O, dried (MgSO$_4$), filtered and concentrated. The crude mixture was purified by flash chromatography (CH$_2$Cl$_2$/MeOH 98:2→97:3) yielding 62 mg of the title compound (47%).

$^1$H NMR (CDCl$_3$) δ 8.85 (d, 1H), 8.11 (s, 1H), 7.41 (m, 10H), 6.54 (bs, 1H), 5.20 (s, 2H), 4.67 (d, 2H), 2.85 (s, 3H), 1.34 (s, 9H).

Example 115

N-(4-tert-Butylbenzyl)-6-hydroxy-2-methyl-1,8-naphthyridine-3-carboxamide 6-(Benzyloxy)-N-(4-tert-butylbenzyl)-2-methyl-1,8-naphthyridine-3-carboxamide (62.0 mg, 0.14 mmol) was dissolved in MeOH (2 ml). Pd (C) (3.1 mg) was added to the solution. The mixture was hydrogenated at atmospheric pressure for 24 h. Then it was filtered through a pad of celite and concentrated under reduced pressure. The residue was washed with CH$_2$Cl$_2$ yielding 37 mg (76%) of the title compound.

$^1$H NMR (DMSO-D$_6$) δ 9.07 (m, 1H), 8.71 (d, 1H), 8.29 (s, 1H), 7.61 (d, 1H), 7.39 (d, 2H), 7.31 (d, 2H), 4.46 (d, 2H), 2.66 (s, 3H), 1.28 (s, 9H).

Example 116

N-(4-tert-Butylbenzyl)-6-cyano-2-methyl-1,8-naphthyridine-3-carboxamide

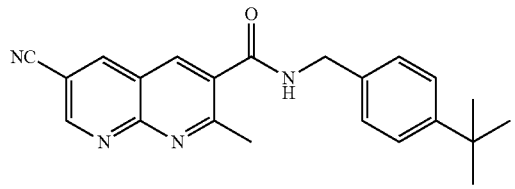 [SMILES: Cc1nc2ncc(C#N)cc2cc1C(=O)NCc1ccc(C(C)(C)C)cc1]

6-Bromo-N-(4-tert-butylbenzyl)-2-methyl-1,8-naphthyridine-3-carboxamide (90 mg, 0.22 mmol), N,N'-dimethylethane-1,2-diamine (24 µl, 0.22 mmol), CuI (4 mg, 0.02 mmol), KI (7 mg, 0.04 mmol) and NaCN (13 mg, 0.26 mmol) were suspended in toluene (2 ml). The mixture was stirred at 120° C. for 48 hours in a closed high-pressure flask. The reaction was cooled, diluted with NH$_4$OH (30 ml) and extracted with CH$_2$Cl$_2$ (3*30 ml). Combined organics were washed with water (30 ml), dried over MgSO$_4$ and evaporated. The product was purified by flash chromatography using CH$_2$Cl$_2$/CH$_3$OH (25:1) as eluent to give 25 mg (32%) of the title compound as pale solids.

$^1$H NMR (CDCl$_3$) δ 9.22 (d, 1H), 8.51 (d, 1H) 8.22 (s, 1H), 7.43 (d, 2H), 7.33 (d, 2H), 4.66 (d, 2H), 2.96 (s, 3H), 1.33 (s, 9H).

Scheme 37

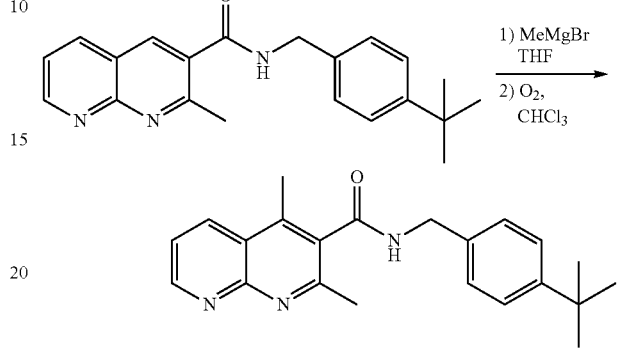

Example 117

N-(4-tert-butylbenzyl)-2,4-dimethyl-1,8-naphthyridine-3-carboxamide

N-(4-tert-butylbenzyl)-2-methyl-1,8-naphthyridine-3-carboxamide (150 mg, 0.45 mmol) was dissolved in THF (anh, 8.0 ml) under N$_2$. Methylmagnesium bromide (4.5 ml of a 1M sln) was added dropwise. The mixture was stirred at r.t. for 2.0 h. The reaction was quenched with NH$_4$Cl (sat). The product was extracted with EtOAc, dried (MgSO$_4$), filtered and concentrated. The residue was dissolved in CHCl$_3$ and O$_2$ (94%) was bubbled through the solution for 3.0 h. The mixture was concentrated and purified by flash chromatography CH$_2$Cl$_2$/MeOH (96:4→95:5) yielding 50.0 mg of the title compound (32%). $^1$H NMR (CDCl$_3$) δ 8.80 (m, 1H), 8.13 (m, 1H), 7.44 (d, 2H), 7.41 (d, 2H), 7.35 (m, 1H), 7.02 (t, 1H), 4.74 (d, 2H), 2.73 (s, 3H), 2.49 (s, 3H), 1.34 (s, 9H).

5-Chloro-2-methyl-N-(3-(trifluoromethyl)benzyl)-1,8-naphthyridine-3-carboxamide

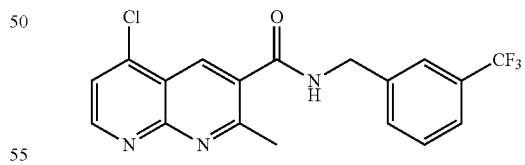

N-(4-Chloro-3-formylpyridin-2-yl)pivalamide (678 mg, 2.82 mmol) and 3-oxo-N-(3-(trifluoromethyl)benzyl)butanamide (2.82 mmol) was dissolved in dry THF (25 ml) and cooled to 0° C. under an atmosphere of nitrogen. Potassium hexamethyldisilazane (14 ml, 7.0 mmol, 0.5 M in toluene) was added dropwise under 15 minutes and the reaction was stirred at 0° C. for 15 minutes followed by 18 hours at room temperature. Reaction was then diluted with NH$_4$Cl (50 ml, sat aq) and extracted with CH$_2$Cl$_2$ (3*30 ml). Combined organics were dried over MgSO$_4$, filtered and evaporated. The crude product was purified by flash chromatography using CH₂Cl₂/CH₃OH (20:1) as eluent to give 0.86 g (80%) of 5-chloro-2-methyl-N-(3-(trifluoromethyl)benzyl)-1,8-naphthyridine-3-carboxamide as a pale syrup.

¹H NMR (CDCl₃) δ 8.69 (d, 1H), 8.18 (s, 1H), 8.12 (br s, 1H), 7.72 (s, 1H), 7.63 (brd, 1H), 7.56 (brd, 1H), 7.49 (m, 1H), 7.38, (d, 1H), 4.75 (d, 2H), 2.72 (s, 3H).

Example 118

5-Methoxy-2-methyl-N-(3-(trifluoromethyl)benzyl)-1,8-naphthyridine-3-carboxamide

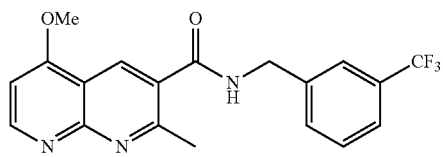 [SMILES: COc1ccnc2nc(C)c(C(=O)NCc3cccc(C(F)(F)F)c3)cc12]

5-Chloro-2-methyl-N-(3-(trifluoromethyl)benzyl)-1,8-naphthyridine-3-carboxamide (100 mg, 0.26 mmol) was dissolved in MeOH (10 ml) together with sodium methoxide (30 mg, 0.55 mmol) and refluxed for 18 hours. The reaction was cooled and evaporated, the residue was purified by flash chromatography using CH₂Cl₂/CH₃OH (20:1→10:1) as eluent to give 77 mg (79%) of 5-methoxy-2-methyl-N-(3-(trifluoromethyl)benzyl)-1,8-naphthyridine-3-carboxamide as a pale mass.

¹H NMR (CDCl₃) δ 8.62 (d, 1H), 8.19 (s, 1H), 7.72 (s, 1H), 7.65 (brd, 1H), 7.57 (brd, 1H), 7.51 (brt, 1H), 6.62, (d, 1H), 4.76 (d, 2H), 3.95 (s, 3H), 2.74 (s, 3H).

Example 119

5-(Dimethylamino)-2-methyl-N-(3-(trifluoromethyl)benzyl)-1,8-naphthyridine-3-carboxamide

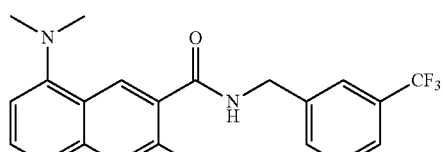

5-Chloro-2-methyl-N-(3-(trifluoromethyl)benzyl)-1,8-naphthyridine-3-carboxamide (100 mg, 0.26 mmol) was dissolved in THF (5 ml) together with methylamine (5 ml, 40% aq) mg, 0.55 mmol) and was stirred at room temperature for 2 hours followed by 18 hours at 50° C. The reaction was cooled and diluted with H₂O (10 ml) and NaCl (5 ml, sat aq) and then extracted with CH₂Cl₂ (4*20 ml). Combined organics were dried over MgSO₄, filtered and evaporated. The residue was purified by flash chromatography using CH₂Cl₂/CH₃OH (20/1→10/1) as eluent to give 70 mg (69%) of 5-(dimethylamino)-2-methyl-N-(3-(trifluoromethyl)benzyl)-1,8-naphthyridine-3-carboxamide as a clear residue.

¹H NMR (CDCl₃) δ 8.42 (brt, 1H), 8.37 (d, 1H), 8.02 (s, 1H), 7.78 (s, 1H), 7.69 (brd, 1H), 7.57 (brd, 1H), 7.51 (m, 1H), 6.46, (d, 1H), 4.80 (d, 2H), 2.97 (s, 6H), 2.65 (s, 3H).

Example 120

2-Methyl-5-morpholino-N-(3-(trifluoromethyl)benzyl)-1,8-naphthyridine-3-carboxamide

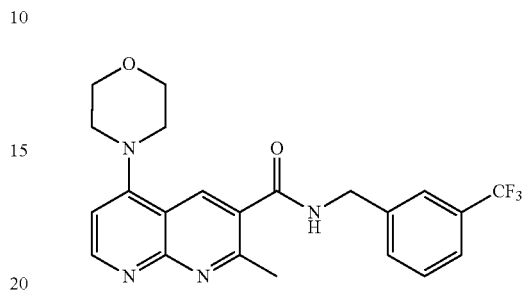

5-Chloro-2-methyl-N-(3-(trifluoromethyl)benzyl)-1,8-naphthyridine-3-carboxamide (100 mg, 0.26 mmol) was dissolved in THF (10 ml) together with morpholine (45 μl, 0.52 mmol) and refluxed for 18 hours. The reaction was cooled and evaporated, the residue was purified by flash chromatography using CH₂Cl₂/CH₃OH (20:1→10:1) as eluent to give 34 mg (30%) of 2-methyl-5-morpholino-N-(3-(trifluoromethyl)benzyl)-1,8-naphthyridine-3-carboxamide as a pale mass.

¹H NMR (CDCl₃) δ 8.71 (d, 1H), 8.16 (s, 1H), 7.72 (s, 1H), 7.65 (br d, 1H), 7.60 (br d, 1H), 7.52 (br t, 1H), 6.75 (d, 1H), 4.79 (d, 2H), 3.91 (t, 2H), 3.16 (t, 2H), 2.74 (s, 3H).

Example 121

6-Chloro-2-methyl-N-(3-(trifluoromethyl)benzyl)-1,8-naphthyridine-3-carboxamide

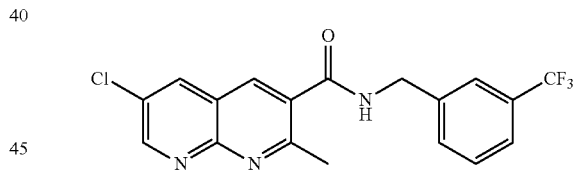

Prepared as above to give 160 mg (9%) white solids.

¹H NMR (CDCl₃) δ 8.77 (brs, 1H), 7.91 (m, 2H), 7.65 (s, 1H), 7.59 (m, 3H), 7.50 (m, 1H), 4.71 (d, 2H), 2.68 (s, 3H).

Scheme 38

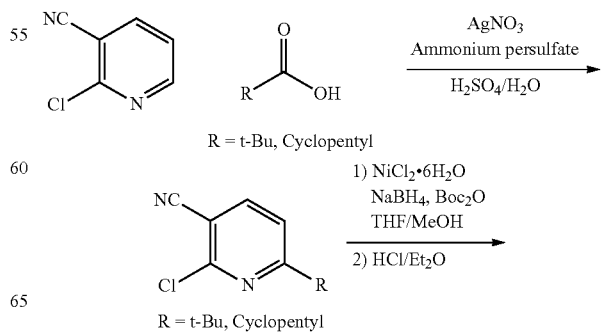

-continued

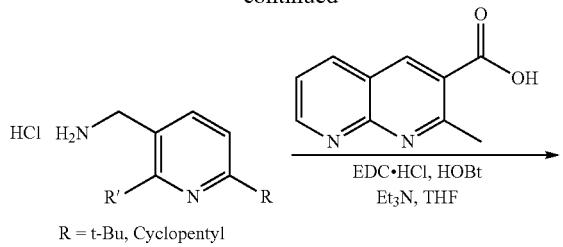

R = t-Bu, Cyclopentyl

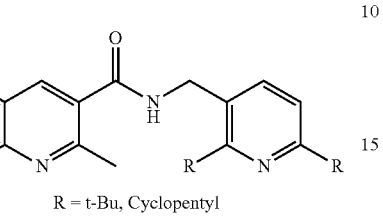

R = t-Bu, Cyclopentyl 6-tert-Butyl-2-chloronicotinonitrile

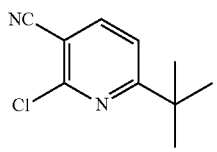

2-Chloronicotinonitrile (2.1 g, 15.2 mmol), pivalic acid (7.7 g, 75.8 mmol) and silver nitrate (0.5 g, 3.0 mmol) were suspended in 10% aqueous $H_2SO_4$ (20 ml). Ammonium persulfate (6.9 g, 30.3 mmol) in $H_2O$ (40 ml) was added to the mixture. The mixture was stirred at r.t. for 36 h. $NH_4OH$ was added until pH=9. The product was extracted with EtOAc. The combined organic extracts were washed with water, dried ($MgSO_4$), filtered and concentrated. Purification was done by flash chromatography (Pet. Ether/EtOAc 9:1) to give the title substance in 38% yield.

$^1$H NMR (CDCl$_3$) δ 7.91 (d, 1H), 7.38 (d, 1H), 1.37 (s, 9H).

2-Chloro-6-cyclopentylnicotinonitrile

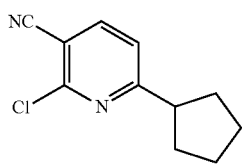 [SMILES: N#Cc1ccc(C2CCCC2)nc1Cl]

This compound was synthesized in 41% yield from 2-chloronicotinonitrile and cyclopentanecarboxylic acid using the same procedure as for 6-tert-butyl-2-chloronicotinonitrile.

$^1$H NMR (CDCl$_3$) d 7.86 (d, 1H), 7.22 (d, 1H), 3.20 (q, 1H), 2.08 (m, 2H), 1.82 (m, 6H).

(6-tert-Butyl-2-chloropyridin-3-yl)methanamine hydrochloride

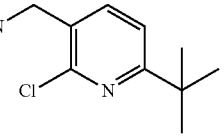

This compound was synthesized following the General procedure F for the reduction of benzonitriles to benzylamines to give the title compound in 27% yield.

$^1$H NMR (CD$_3$OD) δ 7.86 (d, 1H), 7.49 (d, 1H), 4.25 (s, 2H), 1.35 (s, 9H).

(2-Chloro-6-cyclopentylpyridin-3-yl)methanamine hydrochloride

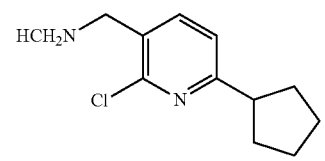

This compound was synthesized following the General procedure F for the reduction of benzonitriles to benzylamines to give the title compound in 32% yield.

$^1$H NMR (CD$_3$OD) δ 7.86 (d, 1H), 7.36 (d, 1H), 4.25 (s, 2H), 3.20 (q, 1H), 2.06 (m, 2H), 1.78 (m, 6H).

Example 122

N-((6-tert-Butyl-2-chloropyridin-3-yl)methyl)-2-methyl-1,8-naphthyridine-3-carboxamide

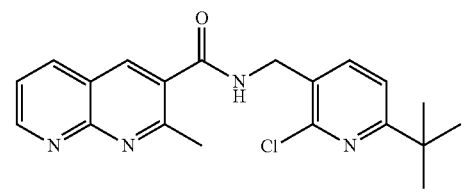 [SMILES: Cc1nc2ncccc2cc1C(=O)NCc1ccc(C(C)(C)C)nc1Cl]

This substance was synthesized following the general amide coupling procedure. Purification was done by flash chromatography (CH$_2$Cl$_2$/MeOH 95:5) to give the title substance in 66% yield.

¹H NMR (CDCl₃) δ 9.09 (dd, 1H), 8.12 (m, 2H), 7.83 (d, 1H), 7.47 (dd, 1H), 7.31 (dd, 1H), 6.80 (t, 1H), 4.73 (d, 2H), 2.88 (s, 3H), 1.35 (s, 9H).

Example 123

N-((2-chloro-6-cyclopentylpyridin-3-yl)methyl)-2-methyl-1,8-naphthyridine-3-carboxamide

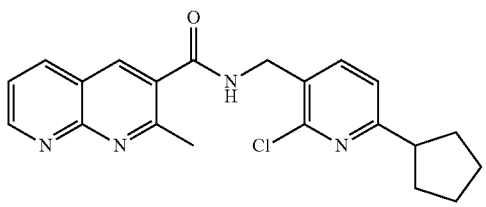 [SMILES: Cc1nc2ncccc2cc1C(=O)NCc1ccc(C2CCCC2)nc1Cl]

This substance was synthesized following the general amide coupling procedure. Purification was done by flash chromatography (CH₂Cl₂/MeOH 95:5) to give the title substance in 89% yield.

¹H NMR (CDCl₃) δ 9.09 (dd, 1H), 8.12 (m, 2H), 7.82 (d, 1H), 7.47 (dd, 1H), 7.17 (d, 1H), 6.84 (t, 1H), 4.73 (d, 2H), 3.17 (q, 1H), 2.87 (s, 3H), 2.10 (m, 2H), 1.75 (m, 6H).

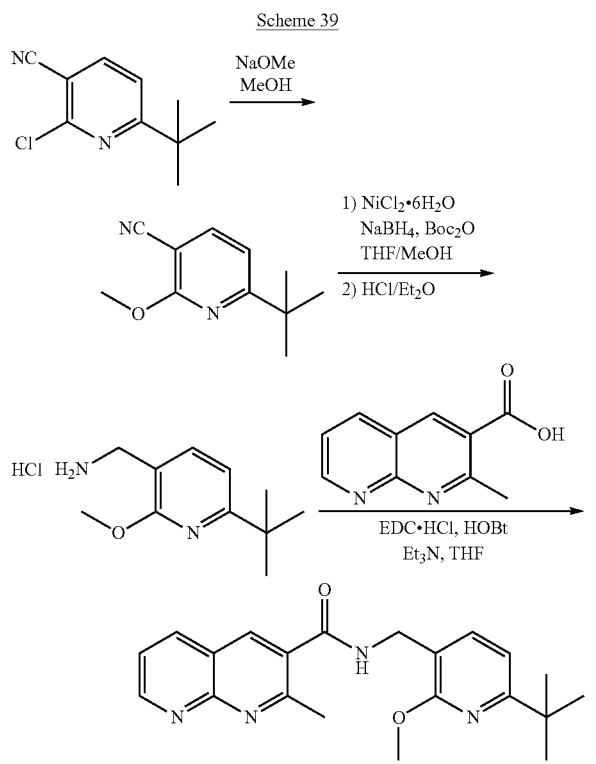

Scheme 39

6-tert-Butyl-2-methoxynicotinonitrile

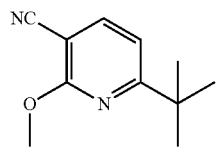

In a screw cap pressure tube, 6-tert-butyl-2-chloronicotinonitrile (410.0 mg, 2.1 mmol) was dissolved in anhydrous MeOH (3.0 ml) under N₂. NaOMe (159.3 mg, 2.9 mmol) was added as a solution in anhydrous MeOH (3.0 ml). The tube was sealed and the mixture refluxed for 20 hours. The mixture was allowed to cool. NH₄Cl (sat.) was added and the product extracted with EtOAc. The combined organic extracts were washed with water, dried (MgSO₄), filtered and concentrated. Purification was done by flash chromatography (Pet. Ether/EtOAc 95:5) to give the title substance in 85% yield.

¹H NMR (CDCl₃) δ 7.78 (d, 1H), 7.97 (d, 1H), 4.05 (s, 3H), 1.34 (s, 9H).

(6-tert-Butyl-2-methoxypyridin-3-yl)methanamine hydrochloride

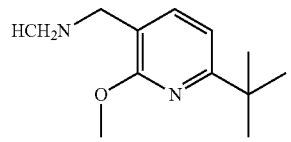

This compound was synthesized following the General procedure F for the reduction of benzonitriles to benzylamines to give the title compound in 50% yield.

¹H NMR (CD₃OD) δ 7.70 (d, 1H), 7.00 (d, 1H), 4.09 (s, 2H), 4.02 (s, 3H), 1.33 (s, 9H).

Example 124

N-((6-tert-Butyl-2-methoxypyridin-3-yl)methyl)-2-methyl-1,8-naphthyridine-3-carboxamide

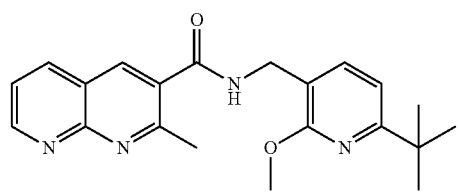 [SMILES: COc1nc(C(C)(C)C)ccc1CNC(=O)c1cc2cccnc2nc1C]

This substance was synthesized following the general amide coupling procedure. Purification was done by flash chromatography (CH₂Cl₂/MeOH 95:5) to give the title substance in 38% yield.

¹H NMR (CDCl₃) δ 9.11 (m, 1H), 8.16 (m, 2H), 7.59 (d, 1H), 7.48 (m, 1H), 6.90 (d, 1H), 6.56 (m, 1H), 4.61 (d, 2H), 4.00 (s, 3H), 2.88 (s, 3H), 1.34 (s, 9H).

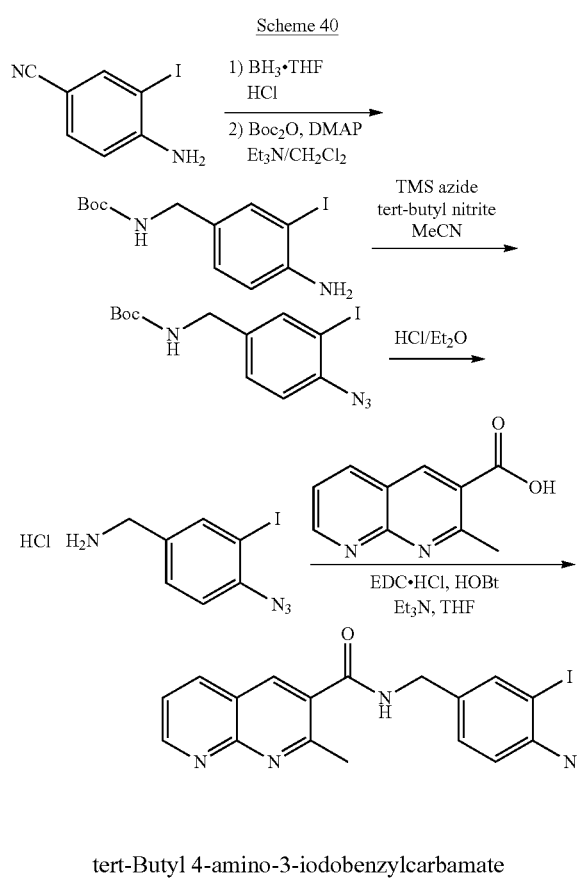

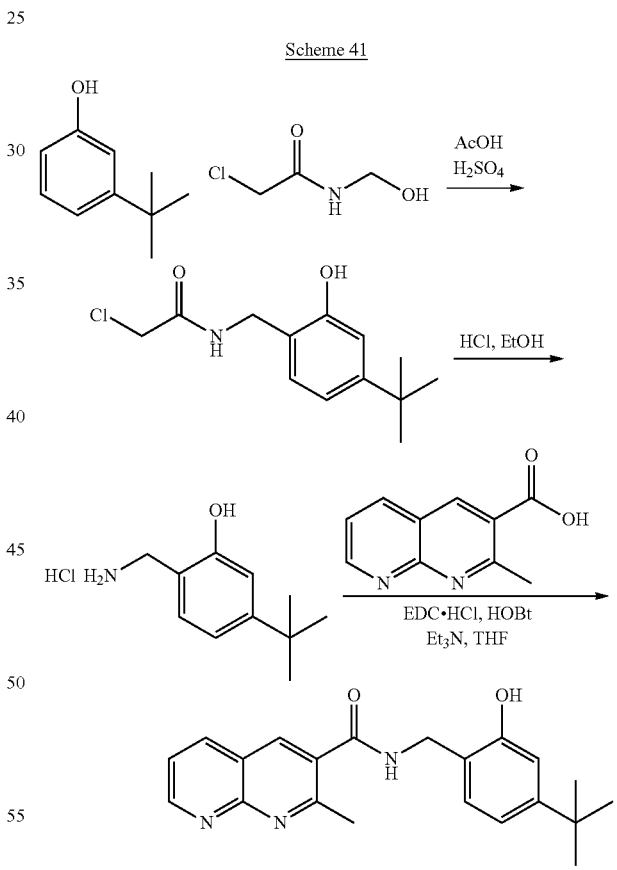

(4-Azido-3-iodophenyl)methanamine hydrochloride tert-Butyl 4-azido-3-iodobenzylcarbamate (936.0 mg, 2.5 mmol) was dissolved in Et$_2$O.HCl (2.0 N in Et$_2$O) (10 ml) was added to the solution. The mixture was stirred at r.t. overnight. The solvent was removed under vacuum and the residue washed with a mixture of CH$_2$Cl$_2$ and MeOH (8:2) affording 350 mg (45%) of the title compound.

$^1$H NMR (CD$_3$OD) δ 7.96 (d, 1H), 7.54 (dd, 1H), 7.33 (d, 1H), 4.08 (s, 2H).

Example 125

N-(4-Azido-3-iodobenzyl)-2-methyl-1,8-naphthyridine-3-carboxamide

This substance was synthesized following the general amide coupling procedure. Purification was done by flash chromatography (CH$_2$Cl$_2$/MeOH 96:4) to give the title substance in 64% yield.

$^1$H NMR (CDCl$_3$) δ 9.04 (dd, 1H), 8.13 (s, 1H), 8.11 (dd, 1H), 7.87 (d, 1H), 7.48 (m, 2H), 7.21 (t, 1H), 7.14 (d, 1H), 4.64 (d, 2H), 2.87 (s, 3H).

tert-Butyl 4-amino-3-iodobenzylcarbamate

In an oven-dried three-necked round bottom flask provided with a reflux condenser was 4-Amino-3-benzonitrile (1.0 g, 4.1 mmol) dissolved in anhydrous THF (10 ml) under N$_2$. BH$_3$.THF was added dropwise. Once the addition was complete the reaction mixture was refluxed for 2 h. The mixture was allowed to cool and HCl (2.0 N aq.) (6.0 ml) was added dropwise. Then the mixture was refluxed for 1.0 h. The solvents were removed under vacuum and residue was suspended in CH$_2$Cl$_2$ (30 ml). DMAP (100.1 mg, 0.8 mmol), Et$_3$N (1.3 ml, 9.4 mmol) and Boc$_2$O (2.7 g, 12.3 mmol) were added and the mixture stirred at r.t. for 1.5 h. H$_2$O was added and the product extracted with EtOAc. The combined organic extracts were dried (MgSO$_4$), filtered and concentrated. The crude product was purified by flash chromatography (CH$_2$Cl$_2$/MeOH 99:1) affording 1.0 g (71%) of the title compound.

$^1$H NMR (CDCl$_3$) δ 7.55 (d, 1H), 7.07 (dd, 1H), 6.70 (d, 1H), 4.76 (bs, 1H), 4.15 (d, 2H), 4.08 (bs, 2H), 1.46 (s, 9H).

tert-Butyl 4-azido-3-iodobenzylcarbamate tert-Butyl 4-amino-3-iodobenzylcarbamate (1.0 g, 2.87 mmol) was dissolved in CH$_3$CN (6.0 ml). The solution was cooled to 0° C., tert-butyl nitrite (444.3 mg, 4.30 mmol) and TMS azide (397.1 mg, 3.45 mmol) were added. The mixture was then stirred at r.t for 2.0 h. The solvents were removed under vacuum and the residue purified by flash chromatography (Pet. Ether/EtOAc 85:15) affording 936 mg (87%) of the title compound.

$^1$H NMR (CDCl$_3$) δ 7.70 (d, 1H), 7.31 (dd, 1H), 7.09 (d, 1H), 4.88 (bs, 1H), 4.25 (d, 2H), 1.47 (s, 9H).

N-(4-tert-Butyl-2-hydroxybenzyl)-2-chloroacetamide

A mixture of 3-tert-butyl phenol (500.0 mg, 3.33 mmol) and 2-chloro-N-(hydroxymethyl)acetamide (411.2 mg, 3.33 mmol) was added in portions to an ice-bath cold solution of acetic acid (3.0 ml) and conc. H$_2$SO$_4$ (0.5 ml). The mixture was stirred at 0-5° C. for 3.0 h. and then it was allowed to warm to r.t. Stirring continued at r.t. for 20 h. The mixture was poured into ice-water, neutralized with solid NaHCO$_3$ and extracted with CH$_2$Cl$_2$. The combined organic extracts were dried (MgSO$_4$), filtered and concentrated. The crude product was purified by flash chromatography; Pet. Ether, EtOAc (9:1→7:3) affording 278 mg (33%) the title compound.

$^1$H NMR (CDCl$_3$) δ 8.60 (s, 1H), 7.39 (bs, 1H), 7.08 (d, 1H), 7.00 (d, 1H), 6.90 (dd, 1H), 4.41 (d, 2H), 4.10 (s, 1H), 1.27 (s, 9H).

2-(Aminomethyl)-5-tert-butylphenol hydrochloride

N-(4-tert-Butyl-2-hydroxybenzyl)-2-chloroacetamide (270.0 mg, 1.06 mmol) was dissolved in a mixture of EtOH (4.0 ml) and conc. HCl (1.3 ml). The mixture was stirred at 85° C. for 3.0 h. The solvents were removed under vacuum to afford 225 mg (98%) of the title compound.

$^1$H NMR (CD$_3$OD) δ 7.19 (d, 1H), 6.96 (d, 1H), 6.93 (dd, 1H), 4.06 (s, 2H), 1.29 (s, 9H).

Example 126

N-(4-tert-butyl-2-hydroxybenzyl)-2-methyl-1,8-naphthyridine-3-carboxamide

This substance was synthesized following the general amide coupling procedure. The crude mixture was washed with CH$_2$Cl$_2$ to give the title substance in 70% yield.

$^1$H NMR (CD$_3$OD) δ 9.04 (dd, 1H), 8.44 (dd, 1H), 8.39 (s, 1H), 7.62 (dd, 1H), 7.22 (d, 1H), 6.89 (m, 2H), 4.53 (s, 2H), 2.81 (s, 3H), 1.29 (s, 9H).

Biological Examples

Biological Example

The usefulness of the compounds, as defined in the embodiments herein, in treating, revoking, mitigating, alleviating and/or preventing a condition of the respiratory apparatus characterized by bronchoconstriction, were evaluated in a complex and relevant in vitro model, which is described in US 2006-0040254 A1 and Skogvall, S., Berglund, M., Dalence-Guzmán, M. F., Svensson, K., Jönsson, P., Persson, C. G. A and Sterner, O., Pulmonary Pharmacology and Therapeutics, vol 20:3, 2007, p. 273-280. All references disclosed herein are hereby incorporated in their entirety by reference.

Lung tissue was obtained from patients undergoing lobectomia or pulmectomia due to lung carcinoma. The tissue was placed in a dissection chamber continuously perfused with 10 ml min$^{-1}$ of a physiological saline solution (PSS) at room temperature. An airway was identified in the cut part of the lobe, and a bronchus of 10-20 mm length, and 1-2 mm diameter was obtained. The bronchus was cut into rings of a width of about 2-3 mm. Each bronchial ring was cleaved to obtain an about rectangular oblong preparation free from cartilage, one end of which was tied to a small steel hook connected to a force transducer, while the other end of the preparation was attached to a fixed hook. This is followed by a period of adjustment, as described below. The preparation was mounted in an atmosphere containing 12% of oxygen and 6% of CO$_2$.

Experimental Chamber

The experimental assay system consists of 8 chambers, each with a volume of 6 ml, and is continuously perfused with solutions at a rate of 3 ml/min at 37° C. The chambers are equipped with force transducers (model AME 801, SensoNor A/S, Horton, Norway) allowing the individual registration of parallel preparations. The force transducers are connected to micrometer screws for stretching of tissue preparations to the desired tone. Recordings from the experiments are sampled and analysed using software from ADInstrumets. The substances to be tested and contractile agent are injected upstream of the preparation(s).

Materials. PPS (physiological saline solution, in mM): NaCl, 117; KCl, 4.87; MgSO$_4$, 0.60; NaHCO$_3$, 25.0; CaCl$_2$, 1.60; glucose, 5.23. The solution is saturated with a mixture of 94% oxygen and 6% carbon dioxide, giving a pH of 7.40±0.05 in the experimental chamber. All substances are prepared as stock solution dissolved in the vehicles ethanol or DMSO. Leukotriene D4 (LTD4; Cayman Ltd.): 10 µl of a 100 µM ethanol stock solution. Substance to be tested: 10-100 µl of a 0.01-0.1 M DMSO stock solution. Solution for establishing the passive tension level: calcium-free PSS+2 mM EGTA. To exclude effects by the test substance vehicle, DMSO was added during the entire experiment except during the presence of test substance.

Test Procedure A

After mounting as described above the preparation is allowed to adjust with a low passive tone in the experimental chamber. The composition of the gas is changed to 94% (v/v) of oxygen. After a short adjustment period, PSS with 10 nM LTD4 is added to the experimental chamber upstream of the preparation (A). The preparation is stretched repeatedly (B) until it exerts a contraction force of around 150 mg. When the contraction has levelled off, LTD4-free solution is administered for 1 hour (C), resulting in a relaxation. A second injection of 10 nM LTD4 (D) makes the preparation return to the tensioned state. At the peak tension leukotriene-free solution is again administered (E). After a third injection of 10 nM LTD4 (F) the preparation returns to the tensioned state. At the peak, PSS with 10 µM of the item to be tested is added, resulting in a relaxation. After 1 h exposure to the test item, 10 nM LTD4 is added, resulting in a contraction (H). If the test item is a bronkorelaxant, a substantially weaker contraction is now observed (H) in comparison with the control LTD4 contraction (F). To obtain a measure of the test substance's bronchorelaxing effect the test and control forces registered in the experiment are compared. During steps C-F and I-J 10 µl DMSO per 100 ml PSS is present to compensate for potential vehicle effects. The experiment is concluded by adding calcium-free solution with addition of 2 mM EGTA for 20 min to establish the passive tension level (I). A bronchus tissue preparation is considered stable and thus fit for the evaluation of test substances if the difference in contraction between contractions D and F is less than 15 percent.

Mounting and stretching preps. 3 units in 12% O$_2$ (10 min).

A. PSS 94% O$_2$ (10 min).

B. PSS+LTD$_4$ 1.0e-8 M (15 min+stretching to plateau at +2 units).

C. PSS+DMSO 10 µl in 100 ml solution (1 h).

D. PSS+DMSO+LTD$_4$ (30 min).

E. PSS+DMSO 10 µl in 100 ml solution (1 h).

F. PSS+DMSO+LTD$_4$ (30 min).

G. PSS+substance 1.0e-5 M (1 h).

H. PSS+substance 1.0e-5 M+LTD$_4$ (30 min).

I. PSS without Ca$^{2+}$+2 mM EGTA (to plateau).

The result, bronchorelaxing efficiency, is calculated as follows: by comparing and obtaining the ratio between the tensioned states (relative to base line) before and after compound treatment, the bronchorelaxing efficiency of the test item is determined. The results are expressed as % remaining contraction (RC).

The remaining contraction, after pre-treatment with various compound examples at a concentration of 1 and 10 μM, of human bronchiols after Leukotriene D4 (10 nM) induced contraction according to the in vitro method described herein above are tabulated below.

Test Procedure B

After mounting as described above the preparation is allowed to adjust with a low passive tone in the experimental chamber. The composition of the gas is changed to 94% (v/v) of oxygen. After a short adjustment period, PSS with 10 nM LTD4 is added to the experimental chamber upstream of the preparation (A). The preparation is stretched repeatedly (B) until it exerts a contraction force of around 150 mg. The preparation is kept at level contraction, plateau, with 10 nM LTD4 for 30 min (C). The preparation is then treated with 0.1 μM of the test item in 10 nM LTD4 PSS for 1 h. This is followed by the sequential treatment with 1 μM of the test item in 10 nM LTD4 PSS for 1 h (E) and finally 10 uM of the test item in 10 nM LTD4 PSS for 1 h (F). The experiment is concluded by adding calcium-free solution with addition of 2 mM EGTA for 20 min to establish the passive tension level base line (G).

The result, bronchorelaxing efficiency, is calculated as follows: by comparing and obtaining the ratio between the tensioned states (relative to base line) at the different concentrations, the bronchorelaxing efficiency of the test item is determined. The results are expressed as % remaining contraction (RC).

By using different inflammatory mediators in either method A or B, it is possible to show if a tested compound is a general dilator or a specific antagonist for a given inflammatory mediator.

In short, lung tissue was obtained from patients undergoing lobectomia or pulmectomia due to lung carcinoma. From the bronchus of this tissue were rectangular oblong preparations obtained. The contraction induced by inflammatory mediators, such as Leukotriene D4, histamine, prostaglandin D2 or acetylcholine, in the presence and absence of the compound to be evaluated, were compared.

The remaining contraction, after pre-treatment with various compound examples at a concentration of 0.1, 1 and 10 μM, of human bronchiols after Leukotriene D4 (10 nM) induced contraction according to the in vitro method described herein above are tabulated below.

Test Procedure A

| Example | % RC 10 μm | % RC 1 μM |
|---------|------------|-----------|
| 17 | 8 | 67 |
| 19 | 17 | 41 |
| 14 | 15 | 76 |
| 2 | 23 | 77 |

Test Procedure B

| Example | % RC 0.1 μM | % RC 1 μM | % RC 10 μM |
|---------|-------------|-----------|------------|
| 4 | 85 | 39 | 4 |
| 101 | 72 | 63 | 27 |
| 62 | 92 | 63 | 17 |
| 109 | 73 | 25 | 1 |

The invention claimed is:
1. A compound according to formula (I),

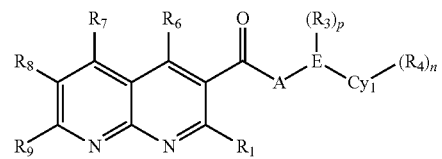

wherein
$R_1$ is selected from the group consisting of Me, NH2, NHMe, CF3, OMe, OCF3, N(Me)$_2$, C(O)H, C(O)Me, C(O)OH, C(O)OMe, C(O)NH$_2$, and NHC(O)Me;
A is NR$_2$, O, or S, wherein R2 is selected from the group consisting of H and C1-C3 alkyl;
E is selected from the group consisting of C1-C3 alkylene, ethene-1,2-diyl, 1-propene-1,3-diyl and 2-propene-1,3-diyl;
if E is selected from the group consisting of ethene-1,2-diyl, 1-propene-1,3-diyl and 2-propene-1,3-diyl, then the stereochemistry of the double-bond may be either E or Z;
the integer "p" is 0 (zero), 1 or 2;
R3 is independently selected from the group consisting of C1-C3 alkyl, C1-C3 alkyleneOC0-C3 alkyl, OMe, C1-5 fluoroalkyl, C0-C3 alkyleneOC1-3 fluoroalkyl, C(O)OC0-C3 alkyl, and C(O)N(C0-C3 alkyl)$_2$, in which the C0-3 alkyl may be the same or different;
R3 may, if present, be connected to any of the carbon atom(s) in E; if "p" is 2, then the two R3 may be the connected to the same carbon atom or to different carbon atoms;
Cy1 is a 5-membered heteroaryl, a 6-membered heteroaryl, or phenyl;
the integer "n" is 0 (zero), 1 or 2;
R4 is independently selected from the group consisting of C1-8 alkyl, C1-5 fluoroalkyl, halo, C0-1 alkylene cyano, C0-8 alkyleneOC0-5 alkyl, SC0-5 alkyl, C0-3 alkyleneSO$_2$C0-5 alkyl, C0-3 alkyleneOC0-3 fluororoalkyl, C0-3 alkyleneNHC0-3 alkyl, C0-3 alkyleneN(C1-5 alkyl)$_2$, in which the C1-5 alkyl may be the same or different, C0-3 alkyleneC(O)OC0-5 alkyl, C0-3 alkyleneOC(O)C0-5 alkyl, C0-3 alkyleneN(C0-3 alkyl)C(O)C0-3 alkyl, C0-3 alkyleneC(O)NHC0-3 alkyl, C0-3 alkyleneC(O)N(C1-5 alkyl)$_2$, in which the C1-5 alkyl may be the same or different, nitro, C(O)C0-C5 alkyl, N(C0-C3 alkyl)SO$_2$C1-C3 alkyl, N(C0-C3 alkyl)SO$_2$C1-C3 fluoroalkyl, OC2-C3alkyleneN(C0-C3 alkyl)$_2$, in which the C0-3 alkyl may be the same or different, and

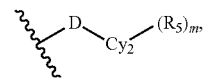

wherein
D is selected from the group consisting of C0-C3 alkylene, C0-1 alkylene OC0-1 alkylene, C0-1 alkylene OC(O)C0-1 alkylene, C0-1 alkylene C(O)OC0-1 alkylene, C0-1 alkylene C(O)N(C0-3 alkyl) C0-1 alkylene, C0-1 alkylene N(C0-3 alkyl)C(O)C0-1 alkylene, NHSO2, SO2NH, SO2, SO, C0-1 alkylene C(O)C0-1 alkylene, C0-1 alkylene N(C0-3 alkyl) C0-1 alkylene and S;

Cy2 is a 5-membered heteroaryl, a 6-membered heteroaryl, phenyl, a 3- to 8-membered non-aromatic heterocycle or a C3-8 non-aromatic carbocycle;

the integer "m" is 0 (zero), 1, 2, 3, 4, or 5; and

R5 is independently selected from C1-5 alkyl, C1-5 fluoroalkyl, halo, C0-1 alkylene cyano, C0-5 alkyleneOC0-5 alkyl, SC0-5 alkyl, C0-3 alkyleneSO₂C0-5 alkyl, C0-3 alkyleneOC1-3 fluoroalkyl, C0-3 alkyleneNHC0-3 alkyl, C0-3 alkyleneN(C1-5 alkyl)₂, in which the C1-5 alkyl may be the same or different, C0-3 alkyleneC(O)OC0-5 alkyl, C0-3 alkyleneOC(O)C0-5 alkyl, C0-3 alkyleneN(C0-3 alkyl)C(O)C0-3 alkyl, C0-3 alkyleneC(O)NHC0-3 alkyl, C0-3 alkyleneC(O)N(C1-5 alkyl)₂, in which the C1-5 alkyl may be the same or different, C0-3 alkyleneC(O)N(C4-5 alkylene), nitro, C(O)C0-C5 alkyl, C(O)C1-C3 fluoroalkyl, N(C0-3 alkyl)SO2C1-C3 alkyl, N(C0-C3 alkyl)SO₂C1-C3 fluoroalkyl, and OC2-C3alkyleneN(C0-C3 alkyl)₂, in which the C0-3 alkyl may be the same or different;

if Cy2 is a 3- to 8-membered non-aromatic heterocycle or a C3-8 non-aromatic carbocycle and "m" is at least 2, then two R5, being attached to the same carbon atom on said 3- to 8-membered non-aromatic heterocycle or said C3-8 non-aromatic carbocycle, may be connected to each other to form a 3, 4 or 5-membered spiro ring; said spiro ring being a non-aromatic carbocycle or a non-aromatic heterocycle;

if Cy2 is a 3- to 8-membered non-aromatic heterocycle or a C3-8 non-aromatic carbocycle and "m" is at least 2, then two R5, being attached to different atoms in said 3- to 8-membered non-aromatic heterocycle or said C3-8 non-aromatic carbocycle, may be connected to each other to form a C0-3 alkylene bridge; Cy2 thus being a bicyclic residue;

if Cy2 is a 3- to 8-membered non-aromatic heterocycle or a C3-8 non-aromatic carbocycle, then R5 may be a double bonded oxygen (=O), being attached to a carbon or sulfur atom in said cycle;

R6, R7, and R8 are independently selected from the group consisting of H, halogen, C1-C3 alkyl, NH(C0-C3 alkyl), C1-3 fluoroalkyl, OC0-C3 alkyl, OC1-3 fluoroalkyl, N(C4-5 alkylene), morpholinyl, N(C1-C3 alkyl)₂, in which the C0-3 alkyl may be the same or different, and cyano;

R9 is selected from the group consisting of H, halogen, C1-C3 alkyl, and C1-3 fluoroalkyl;

as a free base, an acid in its non-charged protonated form, a pharmaceutically addition acceptable salt, a pure stereoisomer, a racemic, diastereomeric or scalemic mixture, a corresponding tautomeric form resulting from a hydrogen shift between two hetero-atoms and/or the corresponding tautomeric form resulting from a keto-enol tautomerization;

with the proviso that the compound is not any of the following:

-continued

2. The compound according to claim 1, wherein R1 is Me, A is NR2, or O, R6, R8 and/or R9 are H, R7 is H or methyl, the integer "p" is 0 (zero) or the integer "p" is 1 and R3 is C1-C3 alkyl, and E is methylene or ethylene.

3. The compound according to claim 2, wherein A is NR2 and R2 is H.

4. The compound according to claim 1, wherein E is methylene, the integer "p" is 1, R3 is methyl and the stereochemistry of the carbon atom in said methylene is "S", if A is given the highest priority, Cy1, the second highest priority and the methyl group the lowest priority.

5. The compound according to claim 1, wherein the integer "n" is 1 or 2.

6. The compound according to claim 1, wherein Cy1 is phenyl or pyridyl.

7. The compound according to claim 1, wherein the integer "n" is 1 and R4 is selected from the group consisting of trifluoromethyl, tert-butyl, halogen, N(C0-3 alkyl)2, in which the C0-3 alkyl may be the same or different, OC1-C3 alkyl and

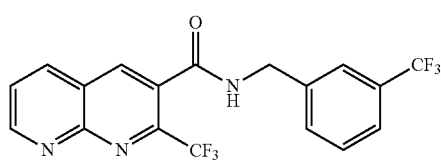

wherein Cy2 is selected from the group consisting of a 5- or a 6-membered non-aromatic heterocycle and a C3-7 non-aromatic carbocycle.

8. The compound according to claim 1, wherein the integer "n" is 2 and at least one of the two R4 is independently selected from the group consisting of trifluoromethyl, tert-butyl, cyano, halogen, N(C0-3 alkyl)2, in which the C0-3 alkyl may be the same or different, OC1-C3 alkyl, and

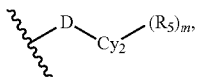

wherein Cy2 is selected from the group consisting of a 5- or 6-membered non-aromatic heterocycle and a C3-7 non-aromatic carbocycle.

9. The compound according to claim 1, wherein the integer "n" is 1 and R4 is

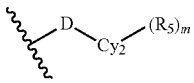

or wherein the integer "n" is 2 and one R4 is

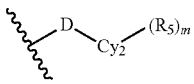

and the other R4 is selected from the group consisting of trifluoromethyl, C1-4 alkyl, halogen, cyano, and —OC0-C3alkyl.

10. The compound according to claim 9, wherein Cy2 is phenyl, pyridyl, a 5- or 6-membered non-aromatic heterocycle or a C3-7 non-aromatic carbocycle.

11. The compound according to claim 9, wherein the integer "m" is 0 (zero), or wherein the integer "m" is 1, 2 or 3, and wherein R5 independently is selected from the group consisting of trifluoromethyl, C1-4 alkyl, and OC1-3 alkyl.

12. The compound according to according to claim 9, wherein Cy2 is 6-membered non-aromatic heterocycle or a 5- or 6-membered non-aromatic carbocycle, "m" is at least 2 and two R5, being attached to the same carbon atom on said 6-membered non-aromatic heterocycle or said 5- or 6-membered non-aromatic carbocycle, are connected to each other to form a 3, 4 or 5-membered spiro ring, or two R5, both being a C1-3 alkyl, are attached to the 4-position (the 1-position being the point of attachment to D) in said 6-membered non-aromatic heterocycle or said 6-membered non-aromatic carbocycle or to the 3-position in said 5-membered non-aromatic carbocycle (the 1-position being the point of attachment to D).

13. The compound according to claim 9, wherein D is selected from the group consisting of a direct bond, —C(O) NH—, —NHC(O)—, C(O), —OCH2-, —CH2O—, —NHSO2-, —O—, and —SO2NH—.

14. The compound according to claim 1, wherein said compound is selected from the group consisting of
2-Methyl-N-(2-(trifluoromethyl)benzyl)-1,8-naphthyridine-3-carboxamide;
2-Methyl-N-(4-(trifluoromethyl)benzyl)-1,8-naphthyridine-3-carboxamide;
N-(4-tert-butylbenzyl)-2-methyl-1,8-naphthyridine-3-carboxamide;
2-Methyl-N-((2-phenylthiazol-4-yl)methyl)-1,8-naphthyridine-3-carboxamide;
2-Methyl-N-(1-(3-(trifluoromethyl)phenyl)propyl)-1,8-naphthyridine-3-carboxamide;
2-Methyl-N-(3-(trifluoromethyl)phenethyl)-1,8-naphthyridine-3-carboxamide;
N-(4-Benzoylbenzyl)-2-methyl-1,8-naphthyridine-3-carboxamide;
2-Methyl-N-((3-phenylisoxazol-5-yl)methyl)-1,8-naphthyridine-3-carboxamide;
2-Methyl-N-(4-(methylsulfonyl)benzyl)-1,8-naphthyridine-3-carboxamide;
N-(4-Chlorobenzyl)-2-methyl-1,8-naphthyridine-3-carboxamide;
N-(4-Chlorophenethyl)-2-methyl-1,8-naphthyridine-3-carboxamide;
N-(4-Fluorobenzyl)-2-methyl-1,8-naphthyridine-3-carboxamide;
N-(3-Chlorobenzyl)-2-methyl-1,8-naphthyridine-3-carboxamide;
2-Methyl-N-(3-(trifluoromethyl)benzyl)-1,8-naphthyridine-3-carboxamide;
2-Methyl-N-((6-phenylpyridin-3-yl)methyl)-1,8-naphthyridine-3-carboxamide;
2-Methyl-N-(1-(3-(trifluoromethyl)phenyl)ethyl)-1,8-naphthyridine-3-carboxamide;
N-(4-Chloro-3-(trifluoromethyl)benzyl)-2-methyl-1,8-naphthyridine-3-carboxamide;
N-(3,5-bis(Trifluoromethyl)benzyl)-2-methyl-1,8-naphthyridine-3-carboxamide;
N-(Biphenyl-4-ylmethyl)-2-methyl-1,8-naphthyridine-3-carboxamide;
N-(Biphenyl-3-ylmethyl)-2-methyl-1,8-naphthyridine-3-carboxamide;
(S)-2-Methyl-N-(1-(3-(trifluoromethyl)phenyl)ethyl)-1,8-naphthyridine-3-carboxamide;
N-(3-Chlorobenzyl)-2-(trifluoromethyl)-1,8-naphthyridine-3-carboxamide;
(R)-2-Methyl-N-(1-(3-(trifluoromethyl)phenyl)ethyl)-1,8-naphthyridine-3-carboxamide;
N-(3-Methoxybenzyl)-2-methyl-1,8-naphthyridine-3-carboxamide;
N-(3-Bromobenzyl)-2-methyl-1,8-naphthyridine-3-carboxamide;
N-(4-Bromobenzyl)-2-methyl-1,8-naphthyridine-3-carboxamide;
N-(4-fluorobenzyl)-2-(trifluoromethyl)-1,8-naphthyridine-3-carboxamide;
(S)—N-(1-(4-bromophenyl)ethyl)-2-methyl-1,8-naphthyridine-3-carboxamide;
(R)—N-(1-(4-bromophenyl)ethyl)-2-methyl-1,8-naphthyridine-3-carboxamide;
2-Methyl-N-(4-(methylthio)benzyl)-1,8-naphthyridine-3-carboxamide;
N-(1-(4-tert-butylphenyl)ethyl)-2-methyl-1,8-naphthyridine-3-carboxamide;
(S)—N-(1-(4-tert-butylphenyl)ethyl)-2-methyl-1,8-naphthyridine-3-carboxamide;
(R)—N-(1-(4-tert-butylphenyl)-2-hydroxyethyl)-2-methyl-1,8-naphthyridine-3-carboxamide;
N-(4-isopropylbenzyl)-2-methyl-1,8-naphthyridine-3-carboxamide;
2-Methyl-N-(3-(phenylcarbamoyl)benzyl)-1,8-naphthyridine-3-carboxamide;
2-Methyl-N-(4-(pyridin-4-yl)benzyl)-1,8-naphthyridine-3-carboxamide;

2-Methyl-N-(4-(pyridin-3-yl)benzyl)-1,8-naphthyridine-3-carboxamide;
N-((4'-Methoxybiphenyl-4-yl)methyl)-2-methyl-1,8-naphthyridine-3-carboxamide;
2-Methyl-N-((2'-(trifluoromethyl)biphenyl-3-yl)methyl)-1,8-naphthyridine-3-carboxamide;
2-Methyl-N-(3-(pyridin-3-yl)benzyl)-1,8-naphthyridine-3-carboxamide;
2-Methyl-N-(3-(pyridin-4-yl)benzyl)-1,8-naphthyridine-3-carboxamide;
N-((4'-Methoxybiphenyl-3-yl)methyl)-2-methyl-1,8-naphthyridine-3-carboxamide;
2-Methyl-N-((2'-(trifluoromethyl)biphenyl-4-yl)methyl)-1,8-naphthyridine-3-carboxamide;
(S)-2-methyl-N-(1-(4-(pyridin-3-yl)phenyl)ethyl)-1,8-naphthyridine-3-carboxamide;
(R)-2-methyl-N-(1-(4-(pyridin-3-yl)phenyl)ethyl)-1,8-naphthyridine-3-carboxamide;
(S)—N-(1-(4-Cyclohexenylphenyl)ethyl)-2-methyl-1,8-naphthyridine-3-carboxamide;
N-(4-(3,6-Dihydro-2H-pyran-4-yl)-3-(trifluoromethyl)benzyl)-2-methyl-1,8-naphthyridine-3-carboxamide;
(S)-2-methyl-N-(1-(4-(piperidin-1-yl)phenyl)ethyl)-1,8-naphthyridine-3-carboxamide;
N-(4-(3,6-Dihydro-2H-pyran-4-yl)-3-(trifluoromethyl)benzyl)-2-methyl-1,8-naphthyridine-3-carboxamide;
N-(4-Cyclohexenyl-3-(trifluoromethyl)benzyl)-2-methyl-1,8-naphthyridine-3-carboxamide;
N-(4-cyclohexylbenzyl)-2-methyl-1,8-naphthyridine-3-carboxamide;
2-Methyl-N-((4-phenylfuran-2-yl)methyl)-1,8-naphthyridine-3-carboxamide;
2-Methyl-N-(4-(pyrrolidin-1-yl)benzyl)-1,8-naphthyridine-3-carboxamide;
2-Methyl-N-(4-(4-methylphenylsulfonamido)-3-(trifluoromethyl)benzyl)-1,8-naphthyridine-3-carboxamide;
N-(4-(1H-Imidazol-1-yl)-3-(trifluoromethyl)benzyl)-2-methyl-1,8-naphthyridine-3-carboxamide;
N-(4-(2-(Dimethylamino)ethoxy)-3-(trifluoromethyl)benzyl)-2-methyl-1,8-naphthyridine-3-carboxamide;
2-Methyl-N-(4-(pyridin-3-ylmethoxy)-3-(trifluoromethyl)benzyl)-1,8-naphthyridine-3-carboxamide;
2-Methyl-N-(4-(piperidin-1-yl)-3-(trifluoromethyl)benzyl)-1,8-naphthyridine-3-carboxamide;
2-Methyl-N-(4-morpholino-3-(trifluoromethyl)benzyl)-1,8-naphthyridine-3-carboxamide;
N-(4-Isopropoxy-3-(trifluoromethyl)benzyl)-2-methyl-1,8-naphthyridine-3-carboxamide;
N-(4-Benzamido-3-(trifluoromethyl)benzyl)-2-methyl-1,8-naphthyridine-3-carboxamide;
2-Methyl-N-(4-(4-methylpiperazin-1-yl)-3-(trifluoromethyl)benzyl)-1,8-naphthyridine-3-carboxamide;
2-Methyl-N-(4-(tetrahydro-2H-pyran-4-yloxy)-3-(trifluoromethyl)benzyl)-1,8-naphthyridine-3-carboxamide;
N-(4-(Dimethylamino)-3-(trifluoromethyl)benzyl)-2-methyl-1,8-naphthyridine-3-carboxamide;
2-Methyl-N-(4-(methyl sulfonyl)-3-(trifluoromethyl)benzyl)-1,8-naphthyridine-3-carboxamide;
N-(4-cyclopentylbenzyl)-2-methyl-1,8-naphthyridine-3-carboxamide;
(S)-2-Methyl-N-(4-(3-methylmorpholino)benzyl)-1,8-naphthyridine-3-carboxamide;
(R)-2-methyl-N-(4-(3-methylmorpholino)benzyl)-1,8-naphthyridine-3-carboxamide;
N-(4-(4-Hydroxypiperidin-1-yl)-3-(trifluoromethyl)benzyl)-2-methyl-1,8-naphthyridine-3-carboxamide;
2-Methyl-N-(4-(1,1,1-trifluoropropan-2-yloxy)benzyl)-1,8-naphthyridine-3-carboxamide;
2-Methyl-N-(4-(2-methylpiperidin-1-yl)benzyl)-1,8-naphthyridine-3-carboxamide
N-(4-(2-(Hydroxymethyl)piperidin-1-yl)benzyl)-2-methyl-1,8-naphthyridine-3-carboxamide;
N-(4-(4-Acetylpiperazin-1-yl)-3-(trifluoromethyl)benzyl)-2-methyl-1,8-naphthyridine-3-carboxamide;
N-(4-(4,4-Dimethylpiperidin-1-yl)benzyl)-2-methyl-1,8-naphthyridine-3-carboxamide;
N-(4-(4,4-dimethylpiperidin-1-yl)-3-fluorobenzyl)-2-methyl-1,8-naphthyridine-3-carboxamide;
N-(3-cyano-4-(4,4-dimethylpiperidin-1-yl)benzyl)-2-methyl-1,8-naphthyridine-3-carboxamide;
N-(4-(Cyclopentyloxy)benzyl)-2-methyl-1,8-naphthyridine-3-carboxamide;
N-(3-fluoro-4-(4-methoxy-4-methylpiperidin-1-yl)benzyl)-2-methyl-1,8-naphthyridine-3-carboxamide;
2-Methyl-N-(4-thiomorpholinobenzyl)-1,8-naphthyridine-3-carboxamide;
N-(4-(8-oxa-3-azabicyclo[3.2.1]octan-3-yl)-3-fluorobenzyl)-2-methyl-1,8-naphthyridine-3-carboxamide;
N-(4-(2,6-dimethylmorpholino)-3-fluorobenzyl)-2-methyl-1,8-naphthyridine-3-carboxamide;
N-(3-fluoro-4-(1,4-dioxa-8-azaspiro[4.5]decan-8-yl)benzyl)-2-methyl-1,8-naphthyridine-3-carboxamide;
N-(4-(4,4-difluoropiperidin-1-yl)-3-fluorobenzyl)-2-methyl-1,8-naphthyridine-3-carboxamide;
2-Methyl-N-(4-(1,1-dioxothiomorpholino)benzyl)-1,8-naphthyridine-3-carboxamide;
2-Methyl-N-(4-(pyridin-3-yl)-3-(trifluoromethyl)benzyl)-1,8-naphthyridine-3-carboxamide;
N-((6-tert-Butylpyridin-3-yl)methyl)-2-methyl-1,8-naphthyridine-3-carboxamide;
2-methyl-N-((5-(piperidin-1-yl)pyridin-2-yl)methyl)-1,8-naphthyridine-3-carboxamide;
2-methyl-N-(4-(tetrahydro-2H-pyran-4-yl)benzyl)-1,8-naphthyridine-3-carboxamide
N-(4-(1-hydroxycyclohexyl)benzyl)-2-methyl-1,8-naphthyridine-3-carboxamide;
2-Methoxy-N-(3-(trifluoromethyl)benzyl)-1,8-naphthyridine-3-carboxamide;
2-(Methylamino)-N-(3-(trifluoromethyl)benzyl)-1,8-naphthyridine-3-carboxamide;
2-Amino-N-(3-(trifluoromethyl)benzyl)-1,8-naphthyridine-3-carboxamide;
2-Methyl-N-(1-(4-(3-(trifluoromethyl)-3H-diazirin-3-yl)phenyl)ethyl)-1,8-naphthyridine-3-carboxamide;
N-(4-(1,2-diazaspiro[2.5]oct-1-en-6-yl)benzyl)-2-methyl-1,8-naphthyridine-3-carboxamide;
N-(4-(1,4-Dioxaspiro[4.5]decan-8-yl)benzyl)-2-methyl-1,8-naphthyridine-3-carboxamide;
2-Methyl-N-(4-(4-oxocyclohexyl)benzyl)-1,8-naphthyridine-3-carboxamide;
N-(1-(4'-methoxybiphenyl-4-yl)ethyl)-2-methyl-1,8-naphthyridine-3-carboxamide;
3-(Trifluoromethyl)benzyl 2-methyl-1,8-naphthyridine-3-carboxylate;
(6-Phenylpyridin-3-yl)methyl 2-methyl-1,8-naphthyridine-3-carboxylate;
(5-Phenylisoxazol-3-yl)methyl 2-methyl-1,8-naphthyridine-3-carboxylate;
(2-Phenylthiazol-4-yl)methyl 2-methyl-1,8-naphthyridine-3-carboxylate;
(6-tert-Butylpyridin-3-yl)methyl 2-methyl-1,8-naphthyridine-3-carboxylate;

Biphenyl-3-ylmethyl 2-methyl-1,8-naphthyridine-3-carboxylate;
(6-Cyclohexylpyridin-3-yl)methyl 2-methyl-1,8-naphthyridine-3-carboxylate;
(S)-1-(4-morpholino-3-(trifluoromethyl)phenyl)ethyl 2-methyl-1,8-naphthyridine-3-carboxylate;
2-Methyl-4-(piperidin-1-yl)-N-(3-(trifluoromethyl)benzyl)-1,8-naphthyridine-3-carboxamide;
2-Methyl-4-oxo-N-(3-(trifluoromethyl)benzyl)-1,4-dihydro-1,8-naphthyridine-3-carboxamide;
4-Methoxy-2-methyl-N-(3-(trifluoromethyl)benzyl)-1,8-naphthyridine-3-carboxamide;
N-(4-tert-butylbenzyl)-2,7-dimethyl-1,8-naphthyridine-3-carboxamide;
N-(4-tert-butylbenzyl)-2,6-dimethyl-1,8-naphthyridine-3-carboxamide;
N-(4-tert-butylbenzyl)-2,5-dimethyl-1,8-naphthyridine-3-carboxamide;
6-Bromo-N-(4-tert-butylbenzyl)-2-methyl-1,8-naphthyridine-3-carboxamide;
6-amino-N-(4-tert-butylbenzyl)-2-methyl-1,8-naphthyridine-3-carboxamide;
N-(4-tert-butylbenzyl)-6-iodo-2-methyl-1,8-naphthyridine-3-carboxamide;
N-(4-tert-Butylbenzyl)-6-hydroxy-2-methyl-1,8-naphthyridine-3-carboxamide;
N-(4-tert-Butylbenzyl)-6-cyano-2-methyl-1,8-naphthyridine-3-carboxamide;
N-(4-tert-butylbenzyl)-2,4-dimethyl-1,8-naphthyridine-3-carboxamide;
5-Methoxy-2-methyl-N-(3-(trifluoromethyl)benzyl)-1,8-naphthyridine-3-carboxamide;
5-(Dimethylamino)-2-methyl-N-(3-(trifluoromethyl)benzyl)-1,8-naphthyridine-3-carboxamide;
2-Methyl-5-morpholino-N-(3-(trifluoromethyl)benzyl)-1,8-naphthyridine-3-carboxamide;
6-Chloro-2-methyl-N-(3-(trifluoromethyl)benzyl)-1,8-naphthyridine-3-carboxamide;
N-((6-tert-Butyl-2-chloropyridin-3-yl)methyl)-2-methyl-1,8-naphthyridine-3-carboxamide;
N-(2-chloro-6-cyclopentylpyridin-3-yl)methyl)-2-methyl-1,8-naphthyridine-3-carboxamide;
N-(6-tert-Butyl-2-methoxypyridin-3-yl)methyl)-2-methyl-1,8-naphthyridine-3-carboxamide;
N-(4-Azido-3-iodobenzyl)-2-methyl-1,8-naphthyridine-3-carboxamide; and
N-(4-tert-butyl-2-hydroxybenzyl)-2-methyl-1,8-naphthyridine-3-carboxamide.

15. A pharmaceutical composition comprising a compound according to claim 1 or a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide and at least one pharmaceutically acceptable excipient.

16. The pharmaceutical composition according to claim 15, wherein said composition comprises a β2-agonist, an anticholinergicum and/or a corticosteroid.

17. A method of treating a disease or condition characterized by bronchoconstriction of the respiratory apparatus selected from the group consisting of asthma, chronic obstructive pulmonary disease, chronic bronchitis, emphysema, bronchiectasis, cystic fibrosis, bronchiolitis and bronchopulmonary dysplasia, comprising administering a mammal, including man in need of such treatment, a therapeutically effective amount of a compound according to claim 1 or a compound selected from the group consisting of 2-(trifluoromethyl)-N-(3-(trifluoromethyl)benzyl)-1,8-naphthyridine-3-carboxamide, N-(pyridin-4-ylmethyl)-2-(trifluoromethyl)-1,8-naphthyridine-3-carboxamide, N-(pyridin-2-ylmethyl)-2-(trifluoromethyl)-1,8-naphthyridine-3-carboxamide, 2-methyl-N-(3-(trifluoromethyl)benzyl)-1,8-naphthyridine-3-carboxamide, 2-methyl-N-(pyridin-4-ylmethyl)-1,8-naphthyridine-3-carboxamide, 2-methyl-N-(pyridin-2-ylmethyl)-1,8-naphthyridine-3-carboxamide and 2-methyl-N-(2-(4-thiazolyl)ethyl)-1,8-naphthyridine-3-carboxamide.

* * * * *